US006678669B2

(12) United States Patent
Lapointe et al.

(10) Patent No.: US 6,678,669 B2
(45) Date of Patent: *Jan. 13, 2004

(54) METHOD FOR SELECTING MEDICAL AND BIOCHEMICAL DIAGNOSTIC TESTS USING NEURAL NETWORK-RELATED APPLICATIONS

(75) Inventors: Jerome Lapointe, Oakland, CA (US); Duane DeSieno, La Jolla, CA (US)

(73) Assignee: Adeza Biomedical Corporation, Sunnyvale, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 658 days.

(21) Appl. No.: 08/912,133
(22) Filed: Aug. 14, 1997
(65) Prior Publication Data
US 2001/0023419 A1 Sep. 20, 2001

Related U.S. Application Data

(63) Continuation-in-part of application No. 08/798,306, filed on Feb. 7, 1997, now abandoned, which is a continuation-in-part of application No. 08/599,275, filed on Feb. 9, 1996, now abandoned.
(60) Provisional application No. 60/011,449, filed on Feb. 9, 1996.

(51) Int. Cl.$^7$ ................................................. G06N 3/02
(52) U.S. Cl. ........................ 706/15; 702/82; 702/121; 702/123
(58) Field of Search ............................ 706/15; 702/82, 702/121, 123

(56) References Cited

U.S. PATENT DOCUMENTS 4,099,587 A  7/1978  Kaufmann ................... 177/210

(List continued on next page.)

FOREIGN PATENT DOCUMENTS

EP           0387630          9/1990

(List continued on next page.)

OTHER PUBLICATIONS

Al–Jumah, A.A.; Arslan, T., Arificial Neural Network Based Multiple Fault Diagnosis in Digital Circuits, Circuits and Systems, 1998. ISCAS '98. Proceedings of the 1998 IEEE International Symposium on, vol.: 2, 1998, pp.: 304–308 vol. 2, Jan. 1998.*

(List continued on next page.)

*Primary Examiner*—Mark R. Powell
*Assistant Examiner*—Wilbert Starks
(74) *Attorney, Agent, or Firm*—Stephanie L. Seidman; Heller Ehrman White & McAuliffe LLP

(57) ABSTRACT

Methods are provided for developing medical diagnostic tests using decision-support systems, such as neural networks. Patient data or information, typically patient history or clinical data, are analyzed by the decision-support systems to identify important or relevant variables and decision-support systems are trained on the patient data. Patient data are augmented by biochemical test data, or results, where available, to refine performance. The resulting decision-support systems are employed to evaluate specific observation values and test results, to guide the development of biochemical or other diagnostic tests, too assess a course of treatment, to identify new diagnostic tests and disease markers, to identify useful therapies, and to provide the decision-support functionality for the test. Methods for identification of important input variables for a medical diagnostic tests for use in training the decision-support systems to guide the development of the tests, for improving the sensitivity and specificity of such tests, and for selecting diagnostic tests that improve overall diagnosis of, or potential for, a disease state and that permit the effectiveness of a selected therapeutic protocol to be assessed are provided. The methods for identification can be applied in any field in which statistics are used to determine outcomes. A method for evaluating the effectiveness of any given diagnostic test is also provided.

251 Claims, 18 Drawing Sheets

U.S. PATENT DOCUMENTS

| | | | |
|---|---|---|---|
| 4,874,963 A | | 10/1989 | Alspector .................... 307/201 |
| 4,965,725 A | | 10/1990 | Rutenberg ............... 364/413.1 |
| 5,036,479 A | * | 7/1991 | Prednis et al. .............. 702/121 |
| 5,096,830 A | | 3/1992 | Senyei et al. ................. 436/65 |
| 5,130,936 A | * | 7/1992 | Sheppard et al. ........... 702/123 |
| 5,157,733 A | | 10/1992 | Takeo et al. .................... 382/6 |
| 5,185,270 A | | 2/1993 | Senyei et al. ............... 436/510 |
| 5,223,440 A | | 6/1993 | Teng et al. .................. 436/510 |
| 5,236,846 A | | 8/1993 | Senyei et al. ................. 436/65 |
| 5,241,620 A | | 8/1993 | Ruggiero ...................... 395/22 |
| 5,249,259 A | | 9/1993 | Harvey ......................... 395/13 |
| 5,251,626 A | | 10/1993 | Nickolls et al. .............. 607/14 |
| 5,281,522 A | | 1/1994 | Senyei et al. ................ 435/7.9 |
| 5,299,284 A | | 3/1994 | Roy ............................. 395/22 |
| 5,301,681 A | | 4/1994 | DeBan et al. ............... 128/736 |
| 5,304,468 A | | 4/1994 | Phillips et al. ................ 435/14 |
| 5,321,492 A | | 6/1994 | Detwiler et al. .............. 356/73 |
| 5,331,550 A | | 7/1994 | Stafford et al. .......... 364/413.2 |
| 5,392,403 A | | 2/1995 | Kaufmann ................... 395/275 |
| 5,405,362 A | | 4/1995 | Kramer et al. ................. 607/5 |
| 5,455,890 A | | 10/1995 | Wang .......................... 395/22 |
| 5,463,548 A | | 10/1995 | Asada et al. ............ 364/413.02 |
| 5,468,619 A | | 11/1995 | Senyei et al. .............. 435/7.94 |
| 5,473,537 A | | 12/1995 | Glazer et al. ............ 364/419.2 |
| 5,481,481 A | * | 1/1996 | Frey et al. ..................... 702/82 |
| 5,491,627 A | | 2/1996 | Zhang et al. ............ 364/413.2 |
| 5,503,161 A | | 4/1996 | Van Den Heuvel ......... 128/773 |
| 5,516,702 A | | 5/1996 | Senyei et al. ............... 436/510 |
| 5,533,519 A | | 7/1996 | Radke et al. ................ 128/777 |
| 5,544,308 A | * | 8/1996 | Giordano et al. ............. 714/26 |
| 5,560,370 A | | 10/1996 | Verrier et al. ............... 128/705 |
| 5,565,364 A | | 10/1996 | Schaefer et al. .............. 436/43 |
| 5,590,665 A | | 1/1997 | Kanai ......................... 128/898 |
| 5,594,637 A | | 1/1997 | Eisenberg et al. .......... 395/202 |
| 5,622,171 A | | 4/1997 | Asada et al. ............ 364/413.01 |
| 5,627,907 A | | 5/1997 | Gur et al. .................... 382/128 |
| 5,687,716 A | | 11/1997 | Kaufmann et al. ......... 128/630 |
| 5,690,103 A | * | 11/1997 | Groth et al. ................. 600/368 |
| 5,817,461 A | * | 10/1998 | Austin et al. ................... 435/6 |
| 5,878,740 A | * | 3/1999 | Videto et al. ............... 600/407 |

FOREIGN PATENT DOCUMENTS

| | | |
|---|---|---|
| EP | 0557831 | 9/1993 |
| EP | 0616291 | 1/1994 |
| EP | 0610805 | 3/1994 |
| EP | 0644414 | 3/1995 |
| WO | 9425933 | 11/1994 |
| WO | 9427490 | 12/1994 |
| WO | 9612187 | 4/1996 |
| WO | 9705553 | 2/1997 |
| WO | 9709678 | 3/1997 |
| WO | 9717891 | 5/1997 |
| WO | 9730996 | 8/1997 |

OTHER PUBLICATIONS

Ouyang, N.; Ikeda,M.; Yamauchi, K., Using a Neural Network to Diagnose Anterior Wall Myocardial Infarction, Neural Networks, 1997., International Conference on, vol.: 1, 1997, pp.: 56–61 vol. 1, Jan. 1997.*

Brownell, T.A., Neural Networks for Sensor Management and Diagnostics, Aerospace and Electronics Conference, 1992. NAECON 1992., Proceedings of the IEEE 1992 National, 1992, pp.: 923–929, Jan. 1992.*

Marko, K.A.; Feldkamp, L.A.; Puskorius, G.V., Automotive Diagnostics Using Trainable Classifiers: Statistical Testing and Paradigm Selection, Neural Networks, 1990., 1990 IJCNN International Joint Conference on, 1990, pp.: 33–38 vol. 1, Jan. 1990.*

Sheppard, J.W.; Simpson, W.R., A Neural Network for Evaluating Diagnostic Evidence, Aerospace and Electronics Conference, 1991. NAECON 1991., Proceedings of the IEEE 1991 National, 1991, pp.: 717–723 vol. 2, Jan. 1991.*

Michel, J.; Mirchandani, G.; Wald, S., Prognosis With Neural Networks Using Statistically Based Feature Sets, Computer–Based Medical Systems, 1992. Proceedings., Fifth Annual IEEE Symposium on, 1992, pp.: 695–702, Jan. 1992.*

Creasy and Resnik, *Maternal–fetal medicine: Principles and practice*, Ch 36, Sec. 18, p. 657, 1989.

Ota and Maki, "Evaluation of autoantibody and CA125 in the diagnosis of endometriosis or adenomyosis", *Medicinal Research Reviews* 18(8):309 (1990).

Database Derwent WPI #009580780, citing European patent 557831 A, Instrument for determining optimum delivery time of foetus.

van Dyne et al., "Using inductive machine learning, expert systems and case based reasoning to predict preterm delivery in pregnant women", Database and Expert Systems Applications, 5th Int'l Conf., DEXA 1994 Proceedings, Athens, Greece, Sep. 7–9, 1994, pp. 690–702.

van Dyne et al., "Using machine learning and expert systems to predict preterm delivery in pregnant women", Proceedings of the Tenth Conference on Artificial Intelligence for Applications, San Antonia, TX, Mar. 1–4, 1994, pp. 344–350.

Benediktsson et al., Parallel consensual neural networks with optimally weighted output, *Proceedings of World Congress on Neural Networks* 3:129–137, 1994.

Kim et al., Ensemble competitive learning neural networks with reduced input dimension, *Intl. J. of Neural Systems* 6(2):133–142, 1995.

Baxt, "Use of an artificial neural network for data analysis in clinical decision–making: The diagnosis of acute coronary occlusion", *Neural Computation*, 2:480–489 (1990).

Baxt, "Use of an artifical neural network for the diagnosis of myocardial infarction", *Annals of Internal Medicine*, 115:843–848 (1991).

Baxt, "Analysis of the clinical variables driving decision in an artificial neural network trained to identify the presence of myocardial infarction", *Annals of Emergency Medicine*, 21: 1439–1444 (1992).

Baxt, "Improving the accuracy of an artificial neural network using multiple differently trained networks", *Neural Computation*, pp. 772–780 (1992).

Baxt, "Complexity, choas and human physiology: the justification for non–linear neural computational analysis", *Cancer Letters*, 77:85–93 (1994).

Baxt, "Application of arificial neural networks to clinical medicine", *Lancet*, 346:1135–1138 (1995).

Baxt, "Bootstrapping confidence intervals for clinical input variable effects in a network trained to indentify the prescence of acute myocardial infarction", *Neural Computation*, 7:624–638 (1995).

P.E. Keller, "Artifical neural networks in medicine", Handout/Technology brief, Pacific Northwest Laboratory.

NTIS Published Search—"Neural networks: Applications" (Sep. 1986–present).

Snow, et al., "Artificial neural networks in the diagnosis and prognosis of prostate cancer: A pilot study", *The Journal of Urology*, 152:1923–1926 (1994).

Alvager, et al., "The use of artificial neural networks in biomedical technologies: An introduction", *Biomedical Instrumentation and Technology* pp. 315–322 (1994).

Arden, "Internal Medicine:Internist", (available at http://www.spi.org/cgi . . . eeit&csum=110562327913 on Dec. 8, 1996).

Beksac, et al., "An artifical intelligent diagnosis system with neural networks to determine genetical disorders and fetal health by using maternal serum markers", *European Journal of Obstetrics and Gynecology and Reproductive Biology* 59:131–136 (1995).

Blinowska, et al., "Diagnostica—A bayesian decision–aid system—applied to hypertension diagnosis", *IEEE Transactions on Biomedical Engineering* 40:230–235 (1993).

Brickley, et al., "Performance of a neural network trained to make third–molar treatment–planning decisions", *Medical Decision Making* 16:153–160 (1996).

Brown, et al., Finite training sample size effects on neural network pattern classification in low–dimensional feature space, pp. 96–101.

Burke, et al., "Artificial neural networks for outcome prediction in cancer", pp. 53–56.

Davis, et al., "Production systems as a representation for a knowledge based consultation program", *Artificial Intelligence* 8:15–45 (1977).

Erickson, "What is cognitive computing?", part 2 of 3, (available at http://www.spi.org/cgi . . . seeit&csum=16068819102 on Dec. 8, 1996).

Fahlman, et al., "The cascade–correlation learning architecture", *Advances in Neural Information Processing Systems 2*, pp. 524–532 (1989).

Fahlman, "Fast learning variations on back–propagation: An empirical study", *Proceedings on the 1988 Connectionist Models Summer School*, Pittsburgh, pp. 38–51 (1988).

Haddawy, "Decision systems and artificial intelligence laboratory", (available at http:/www.cs.uwm.edu/;;public/dsail/ on Nov. 21, 1996).

Kahn, "Mammonet: Mammography decision supports system", (avaiable at http://www.mcw.edu/midas/mammo.html on Nov. 21, 1996).

Keller, et al., "A novel approach to modeling and diagnosing the cardiovascular system" (available at http://www.emsl.pnl.gov:2080/docs/c . . . ural/papers2/keller.wcnn95.abs.html on Nov. 21, 1996).

Kol, et al., "Interpretation of nonstress tests by artificial neural network", *American Journal of Obstetrics and Gynecology* 172:1372–1379 (1995).

Lapuerta, et al., "Use of neural networks in predicting the risk of coronary artery disease", *Computers and Biomedical Research* 28:38–52 (1995).

Maclin, et al., "Using neural networks to diagnose cancer", *Journal of Medical Systems* 15:11–19 (1991).

Mobley, et al., "Artificial neural network predictions of lengths of stay on a post coronary care unit", *Heart and Lung* 24:251–256 (1995).

Pattichis, et al., "Neural network Models in EMG Diagnosis", *IEEE Transactions on Biomedical Engineering* 42:486–495 (1995).

Penny, et al., "Neural networks in Clinical Medicine", *Medical Decision Making* 16:386–398 (1996).

Plate, "Re: neural nets", (available at http://www.gsf.de/msr/sift/msg00649.html on Nov. 21, 1996).

Modai, et al., "Clinical decisions for psychiatric inpatients and their evaluation by trained neural networks", *Methods of Information in Medicine* 32:396–399 (1993).

Roger, et al., "Artificial neural networks for early detection and diagnosis of breast and ovarian cancer", *Cancer Letters* 77:79–83 (1994).

Ruck, et al., "Feature selection in feed–forward neural networks", *Neural Networks Computing* 20:40–48 (1990).

Rutledge, "An overview of medical decision–support systems", (available at http://www.medg.lcs.mit.edu/BIRT/absgeoff.htm on Nov. 21, 1996).

Sammet, "Pattern recognition applied to early diagnosis of heart attacks", (available at http:// www.spi.org/cgi . . . seeit&csum=19641717994 on Dec. 8, 1996.

Siganos, "Neural networks in medicine", (available at http://scorch.doc.ic.ac.uk/~nd/suprise_96/journal/vol2/ds12/article2.html on Nov. 21, 1996).

Solms, et al., "A neural network diagnostic tool for the chronic fatigue syndrome", International Conference on Neural Networks, Paper No. 108).

Stamey, "ProstAsure™: An information resource", (available at http://www.labcorp.com/prost3.htm on Nov. 21, 1996).

Swaine, "Programming Paradigms—part 2", (avaiable at http://www.spi.org/cgi . . . seeit&csum=17808028563 on Dec. 8, 1996).

Turner, "Technology brief: Coronary artery disease diagnosis" (available on http://www.emsl.gov:2080/docs/cie/techbrief/CAD.techbrief.html on Nov. 21, 1996).

Utans, et al., "Input variable selection for neural networks: Applications to predicting the U.S. Business Cycle", IEEE pp. 118–122 (1995).

Weinstein, et al., "Neural networks in the biomedical sciences: A survey of 386 publications since the beginning of 1991", pp. 121–126.

Wenskay, "Neural networks: a prescription for effective protection", *The Computer Lawyer* 8:12–23 (1991).

Widman, "Expert systems in medicine", (available on http://amplatz.uokhsc.edu/acc95–expert–systems.html on Nov. 21, 1996).

Wilding, et al., "Application of Backpropogation neural networks to diagnosis of breast and ovarian cancer", *Cancer Letters* 77:145–153.

Young, "Diagnosis of acute cardiac ischemia", (available on http://www.library.ucs . . . 1/Originals/young.html on Nov. 21, 1996).

"Artificial intelligence systems in routine clinical use", (available on http://www.gretmar.com/ailist/list.html).

"BioComp Systems, Inc.: Systems that learn, adapt and evolve", (available on http://www.bio–comp.com/products.htm on Nov. 21, 1996).

"Multivariate statistical data reduction method", (available on http://www.spi.org/cgi . . . seeit&csum=17396875558 on Dec. 8, 1996).

"Neural informatics pearls of wisdom", (available on http://www.–smi.stanford.edu/people/ . . . hysiology/Neuro_Pearls.html#ANN–app on Nov. 21, 1996).

*Neural Networks & intelligent systems newsletter*, Derwent Direct, Issue 3, (Aug., 1996).

Logical Designs Consulting, Inc., "Thinks™ and ThinksPro™ Neural networks for windows: Your complete neural network development environment".

Moneta et al., Automated diagnosis and disease characterization using neural network analysis, *Instittute of Electrical and Electronics Engineers—Emergent Innovations on Information Transfer Processing and decision Making*, Chicago, vol. 1 of 2: 123–128 (1992).

Nejad et al., Significance measures and data dependency in classification methods, *Instit. Elect. Electron. Engineers Intl. Conference on Neural Network Proceedings*, Australia: 1816–1822 (1995).

Utans, et al., "Selecting neural network architectures via the prediction risk: Application to corporate bond rating prediction", *Proceedings of the First International Conference on Artificial Intelligence Applications on Wall Street, Washington D.C.*, IEEE Computer Society Press. pp. 35–41 (1991).

Diller, W., "Horus computer–enhanced diagnostics", *In Vivo: The Business and Medicine Report*, pp. 3–10, 1997.

Burke, Evaluating artificial neural networks for medical applications, *International Conference on Neural Networks* 4:2494–2495 (1997).

El–Deredy et al., Identification of relevant features in /sup 1/H MR tumour spectra using neural networks, *Fourth International Conference on Artificial Neural Networks* pp. 454–458 (1995).

Furundzic et al., Artificial neural networks for early breast carcinoma detection, *International Workshop on Neural Networks for Identification, Control, Robotics, and Signal/Image Processing* 355–359 (1996).

Gorzalczany, An idea of the application of fuzzy neural networks to medical decision support systems, *Proceedings of the IEEE International Symposium on Industrial Electronics* 1:398–403 (1996).

Kupinski et al., Feature selection and classifiers for the computerized detection of mass lesions in digital mammography, *International Conference on Neural Networks* 4:2460–2463 (1997).

Micheli–Tzanakou et al., Myocardial infarction: diagnosis and vital status prediction using neural networks, *Computers in Cardiology* pp. 229–232 (1993).

Rachid et al., Segmentation of sputum color image for lung cancer diagnosis *International Conference on Image Processing* 1:243–246 (1997).

Shiyi Xu et al., Testability prediction for sequential circuits using neural networks, *Sixth Asian Test Symposium* pp. 48–53 (1997).

Wong et al., Fuzzy neural systems for decision making, *IEEE International Joint Conference on Neural Networks* 2:1625–1637 (1991).

* cited by examiner

FIG. 12

| Pre-Term Delivery Risk Assessment Software: Data Entry Screen | ☒ |
|---|---|

| Lab ID # |
|---|

PATIENT INFORMATION

Name(last) [ ]  First [ ]  M [ ]

DOB [mm/dd/yy]

Ethnic origin: ☐ Caucasian ☐ African American ☐ Asian ☐ Hispanic ☐ Native American ☐ Other Marital status: ☐ Married ☐ Single ☐ Divorced/Seperated ☐ Widowed ☐ Living with partner ☐ Other

PATIENT HISTORY AND CLINICAL INFORMATION

At the time of sampling, was the patient experiencing signs and symptoms of possible preterm labor?   ☐ YES   ☐ NO If yes, please mark all that apply.

☐ Uterine contractions with or without pain
 Number/hr. ☐ <1  ☐ 1-3  ☐ 4-6  ☐ 7-9  ☐ 10-12  ☐ >12

☐ Vaginal bleeding
 ☐ Trace ☐ Med. ☐ Gross

☐ Patient is not "feeling right"

☐ Bleeding during the second or third trimester

☐ Intermittent lower abdominal pain, dull, lowback pain, pelvic pressure

☐ Change in vaginal discharge-amount, color, or consistency

☐ Menstrual-like cramping (with or without diarrhea)

Gestational Age: EGA by first trimester sono [ww.d]   EGA by LMP [ww.d]   EGA at sampling [ww.d]

| Previous Pregnancy: Please mark all that apply: | Current Pregnancy: G: [ ]  P: [ ]  A: [ ] |
|---|---|
| ☐ Previous pregnancy: no complications | ☐ Multiple Gestation ☐ Twins ☐ Triplets ☐ Quads |
| ☐ History of Preterm delivery<br>If Yes, how many? ☐ 1  ☐ 2  ☐ >2 | ☐ Uterine or cervical abnormality |
| ☐ History of Preterm PROM | ☐ Cerclage |
| ☐ History of incompetent cervix | ☐ Gestational Diabetes |
| ☐ History of PIH/preeclampsia | ☐ Hypertensive Disorders |
| ☐ History of SAB prior to 20 wks. | |

Cervical Status immediately following sample collection:
Dilatation(cm) ☐ <1 ☐ 1 ☐ 1-2 ☐ 2 ☐ 2-3 ☐ 3 ☐ >3 ☐ Unk.   Cervical consistency ☐ Firm ☐ Mod ☐ Soft Medications at Time of Test (check all that apply)
☐ Antibiotics ☐ Corticosteroids ☐ Tocolytis ☐ Insulin ☐ Antihypertensives ☐ None ☐ Unknown Qualitative fFN Elisa Test Results: ☐ Positive   ☐ Negative

[ Calculate risk ]   [ Cancel ]

FIG. 13

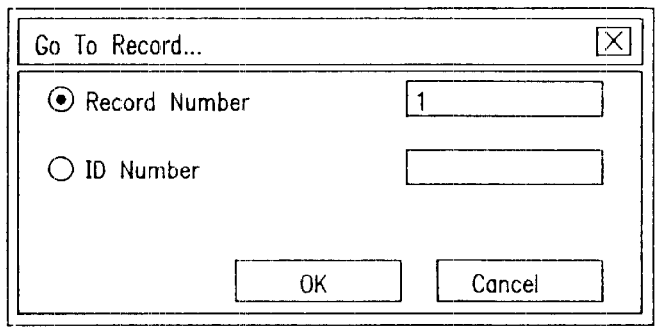
FIG. 14
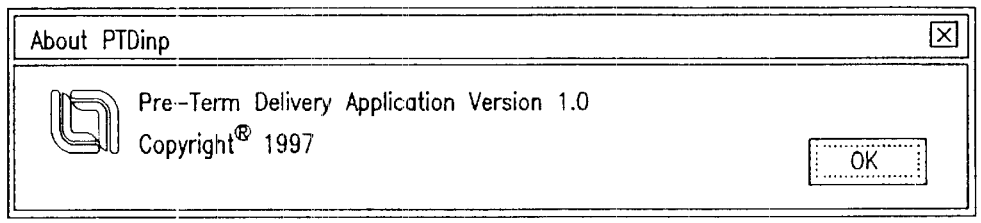
FIG. 15
Pre-Term Delivery Risk Assesment Software:
Test Report Form
| Lab ID # | |
|---|---|
| Patient Name: | |
| Pre-term Delivery Risk <34.6wks: | 0.288432 |
| Pre-term delivery Risk <7 days: | 0.001721 |
| Pre-term Delivery Risk <14 days: | 0.001544 |
FIG. 16A

| Pre-Term Delivery Risk Assessment Software: Data Entry Screen    Lab ID #    ☒ |
|---|

| PATIENT INFORMATION |
|---|

| Name(last)    First    M | Ethnic origin: ☐Caucasian ☐African American ☐Asian |
|---|---|
| DOB  mm/dd/yy | ☐Hispanic ☐Native American ☐Other |
|  | Marital status: ☐Married ☐Single ☐Divorced/Seperated |
|  | ☐Widowed ☐Living with partner ☐Other |

| PATIENT HISTORY AND CLINICAL INFORMATION |
|---|

At the time of sampling, was the patient experiencing signs and symptoms of possible preterm labor?    ☐YES ☐NO If yes, please mark all that apply.

☐Uterine contractions with or without pain   ☐Bleeding during the second or third trimester
Number/hr. ☐<1 ☐1-3 ☐4-6    ☐Intermittent lower abdominal pain, dull, low backpain,
☐7-9 ☐10-12 ☐>12    pelvic pressure ☐Vaginal bleeding    ☐Change in vaginal discharge-amount, color, or
☐Trace ☐Med. ☐Gross    consistency ☐Patient is not feeling right    ☐Menstrual-like cramping (with or without diarrhea)

Gestational Age: EGA by first trimester sono ww.d    EGA by LMP ww.d    EGA at sampling ww.d

| Previous Pregnancy: Please mark all that apply. | Current Pregnancy:  G:    P:    A: |
|---|---|
| ☐ Previous pregnancy: no complications | ☐ Multiple Gestation ☐Twins ☐Triplets ☐Quads |
| ☐ History of Preterm delivery | ☐ Uterine or cervical abnormality |
| If Yes, how many? ☐1 ☐2 ☐>2 | ☐ Cerclage |
| ☐ History of Preterm PROM | ☐ Gestational Diabetes |
| ☐ History of incompetent cervix | ☐ Hypertensive Disorders |
| ☐ History of PIH/preeclampsia |  |
| ☐ History of SAB prior to 20 wks. |  |

Cervical status immediately following sample collection:    ☐Firm  ☐Soft
Dilatation(cm) ☐<1 ☐1 ☐1-2 ☐2 ☐2-3 ☐3 ☐>3 ☐Unknown Cervical consistency ☐Mod Medications at Time of Test(check all that apply)
☐ Antibiotics ☐Corticosteroids  ☐ Tocolytis ☐Insulin ☐ Antihypertensives ☐ None ☐ Unknown Qualitative fFN Elisa Test Results: ☐ Positive    ☐ Negative Pre-term Delivery Risk <34.6wks:    0.288432

Pre-term Delivery Risk <7 days:    0.001721

Pre-term Delivery Risk <14 days:    0.001544

METHOD FOR SELECTING MEDICAL AND BIOCHEMICAL DIAGNOSTIC TESTS USING NEURAL NETWORK-RELATED APPLICATIONS

This application is a continuation-in-part of U.S. application Ser. No. 08/798,306 entitled "METHOD FOR SELECTING MEDICAL AND BIOCHEMICAL DIAGNOSTIC TESTS USING NEURAL NETWORK-RELATED APPLICATIONS" to Jerome Lapointe and Duane DeSieno, filed Feb. 7, 1997, now abandoned. This application is also a continuation-in-part of U.S. application Ser. No. 08/599,275, entitled "METHOD FOR DEVELOPING MEDICAL AND BIOCHEMICAL DIAGNOSTIC TESTS USING NEURAL NETWORKS" to Jerome Lapointe and Duane DeSieno, filed Feb. 9, 1996, now abandoned. U.S. application Ser. No. 08/798,306 is a continuation-in-part of U.S. application Ser. No. 08/599,275. U.S. application Ser. No. 08/599,275, entitled "METHOD FOR DEVELOPING MEDICAL AND BIOCHEMICAL DIAGNOSTIC TESTS USING NEURAL NETWORKS" to Jerome Lapointe and Duane DeSieno, filed Feb. 9, 1996 claims priority under 35 U.S.C. § 119(e) to U.S. provisional application Ser. No. 60/011,449, entitled "METHOD AND APPARATUS FOR AIDING IN THE DIAGNOSIS OF ENDOMETRIOSIS USING A PLURALITY OF PARAMETERS SUITED FOR ANALYSIS THROUGH A NEURAL NETWORK" to Jerome Lapointe and Duane DeSieno, filed Feb. 9, 1996.

The subject matter of each of the above-noted applications and provisional application is herein incorporated in its entirety by reference thereto.

COMPUTER PROGRAM LISTING APPENDIX ON COMPACT DISK

Three computer Appendices containing computer program source code for programs described herein have been submitted concurrently with the filing of this application. The Computer Appendices were converted to Computer Program Listing Compact Disk Appendices pursuant to 37 C.F.R. 1.96(c). Appendices I, II, and III are on compact disks, copy 1 and copy 2, and stored under the file name Appenixl-III.txt, 392KB, created on Apr. 6, 2001. The compact disks, copy 1 and copy 2, are identical. The information submitted on the Compact Disk is in compliance with the American Standard Code for Information Interchange (ASCII) in the IBM-PC machine format compatible with the MS-Windows operating system. The Computer Appendices, which are referred to hereafter as the "Compact Disk Appendices", are each incorporated herein by reference in its entirety.

Thus, a portion of the disclosure of this patent document contains material that is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

This subject matter of the invention relates to the use of prediction technology, particularly nonlinear prediction technology, for the development of medical diagnostic aids. In particular, training techniques operative on neural networks and other expert systems with inputs from patient historical information for the development of medical diagnostic tools and methods of diagnosis are provided.

BACKGROUND OF THE INVENTION

Data Mining, decision support-systems and neural networks A number of computer decision-support systems have the ability to classify information and identify patterns in input data, and are particularly useful in evaluating data sets having large quantities of variables and complex interactions between variables. These computer decision systems which are collectively identified as "data mining" or "knowledge discovery in databases" (and herein as decision-support systems) rely on similar basic hardware components, e.g., personal computers (PCS) with a processor, internal and peripheral devices, memory devices and input/output interfaces. The distinctions between the systems arise within the software, and more fundamentally, the paradigms upon which the software is based. Paradigms that provide decision-support functions include regression methods, decision trees, discriminant analysis, pattern recognition, Bayesian decision theory, and fuzzy logic. One of the more widely used decision-support computer systems is the artificial neural network.

Artificial neural networks or "neural nets" are parallel information processing tools in which individual processing elements called neurons are arrayed in layers and furnished with a large number of interconnections between elements in successive layers. The functioning of the processing elements are modeled to approximate biologic neurons where the output of the processing element is determined by a typically non-linear transfer function. In a typical model for neural networks, the processing elements are arranged into an input layer for elements which receive inputs, an output layer containing one or more elements which generate an output, and one or more hidden layers of elements therebetween. The hidden layers provide the means by which non-linear problems may be solved. Within a processing element, the input signals to the element are weighted arithmetically according to a weight coefficient associated with each input. The resulting weighted sum is transformed by a selected non-linear transfer function, such as a sigmoid function, to produce an output, whose values range from 0 to 1, for each processing element. The learning process, called "training", is a trial-and-error process involving a series of iterative adjustments to the processing element weights so that a particular processing element provides an output which, when combined with the outputs of other processing elements, generates a result which minimizes the resulting error between the outputs of the neural network and the desired outputs as represented in the training data. Adjustment of the element weights are triggered by error signals. Training data are described as a number of training examples in which each example contains a set of input values to be presented to the neural network and an associated set of desired output values.

A common training method is backpropagation or "backprop", in which error signals are propagated backwards through the network. The error signal is used to determine how much any given element's weight is to be changed and the error gradient, with the goal being to converge to a global minimum of the mean squared error. The path toward convergence, i.e., the gradient descent, is taken in steps, each step being an adjustment of the input weights of the processing element. The size of each step is determined by the learning rate. The slope of the gradient descent includes flat and steep regions with valleys that act as local minima, giving the false impression that convergence has been achieved, leading to an inaccurate result.

Some variants of backprop incorporate a momentum term in which a proportion of the previous weight-change value is added to the current value. This adds momentum to the algorithm's trajectory in its gradient descent, which may prevent it from becoming "trapped" in local minima. One backpropagation method which includes a momentum term is "Quickprop", in which the momentum rates are adaptive. The Quickprop variation is described by Fahlman (see,"Fast Learning Variations on Back-Propagation: An Empirical Study", *Proceedings on the* 1988 *Connectionist Models Summer School*, Pittsburgh, 1988, D. Touretzky, et al., eds., pp.38-51, Morgan Kaufmann, San Mateo, Calif.; and, with Lebriere, "The Cascade-Correlation Learning Architecture", *Advances in Neural Information Processing Systems* 2,(Denver, 1989), D. Touretzky, ed., pp. 524-32. Morgan Kaufmann, San Mateo, Calif.). The Quickprop algorithm is publicly accessible, and may be downloaded via the Internet, from the Artificial Intelligence Repository maintained by the School of Computer Science at Carnegie Mellon University. In Quickprop, a dynamic momentum rate is calculated based upon the slope of the gradient. If the slope is smaller but has the same sign as the slope following the immediately preceding weight adjustment, the weight change will accelerate. The acceleration rate is determined by the magnitude of successive differences between slope values. If the current slope is in the opposite direction from the previous slope, the weight change decelerates. The Quickprop method improves convergence speed, giving the steepest possible gradient descent, helping to prevent convergence to a local minimum.

When neural networks are trained on sufficient training data, the neural network acts as an associative memory that is able to generalize to a correct solution for sets of new input data that were not part of the training data. Neural networks have been shown to be able to operate even in the absence of complete data or in the presence of noise. It has also been observed that the performance of the network on new or test data tends to be lower than the performance on training data. The difference in the performance on test data indicates the extent to which the network was able to generalize from the training data. A neural network, however, can be retrained and thus learn from the new data, improving the overall performance of the network.

Neural nets, thus, have characteristics that make them well suited for a large number of different problems, including areas involving prediction, such as medical diagnosis.

Neural Nets and Diagnosis

In diagnosing and/or treating a patient, a physician will use patient condition, symptoms, and the results of applicable medical diagnostic tests to identify the disease state or condition of the patient. The physician must carefully determine the relevance of the symptoms and test results to the particular diagnosis and use judgement based on experience and intuition in making a particular diagnosis. Medical diagnosis involves integration of information from several sources including a medical history, a physical exam and biochemical tests. Based upon the results of the exam and tests and answers to the questions, the physician, using his or her training, experience and knowledge and expertise, formulates a diagnosis. A final diagnosis may require subsequent surgical procedures to verify or to formulate. Thus, the process of diagnosis involves a combination of decision-support, intuition and experience. The validity of a physician's diagnosis is very dependent upon his/her experience and ability.

Because of the predictive and intuitive nature of medical diagnosis, attempts have been made to develop neural networks and other expert systems that aid in this process. The application of neural networks to medical diagnosis has been reported. For example, neural networks have been used to aid in the diagnosis of cardiovascular disorders (see, e.g., Baxt (1991) "Use of an Artificial Neural Network for the Diagnosis of Myocardial Infarction," *Annals of Internal Medicine* 115:843; Baxt (1992) "Improving the Accuracy of an Artificial Neural Network Using Multiple Differently Trained Networks," *Neural Computation* 4:772; Baxt (1992), "Analysis of the clinical variables that drive decision in an artificial neural network trained to identify the presence of myocardial infarction," *Annals of Emergency Medicine* 21:1439; and Baxt (1994) "Complexity, chaos and human physiology: the justification for non-linear neural computational analysis," *Cancer Letters* 77:85). Other medical diagnostic applications include the use of neural networks for cancer diagnosis (see, e.g., Maclin, et al. (19910 "Using Neural Networks to Diagnose Cancer" *Journal of Medical Systems* 15:11-9; Rogers, et al. (1994) "Artificial Neural Networks for Early Detection and Diagnosis of Cancer" *Cancer Letters* 77:79-83; Wilding, et al. (1994) "Application of Backpropogation Neural Networks to Diagnosis of Breast and Ovarian Cancer" *Cancer Letters* 77:145-53), neuromuscular disorders (Pattichis, et al. (1995) "Neural Network Models in EMG Diagnosis", *IEEE Transactions on Biomedical Engineering* 42:5:486-495), and chronic fatigue syndrome (Solms, et al (1996) "A Neural Network Diagnostic Tool for the Chronic Fatigue Syndrome", International Conference on Neural Networks, Paper No. 108). These methodologies, however, fail to address significant issues relating to the development of practical diagnostic tests for a wide range of conditions and does not address the selection of input variables.

Computerized decision-support methods other than neural networks have been reported for their applications in medical diagnostics, including knowledge-based expert systems, including MYCIN (Davis, et al., "Production Systems as a Representation for a Knowledge-based Consultation Program", *Artificial Intelligence,* 1977; 8:1:15-45) and its progeny TEIRESIAS, EMYCIN, PUFF, CENTAUR, VM, GUIDON, SACON, ONCOCIN and ROGET. MYCIN is an interactive program that diagnoses certain infectious diseases and prescribes anti-microbial therapy. Such knowledge-based systems contain factual knowledge and rules or other methods for using that knowledge, with all of the information and rules being pre-programmed into the system's memory rather than the system developing its own procedure for reaching the desired result based upon input data, as in neural networks. Another computerized diagnosis method is the Bayesian network, also known as a belief or causal probabilistic network, which classifies patterns based on probability density functions from training patterns and a priori information. Bayesian decision systems are reported for uses in interpretation of mammograms for diagnosing breast cancer (Roberts, et al., "MammoNet: A Bayesian Network diagnosing Breast Cancer", Midwest Artificial Intelligence and Cognitive Science Society Conference, Carbondale, Ill., April 1995) and hypertension (Blinowska, et al. (1993) "Diagnostica—A Bayesian Decision-Aid System—Applied to Hypertension Diagnosis", *IEEE Transactions on Biomedical Engineering* 40:230-35) Bayesian decision systems are somewhat limited in their reliance on linear relationships and in the number of input data points that can be handled, and may not be as well suited for decision-support involving non-linear relationships between variables. Implementation of Bayesian methods using the processing elements of a neural network can overcome some of these limitations (see, e.., Penny, et al. (1996) In "Neural Networks in Clinical Medicine", Medical Decision-support, 1996; 16:4: 386-98). These methods have been used, by mimicking the physician, to diagnose disorders in which important variables are input into the system. It, however, would be of interest to use these systems to improve upon existing diagnostic procedures.

Endometriosis

Endometriosis is the growth of uterine-like tissue outside of the uterus. It affects about 15-30 percent of reproductive age women. The cause(s) of endometriosis are not known, but it may result from retrograde menstruation, the reflux of endometrial tissue and cells (menstrual debris) from the uterus into the peritoneal cavity. While retrograde menstruation is thought to occur in most or all women, it is unclear why some women develop endometriosis and others do not.

Not all women with endometriosis exhibit symptoms or suffer from the disease. The extent or severity of endometriosis does not correlate with symptoms. Some women with severe disease may be completely asymptomatic, whereas others with minimal disease may suffer from excruciating pain. Symptoms, such as infertility, pelvic pain, dysmenorrhea and past occurrence of endometriosis, that have been associated with endometriosis often occur in women who do not have endometriosis. In other instances, these symptoms may be present, and the women do have endometriosis. Although an association between these symptoms and endometriosis appears to exist, the correlation is far from perfect, the interplay with these and other factors are complex. Clinicians often perform diagnostic laparoscopies on patients whom they believe are excellent candidates for having endometriosis based a combination of the above indications. Endometriosis, however, is not present in a significant proportion of these women. Thus, endometriosis represents an example of a disease state in which a physician must draw upon experience using a complex set of information to formulate a diagnosis. The validity of the diagnosis is related to the experience and ability of the physician.

As a result, determining if a woman has endometriosis from symptoms alone has not been possible. Within the medical community, the diagnosis of endometriosis is confirmed only by direct visualization of endometrial lesions during surgery. Many physicians often impose a further restriction and demand that the suspected lesions be verified as being endometrial-like (glands and stroma) using histology on endometrial biopsied tissue. Thus, a non-invasive diagnostic test for endometriosis would be of significant benefit.

Therefore, it is an object herein to provide a non-invasive diagnostic aid for endometriosis. It is also an object herein to provide methods to select important variables to be used in decision-support systems to aid in diagnosis of endometriosis and other disorders and conditions. It is also an object herein to identify new variables, identify new biochemical tests and markers for diseases and to design to new diagnostic tests that improve upon existing diagnostic methodologies.

SUMMARY OF THE INVENTION

Methods using decision-support systems for the diagnosis of and for aiding in the diagnosis of diseases, disorders and other medical conditions are provided. The methods provided herein, include a method of using patient history data and identification of important variables to develop a diagnostic test; a method for identification of important selected variables; a method of designing a diagnostic test; a method of evaluating the usefulness of diagnostic test; a method of expanding clinical utility of diagnostic test, and a method of selecting a course of treatment by predicting the outcome of various possible treatments. Also provided are disease parameters or variables to aid in the diagnosis of disorders, including any disorders that are difficult to diagnose, such as endometriosis, predicting pregnancy related events, such as the likelihood of delivery within a particular time period, and other such disorders relevant to women's health. It is understood that although women's disorders are exemplified herein, the methods herein are applicable to any disorder or condition.

Also provided are means to use neural network training to guide the development of the tests to improve their sensitivity and specificity, and to select diagnostic tests that improve overall diagnosis of, or potential for, a disease state or medical condition. Finally, a method for evaluating the effectiveness of any given diagnostic test is described.

Thus, provided herein is a method for identifying variables or sets of variables that aid in the diagnosis of disorders or conditions. In the methods for identifying and selection of important variables and generating systems for diagnosis, patient data or information, typically patient history or clinical data are collected and variables based on this data are identified. For example, the data includes information for each patient regarding the number of pregnancies each patient has had. The extracted variable is, thus, number of pregnancies. The variables are analyzed by the decision-support systems, exemplified by neural networks, to identify important or relevant variables.

Methods are provided for developing medical diagnostic tests using computer-based decision-support systems, such as neural networks and other adaptive processing systems (collectively, "data mining tools"). The neural networks or other such systems are trained on the patient data and observations collected from a group of test patients in whom the condition is known or suspected; a subset or subsets of relevant variables are identified through the use of a decision-support system or systems, such as a neural network or a consensus of neural networks; and another set of decision-support systems is trained on the identified subset(s) to produce a consensus decision-support system based test, such as a neural net-based test for the condition. The use of consensus systems, such as consensus neural networks, minimizes the negative effects of local minima in decision-support systems, such as neural network-based systems, thereby improving the accuracy of the system.

Also, to refine or improve performance, the patient data can be augmented by increasing the number of patients used. Also biochemical test data and other data may be included as part of additional examples or by using the data as additional variables prior to the variable selection process.

The resulting systems are used as an aid in diagnosis. In addition, as the systems are used patient data can be stored and then used to further train the systems and to develop systems that are adapted for a particular genetic population. This inputting of additional data into the system may be implemented automatically or done manually. By doing so the systems continually learn and adapt to the particular environment in which they are used. The resulting systems have numerous uses in addition to diagnosis, which includes assessing the severity of a disease or disorder, predicting the outcome of a selected treatment protocol. The systems may also be used to assess the value of other data in a diagnostic procedure, such as biochemical test data and other such data, and to identify new tests that are useful for diagnosing a particular disease.

Thus, also provided are methods for improving upon existing biochemical tests, identifying relevant biochemical tests and for developing new biochemical tests to aid in diagnosis of disorders and conditions. These methods involve assessing the effect of a particular test or a potential new test on the performance of the decision-support system based test. If addition of information from the test improves performance, such test will have relevance in diagnosis.

The disorders and conditions that are of particular interest herein and to which the methods herein may be readily applied, are gynecological conditions and other conditions that impact on fertility, including but not limited to endometriosis, infertility, prediction of pregnancy-related events, such as the likelihood of delivery within a particular time period, and pre-eclampsia. It is understood, however, that the methods herein are applicable to any disorder or condition.

The methods are exemplified with reference to neural networks, however, it is understood that other data mining tools, such as expert systems, fuzzy logic, decision trees, and other statistical decision-support systems which are generally non-linear, may be used. Although the variables provided herein are intended to be used with decision-support systems, once the variables are identified, then a person, typically a physician, armed with knowledge the important variables can use them to aid in diagnosis in the absence of a decision-support system or using a less complex linear system of analysis.

As shown herein, variables or combinations thereof that heretofore were not known to be important in aiding in diagnosis are identified. In addition, patient history data, without supplementing biochemical test data, can be used to diagnose or aid in diagnosing a disorder or condition when used with the decision-support systems, such as the neural nets provided herein. Furthermore, the accuracy of the diagnosis with or without biochemical data may be sufficient to obviate the need for invasive surgical diagnostic procedures.

Also provided herein is a method of identifying and expanding clinical utility of diagnostic test. The results of a particular test, particular one that had heretofore not been considered of clinical utility with respect to the disorder or condition of interest, are combined with the variables and used with the decision-support system, such as a neural net. If the performance, the ability to correctly diagnose a disorder, of the system is improved by addition of the results of the test, then the test will have clinical utility or a new utility.

Similarly, the resulting systems can be used to identify new utilities for drugs or therapies and also to identify uses for particular drugs and therapies. For example, the systems can be used to select subpopulations of patients for whom a particular drug or therapy is effective. Thus, methods for expanding the indication for a drug or therapy and identifying new drugs and therapies are provided.

In specific embodiments, neural networks are employed to evaluate specific observation values and test results, to guide the development of biochemical or other diagnostic tests, and to provide the decision-support functionality for the test.

A method for identification of important variables (parameters) or sets thereof for use in the decision-support systems is also provided. This method, while exemplified herein with reference to medical diagnosis, has broad applicability in any field, such as financial analysis, in which important parameters or variables are selected from among a plurality.

In particular, a method for selecting effective combinations of variables is provided. The method involves: (1) providing a set of "n" candidate variables and a set of "selected important variables", which initially is empty; (2) ranking all candidate variables based on a chi square and sensitivity analysis; (3) taking the highest "m" ranked variables one at a time, where m is from 1 up to n, and evaluating each by training a consensus of neural nets on that variable combined with the current set of important variables; (4) selecting the best of the m variables, where the best variable is the one that gives the highest performance, and if it improves performance in comparison to the performance of the selected important variables, adding it to the "selected important variable" set, removing it from the candidate set and continuing processing at step (3), otherwise going to step (5); (5) if all variables on the candidate set have been evaluated, the process is complete, otherwise continue taking the next highest "m" ranked variables one at a time, and evaluating each by training a consensus of neural nets on that variable combined with the current set of important selected variables and performing step (4). The final set of important selected variables will contain a plurality, typically more than three to five or more variables.

In a particular embodiment, the sensitivity analysis involves: (k) determining an average observation value for each of the variables in an observation data set; (I) selecting a training example, and running the example through a decision-support system to produce an output value, designated and stored as the normal output; (m) selecting a first variable in the selected training example, replacing the observation value with the average observation value of the first variable; running the modified example in the decision-support system in the forward mode and recording the output as the modified output; (n) squaring the difference between the normal output and the modified output and accumulating it as a total for each variable, in which this total is designed the selected variable total for each variable; (o) repeat steps (m) and (n) for each variable in the example; (p) repeating steps (l)-(n) for each example in the data set, where each total for the selected variable represents the relative contribution of each variable to the determination of the decision-support system output. This total will be used to rank each variable according to its relative contribution to the determination of the decision-support system output.

As shown herein, computer-based decision-support systems such as neural networks reveal that certain input factors, which were not initially considered to be important, can influence an outcome. This ability of a neural network to reveal the relevant input factors permits its use in guiding the design of diagnostic tests. Thus a method of designing a diagnostic test, and a method of evaluating utility of diagnostic test are also provided. In each instance, the data from the test or possible test is added to the input of the decision-support system. If the results are improved when the data are included in the input, then the diagnostic test may have clinical utility. In this manner, tests that heretofore were not known to be of value in diagnosis of a particular disorder are identified, or new tests can be developed. Neural networks can add robustness to diagnostic tests by discounting the effects of spurious data points and by identifying other data points that might be substituted, if any.

Networks are trained on one set of variables and then clinical data from diagnostic or biochemical test data and/or additional patient information are added to the input data. Any variable that improves the results compared to their absence is (are) selected. As a result, particular tests that heretofore were of unknown value in diagnosing a particular disorder can be shown to have relevance. For example, the presence or absence of particular spots on a western blot of serum antibodies can be correlated with a disease state. Based on the identity of particular spots (i.e., antigens) new diagnostic tests can be developed.

An example of the application of the prediction technology to aid in the diagnosis of disease and more particularly the use of neural network techniques with inputs from various information sources to aid in the diagnosis of the disease endometriosis is provided. A trained set of neural networks operative according to a consensus of networks in a computer system is employed to evaluate specific clinical associations, for example obtained by survey, some of which may not generally be associated with a disease condition. This is demonstrated with an exemplary disease condition endometriosis, and factors used to aid in the diagnosis of endometriosis are provided. The neural network training is based on correlations between answers to questions furnished by physicians of a significant number of clinical patients whose disease condition has been surgically verified, herein termed clinical data.

A plurality of factors, twelve to about sixteen, particularly a set of fourteen factors, in a specific trained neural network extracted from a collection of over forty clinical data factors have been identified as primary indicia for endometriosis. The following set of parameters: age, parity (number of births), gravidity (number of pregnancies), number abortions, smoking (packs/day), past history of endometriosis, dysmenorrhea, pelvic pain, abnormal pap/dysplasia, history pelvic surgery, medication history, pregnancy hypertension, genital warts and diabetes were identified as being significant. Other similar sets of parameters were also identified. Subsets of these variables also may be employed in diagnosing endometriosis.

In particular, any subset of the selected set of parameters, particularly the set of fourteen variables, that contain one (or more) of the following combinations of three variables can be used with a decision-support system for diagnosis of endometriosis:

a) number of births, history of endometriosis, history of pelvic surgery;

b) diabetes, pregnancy hypertension, smoking;

c) pregnancy hypertension, abnormal pap smear/dysplasia, history of endometriosis;

d) age, smoking, history of endometriosis;

e) smoking, history of endometriosis, dysmenorrhea;

f) age, diabetes, history of endometriosis;

g) pregnancy hypertension, number of births, history of endometriosis;

h) Smoking, number of births, history of endometriosis;

i) pregnancy hypertension, history endometriosis, history of pelvic surgery;

j) number of pregnancies, history of endometriosis, history of pelvic surgery;

k) number of births, abnormal PAP smear/dysplasia, history of endometriosis;

l) number of births, abnormal PAP smear/dysplasia, dysmenorrhea;

m) history of endometriosis, history of pelvic surgery, dysmenorrhea; and n) number of pregnancies, history of endometriosis, dysmenorrhea.

Diagnostic software and exemplary neural networks that use the variables for diagnosis of endometriosis and the risk of delivery before a specified time are also provided. Software generates a clinically useful endometriosis index is provided as software that generates an index for assessing the risk are provided.

In other embodiments, the performance of a diagnostic neural network system used to test for endometriosis is enhanced by including variables based on biochemical test results from a relevant biochemical test as part of the factors (herein termed biochemical test data, which includes tests from analyses and data such as vital signs, such as pulse rate and blood pressure) used for training the network. An exemplary network that results therefrom is an augmented neural network that employs fifteen input factors, including results of the biochemical test and the fourteen clinical parameters. The set of weights of the eight augmented neural networks differ from the set of weights of the eight clinical data neural networks. The exemplified biochemical test employs an immuno-diagnostic test format, such as the ELISA diagnostic test format.

The methodology applied to endometriosis as exemplified herein can be similarly applied and used to identify factors for other disorders, including, but not limited to gynecological disorders and female-associated disorders, such as, for example, infertility, prediction of pregnancy related events, such as the likelihood of delivery within a particular time period, and pre-eclampsia. Neural networks, thus, can be trained to predict the disease state based on the identification of factors important in predicting the disease state and combining them with biochemical data.

The resulting diagnostic systems may be adapted and used not only for diagnosing the presence of a condition or disorder, but also the severity of the disorder and as an aid in selecting a course of treatment.

BRIEF DESCRIPTION OF THE DRAWINGS

FIG. 12 depicts an exemplary screen showing main menu, tool bar and results display in the user interface using the software (Appendix III for assessing preterm delivery;

FIG. 13 depicts an exemplary Edit Record dialog box in preterm delivery software;

FIG. 14 depicts an exemplary Go To dialog box in the software;

FIG. 15 depicts an exemplary Help About dialog box in the software;

FIGS. 16A and 16B shows exemplary outputs from the software, FIG. 16B includes the input data as well;

DETAILED DESCRIPTION OF PREFERRED EMBODIMENTS

Definitions

Figure 1:
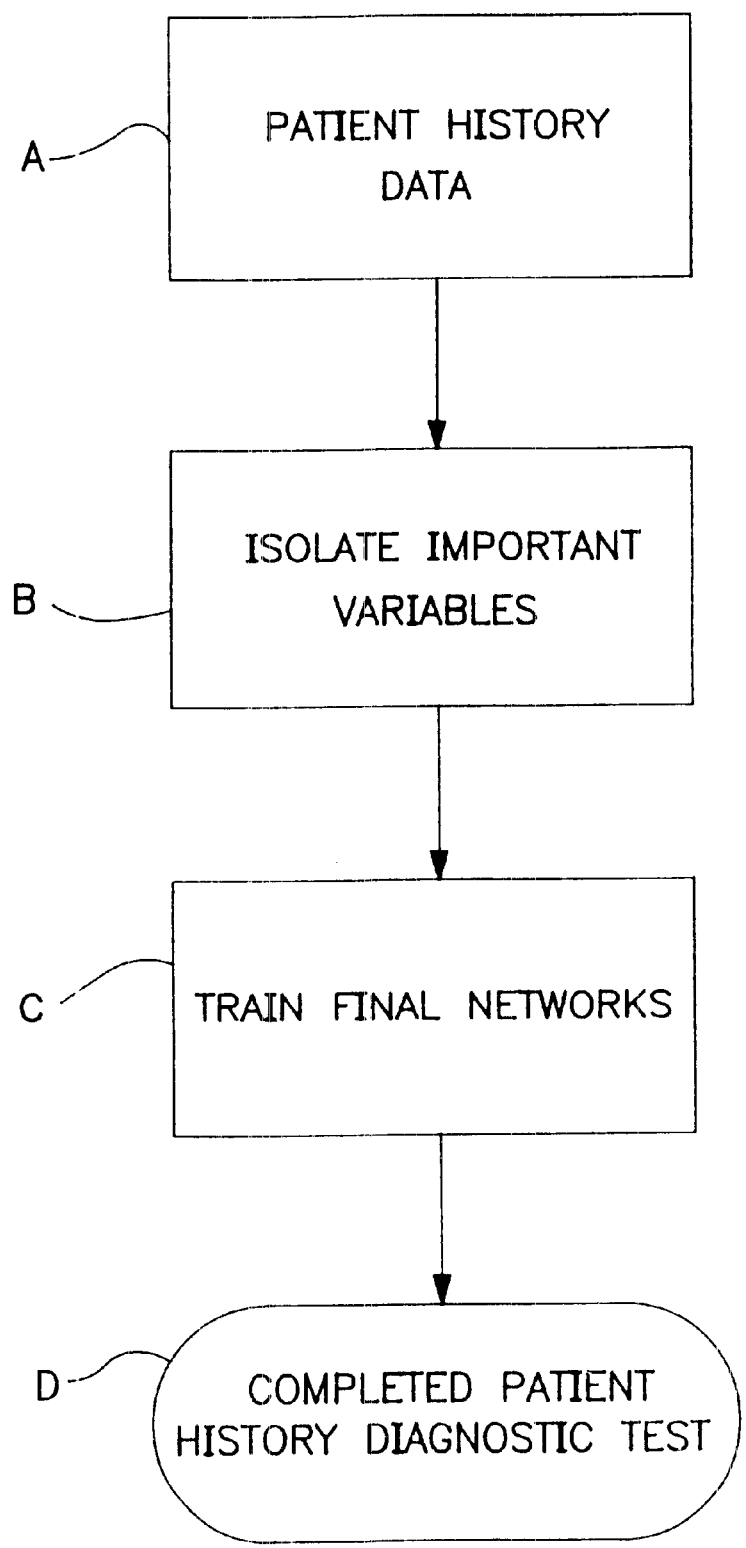
FIG. 1 is a flow chart for developing a patient-history-based diagnostic test process.

Unless defined otherwise, all technical and scientific terms used herein have the same meaning as is commonly understood by one of skill in the art to which this invention belongs. All patents and publications referred to herein are incorporated by reference.

As used herein, a decision-support system, also referred to as a "data mining system" or a "knowledge discovery in data system", is any system, typically a computer-based system, that can be trained on data to classify the input data and then subsequently used with new input data to make decisions based on the training data. These systems include, but are not limited, expert systems, fuzzy logic, non-linear regression analysis, multivariate analysis, decision tree classifiers, Bayesian belief networks and, as exemplified herein, neural networks.

As used herein, an adaptive machine learning process refers to any system whereby data are used to generate a predictive solution. Such processes include those effected by expert systems, neural networks, and fuzzy logic.

As used herein, expert system is a computer-based problem solving and decision-support system based on knowledge of its task and logical rules or procedures for using the knowledge. Both the knowledge and the logic are entered into the computer from the experience of human specialists in the area of expertise.

As used herein, a neural network, or neural net, is a parallel computational model comprised of densely interconnected adaptive processing elements. In the neural network, the processing elements are configured into an input layer, an output layer and at least one hidden layer. Suitable neural networks are known to those of skill in this art (see, e.g., U.S. Pat. Nos. 5,251,626; 5,473,537; and 5,331,550, Baxt (1991) "Use of an Artificial Neural Network for the Diagnosis of Myocardial Infarction," *Annals of Internal Medicine* 115:843; Baxt (1992) "Improving the Accuracy of an Artificial Neural Network Using Multiple Differently Trained Networks," *Neural Computation* 4:772; Baxt (1992) "Analysis of the clinical variables that drive decision in an artificial neural network trained to identify the presence of myocardial infarction," *Annals of Emergency Medicine* 21:1439; and Baxt (1994) "Complexity, chaos and human physiology: the justification for non-linear neural computational analysis," *Cancer Letters* 77:85).

As used herein, a processing element, which may also be known as a perceptron or an artificial neuron, is a computational unit which maps input data from a plurality of inputs into a single binary output in accordance with a transfer function. Each processing element has an input weight corresponding to each input which is multiplied with the signal received at that input to produce a weighted input value. The processing element sums the weighted inputs values of each of the inputs to generate a weighted sum which is then compared to the threshold defined by the transfer function.

As used herein, transfer function, also known as a threshold function or an activation function, is a mathematical function which creates a curve defining two distinct categories. Transfer functions may be linear, but, as used in neural networks, are more typically non-linear, including quadratic, polynomial, or sigmoid functions.

As used herein, backpropogation, also known as backprop, is a training method for neural networks for correcting errors between the target output and the actual output. The error signal is fed back through the processing layer of the neural network, causing changes in the weights of the processing elements to bring the actual output closer to the target output.

As used herein, Quickprop is a backpropogation method that was proposed, developed and reported by Fahlman ("Fast Learning Variations on Back-Propagation: An Empirical Study", *Proceedings on the* 1988 *Connectionist Models Summer School*, Pittsburgh, 1988, D. Touretzky, et al., eds., pp.38-51, Morgan Kaufmann, San Mateo, Calif.; and, with Lebriere, "The Cascade-Correlation Learning Architecture", Advances in Neural Information Processing Systems 2,(Denver, 1989), D. Touretzky, ed., pp. 524-32. Morgan Kaufmann, San Mateo, Calif.).

As used herein, diagnosis refers to a predictive process in which the presence, absence, severity or course of treatment of a disease, disorder or other medical condition is assessed. For purposes herein, diagnosis will also include predictive processes for determining the outcome resulting from a treatment.

As used herein, a patient or subject includes any mammals for whom diagnosis is contemplated. Humans are the preferred subjects.

As used herein, biochemical test data refers to the results of any analytical methods, which include, but are not limited to:, immunoassays, bioassays, chromatography, data from monitors, and imagers; measurements and also includes data related to vital signs and body function, such as pulse rate, temperature, blood pressure, the results of, for example, EKG, ECG and EEG, biorhythm monitors and other such information. The analysis can assess for example, analytes, serum markers, antibodies, and other such material obtained from the patient through a sample.

As used herein, patient historical data refers to data obtained from a patient, such as by questionnaire format, but typically does not include biochemical test data as used herein, except to the extent such data is historical, a desired solution is one that generates a number or result whereby a diagnosis of a disorder can be generated.

As used herein, wherein a training example includes the observation data for a single diagnosis, typically the observation data related to one patient.

As used herein, the parameters identified from patient historical data are herein termed observation factors or values or variables. For example, patient data will include information with respect to individual patient's smoking habits. The variable associated with that will be smoking.

As used herein, partition means to select a portion of the data, such as 80%, and use it for training a neural net and to use the remaining portion as test data. Thus, the network is trained on all but one portion of the data. The process can then be repeated and a second network trained. The process is repeated until all partitions are used as used as test data and training data.

As used herein, the method of training by partitioning the available data into a plurality of subsets is generally referred to as the "holdout method" of training. The holdout method is particularly useful when the data available for network training is limited.

As used herein, training refers to the process in which input data are used to generate a decision-support system. In particularly, with reference to neural nets, training is a trial-and-error process involving a series of iterative adjustments to the processing element weights so that a particular processing element provides an output which, when combined with the outputs of other processing elements, generates a result which minimizes the resulting error between the outputs of the neural network and the desired outputs as represented in the training data.

As used herein, a variable selection process is a systematic method whereby combinations of variables that yield predictive results are selected from any available set. Selection is effected by maximizing predictive performance of subsets such that addition of additional variables does not improve the result. The preferred methods provided herein advantageously permit selection of variables without considering all possible combinations.

As used herein, a candidate variable is a selected item from collected observations from a group of test patients for the diagnostic embodiments or other records, such as financial records, that can be used with the decision-support system. Candidate variables will be obtained by collecting data, such as patient data, and categorizing the observations as a set of variables.

As used herein, important selected variables refer to variables that enhance the network performance of the task at hand. Inclusion of all available variables does not result in the optimal neural network; some variables, when included in network training, lower the network performance. Networks that are trained only with relevant parameters result in increased network performance. These variables are also referred to herein as a subset of relevant variables.

As used herein, ranking refers to a process in which variables are listed in an order for selection. Ranking may be arbitrary or, preferably, is ordered. Ordering may be effected, for example, by a statistical analysis that ranks the variables in order of importance with respect to the task, such as diagnosis, or by a decision-support system based analysis. Ranking may also be effected, for example, by human experts, by rule based systems, or any combination of any of these methods.

As used herein, a consensus of neural networks refers to the linear combination of outputs from a plurality of neural networks where the weight on each is outputs is determined arbitrarily or set to an equal value.

As used herein, a greedy algorithm is a method for optimizing a data set by determining whether to include or exclude a point from a given data set. The set begins with no elements and sequentially selects an element from the feasible set of remaining elements by myopic optimization, in which, given any partial solution, another value that improves the object the most is selected.

As used herein, a genetic algorithm is a method that begins with an initial population of randomly generated neural networks which are run through a training cycle and ranked according to their performance in reaching the desired target. The poor-performing networks are removed from the population, with the fitter networks being retained and selected for the crossover process to offspring that retain the desirable characteristics of the parent networks.

As used herein, performance of a system is said to be improved or higher when the results more accurately predict or determine a particular outcome. It is also to be understood that the performance of a system will typically be better as more training examples are used. Thus, the systems herein will improve over time as they are used and more patient data is accumulated and then added to the systems as training data.

As used herein, sensitivity=TP/(TP+FN); specificity is TN/(TN+FP), where TP=true positives; TN=true negatives; FP=false positives; and FN=false negative. Clinical sensitivity measures how well a test detects patients with the disease; clinical specificity measures how well a test correctly identifies those patients who do not have the disease.

As used herein, positive predictive value (PPV) is TP/(TP+FP); and negative predictive value (NPV) is TN/(TN+FN). Positive predictive value is the likelihood that a patient with a positive test actually has the disease, and negative predictive value is the likelihood that a patient with a negative test result does not have the disease.

As used herein, fuzzy logic is an approach to deal with systems that cannot be described precisely. Membership functions (membership in a data set) are not binary in fuzzy logic systems; instead membership function may take on fractional values. Therefore, an element can be simultaneously contained in two contradictory sets, albeit with different coefficients of set membership. Thus, this type of approach is useful for answering questions in which there is no yes or answer. Thus, this type of logic is suitable for categorizing responses from patient historical questionnaires, in which the answer is often one of degree.

1. General considerations and general methodology

It has been determined that a number of techniques can be used to train neural networks for analyzing observation values such as patient history and/or biochemical information. Depending upon the characteristics of the available data and the problem to be analyzed, different neural network training techniques can be used. For example, where large amounts of training inputs are available, methodology may be adopted to eliminate redundant training information.

As shown herein, neural networks may also reveal that certain input factors that were not initially considered to be important can influence an outcome, as well as reveal that presumably important factors are not outcome determinative. The ability of neural networks to reveal the relevant and irrelevant input factors permit their use in guiding the design of a diagnostic test. As shown herein, neural networks, and other such data mining tools, are a valuable advance in diagnostics, providing an opportunity to increase the sensitivity and specificity of a diagnostic test. As shown herein, care must be taken to avoid the potential of poor-accuracy answer due to the phenomenon of local minima. The methods herein provide a means to avoid this problem or at least minimize it.

In developing the developing diagnostic procedures, and in particular diagnostic tests that are based solely or in part on patient information, a number of problems have been solved. For example, there is generally a limited amount of data because there is a limited number of patients where training data are available. To solve this, as described below, the patient information is partitioned when training the network. Also, there is generally a large number of input observation factors available for use in connection with the available data, so methods for ranking and selecting observations were developed.

Also, there are generally large number of binary (true/false) input factors in the available patient data, but these factors are generally sparse in nature (values that are positive or negative in only a small percentage of cases of the binary input factors in the available patient data). Also there is a high degree of overlap between the positive and negative factors of the condition being diagnosed.

These characteristics and others impact the choice of procedures and methods used to develop a diagnostic test. These problems are addressed and solved herein.

2. Development of patient history diagnostic test

Diagnostic test

Methods for diagnosis based solely on patient history data are provided. As demonstrated herein, it is possible to provide decision-support system that rely only on patient history information but that aid in diagnosis. Consequently, the resulting systems can then be used to improve the predictive ability of biochemical test data, to identify new disease markers, to develop biochemical tests, to identify tests that heretofore were not thought to be predictive of a particular disorder.

The methods may also be used to select an appropriate course of treatment by predicting the result of selected course of treatment and to predict status following therapy. The input variables for training would be derived from, for example, electronic patient records, that indicate diagnoses and other available data, including selected treatments and outcomes. The resulting decision-support system would then be used with all available data to, for example, categorize women into different classes that will respond to different treatments and predict the outcome of a particular treatment. This permits selection of a treatment or protocol most likely to be successful.

Similarly, the systems can be used to identify new utilities for drugs or therapies and also to identify uses for particular drugs and therapies. For example, the systems can be used to select subpopulations of patients for whom a particular drug or therapy is effective. Thus, methods for expanding the indication for a drug or therapy and identifying new drugs and therapies are provided.

Collection of patient data, generation of variables and overview To exemplify the methods herein, FIG. 1 sets forth a flow chart for developing a patient-history-based diagnostic test process. The process begins with collection of patient history data (Step A). Patient history data or observation values are obtained from patient questionnaires, clinical results, in some instances diagnostic test results, and patient medical records and supplied in computer-readable form to a system operating on a computer. In the digital computer, the patient history data are categorized into a set of variables of two forms: binary (such as true/false) values and quantitative (continuous) values. A binary-valued variable might include the answer to the question, "Do you smoke?" A quantitative-valued variable might be the answer to the question, "How many packs per day do you smoke?" Other values, such as membership functions, may also be useful as input vehicles.

The patient history data will also include a target or desired outcome variable that would be assumed to be indicative of the presence, absence, or severity of the medical condition to be diagnosed. This desired outcome information is useful for neural network training. The selection of data to be included in the training data can be made with the knowledge or assumption of the presence, severity, or absence of the medical condition to be diagnosed. As noted herein, diagnosis may also include assessment of the progress and/or effectiveness of a therapeutic treatment.

The number of variables, which can be defined and thus generated, can be unwieldy. Binary variables are typically sparse in that the number of positive (or negative) responses is often a small percentage of the overall number of responses. Thus, in instances in which there is a large number of variables and a small number of patient cases available in a typical training data environment, steps are taken to isolate from the available variables a subset of variables important to the diagnosis (Step B). The specific choice of the subset of variables from among the available variables will affect the diagnostic performance of the neural network.

The process outlined herein has been found to produce a subset of variables which is comparable or superior in sensitivity and reliability to the subset of variables typically chosen by a trained human expert, such as a physician. In some instances, the variables are prioritized or placed in order of rank or relevance.

Thereafter, the final neural networks to be used in the diagnostic procedure are trained (Step C). In preferred embodiments, a consensus (i.e. a plurality) of networks are trained. The resulting networks form the decision-support functionality for the completed patient history diagnostic test (Step D).

Method for isolation of important variables

A method for isolation of important variables is provided herein. The method permits sets of effective variables to be selected without comparing every possible combination of variables. The important variables may be used as the inputs for the decision-support systems.

Isolation of important or relevant variables -ranking the variables

Figure 3A:
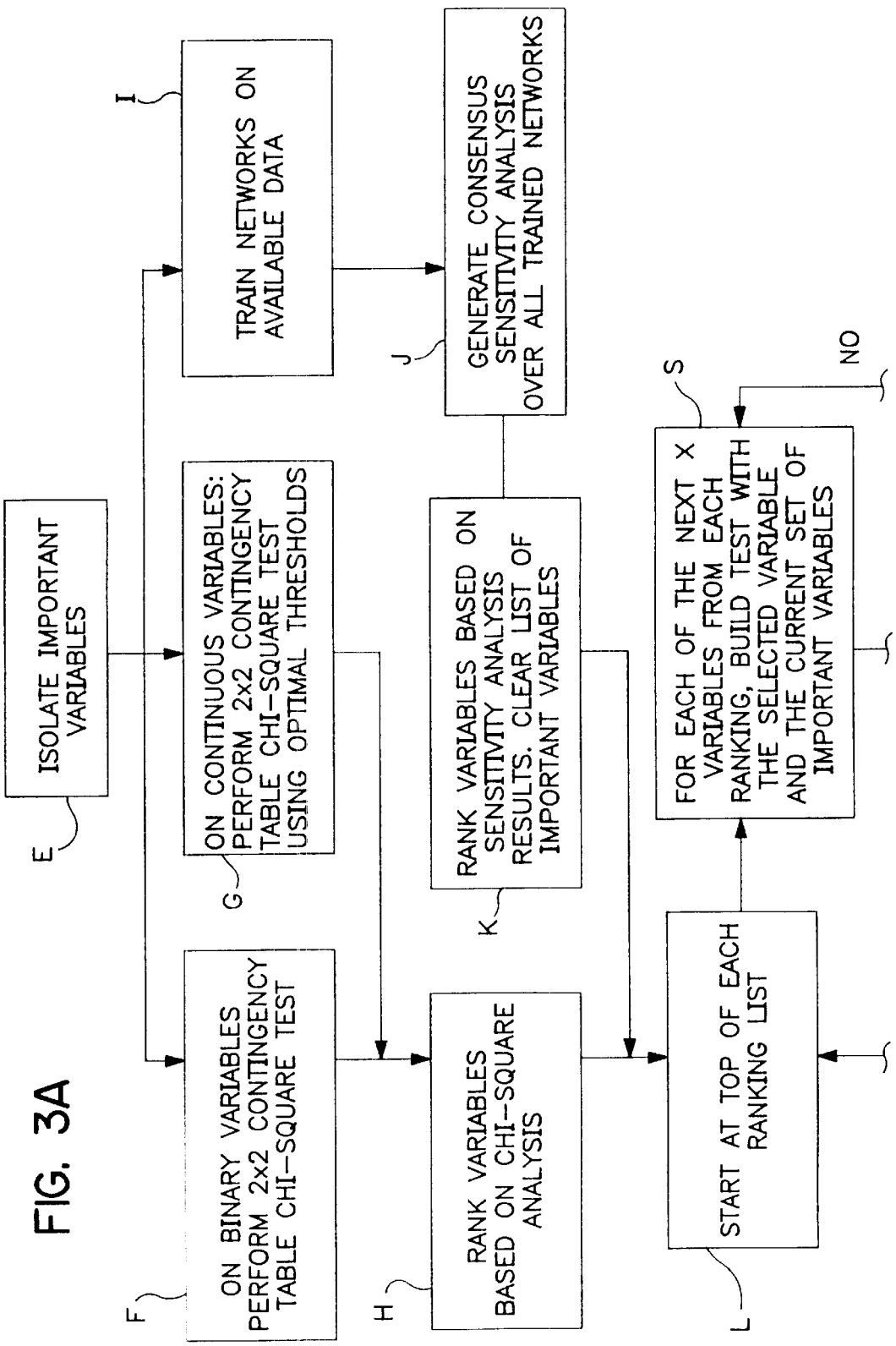
FIG. 3 is a flow chart of the process for isolating important variables.
Figure 3B:
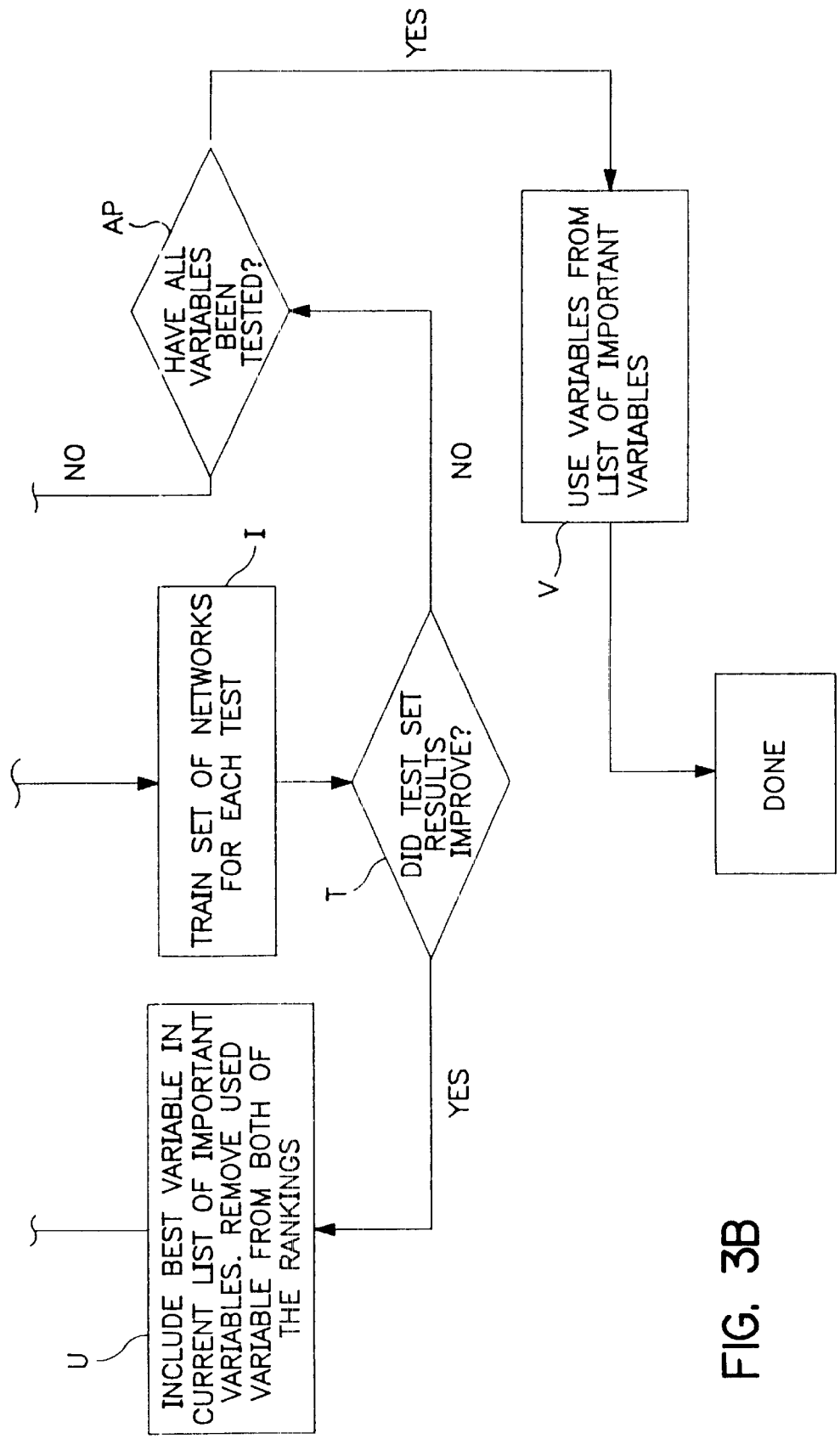

FIGS. 3A–B provides a flow chart of the process for isolating the important or relevant variables (Step E) within a diagnostic test. Such a process is typically conducted using a digital computer system to which potentially relevant information has been provided. This procedure ranks the variables in order of importance using two independent methods, then selects a subset of the available variables from the uppermost of the ranking. As noted above, other ranking methods can be used by those of skill in the art in place of chi square or sensitivity analysis. Also, if x is set to N (the total number of candidate variables), then ranking can be arbitrary.

The system trains a plurality of neural networks on the available data (Step I), as explained hereinafter, then generates a sensitivity analysis over all trained networks to determine to what extent each input variable was used in the network to perform the diagnosis (Step J). A consensus sensitivity analysis of each input variable is determined by averaging the individual sensitivity analysis results for each of the networks trained. Based upon sensitivity, a ranking order for each of the variables available from the patient history information is determined (Step K).

Ranking the variables

In preferred embodiments, the variables are ranked using a statistical analysis, such as a chi square analysis, and/or a decision-support system-based analysis, such as a sensitivity analysis. A sensitivity analysis and chi square analysis are used, in the exemplary embodiment to rank variables. Other statistical methods and/or decision-support system-based, including but not limited to regression analysis, discriminant analysis and other methods known to those of skill in the art, may be used. The ranked variables may be used to train the networks, or, preferably, used in the method of variable selection provided herein.

The method employs a sensitivity analysis in which each input is varied and the corresponding change in output is measured (see, also, Modai, et al., (1993) "Clinical Decisions for Psychiatric Inpatients and Their Evaluation by Trained Neural Networks", *Methods of Information in Medicine* 32:396-99; Wilding et al. (1994) "Application of Backpropogation Neural Networks to Diagnosis of Breast and Ovarian Cancer", *Cancer Letters* 77:145-53; Ruck et al. (1990) "Feature Selection in Feed-Forward Neural Networks", *Neural Network Computing* 20:40-48; and Utans, et al. (1993) "Selecting Neural Network Architectures Via the Prediction Risk: Application to Corporate Bond Rating Prediction"; *Proceedings of the First International Conference on Artificial Intelligence Applications on Wall Street. Washington, D.C.*, IEEE Computer Society Press. pp. 35-41; Penny et al. (1996) In "Neural Networks in Clinical Medicine", *Medical Decision-support* 4:386-398). Such methods, which have heretofore not been used to select important variables, as described herein. For example, sensitivity analysis has bee reported to be used to develop a statistical approach to determine the relationships between the variables, but not for selection of important variables (see, Baxt et al. (1995) "Bootstrapping Confidence Intervals for Clinical Input Variable Effects in a Network Trained to Identify the Presence of Myocardial Infarction," *Neural Computation* 7: 624-38). Any such sensitivity analyses may be used as described herein as part of the selection of important variables as an aid to diagnosis.

Step K, FIG. 3A, provides an outline of the sensitivity analysis. Each network or a plurality of trained neural networks (networks $N_1$ through $N_n$) is run in the forward mode (no training) for each training example $S_x$ (input data group for which true output is known or suspected; there must be at least two training examples), where "x" is the number of training examples. The output of each network $N_1$–$N_n$ for each training example $S_x$ is recorded, i.e., stared in memory. A new training example is defined containing the average value for each input variable within all training examples. One at a time, each input variable within each original training example $S_x$ is replaced with its corresponding average value $V_{1(avg)}$ through $V_{y(avg)}$, where "y" is the number of variables, and the modified training example $S_x'$ is again executed through the multiple networks to produce a modified output for each network for each variable. The differences between the output from the original training example $S_x$ and the modified output for each input variable are the squared and summed (accumulated) to obtain individual sums corresponding to each input variable. To provide an illustration, for example, for 10 separate neural networks $N_1$–$N_{10}$ and 5 different training examples $S_1$–$S_5$, each having 5 variables $V_1$–$V_{15}$, each of the 5 training examples would be run through the 10 networks to produce 50 total outputs. Taking variable $V_1$ from each of the training examples, an average value $V_{1(avg)}$ is calculated. This averaged variable $V_{1(avg)}$ is substituted into each of the 5 training examples to create modified training examples $S_1'$–$S_5'$ and they are again run through the 10 networks. Fifty modified output values are generated by the networks $N_1$–$N_{10}$ for the 5 training examples, the modification being the result of using the average value variable $V_{1(avg)}$. The difference between each of the fifty original and modified output values is calculated, i.e., the original output from training $S_4$ in network $N_6$: $OUT(S_4N_6)$ is subtracted from the modified output from training example $S_4$ in network $N_6$, OUT $(S_4'N_6)$. That difference value is squared $[OUT(S_4'N_a)-QUT(S_4N_a)]^2_{vi}$. This value is summed with the squared difference values for all combinations of networks and training examples for the iteration in which variable $V_1$ was substituted with its average value $V_{1(avg)}$, i.e., $$\sum_{x=1}^{5}\sum_{n=1}^{10}[OUT(S_x'N_n)-OUT(S_xN_n)]^2_{V_I}.$$

Next, the process is repeated for variable #2, finding the differences between the original and modified outputs for each combination of network and training example, squaring, then summing the differences. This process is repeated for each variable until all 15 variables have been completed.

Each of the resultant sums is then normalized so that if all variables contributed equally to the single resultant output, the normalized value would be 1.0. Following the preceding example, the summed squared differences for each variable are summed to obtain a total summed squared difference for all variables. The value for each variable is divided by the total summed square difference to normalize the contribution from each variable. From this information, the normalized value for each variable can be ranked in order of importance, with higher relative numbers indicating that the corresponding variable has a greater influence on the output. The sensitivity analysis of the input variables is used to indicate which variables played the greatest roles in generating the network output.

It has been found herein that using consensus networks to perform sensitivity analysis improves the variable selection process. For example, if two variables are highly correlated, a single neural network trained on the data might use only one of the two variables to produce the diagnosis. Since the variables are highly correlated, little is gained by including both, and the choice of which to include is dependent on the initial starting conditions of the network being trained. Sensitivity analysis using a single network might show that only one, or the other, is important. Sensitivity analysis derived from a consensus of multiple networks, each trained using different initial conditions, may reveal that both of the highly correlated variables are important. By averaging the sensitivity analysis over a set of neural networks, a consensus is formed that minimizes the effects of the initial conditions.

Chi-square contingency table

When dealing with sparse binary data, a positive response on a given variable might be highly correlated to the condition being diagnosed, but occur so infrequently in the training data that the importance of the variable, as indicated by the neural network sensitivity analysis, might be very low. In order to catch these occurrences, the Chi-square contingency table is used as a secondary ranking process. A 2X2 contingency table Chi-square test on the binary variables, where each cell of the table is the observed frequency for the combination of the two variables (FIG. 3A, Step F) is performed. A 2X2 contingency table Chi-square test is performed on the continuous variables using optimal thresholds (which might be empirically-determined) (Step G)> The binary and continuous variables that have been based on Chi-square analysis are ranked (Step H).

The standard Chi-square 2×2 contingency table operative on the binary variables (Step F) is used to determine the significance of the relationship between a specific binary input variable and the desired output (as determined by comparing the training data with the known single output result). Variables that have a low Chi-square value are typically unrelated to the desired output.

For variables that have continuous values, a 2×2 contingency table can be constructed (Step G) by comparing the continuous variable to a threshold value. The threshold value is modified experimentally to yield the highest possible Chi-square value.

The Chi-square values of the continuous variables and of the binary variables can then be combined for common ranking (Step H). A second level of ranking can then be performed that combines the Chi-square-ranked variables with the sensitivity-analysis-ranked variables (Step L). This combining of rankings allows variables that are significantly related to the output but that are sparse (i.e, values that are positive or negative in only a small percentage of cases) to be included in the set of important variables. Otherwise, important information in such a non-linear system could easily be overlooked.

Selection of important variables from among the ranked variables

As noted above, important variables are selected from among the identified variables. Preferably the selection is effected after ranking the variables at which time a second level ranking process is invoked. A method for identification of important variables (parameters) or sets thereof for use in the decision-support systems is also provided. This method, while exemplified herein with reference to medical diagnosis, has broad applicability in any field, such as financial analysis and other endeavors that involve statistically-based prediction, in which important parameters or variables are selected from among a plurality.

In particular, a method for selecting effective combinations of variables is provided. After (1) providing a set of "n" candidate variables and a set of "selected important variables", which initially is empty; and (2) ranking all candidate variables based on a chi square and sensitivity analysis, as described above, the method involves: (3) taking the highest "m" ranked variables one at a time, where m is from 1 up to n, and evaluating each by training a consensus of neural nets on that variable combined with the current set of important variables; (4) selecting the best of the m variables, where the best variable is the one that most improves performance, and if it improves performance, adding it to the "selected important variable" set, removing it from the candidate set and continuing processing at step (3) otherwise continuing by going to step (5); (5) if all variables on the candidate set have been evaluated, the process is complete, otherwise continue taking the next highest "m" ranked variables one at a time, and evaluating each by training a consensus of neural nets on that variable combined with the current set of important selected variables and performing step (4).

In particular, the second level ranking process (Step L) starts by adding the highest ranked variable from the sensitivity analysis (Step K) to the set of important variables (Step H). Alternatively, the second level ranking process could be started with an empty set and then testing the top several (x) variables from each of the two sets of ranking. This second level ranking process uses the network training procedure (Step I) on a currently selected partition or subset of variables from the available data to train a set of neural networks. The ranking process is a network training procedure using the current set of "important" variables (which generally will initially be empty) plus the current variable being ranked or tested for ranking, and uses a greedy algorithm to optimize the set of input variables by myopically optimizing the input set based upon the previously identified important variable(s), to identify the remaining variable(s) which improve the output the most.

Figure 4:
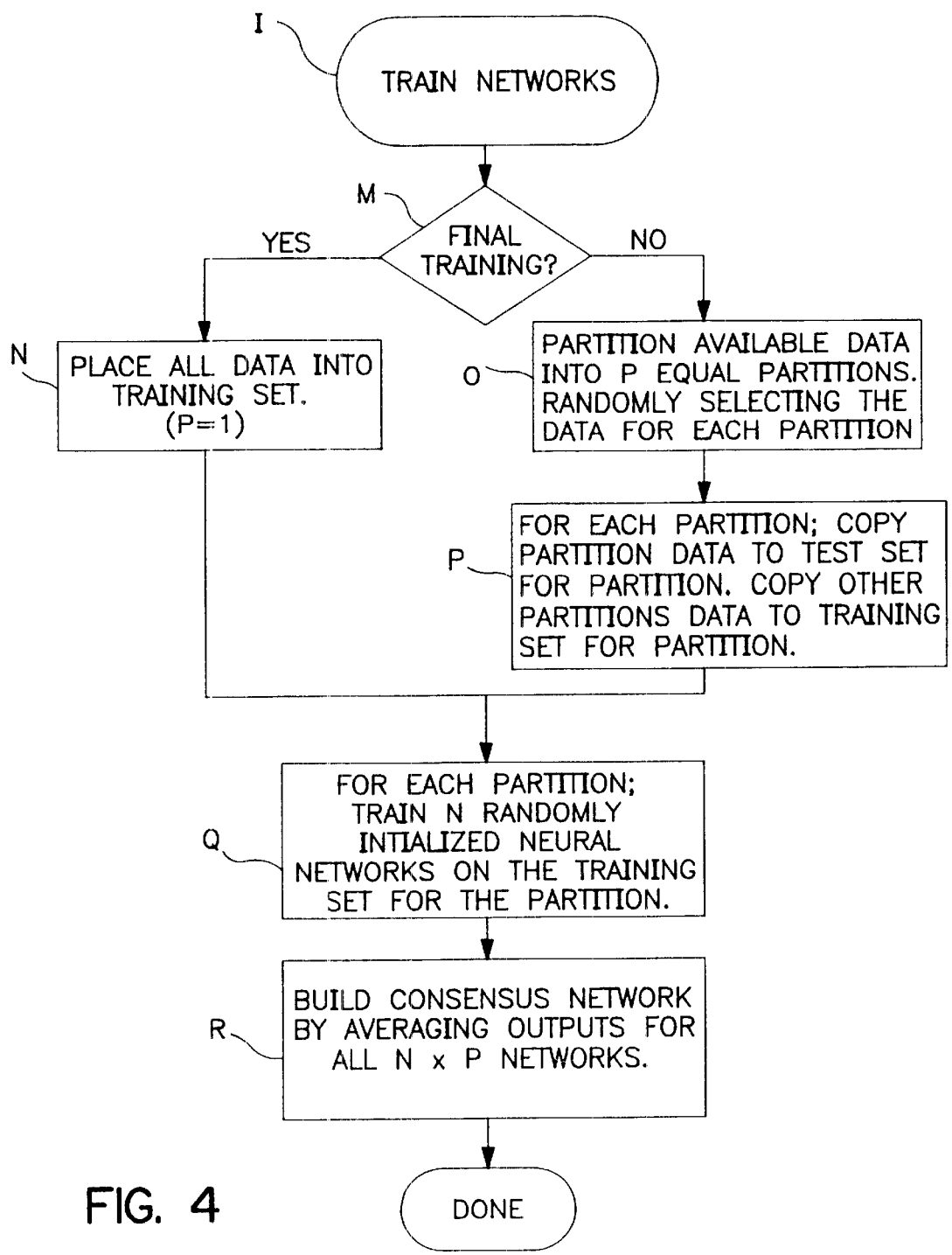
FIG. 4 is a flow chart on the process of training one or a set of neural networks involving a partitioning of variables.

This training process is illustrated in FIG. 4. The number of inputs used by the neural network is controlled by excluding inputs which are found to not contribute significantly to the desired output, i.e., the known target output of the training data. A commercial computer program, such as ThinksPro™ neural networks for Windows™ (or Train-Dos™ the DOS version) by Logical Designs Consulting, Inc, La Jolla, Calif., or any other such program that one of skill in the art can develop may be used to vary the inputs and train the networks.

A number of other commercially available neural network computer programs may be used to perform any of the above operations, including Brainmaker™, which is available from California Scientific Software Co., Nevada Adaptive Solutions, Beaverton, Oreg.; Neural Network Utility/2™, from NeuralWare, Inc., Pittsburgh, Pa.; NeuroShell™ and Neuro-Windows™, from Ward Systems Group, Inc., Frederick, Md. Other types of data mining tools, i.e., decision-support systems, that will provide the function of variable selection and network optimization may be designed or other commercially available systems may be used. For example, NeuroGenetic Optimizer™ from Bio-Comp Systems, Inc., Redmond, Wash.; and Neuro Forecaster/GENETICA, from New Wave Intelligent Business Systems (NIB5) Pte Ltd., Republic of Singapore, use genetic algorithms that are modelled on natural selection to eliminate poor-performing nodes within network population while passing on the best performing rates to offspring nodes to "grow" an optimized network and to eliminate input variables which do not contribute significantly to the outcome. Networks based on genetic algorithms use mutation to avoid trapping in local minima and use crossover processes to introduce new structures into the population.

Knowledge discovery in data (KDD) is another data mining tool, decision-support system, designed to identify significant relationship is that exist among variables, and are useful when there are many possible relationships. A number of KDD systems are commercially available including Darwin™, from Thinking Machines, Bedford, Mass.; Mineset™, from Silicon Graphics, Mountain View, Calif., and Eikoplex™ from Ultragem Data Mining Company, San Francisco, Calif.. (Eikoplex™ has been used to provide classification rules for determining the probability of the presence of heart disease.) Others may be developed by those of skill in the art.

Proceeding with the ranking procedure, if, for example, x is set to 2, then the top two variables from each of the two ranking sets will be tested by the process (FIG. 3A, Steps L, S), and results are checked to see if the test results show improvement (Step T). If there is an improvement, the single best performing variable is added to the set of "Important" variables, and then that variable is removed from the two rankings (FIG. 38, Step U) for further testing (Step S). If there is no improvement, then the process is repeated with the next x variables from each set until an improvement is found or all of the variables from the two sets have been tested. This process is repeated until either the source sets are empty, i.e., all relevant or important variables have been included in the final network, or all of the remaining variables in the sets being tested are found to be below the performance of the current list of important variables. This process of elimination greatly reduces the number of subsets of the available variables which must be tested in order to determine the set of important variables. Even in the worst case, with ten available variables, the process would test only 34 subsets where $x=2$ and only 19 subsets of the 1024 possible combinations if $x=1$. Thus, where there are 100 available variables, only 394 subsets would be tested where $x=2$. The variables from the network with the best test performance are thus identified for use (FIG. 3B, Step V).

Then the final set of networks is trained to perform the diagnosis (FIG. 4, Steps M, N, Q, R). Typically, a number of final neural networks are trained to perform the diagnosis. It is this set of neural networks (a that can form the basis of a deliverable product to the end user. Since different initial conditions (initial weights) can produce differing outputs for a given network, it is useful to seek a consensus. (The different initial weights are used to avoid error from trapping in local minima.) The consensus is formed by averaging the outputs of each of the trained networks which then becomes the single output of the diagnostic test.

Training a consensus of networks

FIG. 4 illustrates the procedure for the training of a consensus of neural networks. It is first determined whether the current training cycle is the final training step (Step M). If yes, then all available data are placed into the training data set (i.e., P=1) (Step N). If no, then the available data are divided into P equal-sized partitions, randomly selecting the data for each partition (Step 0). In an exemplary embodiment, for example five partitions, e.g., $P_1$-$P_5$ are created from the full set of available training data. Then two constructions are undertaken (Step P). First, one or more of the partitions are copied to a test file and the remaining partitions are copied to a training file. Continuing the exemplary embodiment of five partitions, one of the partitions, e.g., $P_1$, representing 20% of the total data set, is copied to the test file. The remaining four files, $P_2$-$P_4$, are identified as training data. A group of N neural networks is trained using the training partitions, each network having different starting weights (Step Q). Thus, in the exemplary embodiment, there will be 20 networks (N=20) with starting weights selected randomly using 20 different random number seeds. Following completion of training for each of the 20 networks, the output values of all 20 networks are averaged to provide the average performance on the test data for the trained networks. The data in the test file (partition $P_1$) is then run through the trained networks to provide an estimate of the performance of the trained networks. The performance is typically determined as the mean squared error of prediction, or misclassification rate. A final performance estimate is generated by averaging the individual performance estimates of each network to produce a completed consensus network (Step R). This method of training by partitioning the available data into a plurality of subsets is generally referred to as the "holdout method" of training. The holdout method is particularly useful when the data available for network training is limited.

Test set performance can be empirically maximized by performing various experiments that identify network parameters that maximize test set performance. The parameters that can be modified in this set of experiments are 1) the number of hidden processing elements, 2) the amount of noise added to the inputs, 3) the amount of error tolerance, 4) the choice of learning algorithm, 5) the amount of weights decay, and 6) the number of variables. A complete search of all possible combinations is typically not practical, due to the amount of processing time that is required. Accordingly, test networks are trained with training parameters chosen empirically via a computer program, such as ThinksPro™ or a user developed program, or from the results of existing test results generated by others who are working in the field of interest. Once a "best" configuration is determined, a final set of networks can be trained on the complete data set.

3. Development of biochemical diagnostic test

A similar technique for isolating variables may be used to build or validate a biochemical diagnostic test, and also to combine a biochemical diagnostic test data with the patient history diagnostic test to enhance the reliability of a medical diagnosis.

The selected biochemical test can include any test from which useful diagnostic information may be obtained in association with a patient and/or patient's condition. The test can be instrument or non-instrument based and can include the analysis of a biological specimen, a patient symptom, a patient indication, a patient status, and/or any change in these factors. Any of a number of analytical methods can be employed and can include, but are not limited to, immunoassays, bioassays, chromatography, monitors, and imagers. The analysis can assess analytes, serum markers, antibodies, and the like obtained from the patient through a sample. Further, information concerning the patient can be supplied in conjunction with the test. Such information includes, but is not limited to, age, weight, blood pressure, genetic history, and the other such parameters or variables.

The exemplary biochemical test developed in this embodiment employs a standardized test format, such as the Enzyme Linked Immunosorbent Assay or ELISA test, although the information provided herein may apply to the development of other biochemical or diagnostic tests and is not limited to the development of an ELISA test (see, e.g., *Molecular Immunology: A Textbook*, edited by Atassi et al. Marcel Dekker Inc., New York and Basel 1984, for a description of ELISA tests). Information important to the development of the ELISA test can be found in the Western Blot test, a test format that determines antibody reactivity to proteins in order to characterize antibody profiles and extract their properties.

A Western Blot is a technique used to identify, for example, particular antigens in a mixture by separating these antigens on polyacrylamide gels, blotting onto nitrocellulose, and detecting with labeled antibodies as probes. (See, for example, *Basic and Clinical Immunology*, Seventh Edition, edited by Stites and Terr, Appleton and Large 1991, for information on Western Blots.) It is, however, sometimes undesirable to employ the Western Blot test as a diagnostic tool. If instead, ranges of molecular weight that contain relevant information to the diagnosis can be pre-identified then this information can be "coded" into an equivalent ELISA test.

Figure 5:
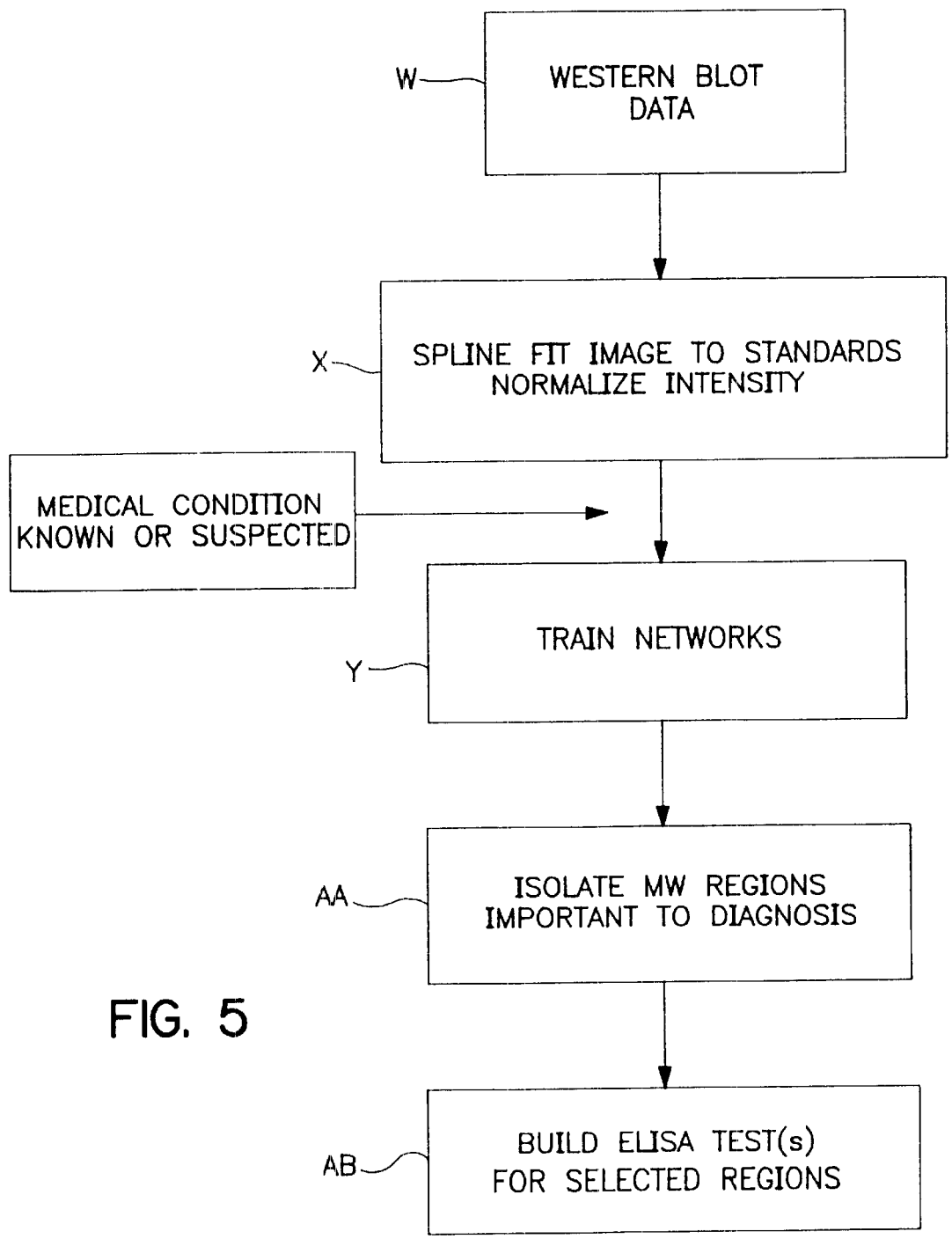
FIG. 5 is a flow chart for developing a biochemical diagnostic test.

In this example, the development of an effective biochemical diagnostic test is dependent upon the availability of Western Blot data for the patients for which the disease condition is known or suspected. Referring to FIG. 5, Western Blot data are used as a source (Step W), and the first step in processing the Western Blot data are to pre-process the Western Blot data for use by the neural network (Step X). Images are digitized and converted to fixed dimension training records by using a computer to perform the spline interpolation and image normalization. It is necessary to align images on a given gel based only on information in the image in order to use data from multiple Western Blot tests. Each input of a neural network needs to represent a specific molecular weight or range of molecular weights accurately. Normally, each gel produced contains a standards image for calibration, wherein the proteins contained are of a known molecular weight, so that the standards image can also be used for alignment of images contained within the same Western Blot. For example, a standard curve can be used to estimate the molecular weight range of other images on the same Western Blot and thereby align the nitrocellulose strips.

The process for alignment of images is cubic spline interpolation. This is a method which guarantees smooth transitions at the data points represented by the standards. To avoid possible performance problems due to extrapolation, termination conditions are set so that extrapolation is linear. This alignment step minimizes the variations in the estimates of molecular weight for a given band on the output of the Western Blot.

The resultant scanned image is then processed to normalize the density of the image by scaling the density so that the darkest band has a scaled density of 1.0 and the lightest band is scaled to 0.0. The image is then processed into a fixed length vector of numbers which become the inputs to a neural network, which at the outset must be trained as hereinafter explained.

A training example is built in a process similar to that previously described where the results generated from the processing of the Western Blot data are trained (Step Y). To minimize the recognized problems of dependency on starting weights, redundancy among interdependent variables, and desensitivity resulting from overtraining a network, it is helpful to train a set of neural networks (consensus) on the data by the partitioning method discussed previously.

From the sensitivity analysis of the training runs on the processed Western Blot data, regions of significantly contributing molecular weights (MW) can be determined and identified (Step AA). As part of the isolation step, inputs in contiguous regions are preferably combined into "bins" as long as the sign of the correlation between the input and the desired output is the same. This process reduces the typical 100-plus inputs produced by the Western Blot, plus the other inputs, to a much more manageable number of inputs of less than about twenty.

In a particular embodiment, it may be found that several ranges of molecular weight may correlate with the desired output, indicative of the condition being diagnosed. A correlation may be either positive or negative. A reduced input representation may be produced by using a Gaussian region centered on each of the peaks found in the Western Blot training, with a standard deviation determined so that the value of the Gaussian was below 0.5 at the edges of the region.

In a specific embodiment, the basic operation to generate the neural network input is to perform a convolution between the Gaussian and the Western Blot image, using the log of the molecular weight for calculation.

The data may be tested using the holdout method, as previously described. For example, five partitions might be used where, in each partition, 80% of the data are used for training and 20% of the data are used for testing. The data are shuffled so that each of the partitions is likely to have examples from each of the gels.

Once the molecular weight regions important to diagnosis have been identified (Step AA), one or more tests for the selected region or regions of molecular weight may be built (Step AB). The ELISA biochemical test is one example. The selected region or regions of molecular weight identified as important to the diagnosis may then be physically identified and used as a component of the ELISA biochemical test. Whereas regions of the same correlation sign may, or may not, be combined into a single ELISA test, regions of differing correlation signs should not be combined into a single test. The value of such a biochemical test may then be determined by comparing the biochemical test result with the known or suspected medical condition.

Figure 2:
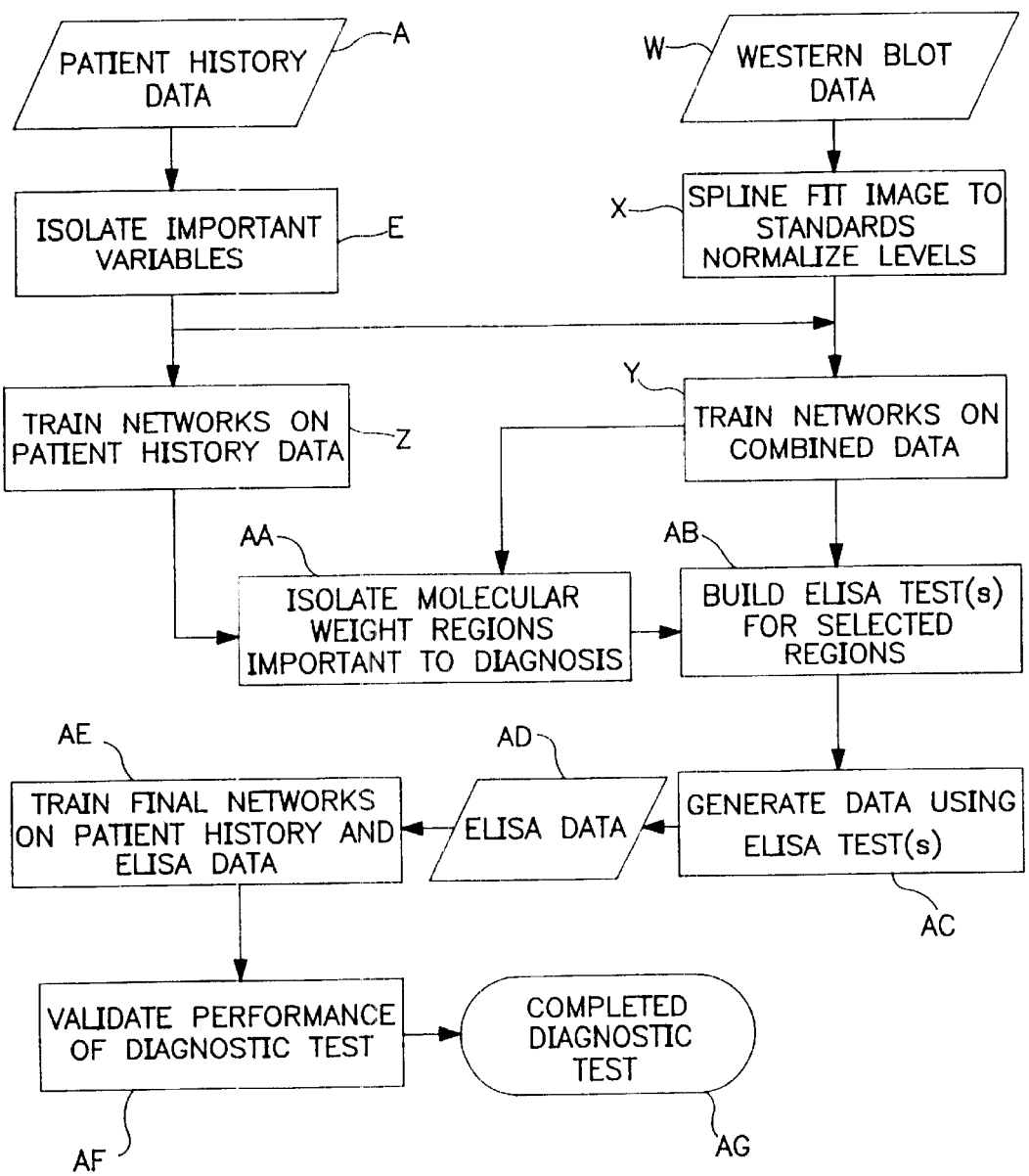
FIG. 2 is a flow chart for developing a biochemical diagnostic test.

In this example, the development of a biochemical diagnostic test may be enhanced by combining patient data and biochemical data in a process shown in FIG. 2. Under these conditions, the patient history diagnostic test is the basis for the biochemical diagnostic test. As explained herein, the variables that are identified as important variables are combined with data derived from the Western Blot data in order to train a set of neural networks to be used to identify molecular weight regions that are important to a diagnosis.

Referring to FIG. 2, Western Blot data are used as a source (Step W) and pre-processed for use by the neural network as described previously (Step X). A training example is built in a process similar to that previously described wherein the important variables from the patient history data and the results generated from the processing of the Western Blot data are combined and are trained using the combined data (Step Y). In parallel, networks are trained on patient history data, as described above (Step Z).

To minimize the recognized problems of dependency on starting weights, redundancy among interdependent variables, and desensitivity resulting from overtraining a network, it was found that it was preferable to train a set of neural networks (consensus set) on the data by the partitioning method. From the sensitivity analysis of the training runs on patient history data alone and on combined data, regions of significantly contributing molecular weights can be determined and identified as previously described (Step AA). As a further step in the isolation process, a set of networks is thereafter trained using as inputs the combined patient history and bin information in order to isolate the important bins for the Western Blot data. The "important bins" represent the important regions of molecular weight related to the diagnosis considering the contribution of patient history information. These bins are either positively or negatively correlated with the desired output of the diagnosis.

Once the molecular weight regions important to diagnosis have been identified (Step AA), one or more tests for the selected region or regions may be built and validated as previously described (Step AB). The designed ELISA tests are then produced and used to generate ELISA data for each patient in the database (Step AC). Using ELISA data and the important patient history data as input, a set of networks is trained using the partition approach as described above (Step AE). The partition approach can be used to obtain an estimate of the lower bound of the biochemical test. The final training (Step AE) of a set of networks, i.e., the networks to be used as a deliverable product, is made using all available data as part of the training data. If desired, new data may be used to validate the performance of the diagnostic test (Step AF). The performance on all the training data becomes the upper bound on the performance estimate for the biochemical test. The consensus of the networks represents the intended diagnostic test output (AG). This final set of neural networks can then be used for diagnosis.

4. Improvement of neural network performance

An important feature of the decision-support systems, as exemplified with the neural networks, and methods provided herein is the ability to improve performance. The training methodology outlined above may be repeated as more information becomes available. During operation, all input and output variables are recorded and augment the training data in future training sessions. In this way, the diagnostic neural network may adapt to individual populations and to gradual changes in population characteristics.

If the trained neural network is contained within an apparatus that allows the user to enter the required information and outputs to the user the neural network score, then the process of improving performance through use may be automated. Each entry and corresponding output is retained in memory. Since the steps for retraining the network can be encoded into the apparatus, the network can be re-trained at any time with data that are specific to the population.

5. Method for evaluating the effectiveness of a diagnostic test course of treatmentt Typically, the effectiveness or usefulness of a diagnostic test is determined by comparing the diagnostic test result with the patient medical condition that is either known or suspected. A diagnostic test is considered to be of value if there is good correlation between the diagnostic test result and the patient medical condition; the better the correlation between the diagnostic test result and the patient medical condition, the higher the value placed on the effectiveness of the diagnostic test. In the absence of such a correlation, a diagnostic test is considered to be of lesser value. The systems provided herein, provide a means to assess the effectiveness of a biochemical test by determining whether the variable that corresponds to that test is an important selected variable. Any test that yields data that improves the performance of the system is identified.

Figure 6:
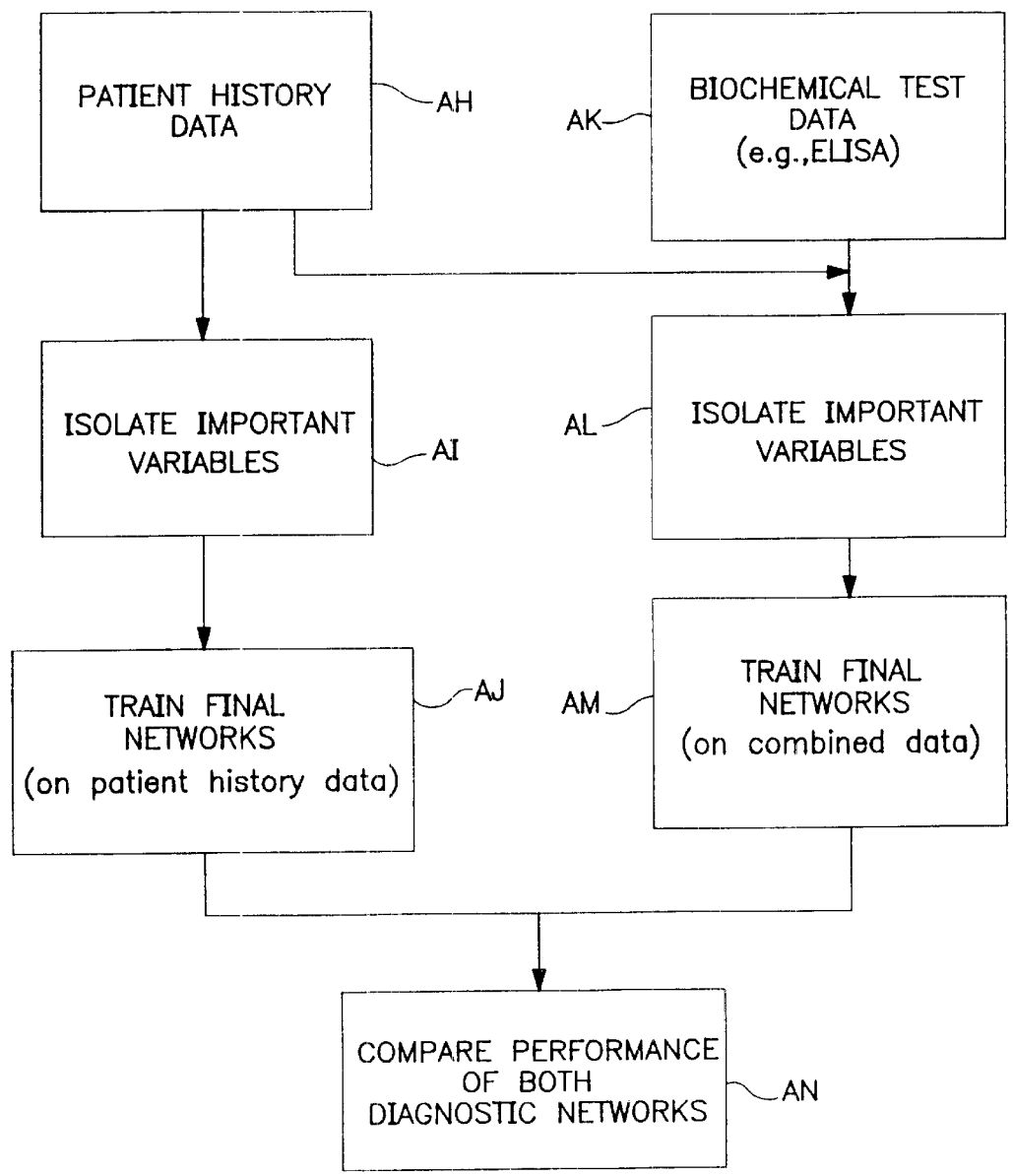
FIG. 6 is a flow chart for determining the effectiveness of a biochemical diagnostic test.

A method by which the effectiveness of a diagnostic test may be determined, independent of the correlation between the diagnostic test result and the patient medical condition (FIG. 6) is described below. A similar method may be used to assess the effectiveness of a particular treatment.

In one embodiment, the method compares the performance of a patient history diagnostic neural network trained on patient data alone, with the performance of a combined neural network trained on the combination of patient historical data and biochemical test data, such as ELISA data. Patient history data are used to isolate important variables for the diagnosis (Step AH), and final neural networks are trained (Step AJ), all as previously described. In parallel, biochemical test results are provided for all or a subset of the patients for whom the patient data are known (Step AK), and a diagnostic neural network is trained on the combined patient and biochemical data by first isolating important variables for the diagnosis (Step AL), and subsequently training the final neural networks (Step AM), all as previously described.

The performance of the patient history diagnostic neural network derived from Step AJ is then compared with the performance of the combined diagnostic neural network derived from Step AM, in Step AN. The performance of a diagnostic neural network may be measured by any number of means. In one example, the correlations between each diagnostic neural network output to the known or suspected medical condition of the patient are compared. Performance can then be measured as a function of this correlation. There are many other ways to measure performance. In this example, any increase in the performance of the diagnostic neural network derived from Step AM over that derived from Step AJ is used as a measure of the effectiveness of the biochemical test.

A biochemical test in this example, and any diagnostic test in general, that lacks sufficient correlation between that test result and the known or suspected medical condition, is traditionally considered to be of limited utility. Such a test may be shown to have some use through the method described above, thereby enhancing the effectiveness of that test which otherwise might be considered uninformative. The method described herein serves two functions: it provides a means of evaluating the usefulness of a diagnostic test, and also provides a means of enhancing the effectiveness of a diagnostic test.

6. Application of the methods to identification of variables for diagnosis and development of diagnostic tests The methods and networks provided herein provide a means to, for example, identify important variables, improve upon existing biochemical tests, develop new tests, assess therapeutic progress, and identify new disease markers. To demonstrate these advantages, the methods provided have been applied to endometriosis and to pregnancy related events, such as the likelihood of labor and delivery during a particular period.

Endometriosis

The methods described herein, have provided a means to develop a non-invasive methodology for the diagnosis of endometriosis. In addition, the methods herein provide means to develop biochemical tests that provide data indicative of endometriosis, and also to identify and develop new biochemical tests.

The methodology for variable selection and use of decision-support systems, has been applied to endometriosis. A decision-support system, in this instance, a consensus of neural networks, has been developed for the diagnosis of endometriosis. In the course of this development, which is detailed in the EXAMPLES, it was found that it was possible to develop neural networks capable of aiding in the diagnosis of endometriosis that only rely on patient historical data, i.e., data that can be obtained from a patient by questionnaire format. It was found that biochemical test data could be used to enhance the performance of a particular network, but it was not essential to its value as a diagnostic tool. The variable selection protocol and neural nets provide a means to select sets of variables that can be inputted into the decision-support system to provide a means to diagnose endometriosis. While some of the identified variables, include those that have traditionally been associated with endometriosis, others of the variables have not. In addition, as noted above, variables, such as pelvic pain and dysmenorrhea that have been associated with endometriosis are not linearly correlated with it to permit diagnosis.

Exemplary decision-support system are described in the Example. For example, one neural net, designated pat07 herein, is described in Example 14. Comparison of the output of the pat07 network output with the probability of having endometriosis yields a positive correlation (see Table 1). The pat07 network can predict the likelihood of a woman having endometriosis based on her pat07 score. For example, if a woman has a pat07 score of 0.6, then she has a 90% probability of having endometriosis; if her pat07 score is 0.4, then she has a 10% probability of having endometriosis. The dynamic range of pat07 output when applied to the database was about 0.3 to about 0.7. Theoretically, the output values can range from 0 to 1, but values below 0.3 or above 0.7 were not observed. Over 800 women have been evaluated using the pat07 network, and its performance can be summarized as follows:

TABLE 1

| Pat07 Score | Endometriosis (% of Total) |
| --- | --- |
| <0.40 | 10 |
| 0.40–0.45 | 30 |
| 0.45–0.55 | 50 |
| 0.55–0.60 | 70 |
| >0.60 | 90 |

The pat07 network score is interpreted as the likelihood of having endometriosis, and not whether or not a woman is diagnosed with endometriosis. The likelihood is based on the relative incidence of endometriosis found in each score group. For example, in the group of women with pat07 network score of 0.6 or greater, 90% of these women had endometriosis, and 10% of these women did not. This likelihood relates to the population of women at infertility clinics. Software programs have been developed that contain the pat07 network.

One program, referred to as adezacrf.exe, provides a single screen windows interface that allows the user to obtain the pat07 network score for a woman. User enters values for all 14 variables, pat07 network score is calculated following every keystroke. Another program, designated adzcrf2.exe, is almost exactly the same as adezacrf.exe, except that it allows for one additional input: the value of an ELISA test. This program and network is a specific example of a method of expanding clinical utility of a diagnostic test. The ELISA test results did not correlate with endometriosis. By itself, the ELISA test does not have clinical utility. As another input parameter, the ELISA test improved network performance, so that one may assert that incorporating the ELISA result as an input for network analysis expanded the clinical utility of that ELISA test. Another program (provided herein in the Appendix II, designated adzcrf2.exe, provides a multiple screen windows interface that allows the user to obtain the pat07 network score for a woman. The multiple data entry screens guides the user to enter all patient historical data, and not just those parameters required as inputs for pat07. Pat07 score is calculated after all data are entered and accepted as correct by the user. This program also saves the data entered in *.fdb files, can import data, calculate pat07 scores on imported data, and export data. The user can edit previously entered data. All three of the above programs serve as specific examples of the diagnostic software for endometriosis.

Figure 11:
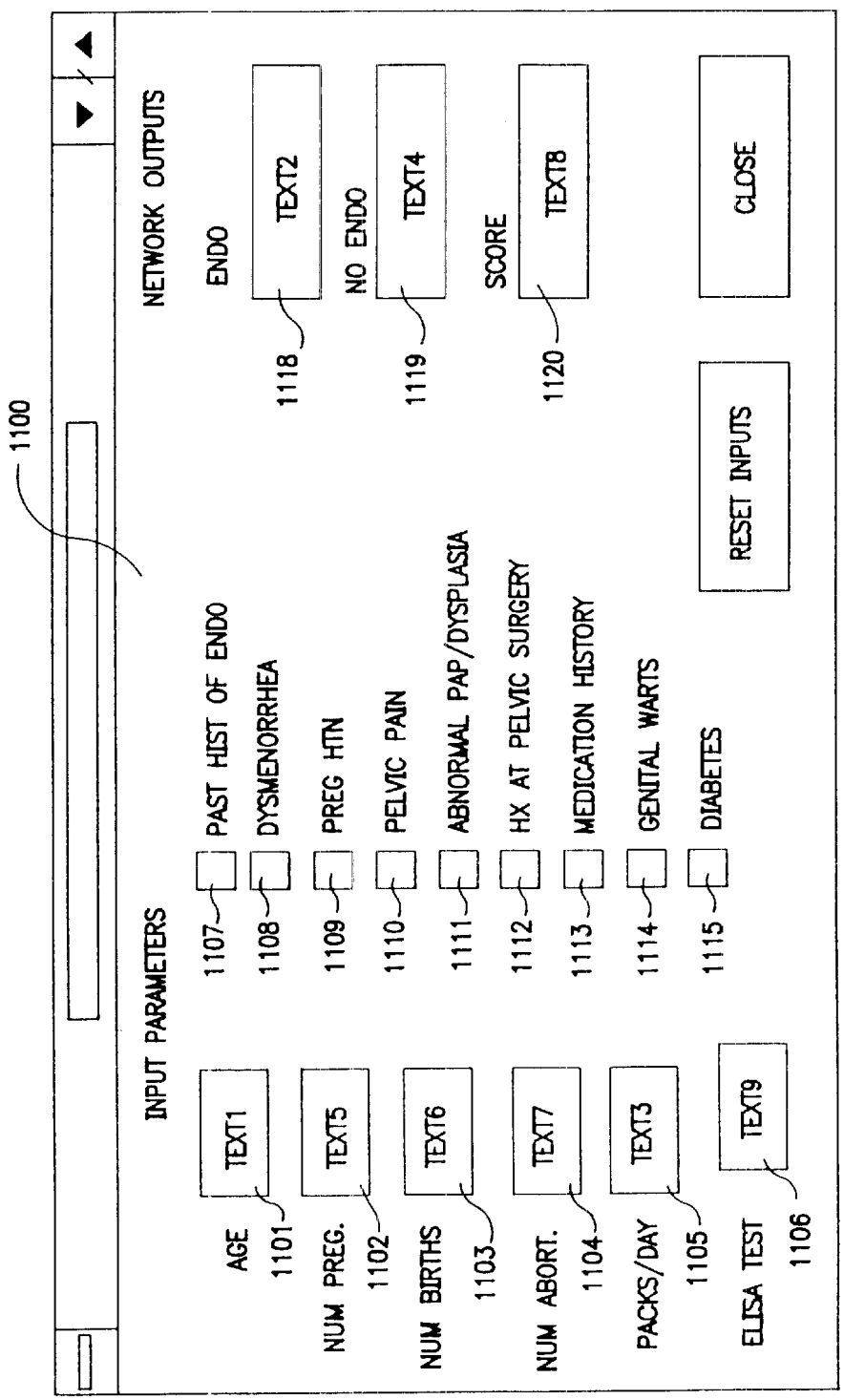
FIG. 11 is a depiction of an exemplary interface screen of the user interface in the diagnostic endometriosis index.

FIG. 11 illustrates an exemplary interface screen used in the diagnostic software for endometriosis. The display 1100, which is provided as a MicroSoft Window™-type display, provides a template for entry of numerical values for each of the important variables which have been determined for diagnosis of endometriosis. Input of data to perform a test is accomplished using a conventional keyboard alone, or in combination with a computer mouse, a trackball or joystick. For purposes of this description, a mouse/keyboard combination will be used.

Each of the text boxes 1101–1106 is for entry of numerical values representative of the important variables Age (box 1011); Number of Pregnancies (box 1102); Number of Births (box 1103); Number of Abortions (box 1104); Number of Packs of Cigarettes Smoked per Day (box 1105); and ELISA test results (box 1106). To enter the subject patient's age, the user moves the mouse so that the pointer on the screen is in box 1101, then clicks on that location. Entry of the number representative of the patient's age is done using the keyboard. The remaining boxes are accessed by pointing and clicking at the selected box.

Boxes 1107–1115 are important selected variables for which the data are binary, i.e., either "yes" or "no". The boxes and the variables are correlated as follows:

| BOX | VARIABLE |
|---|---|
| 1107 | Past History of Endometriosis |
| 1108 | Dysmenorrhea |
| 1109 | Hypertension During Pregnancy |
| 1110 | Pelvic Pain |
| 1111 | Abnormal PAP/Dysplasia |

| BOX | VARIABLE |
|---|---|
| 1112 | History of Pelvic Surgery |
| 1113 | Medication History |
| 1114 | Genital Warts |
| 1115 | Diabetes |

A "yes" to any one of these variables can be indicated by pointing at the corresponding box and clicking the mouse button to indicate an "X" within the box.

The network automatically processes the data after every keystroke, so changes will be seen in the output values displayed in text boxes 1118–1120 after every entry into the template 1100. Text box 1118, labelled "Endo" provides consensus network output for the presence of endometriosis; text box 1119, labelled "No Endo" provides consensus network output for the absence of endometriosis; and text box 1120 provides a relative score indicative of whether or not the patient has endometriosis. It is noted that the score in the text box 1120 is an artificial number derived from boxes 1118 and 1119 that makes it easier for the physician to interpret results. As presently set, a value in this box in the positive range up to 25 is indicative of having endometriosis, and a value in the negative range down to -25 will be indicative of not having endometriosis. The selected transformations permits the physician to readily interpret the pat07 output more readily.

As described in the Examples, the pat07 is not the only network that is predictive of endometriosis. Other networks, designated pat08 through pat23a have been developed. These are also predictive of endometriosis. All these networks perform very similarly, and can readily be used in place of pat07. Thus, by following the methodology used to develop pat07, other similarly functioning neural nets can be and have been developed. Pat08 and pat09 are the most similar to pat07: these networks were developed by following the protocol outlined above, and were allowed to select important variables from the same set as that used for development of pat07.

It was found that the initial weighting of variables can have effects on the outcome of the variable selection procedure, but not in the ultimate diagnostic result. Pat08 and pat09 used the same database of patient data as pat07 to derive the disease relevant parameters. Pat10 through pat23a were training runs originally designed to elucidate the importance of certain parameters: history of endometriosis, history of pelvic surgery, dysmenorrhea and pelvic pain. For development of these, the importance of a variable was assessed by withholding that variable from the variable selection process. It was found that the variable selection process and training the final consensus networks, network performance did not significantly deteriorate.

Thus, although a particular variable, or set of variables, may have appeared to be significant in predicting endometriosis, networks trained in the absence of such variables do not have a markedly reduced ability to predict endometriosis. These results to demonstrate (1) the effectiveness of the methodology for variable selection and consensus network training;, and (2) the adaptability of networks in general. In the absence of one type of data, the network found other variable(s) from which to extract that information. In the absence of one variable, the network selected different variables in its place and maintained performance.

Patients suspected of having endometriosis typically must undergo exploratory surgery to diagnose the disease. The ability to diagnose this disorder reliably using patient history information and optionally biochemical test data, such as western blot data, provides a highly desirable alternative to surgery. The methods herein and identified variables provide a means to do so.

Data related to the diagnosis of the disease of endometriosis has been gathered. The data includes, patient history data, western blot data and ELISA data. Application of the methodology herein, as shown in the EXAMPLES, demonstrated that patient history data alone can be predictive of endometriosis.

To assess the performance of the variable selection protocol and to ascertain where the 14 variable network (pat07) ranked (in performance) compared to all possible combinations of the 14 variables, networks were trained on every possible combination of the variables (16,384 combinations). Also, the variable selection protocol was applied to the set of 14 variables. From among the 14, 5 variables were selected. These are pregnancy hypertension, number of births, abnormal PAP/dysplasia, history of endometriosis and history of pelvic surgery. This combination ranked as the 68th best performing combination out the 16,384 (99.6 percentile) possible combinations, thereby demonstrating the effectiveness of variable selection protocol. Also, the combination that includes all 14 variables was ranked 718 th out the 16,384 possible combinations (95.6 percentile).

These results also show that subsets of the 14 variables are useful. In particular, any subset of the selected set of parameters, particularly the set of fourteen variables, that contain one (or more) of the following combinations of three variables can be used with a decision-support system for diagnosis of endometriosis:

a) number of births, history of endometriosis, history of pelvic surgery;

b) diabetes, pregnancy hypertension, smoking;

c) pregnancy hypertension, abnormal pap smear/dysplasia, history of endometriosis;

d) age, smoking, history of endometriosis;

e) smoking, history of endometriosis, dysmenorrhea;

f) age, diabetes, history of endometriosis;

g) pregnancy hypertension, number of births, history of endometriosis;

h) Smoking, number of births, history of endometriosis;

i) pregnancy hypertension, history endometriosis, history of pelvic surgery;

j) number of pregnancies, history of endometriosis, history of pelvic surgery;

k) number of births, abnormal PAP smear/dysplasia, history of endometriosis;

l) number of births, abnormal PAP smear/dysplasia, dysmenorrhea;

m) history of endometriosis, history of pelvic surgery, dysmenorrhea; and n) number of pregnancies, history of endometriosis, dysmenorrhea.

As shown in the examples, other sets of important selected variables that perform similarly to the enumerated 14 variables can be obtained. Other smaller subsets thereof may be also be identified.

Predicting pregnancy related events, such as the likelihood of delivery within a particular time period The methods herein may be applied to any disorder or condition, and are particularly suitable for conditions in which no diagnostic test can be adequately correlated or for which no biochemical test or convenient biochemical test is available. For example, the methods herein have been applied to predicting pregnancy related events, such as the likelihood of delivery within a particular time period.

Determination of impending birth is of importance, example, for increasing neonatal survival of infants born before 34 weeks. The presence of fetal fibronectin in secretion samples from the vaginal cavity or the cervical canal from a pregnant patient after week 20 of pregnancy is associated with a risk of labor and delivery before 34 weeks. Methods and kits for screening for fetal fibronectin in body fluids and tissues, particularly in secretion samples from the vaginal cavity or the cervical canal, of a pregnant patient after week 20 of pregnancy are available (see, U.S. Pat. Nos. 5,516,702, 5,468,619, and 5,281,522, and 5,096,830; see, also U.S. Pat. Nos. 5,236,846, 5,223,440, 5,185,270).

The correlation between the presence of fetal fibronectin in these secretions and the labor and delivery before 34 weeks is not perfect; there are significant false-negative and false-positive rates. Consequently, to address the need for methods to assess the likelihood of labor and delivery before 34 weeks and to improve the predictability of the available tests, the methods herein have been applied to development of a decision-support system that assesses the likelihood of certain pregnancy related events. In particular, neural nets for predicting delivery before (and after) 34 weeks of gestation have been developed. Neural networks and other decision-support systems developed as described herein can improve the performance of the fetal fibronectin (fFN) test by lowering the number of false positives. The results, which are shown in EXAMPLE 13, demonstrate that use of the methods herein can improve the diagnostic utility of existing tests by improving predictive performance. EXEMPLARY neural networks and implementing software (Appendix II) are also provided herein.

PreTerm Delivery Risk Assessment Software

The Pre-term Delivery Risk Assessment Software (designated ptdinp.exe in Appendix III) program provides a means to input patient historical information and fFN test results into a database of fixed length ASCII records, and to perform the calculations necessary to generate inputs to three neural network tests used to evaluate the patients risks related to pre-term delivery. The software generates outputs that define the risk of preterm delivery. The Preterm Delivery Risk Assessment Software provided herein classifies the fFN ELISA positive results into 3 clinically distinct groups. In so doing, more than 50% of the fFN ELISA false positive results can be immediately identified. Moreover, about 35% of the true positive results can be rescued. The combination of the Preterm Delivery Risk Assessment Software with the ELISA test result provides new information which the clinician can use to improve the management of symptomatic patients. In particular, risk of delivery less than or equal to 34 week, 6 days, risk of delivery less than or equal to 7 days from time of sampling for fFN, and risk of delivery less than or equal to 14 days from time of sampling for fFN. The exemplified software uses neural networks designated EGA6, EGA7f and EGA14f (see Examples) herein, but can be used with any nets provided herein or developed based on the methods provided herein. The source code for the software is set forth in Appendix Ill.

The following is a description of the operation, inputs and outputs of the software.

A. User Interface

A typical user interface is depicted in FIGS. 12-15 and exemplary printed outputs are depicted in FIGS. 16A and 16B.

Main Menu

Figure 12:
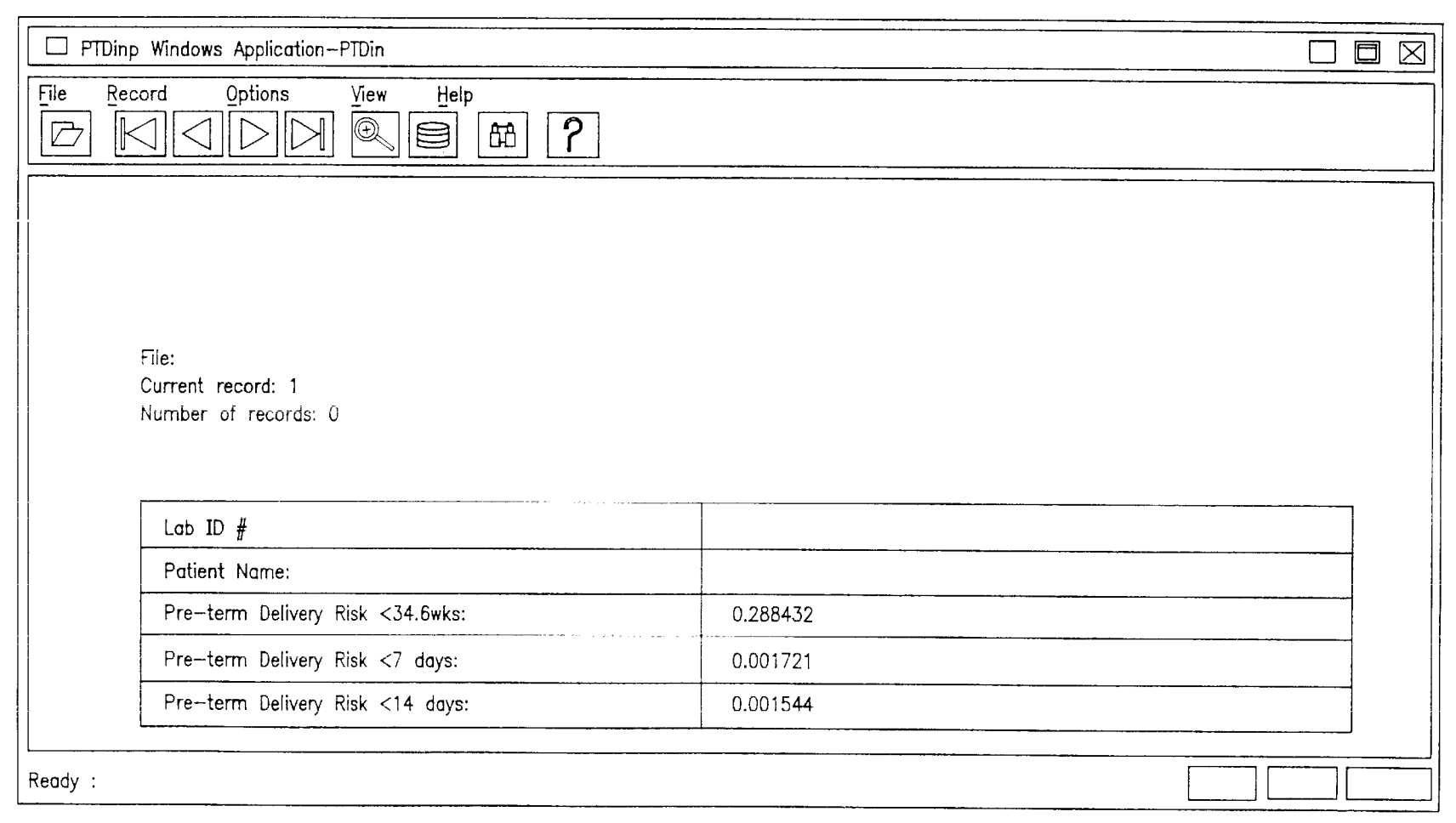

The main menu, tool bar and results display appear as shown in FIG. 12. The various fields in the main window are calculated as follows:

File: The name of the fdb file opened by the user.

Current Record: The record number counting from 1 that is currently displayed.

Number of records: The count of records contained in the open file.

Lab ID #: The contents of the associated field in the fixed length data record entered by the user.

Patient Name: The first, middle initial, and last name of the patient from the fixed length data record.

Pre-term Delivery Risk≦34 weeks 6 days, which is the consensus score from the ega6 set of neural networks.

Pre-term Delivery Risk≦7 days: The consensus score from the egad7f set of neural networks.

Pre-term Delivery Risk≦14 days: The consensus score from the egad14f set of neural networks.

The File item on the main menu contains the following sub menu items and functions;

Open: Open a fixed length database file (.fdb) for entry and examination.

Print: Print the current record in one of the two formats as specified in the Options menu.

Print Setup: Provides standard Windows support for print functions setup.

Print Preview: Provides standard Windows support for print viewing.

MRU List: Provides a list of the four Most Recently Used files.

Exit: To Exit the program.

The Record item on the main menu will contain the following sub menu items and functions:

First Record: Display the first record in the database file.

Next Record: Display the next record in the database file.

Previous Record: Display the previous record in the database file.

Last Record: Display the last record in the database file.

Go to Record: Opens a dialog to go to a specific record number or search for a specific Lab ID #.

Edit Record: Opens a dialog to allow the examination and modification of data in the displayed record.

New Record: Creates a new record at the end of the database and automatically edits the record.

The Options item on the main menu will contain the following sub menu items and functions;

Print full form: When checked, the print function will print the full record as shown in the edit record dialog box. When unchecked, the print function will print the information shown in the main window. The default setting is unchecked.

Clear sub fields: When checked, sub fields will be cleared when field is unchecked in the edit dialog. The default setting is checked.

The View item on the main menu will contain the following sub menu items and functions:

Toolbar: Standard Windows Toolbar appears when checked.

Status Bar: Standard Windows Status Bar appears when checked.

The Help item on the main menu will contain the following sub menu items and functions;

About PTDinp: Provide version number, program icon, and developer of the program.

Tool Bar buttons will be provided for the following functions:
File Open
View First Record
View Previous Record
View Next Record
View Last Record
Edit Record
New Record
Go To Record
Help About
Edit Dialog An exemplary Edit Record dialog box is set forth in FIG. 13. Through this dialog the user can exam, change or input patient specific data into a fixed length database record. The table below provides the size and location of each item in the fixed length database record. For entry into the dialog box relevant items are checked; all checked items are assigned a value of 1, all others are assigned a value of 0. The alphanumeric fields in the dialog box, such as Lab ID #, name, date of birth, EGA boxes, G (gravity), P (parity), A (abortions) are assigned the entered values. The table set forth (True=checked, false=unchecked) below summarizes how the information entered into the dialog box is converted for storage in the fixed length database record.

| NAME | POSITION | WIDTH | DESCRIPTION |
|---|---|---|---|
| LAB ID # | 1 | 12 | ACSII text |
| LAST NAME | 13 | 24 | ACSII text |
| FIRST NAME | 37 | 24 | ACSII text |
| MIDDLE INITIAL | 61 | 2 | ACSII text |
| DATE OF BIRTH | 93 | 10 | ACSII mm/dd/yy |
| ETHNIC ORIGIN WHITE | 103 | 2 | 0 = FALSE 1 = TRUE |
| ETHNIC ORIGIN BLACK | 105 | 2 | 0 = FALSE 1 = TRUE |
| ETHNIC ORIGIN ASIAN | 107 | 2 | 0 = FALSE 1 = TRUE |
| ETHNIC ORIGIN HISPANIC | 109 | 2 | 0 = FALSE 1 = TRUE |
| ETHNIC ORIGIN NATIVE AMERICAN | 111 | 2 | 0 = FALSE 1 = TRUE |
| ETHNIC ORIGIN OTHER | 113 | 2 | 0 = FALSE 1 = TRUE |
| MARITAL STATUS | 115 | 2 | 1 = Single (only one box can be checked) 2 = Married 3 = Divorced 4 = Widowed 5 = Living with partner 6 = Other |
| Symptoms of Preterm labor | 117 | 2 | 0 = No 1 = Yes |
| Vaginal Bleeding | 119 | 2 | 0 = N/A (check if sub field checked) 1 = Trace 2 = Medium 3 = Gross |
| Uterine Contractions | 121 | 2 | 0 = FALSE 1 = TRUE |
| Intermittent lower abdominal pain, dull low back pain | 123 | 2 | 0 = FALSE 1 = TRUE |
| Bleeding during the second or third trimester | 125 | 2 | 0 = FALSE 1 = TRUE |
| Menstrual-like or intestinal cramping | 127 | 2 | 0 = FALSE 1 = TRUE |
| Change in vaginal discharge | 129 | 2 | 0 = FALSE 1 = TRUE |

-continued

| NAME | POSITION | WIDTH | DESCRIPTION |
|---|---|---|---|
| Patient is not "feeling right" | 131 | 2 | 0 = FALSE 1 = TRUE |
| Number/hr. | 133 | 2 | 0 = Uterine Contractions FALSE 1 = "<1" 2 = "1–3" 3 = "4–6" 4 = "7–9" 5 = "10–12" 6 = ">12" |
| EGA by SONO | 135 | 8 | ACSII weeks.days format |
| EGA by LMP | 143 | 8 | ACSII weeks.days format |
| EGA at Sampling | 151 | 8 | ACSII weeks.days format |
| GRAVITY (G:) | 159 | 2 | ASCII number |
| PARITY (P:) | 161 | 2 | ASCII number |
| ABORTIONS (A:) | 163 | 2 | ASCII number |
| Number of Pre-term delivery | 165 | 2 | 0 = NONE 1 = "1" 2 = "2" 3 = ">2" |
| No previous pregnancies | 167 | 2 | 1 = "Gravity = 0" |
| Previous pregnancies with no complications | 169 | 2 | 0 = FALSE 1 = TRUE |
| History of Pre-term delivery | 171 | 2 | 0 = FALSE 1 = TRUE |
| History of pre-term PROM | 173 | 2 | 0 = FALSE 1 = TRUE |
| History of in-competent cervix | 175 | 2 | 0 = FALSE 1 = TRUE |
| History of PIH/preeclampsia | 177 | 2 | 0 = FALSE 1 = TRUE |
| History of SAB prior to 20 weeks | 179 | 2 | 0 = FALSE 1 = TRUE |
| Multiple Gestation | 181 | 2 | 0 = NONE (unchecked) 1 = "Twins" 2 = "Triplets" 3 = "Quads" |
| Uterine or cervical abnormality | 183 | 2 | 0 = FALSE 1 = TRUE |
| Cerclage | 185 | 2 | 0 = FALSE 1 = TRUE |
| Gestational Diabetes | 187 | 2 | 0 = FALSE 1 = TRUE |
| Hypertensive Disorders | 189 | 2 | 0 = FALSE 1 = TRUE |
| Dilation | 191 | 2 | 0 = Unk. Or None checked 1 = "<1" 2 = "1" 3 = "1–2" 4 = "2" 5 = "2–3" 6 = "3" 7 = ">3" |
| Cervical Consistency | 193 | 2 | blank = (unchecked) 1 = "Firm" 2 = "Mod" 3 = "Soft" |
| Antibiotics | 195 | 2 | 0 = FALSE 1 = TRUE |
| Corticosteroids | 197 | 2 | 0 = FALSE 1 = TRUE |
| Tocolytis | 199 | 2 | 0 = FALSE 1 = TRUE |
| Insulin | 201 | 2 | 0 = FALSE 1 = TRUE |
| Antihypertensives | 203 | 2 | 0 = FALSE 1 = TRUE |
| Medication: None | 205 | 2 | 0 = FALSE 1 = TRUE |
| Medication: Unknown | 207 | 2 | 0 = FALSE 1 = TRUE |
| Qualitative fFN Result | 209 | 2 | 0 = FALSE 1 = TRUE |
| <34.6 Net Output Positive | 211 | 20 | ASCII coded float |
| <34.6 Net Output Negative | 231 | 20 | ASCII coded float |
| <7 Day Net Output Positive | 251 | 20 | ASCII coded float |
| <7 Day Net Output Negative | 271 | 20 | ASCII coded float |
| <14 Day Net Output Positive | 291 | 20 | ASCII coded float |
| <14 Day Net Output Negative | 311 | 20 | ASCII coded float |

Go To Dialog

The Go To dialog box is shown in FIG. 14. The user may enter either the record number or the Lab ID number. When OK is pressed the record is found and displayed based on the information contained in a database record.

Help About Dialog

The Help About dialog box, which can provide information, such as the title of the software, version and copyright information, is shown in FIG. 15.

B. Pre-term Delivery Risk Evaluation

1. Loading the Networks

When a new database is opened or the program is first run, the neural networks associated with the risk evaluations are loaded. For each risk evaluation there are 8 neural networks that must be loaded. This is performed by repeated calls to the LoadNet function of the ThinksPro TKSDLL.DLL (a WINDOWS™ dynamic link library). Other suitable programs can be used to run the neural networks described herein. The LoadNet function automatically loads the weights associated with each network.

For the ≦34 weeks, 6 days evaluation the following nets (described in the Examples) are loaded.
Ega6_0
Ega6_1
Ega6_2
Ega6_3
Ega6_4
Ega6_5
Ega6_6
Ega6_7.

For the ≦7 days evaluation the following nets are loaded:
Egad7f0
Egad7f1
Egad7f2
Egad7f3
Egad7f4
Egad7f5
Egad7f6
Egad7f7

For the ≦14 days evaluation the following nets are loaded:
Egad14f0
Egad14f1
Egad14f2
Egad14f3
Egad14f4
Egad14f5
Egad14f6
Egad14f7

2. Processing the Inputs and Outputs

To run the evaluation of the pre-term delivery risks, data from the database record must be processed for use by the neural networks. The networks are run for a given evaluation when the "calculate risk" button is pressed in the edit record dialog (FIG. 13). The positive outputs (described below) of each network are averaged together to produce the value that is displayed, printed and placed in the database. The negative outputs (described below) are averaged and the result is placed in the database only.

a. For the ≦34 weeks, 6 days (referred to herein as 34.6) evaluation

The ≦34.6 networks use 11 inputs generated from the database record. These inputs are calculated as follows.

1. Ethnic Origin White: 1.0 input if TRUE, 0.0 input if FALSE.
2. Marital Status Living with Partner: 1.0 input if TRUE, 0.0 input if FALSE.
3. EGA by SONO: Convert from weeks.days to weeks.
4. Val1=EGA by LMP: Convert from weeks.days to weeks. Val2=EGA by SONO: Convert from weeks.days to weeks. If Val2<=13.0 then input is Val2; Else if the difference between Val1 and Val2 is >2 then input is Val1. Else input is Val2.

5. EGA at Sample: Convert from weeks.days to weeks.
6. If Dilatation none then input is 0.0.
   If Dilatation<1 then input is 0.0.
   If Dilatation 1 then input is 1.0.
   If Dilatation 1-2 then input is 1.5.
   If Dilatation 2 then input is 2.0.
   If Dilatation 2-3 then input is 2.0.
   If Dilatation 3 then input is 3.0.
   If Dilatation>3 then input is 3.0.
7. If Number of Preterm Delivery=0 then input is 0.0.
If Number of Preterm Delivery=1 then input is 1.0.
   If Number of Preterm Delivery=2 then input is 2.0.
If Number of Preterm Delivery>2 then input is 3.0.
8. Vaginal Bleeding: 1.0 input if TRUE, 0.0 input if FALSE.
9. If Cervical Consistency unchecked then input is 1.823197.
   If Cervical Consistency Firm then input is 1.0.
   If Cervical Consistency Mod then input is 2.0.
   If Cervical Consistency Soft then input is 3.0.
10. Previous pregnancies with no complications: 1.0 input if TRUE, 0.0 input if FALSE.
11. FFN Result: 1.0 input if Positive, 0.0 input if negative.
   b. For the ≦7 days evaluation The ≦7 day networks use 7 inputs generated from the database record. These inputs are calculated as follows.
1. Ethnic Origin White: 1.0 input if TRUE, 0.0 input if FALSE.
2. Uterine Contractions: 1.0 input if TRUE, 0.0 input if FALSE.
3. Number of Abortions: Convert to float.
4. Vaginal Bleeding: 1.0 input if TRUE, 0.0 input if FALSE.
5. If Number/hr unchecked then input 0.0.
   If Number/hr<1 then input 1.0.
   If Number/hr 1-3 then input 2.0.
   If Number/hr 4-6 then input 3.0.
   If Number/hr 7-9 then input 4.0.
   If Number/hr 10-12 then input 5.0.
   If Number/hr>12 then input 6.0.
6. No previous pregnancies: 1.0 input if TRUE, 0.0 input if FALSE.
7. fFN Result: 1.0 input if Positive, 0.0 input if negative.
   c. For the ≦14 days evaluation The ≦14 day networks use 7 inputs generated from the database record. These inputs are calculated as follows.
1. Ethnic Origin Native American: 1.0 input if TRUE, 0.0 input if FALSE.
2. Marital Status Living with Partner: 1.0 input if TRUE, 0.0 input if FALSE.
3. Uterine Contractions: 1.0 input if TRUE, 0.0 input if FALSE.
4. If Dilatation none then input is 0.0.
   If Dilatation<1 then input is 0.0.
   If Dilatation 1 then input is 1.0.
   If Dilatation 1-2 then input is 1.5.
   If Dilatation 2 then input is 2.0.
   If Dilatation 2-3 then input is 2.0.
   If Dilatation 3 then input is 3.0.
   If Dilatation>3 then input is 3.0.
5. If Number/hr unchecked then input 0.0.
   If Number/hr<1 then input 1.0.
   If Number/hr 1-3 then input 2.0.
   If Number/hr 4-6 then input 3.0.
   If Number/hr 7-9 then input 4.0.
   If Number/hr 10-12 then input 5.0.
   If Number/hr>12 then input 6.0.
6. No previous pregnancies: 1.0 input if TRUE, 0.0 input if FALSE.
7. FFN Result: 1.0 input if Positive, 0.0 input if negative.

3. Print Functions and Output interpretation

Based on the print full form option (options menu), print the full form if the option is checked and the results only if the option is not checked. FIGS. 16A and 16B show exemplary output formats, with the risk indices for each net, which are interpreted according to the following tables:

Risk of Preterm Delivery (Delivery before 34 weeks 6 days gestation)

| Risk Index | Interpretation |
|---|---|
| ≦.30 | low risk |
| >.30 | high risk |

Risk of Delivery within 14 days of sampling for fFN Qual ELISA.

| Risk Index | Interpretation |
|---|---|
| ≦0.10 | low risk |
| 0.10–0.40 | moderate risk |
| >0.40 | high risk |

Risk of Delivery within 7 days of sampling for fFN Qual ELISA.

| Risk Index | Interpretation |
|---|---|
| ≦0.05 | low risk |
| 0.05–0.60 | moderate risk |
| >0.60 | high risk |

D. Software Performance

As demonstrated below, the Preterm Delivery Risk Assessment Software supplements the fFN ELISA results in a clinically useful manner. By combining patient history and symptom information with the fFN ELISA test results, the software is able to more accurately assess the risk of preterm delivery. The data presented above suggest that the software is more capable of discriminating those women truly at risk for preterm delivery: whereas the fFN ELISA test has relatively high false positive rates and low positive predictive value, the software test reduces false positive observations by over 50% and doubles predictive value of the positive result. The fFN ELISA test allowed clinicians to identify those patients not at risk for preterm delivery. Given the significant increase in relative risk and the risk classification of the software test, the clinician may now identify those women who are at risk for preterm delivery. This capability represents a new advance in the clinical management of women who are experiencing symptoms of preterm labor.

In particular, the performance of the Preterm Delivery Risk Assessment Software has been evaluated on 763 women experiencing at least one of the following symptoms of preterm labor:

1. Uterine contractions, with or without pain.
2. Intermittent lower abdominal pain, dull, low backache, pelvic pressure.
3. Bleeding during the second or third trimester.
4. Menstrual-like or intestinal cramping, with or without diarrhea.
5. Change in vaginal discharge—amount, color or consistency.
6. Not "feeling right".

All 763 women were tested for fFN using the Qualitative fFN ELISA test. Based solely on the ELISA test, 149 women tested positive for fFN of which only 20 (13.4%) delivered within 7 days and 25 (16.8%) delivered within 14 days.

The low positive predictive value of the fFN ELISA test is enhanced by the Preterm Delivery Risk Assessment Software, which combines the fFN ELISA result with other patient information.

Table 1 compares the performance of the Qualitative fFN ELISA Test with the Preterm Delivery Risk Assessment Software Test for predicting delivery before 35 weeks completed gestation. The number of false positive observations decreased from 105 to 42, or about 60%. The decrease in false positive results is accompanied by a corresponding increase in true negative results, from 584 for the fFN ELISA to 647 for the software test. Moreover, a reduction in false negative results was also observed, from 30 for the ELISA test to 25 for the software test. Accordingly, the sensitivity and the specificity of the ELISA test are augmented by the software from 59.5% to 66.2% and from 84.8% to 90.4%, respectively. The positive predictive nearly doubles, increasing from 29.5% to 53.9%, and both the odds ratio and relative risk are increased substantially.

TABLE 1

| MEASURE | QUAL fFN ELISA TEST | RISK ASSESSMENT SOFTWARE TEST |
|---|---|---|
| True Positive | 44 | 49 |
| False Positive | 105 | 42 |
| True Negative | 584 | 647 |
| False Negative | 30 | 25 |
| Sensitivity | 59.5% | 66.2% |
| Specificity | 84.8% | 96.3% |
| Pos PV | 29.5% | 53.9% |
| Neg PV | 95.1% | 96.3% |
| Odds Ratio | 8.2 | 30.2 |
| Relative Risk | 6.0 | 14.6 |

Performance comparison of Qualitative fFN ELISA Test and the Preterm Delivery Risk Assessment Software Test relative to risk of preterm delivery before 35 completed weeks of gestation. The Risk Assessment Software combines fFN ELISA Test results with patient history and symptom information to provide a more accurately assess risk of preterm delivery (before 35 completed weeks of gestation).

Table 2 compares the performance of the two tests relative to risk of preterm delivery within 7 days. The largest difference between the two tests is in the reduction of false positive test results of the software when compared to the ELISA test. The software decreased the number of false positive observations from 129 to 57, or about 56%. Accompanying this decrease in false positive results is the matching increasing in true negative results, from 611 to 683. The true positive and false negative results remained essentially unchanged. The sensitivity and specificity of the software test is much higher than the ELISA test. Compare the sensitivity of 91.3% for the software with 87.0% for the ELISA, and the specificity of 92.3% for the software with 92.3% for the ELISA. Furthermore, the software test doubles the positive predictive value, increasing form 13.4% to 26.9%. Finally, the odds ratio is quadrupled and the relative risk more than tripled by the software.

TABLE 2

| MEASURE | QUAL fFN ELISA TEST | RISK ASSESSMENT SOFTWARE TEST |
|---|---|---|
| True Positive | 20 | 21 |
| False Positive | 129 | 57 |
| True Negative | 611 | 683 |
| False Negative | 3 | 2 |
| Sensitivity | 87.0% | 91.3% |
| Specificity | 82.6% | 92.3% |
| Pos PV | 13.4% | 26.9% |
| Neg PV | 99.5% | 99.7% |
| Odds Ratio | 31.6 | 125.8 |
| Relative Risk | 27.4 | 89.7 |

Performance comparison of Qualitative fFN ELISA Test and the Preterm Delivery Risk Assessment Software Test relative to risk of preterm delivery within 7 days.

Table 3 compares the performance of the two test relative to risk of preterm delivery within 14 days. Once again, the software decreases false positive test results when compared to the ELISA test, from 124 to 55, or about 53%. This decrease in false positive results is matched by the corresponding increase in true negative results, from 609 to 678. The number of true positive and false negative results were unchanged. Whilst the sensitivity of the test was unaffected, the specificity of the test rose nearly 10 points, increasing from 83.1% to 92.5%. As seen before, the positive predictive value nearly doubled, increasing from 16.8% to 31.3%, and the odds ratio and relative risk increased substantially from 24.6 to 61.6 and from 20.7 to 44.7, respectively.

TABLE 3

| MEASURE | QUAL fFN ELISA TEST | RISK ASSESSMENT SOFTWARE TEST |
|---|---|---|
| True Positive | 25 | 25 |
| False Positive | 124 | 55 |
| True Negative | 609 | 678 |
| False Negative | 5 | 5 |
| Sensitivity | 83.3% | 83.3% |
| Specificity | 83.1% | 92.5% |
| Pos PV | 16.8% | 31.3% |
| Neg PV | 99.2% | 99.3% |
| Odds Ratio | 24.6 | 61.6 |
| Relative Risk | 20.7 | 44.7 |

Performance comparison of Qualitative fFN ELISA Test and the Preterm Delivery Risk Assessment Software Test relative to risk of preterm delivery within 14 days.

The following examples are included for illustrative purposes only and are not intended to limit the scope of the invention.

EXAMPLE 1

Evaluation of Patient History Data for Relevant Variables

This examples demonstrates selection of the candidate variables.

Requirements

Evaluation of the patient history to determine which variables are relevant to the diagnosis. This example is performed by performing a sensitivity analysis on each of the variables to be used in the diagnosis. Two methods can be used to perform this analysis. The first is to train a network on all the information and determine from the network weights, the influence of each input on the network output. The second method is to compare the performance of two networks, one trained with the variable included and the second trained with the variable eliminated. This training would be performed for each of the suspected relevant variables. Those that did not contribute to the performance will be eliminated. These operations are performed to lower the dimension of the inputs to the network. When training with limited amounts of data, a lower input dimension will increase the generalization capabilities of the network.

Analysis of Data

The data used for this example included 510 patient histories. Each record contained 120 text and numeric fields. Of these fields, 45 were identified as being known before surgery and always containing information. These fields were used as the basic available variables for the analysis and training of networks. A summary of the variables used in this example was as follows:

| | |
|---|---|
| 1. age (preproc)- Preprossed to normalize the age to fall between 0 and 1 | 24. Uterine/Tubal Anomalies26. Ectopic Preg |
| 2. Diabetes | 25. Fibroids |
| 3. Preg Induced DM | 26. Ectopic Preg. |
| 4. Hypertension | 27. Dysfunctional Uterine Bld. |
| 5. Preg hyperplasia | 28. Ovarian Cyst |
| 6. Autoimmune Disease | 29. Polycystic Ovarian Synd |
| 7. Transplant | 30. Abnormal PAP/Dysplasia |
| 8. Packs/Day | 31. Gyn Cancer |
| 9. Drug Use | 32. Other HX |
| 10. #Preg | 33. Past HX of Endo |
| 11. #Birth | 34. Hist of Pelvic Surgery |
| 12. #Abort | 35. Medication History |
| 13. Hist of Infertility | 36. Current Exog. Hormone |
| 14. Ovulatory | 37. Pelvic Pain |
| 15. Anovulatory | 38. Abnormal Pain |
| 16. Unknown | 39. Menstrual Abnormalities |
| 17. Oligoovulatory | 40. Dysmenorrhea |
| 18. Hormone Induced | 41. Dyspaarunia |
| 19. Herpes | 42. Infertility |
| 20. Genital Warts | 43. Adnneaxal Masses/Thickening |
| 21. Other sexually transmitted diseases (STD) | 44. Undetermined |
| 22. Vag Infections | 45. Other Symptoms |
| 23. Pelvic inflammatory disease (PID) | |

Methodology Used

The most commonly used method for determining the importance of variables is to train a neural network on the data with all the variables included. Using the trained network as the basis, a sensitivity analysis is performed on the network and the training data. For each training example the network is run in the forward mode (no training). The network outputs were recorded. The for each input variable, the network is rerun with the variable replaced by it's average value over the training example. The difference in output values is squared and accumulated. This process is repeated for each training example. The resulting sums are then normalized so that the sum of the normalized values equals the number of variables. In this way, if all variables contribute equally to the output, their normalized value would be 1.0. The normalized value can then be ranked in order of importance.

There are several problems with the above approach. First, it is dependent on the neural network solution found. If different network starting weights are used, a different ranking might be found. Secondly, if two variables are highly correlated, the use of either would contain sufficient information. Depending on the network training run, only one of the variables might be identified as important. The third problem is that an overtrained network can distort the true importance of a variable.

To minimize the effects of the above problems, several networks were trained on the data. The training process was refined to produce the best possible test set performance so that the networks had learned the underlying relationship between the inputs and the desired outputs. By the end of this process, both a good set of networks would be available and the training configuration for the final trained networks would be established. The sensitivity analysis was performed on each of the networks trained and the normalized values were averaged. For this example, a training run included 15 networks trained on five partitions of the available data using a holdout method.

Once the ranking of variables has been established, test runs are made to determine the effects of eliminating variables has on the test set performance. Eliminating a variable that has a small contribution should lower the test set performance. When overtraining is an issue, due to limited training data, eliminating variables can actually improve the test set performance. To save on processing time, groups of variables can be eliminated in a test based on the ranking.

Results

The rankings or variables are as follows and are reported for networks trained in run pat05.

| | | |
|---|---|---|
| 01. | 35 | Medication History |
| 02. | 33. | Past history of Endo |
| 03. | 11 | #Birth |
| 04. | 37. | Pelvic Pain |
| 05. | 40. | Dysmenorrhea |
| 06. | 34. | Hist of Pelvic Surgery |
| 07. | 1. | Age(preproc) |
| 08. | 13. | Hist of Infert |
| 09. | 8. | Packs/Day |
| 10. | 36. | Current Exog. Hormones |
| 11. | 42. | Infertility |
| 12. | 18. | Hormone Induced |
| 13. | 15. | Anovulatory |
| 14. | 14. | Ovulatory |
| 15. | 43. | Adnnexal Masses/Thickening |
| 16. | 45. | Other Symptoms |
| 17. | 30 | Abnormal PAP/Dysplasia |
| 18. | 26. | Ectopic Preg. |
| 19. | 19. | Herpes |
| 20. | 39. | Menstrual Abnormalities |
| 21. | 12. | #Abort |
| 22. | 41. | Dyspaarunia |
| 23. | 24. | Uterine/Tubal Anomalies |
| 24. | 31. | Gyn Cancer |
| 25. | 32. | Other history |
| 26. | 10. | #Preg |
| 27. | 28. | Ovarian Cyst |
| 28. | 25. | Fibroids |
| 29. | 22. | Vag Infections |
| 30. | 16. | Unknown |
| 31. | 27. | Dysfunctional Uterine Bld. |
| 32. | 38. | Abdominal Pain |
| 33. | 5. | Preg hyperplasia |
| 34. | 9. | Drug Use |
| 35. | 20. | Genital Warts |
| 36. | 3. | Preg Induced DM |
| 37. | 4. | Hypertension |
| 38. | 21. | Other STD |
| 39. | 23. | PID |
| 40. | 44. | Undetermined |
| 41. | 2. | Diabetes |
| 42. | 17. | Oligoovulatory |
| 43. | 6. | Autoimmune Disease |
| 44. | 29. | Polycystic Ovarian Synd |
| 45. | 7. | Transplant |

Subsets of the variables were tested and the final set of 14 variables to be used to train the pat07 networks [see, Examples 13 and 14]. Some variables were used that were not in the above top 14. This occurred to improve the test set performance. The rankings for the pat07 networks are as follows:

| 01. | 10. | Past history of Endo |
| --- | --- | --- |
| 02. | 6. | #Birth |
| 03. | 14. | Dysmenorrhea |
| 04. | 1. | Age(preproc) |
| 05. | 13. | Pelvic Pain |
| 06. | 11. | Hist of Pelvic Surgery |
| 07. | 4. | Packs/Day |
| 08. | 12. | Medication History |
| 09. | 5. | #Preg |
| 10. | 7. | #Abort |
| 11. | 9. | Abnormal PAP/Dysplasia |
| 12. | 3. | Preg hyperplasia |
| 13. | 8. | Genital Warts |
| 14. | 2. | Diabetes |

Conclusions

The set of variables identified in this example appear to be reasonable based on the testing and information.

EXAMPLE 2

Train Networks on Patient History Data

This example, using the above 14 variables, demonstrates methods for setting and optimizing various parameters.

Requirements

At the completion of the above examples, train a set of networks on the reduced patient history and record their performance. Experiments were run to determine the best configuration and parameters for training of the networks. An analysis of the performance was performed to determine the number of false positive and false negatives, to see if a given subset of the patients can be reliably diagnosed. Since there was limited data, the estimated performance was determined by leaving out small portions of the database (25%) for testing and training on the remaining data. This method was repeated until all of the data has been used as test data in one of the networks. The combined results on the test data then become the performance estimate. A final network was be trained using all of the available data as training data.

Methodology Used

When dealing with small training examples, the holdout method is effective in providing test information useful in determining network configuration and parameter settings. In order to maximize the data available for training without a big increase in processing time a 20% holdout was used instead of the proposed 25%. This produced 5 partitions of the data instead of 4 and made 80% of the data for training in each partition.

To minimize the effects of the random starting weights, several networks were trained in the full training runs. In theses runs three networks were trained in each of the five partitions of data, each from a different random start. The outputs of the networks were averaged to form a consensus result that has a lower variance than could be obtained from a single network.

A number of experiments were performed to find network parameters that would maximize the test set performance. The parameters modified in this process were as follows;

1. Number of hidden processing elements.
2. Amount of Noise added to the inputs.
3. Amount of Error tolerance.
4. Learning algorithm used.
5. Amount of Weights decay used.
6. Number of input variables used.

A complete search of all possible combinations of 45 variables was not feasible because of the amount of CPU time needed for the tests. Test networks were trained with parameters chosen from based on parameters known by those of skill in the art to be important in this area and based on results of prior tests. Other sets of variables would also have been suitable. Also, as shown elsewhere herein, combinations of all of the selected 14 variables have been tested. Once the best configuration was determined, a final set of networks was trained on the complete data set of 510 patients. In the final set of networks, a consensus of eight networks was made to produce the final statistics.

Results

The final holdout training run was pat06 with 14 variables. The performance on the test data was 68.23%. The full training run was pat07 with the same network configuration as pat06. The performance on the training data was 72.9%. Statistics were generated on the last training run based on the use of a cutoff in the network output values. If the network output was below the cutoff, the example was rejected from consideration. The following table is a summary of the results for the consensus of eight networks in the pat07. A test program named adzcrf was produced to demonstrate this final training.

| Cutoff | 0.00 | 0.02 | 0.075 | 0.075 | 0.10 |
| --- | --- | --- | --- | --- | --- |
| Sensitivity | .828179 | .835821 | .872247 | .943750 | .956522 |
| Specificity | .598174 | .627660 | .630137 | .638298 | .745098 |
| PPV | .732523 | .761905 | .785714 | .816216 | .871287 |
| NPV | .723757 | .728395 | .760331 | .869565 | .904762 |
| Odds Ratio | 2.695 | 3.000 | 3.494 | 4.907 | 7.412 |
| % Rejected | 0 | 10.58 | 26.86 | 50.20 | 71.96 |

PPV = positive predictive value;,
NPV = negative predictive value

EXAMPLE 3

Preprocessing and input Western Blot Data Requirements

The antigen data, from Western Blots, for the patients that was originally delivered to Logical Designs provided information on only the peak molecular weights and their associated intensities. Analysis of this data and of the original images from which the data was taken, suggests that it may be possible to use the original image digitized in a way that could provide more information to the neural network. In examining the original images for two experiments, it preprocessing of the image data decreases the variability of the position of a specific molecular weight in the image. This preprocessing will use a polynomial fit through the standards image to produce a modified image. Preprocessing of the images will also include steps to normalize the background level and contrast of the images.

Once the preprocessing is complete, the image data could be used as is, or the peak molecular weights could be extracted. From resulting images, inputs to the neural network will be generated. As a typical image is about 1000 pixels long, methods to reduce the number of inputs will be investigated. As the image would be coded directly into the network inputs using the full or reduced dimension (resolution) images, a neural network will be trained with supervised learning to aid in the determination of the ranges of molecular weights that are related to the determination of the disease. This Example focuses on using the image as a whole in the input to the network.

Methodology Used

Using a correlation technique, similar features on images of Western blots were matched and a correlation plot was produced. From those plots, it was concluded that there was too much variation in matches on the correlation plots of two samples to accurately align the samples. Since each input of the network needed to accurately represent a molecular weight value, it was decided that only information from the standards image would be used for alignment of images.

A quadratic fit was performed on the standards image to generate a means to translate relative mobility information to molecular weight. After plotting a curve of relative mobility to the log of the molecular weight and examining the RSQR values, it was concluded that the quadratic fit was not accurate enough for performing this translation. The calculated weight for a standard molecule varied from gel to gel using the quadratic fit.

Several methods were tried to improve the translation of relative mobility to molecular weight. Cubic spline interpolation was selected. This method guarantees smooth transitions at the data points and is rapidly calculated. The only concern is how the method performs on values of relative mobility outside the intervals covered by the standards. If termination conditions are set properly, the extrapolation problem seems to be avoided. This was the selected method.

Using spline interpolation, the images were converted to fixed dimension training records. At this point, image intensity normalization had to be considered. Two alternatives were considered. The first was to perform no normalization. The second was to process the images so that the maximum value across the image was set to 1.0 and the minimum value was set to 0.0. Networks were trained on each alternative and the results were compared. With no noise added to the inputs, the preprocessed image network had a training example performance of 97% while the performance for no preprocessing was 79%. When noise was added, the two alternative gave similar results. The choice was made to use the preprocessed images for further training runs. This choice insured that a given network input would consistently be associated with a specific molecular weight within the tolerances achievable using the Western Blot method.

Using the above choices, a series of eight neural networks were trained to provide information on the importance of different molecular weights on the prediction of the Endo present variable. In order to permit an analysis of the direction of correlation, only a single hidden processing element was used in the training. A sensitivity analysis was performed on each of the networks and the resulting consensus was plotted using Excel.

The weights of the network were then averaged together to generate a consensus value for each weight. Since the interconnection weight from the hidden clement to the output could be either positive or negative. The weights were transformed so that all the output connections had the same sign. The weights were then averaged and the results plotted using Excel.

Results

The analysis of the Western Blot data was performed using a cubic spline interpolation for image alignment to the network inputs and Max/Min image preprocessing. Given that a certain amount of variability can be expected in the accuracy of alignment of the images, due to the Western Blot methodology, this approach is believed to give better results that the polynomial fit originally used.

The plot of the sensitivity analysis and of the weights for the final consensus networks indicated that there are regions on the Western Blot that can aid in the prediction and diagnosis of the disease. The width of the regions of positive and negative correlation, as seen in the network weights, also indicates that the results shown are significant. If the peaks had been very narrow, one would have to conclude that the peaks were artifacts of the training process, similar to overtraining, and not form the underlying process being learned. The regions that appear important are as follows:

Positive Correlation:
   131503.98 - 34452.12
   62548.87 - 65735.97
   84279.36 - 89458.49

Negative Correlation:
   19165.9 - 20142.47
   50263.36 - 53352.14
   67725.77 - 78614.77

While there were a number of positive and negative peaks, these appeared to be the most likely regions for inclusion into two ELISA tests. One test will focus on the positive regions and the other on the negative regions. The two resulting values can then be combined with the patient history data as input to the neural networks.

Conclusions

The neural network was able to find regions on the Western Blot that correlate with the presence of the disease.

EXAMPLE 4

Investigate Fixed Input Dimension for Western Blot Data

Requirements

Using peak molecular weights extracted from the preprocessed image, methods to reduce the varying dimension of the western blot data for a patient to a fixed dimension for the neural network will be investigated. This approach is desirable in that it will have substantially fewer network inputs than the full image approach. The basic problem is that the test yields a varying number of molecular weights that might by interrelated. Comparison of results from Example and this example will indicate that patterns of molecular weights exist or if the weights are unrelated. Since there is some variability in the weight data the approach to the processing of this data will be similar to a fuzzy membership function, even though the classification will be performed with a neural network.

Additional Requirements

Fractions are identified from the Western blot data. Since production of these fractions is reproducible, the effectiveness of the use of this information will be determined by processing the Western blot image data into bins corresponding to the molecular weights of the fractions.

Methodology Used

From the results of Example 5, several ranges in molecular weight were determined to correlate with the disease. A reduced input representation was produced by using a gaussian region centered on each of the peaks found in Example 5. The standard deviation of the gaussian was determined so that the value of the gaussian was below 0.5 at the edges of the region. The basic operation performed to generate the neural network input was to perform a convolution between the gaussian and the Western blot image. The calculations were all performed using the log of the molecular weight.

A separate software program was produced. The program performed the convolution on the normalized images with respect to molecular weight and intensity. The parameters for calculation of the network inputs are contained in a table in the binproc program. In binproc the mean and std. deviation are stored in the table. The program is recompiled when the table values are changed. The program has a test mode that produces an output file that allows the gaussians to be plotted an compared to the Western Blot images, using Excel. Plots of regions are included in the documentation.

When working with 36 fractions, binproc.c was again modified to translate the positions of the fractions into table values for binproc. This modified program is called fproc.d. It's purpose is to perform the spline interpolation required to normalize the molecular weight value based on the standards. Binproc2.c was produced from binproc, replacing the mean and std. deviation tables with min. and max. tables which correspond to the endpoints of the fractions in the files supplied.

In order to test any of the data files produced by the above programs, the holdout methods was used with 80% of the data being used for training and the remaining 20% to be used for testing. Once the training data are produced form the Western Blot data, a random number column and the Patient ID column was added in the Excel spreadsheet. The data was then sorted on the random number column. This in effect shuffles the data. In this way, it is likely that each partition has examples from each of the gels. With these percentages, five separate training and test files were produced os as to allow a network performance to be estimated from the combined test set results.

Using ThinksPro™ the number of inputs used by the network could be varied by excluding inputs. Excluded inputs are not presented to the network during training. Using the sensitivity analysis as a guide, unimportant inputs are eliminated. Decreasing the dimension of the input space becomes even more important when the number of training examples is small. This method is the same as was used for eliminating variables in the patient history training runs. At the current time, this process is performed manually.

Results

In Example 5, networks trained on all the data were used to determine what ranges of molecular weights were important to the classification process. In this Example, the holdout method was used to train networks so that the test set performance could be estimated. The first set of test were based on regions identified in Example 5. The second set of tests were made using the fractions identified in the four ishgel files.

The initial consensus runs based on the top six regions found in Example 5 yielded poor performance (50%). Analysis of the input data generated, indicated that the regions used to generate the input data were too narrow to capture the important information from the image data. The regions were widened and the top ten regions from Example 5 were included instead of the top six. A test on the ten wider regions indicated slightly better performance. Using sensitivity analysis, three of the ten regions were eliminated and a complete test as run. The performance on the six of the ten wider regions improved to 54.5%.

As the number of inputs to the network was further decreased, the test set performance (estimated with the holdout method) continued to increase. The best performance was achieved from using only one of the regions, with molecular weight ranging from 66392.65 to 78614.74. The performance estimate was 58.5% on test data using the holdout method.

This process was applied again using, as a start, 36 regions based on identified fractions. There was a great deal of overlap in the 36 fractions. The top 7 fractions were determined from the 36 using sensitivity analysis. Similar performance of 58% was achieved using the subset of the fractions.

Conclusions

None of the tests yielded results that were very high. The primary reason for this is likely to be the limited amount of training data available for this Example. Results from previous Examples indicated that as the number of patients in the training sample decreased, that the performance on validation data also decreased. This relationship is illustrated in the following table.

| Network | Patients | Estimated Performance |
|---|---|---|
| Patient History | 510 | 68.23 (pat06) |
| Elisa using patient history data only | 350 | 62.76 |
| Western Blot | 200 | 58.0 |

Better results were achieved on the ELISA/patient historical data when including the Elisa variables, even with the reduced number of patients. This showed the value of the ELISA variable.

It appears that a number of regions can be determined as being important to the classification of the disease. Substantially different sets of regions has yielded similar results, indicating that there may be patterns in the Western Blot data that indicate the presence of the disease. With a small database of patients, it is more difficult to isolate these patterns.

It is clear that increasing the size of the database for Western Blot data will improve the performance of the networks trained on this data. When combining Western Blot data with patient historical data, the input dimension of the network will increase. The increase in input dimension usually requires more training examples to ensure generalization.

EXAMPLE 5

Train Networks Using Western Blot Data

The purpose of this example was to train a set of networks to determine the performance estimate for the diagnosis using only western blot data. Experiments were run to determine the best configuration and parameters for training of the networks. The method described in Example 2 above was be used for this performance estimate. A final network was trained using all of the available data as training data. The output of this trained network (antigen index) was used as an input to the network generated in the combined data phase.

Methodology Used

Several methods were used to find the best performing set of inputs for the available training data. From previous Examples, the use of the sensitivity analysis was shown to produce good results in identifying the importance of each of the inputs variables. The number of networks were trained on combinations of variables manually determined from the sensitivity analysis.

In preparing an automated procedure, the use of a 2×2 contingency table Chi square analysis of the variables was used to provide an alternative ranking of the importance of the variables. Since the inputs were continuous, a threshold was used for each input to generate the information needed for the contingency table. The Chi-square value varies depending on the setting of the threshold. The threshold value used in the ranking of variables was chosen to maximize the Chi square statistic.

The training runs made during the development of the automated procedure were chosen from these rankings. At the time that the training runs were made, an automated procedure had not been formulated. To save on overall processing time, only one partition of the training data was used. Combinations of variables that performed well in the first partition of the training and test data were then tried on remaining the partitions.

One method suggested in the literature for finding the best set of inputs has been to use a genetic algorithm to determine the highest performing set of inputs. Genetic algorithms typically require thousands of iterations to converge to a good solution. In working with the Western Blot data, this would represent a large amount of computer time, even with the small training example size. For 10 variables, an enumeration of all combinations would require 1024 training runs. An alternative to the genetic algorithm was attempted. In this alternative method, a neural network was trained to predict the test set RMS Error based on the set of inputs chosen. The training examples used for this experiment were the results of training runs on the first partition of the Western Blot data. The predictor network was then tested with all combinations to determine the predicted minimum combination. That input combination was then used to train a network on the Western Blot data. The main drawback of this method and the genetic algorithm approach is that the sensitivity analysis information, found to be very effective is ignored in the process.

Results

The basic rankings for the 10 variables (bins) in the Western Blot Data are based on a consensus of 8 networks trained on the full database of 200 examples. The results are as follows:

| | |
|---|---|
| 7 | 1.182073 |
| 9 | 1.055611 |
| 3 | 1.053245 |
| 8 | 1.039028 |
| 6 | 1.027239 |
| 10 | 1.023135 |
| 4 | 0.978769 |
| 5 | 0.952821 |
| 2 | 0.899936 |
| 1 | 0.788143 |

The rankings of the 10 variables based on the Chi-square analysis are as follows:

| | |
|---|---|
| 3 | 4.380517 |
| 9 | 3.751625 |
| 7 | 3.372731 |
| 2 | 3.058437 |
| 6 | 3.022164 |
| 5 | 2.787982 |
| 10 | 1.614931 |
| 4 | 1.225725 |
| 1 | 0.975502 |
| 8 | 0.711958 |

During the analysis of the Western Blot data, a number of networks were trained on the first partition(s) of the training data. The test results, which are ranked below, show the variables that were included in the training run.

| Variables | | | | | | | | | | Test Error | |
|---|---|---|---|---|---|---|---|---|---|---|---|
| 1 | 2 | 3 | 4 | 5 | 6 | 7 | 8 | 9 | 10 | | |
| 0 | 0 | 0 | 1 | 0 | 1 | 0 | 0 | 1 | 1 | 0.49291 | |
| 0 | 0 | 1 | 0 | 0 | 0 | 1 | 0 | 1 | 0 | 0.49374 | |
| 0 | 0 | 0 | 0 | 1 | 0 | 0 | 1 | 0 | 1 | 0.49831 | |
| 1 | 0 | 0 | 0 | 0 | 1 | 0 | 0 | 0 | 1 | 0.50036 | (11) |
| 0 | 0 | 1 | 0 | 0 | 0 | 0 | 0 | 0 | 0 | 0.50145 | |
| 0 | 0 | 0 | 0 | 0 | 1 | 0 | 0 | 0 | 1 | 0.50164 | (13) |
| 0 | 0 | 0 | 0 | 0 | 0 | 0 | 0 | 0 | 1 | 0.50174 | (5) |
| 0 | 0 | 0 | 0 | 0 | 0 | 1 | 0 | 0 | 0 | 0.50182 | |
| 0 | 0 | 0 | 0 | 1 | 0 | 0 | 0 | 0 | 0 | 0.50295 | (8) |
| 0 | 0 | 1 | 0 | 1 | 0 | 1 | 0 | 0 | 0 | 0.50285 | |
| 0 | 0 | 0 | 0 | 0 | 0 | 0 | 0 | 1 | 0 | 0.50323 | |
| 0 | 0 | 0 | 0 | 0 | 1 | 0 | 0 | 0 | 0 | 0.50360 | (7) |
| 0 | 0 | 1 | 0 | 0 | 0 | 1 | 0 | 0 | 1 | 0.50587 | |
| 0 | 1 | 1 | 0 | 0 | 0 | 0 | 1 | 0 | 0 | 0.50682 | (3) |
| 0 | 0 | 1 | 0 | 0 | 0 | 0 | 0 | 1 | 0 | 0.50707 | |
| 0 | 0 | 0 | 1 | 1 | 1 | 0 | 0 | 1 | 1 | 0.50823 | |
| 1 | 0 | 0 | 0 | 1 | 1 | 1 | 0 | 0 | 0 | 0.50853 | (2) |
| 0 | 0 | 0 | 0 | 1 | 0 | 1 | 0 | 0 | 0 | 0.50995 | (1) |
| 1 | 1 | 0 | 0 | 0 | 0 | 0 | 0 | 0 | 0 | 0.51158 | (9) |
| 0 | 0 | 0 | 0 | 0 | 1 | 0 | 1 | 0 | 0 | 0.51163 | |
| 0 | 0 | 0 | 0 | 1 | 1 | 0 | 0 | 0 | 0 | 0.51372 | (10) |
| 0 | 0 | 0 | 0 | 0 | 0 | 1 | 1 | 0 | 0 | 0.51909 | |
| 1 | 0 | 0 | 1 | 0 | 0 | 0 | 1 | 0 | 0 | 0.52084 | (4) |
| 1 | 1 | 0 | 1 | 0 | 1 | 0 | 0 | 0 | 1 | 0.52950 | |
| 0 | 1 | 0 | 0 | 0 | 1 | 0 | 1 | 0 | 0 | 0.52978 | |
| 0 | 0 | 0 | 1 | 0 | 1 | 0 | 1 | 0 | 0 | 0.53196 | |
| 0 | 0 | 1 | 1 | 0 | 0 | 0 | 1 | 1 | 0 | 0.54841 | |
| 0 | 0 | 1 | 0 | 0 | 1 | 0 | 1 | 0 | 0 | 0.54934 | (14) |
| 0 | 1 | 0 | 1 | 0 | 0 | 0 | 0 | 0 | 1 | 0.55178 | (12) |
| 1 | 1 | 0 | 0 | 0 | 1 | 1 | 0 | 0 | 0 | 0.55290 | (6) |
| 1 | 0 | 1 | 0 | 0 | 0 | 0 | 1 | 0 | 1 | 0.56664 | |
| 0 | 0 | 1 | 1 | 0 | 1 | 0 | 1 | 1 | 1 | 0.59937 | |

() indicates combination was generated by prediction network training process.

In looking at the above test runs, it is clear that the more important variables in the rankings contributed to lower test set errors and that the more variables included, the lower the test set results. This shows the importance of choosing the best subset of variables in developing a high performance neural network.

Several combinations of variables were used to train networks on all partitions of the training data. The results of these runs are shown below.

| VARIABLES | TIME SET PERFORMANCE |
|---|---|
| 3 | 57.5% |
| 3, 9 | 53.5% |
| 3, 7, 9 | 53.0% |
| 4, 6, 9, 10 | 57.0% |

Since both rankings of variables showed 3, 7, and 9 as important, it is likely that this combination would give higher than 57.5% provided there was enough training data. Training example performance for this combination was 63.9%, showing the level of overtraining that occurred. Several of the first partition networks shown above had combinations of variables chosen by a neural network trained to predict the test performance. Those networks are indicated by a number in the last column. This number indicates the sequence in which tests were run. Combinations without a number were chosen manually from the rankings. It is likely that is this process were continued that the predictor network would eventually find the best combination. Since there are many factors that can effect the test set performance, it is likely that there is a lot of "noise" in the test set results. For this method to work better, a consensus approach may be needed to generate the training values for the predicted test set error. This problem would also be seen when using the consensus approach.

Conclusion

The process of using the sensitivity and contingency table rankings of variables is an effective and efficient technique for picking a set of variables to maximize the neural network performance. The top 3 variables under both rankings were the same, indicating that these methods are performing well. This method appears to work with the Western Blot data but should work well on any form of data, making this a general purpose neural network technique that can also be applied to patient history data.

The above results indicate more data would improve the level of performance. The sensitivity analysis shows little variation in the relative values of variables. Most of the variables contribute to the solution. This should be expected since the bins were chosen based on an analysis of neural network weights trained on the full Western Blot images. By using all or most of the variables, however, the neural networks quickly get into an overtraining situation. This can be avoided by adding data to the training example.

Tests with the neural network guided selection of variables proved to be less effective than the ranking approach. While the ranking approach was clearly the most effective, the neural network guided approach should also be able to eventually discover the best set of variables. Because it is a more direct approach than a genetic algorithm, it is likely to perform better than the genetic algorithm on similar data. The major drawback of this method is that it does not use the sensitivity analysis information to aid in the search.

EXAMPLE 6

Combine Patient History and ELISA Data Requirements

Using the processing developed in the above examples, train a set of networks on the combination of Patient History Data and ELISA Data. An index generated from an ELISA test, based on the use of the entire set of antigens will be used to determine the improvement in performance achieved by combining this information with the patient historical data.

Additional Requirements

In addition to the above requirements, a comparison between the data from several ELISAs, ELISA 100 and ELISA 200 data and ELISA 2 data, and an analysis of the interrelationships of variables were performed to help determine to what variables the original ELISA tests related.

Methodology Used

In order to determine the improvement in the diagnostic test performance achieved by the inclusion of ELISA test results, several trainings were made using the holdout methods described in EXAMPLE 2. The partitions of the data were made so that in each partition, 80% of the data was used for training and the remaining 20% was used for testing.

To minimize the effects of the random starting weights, several networks were trained in the full training runs. In these runs three networks were trained in each of the five partitions of data, each from a different random start. The outputs of the networks were averaged to form a consensus result that has a lower variance than could be obtained from a single network. Since the number of patients for which all forms of ELISA data was available was 325, new training runs with the original 14 variables were made to provide an accurate means of comparing the effects of the ELISA data on the diagnosis of the disease. Analysis of the ELISA 2 data showed a large range of values for the test. Plots showing the relation of ELISA 2 to the ELISA 1 00 data suggested that the log of the ELISA 2 data might be better than the raw value.

The comparison training runs were organized as follows:
Run 1:ELISA 100, ELISA 200, log (ELISA 2) and the original 14 variables.
Run 2:(ELISA 2) and the original 14 variables
Run 3: The original 14 variables After making these comparison runs, a final set of networks was trained on the complete data set of 325 patients. In the final set of networks, a consensus of eight networks was made to produce the final statistics. The final run statistics are reported only on the training data and represent an upper bound on the true performance. The results from the last holdout run represent a possible lower bound on the performance.

From the training data each of the 65 variables, including not available for a diagnosis, were built into a training example of 325 training examples. The TrainDos training program was modified to automate the generation of networks to provide relationships between the variables. In each of 65 networks, one of the variables was predicted by remaining 64. A sensitivity analysis was performed for each network to indicate the importance of each variable in making the prediction.

Results

The consensus results for the three comparison runs are as follows:

| | |
|---|---|
| Run 1: All ELISA variables (CRFE: 1) | 66.46% |
| Run 2: Log of ELISA 2 (CRFEL2) | 66.77% |
| Run 3: No ELISA Variables (CRFEL0) | 62.76% |

Comparison of Run 1 and Run 2 show that the addition of ELISA 100 and ELISA 200 data to ELISA 2 data had no effect. Therefore, ELISA 100 and ELISA 200 variables could be eliminated.

Comparisons of Run 2 and 3 showed that an input based on the ELISA test improved the diagnosis of the disease.

Comparison of Run 3 to pat06 showed a 5.47% drop in test performance. This could only be due to the decrease in the number of patients available on training. This also suggest that an increase in training data above 500 is likely to have a significant effect on the performance of the neural network on test data.

Based on these results, final networks were trained. Eight networks were trained on the 325 patients. The performance on the training data was 72.31 %. While this is similar results to the pat07 runs, it is clear that the improvement due to ELISA 2 data are being offset by a decrease in the amount of available training data.

Sensitivity Analysis results showed that the ELISA 2 variable ranked 7 out of the 15 variables used.

Plots of the hidden processing element outputs were made from the log files of the eight trained networks. A means was found so that the desired output could be indicated on the plots. By comparing the eight networks, it is clear that each performed the task in a different way. Some clustering of data points is seen in a few plots. Since this did not occur consistently, no conclusions could be drawn.

Statistics were generated on the last training run based on the use of a cutoff in the network output values. If the network output was below the cutoff, the example was rejected from consideration. The following table is a summary of the results for the consensus of eight networks in CRFLE2.

| Cutoff | 0.00 | 0.02 | 0.05 | 0.075 | 0.10 |
|---|---|---|---|---|---|
| Sensitivity | .7790 | .7911 | .9016 | .9596 | .9595 |
| Specificity | .6549 | .6552 | .7200 | .7755 | .8529 |
| PPV | .7421 | .7576 | .8397 | .8962 | .9342 |

-continued

| | | | | | |
|---|---|---|---|---|---|
| NPV | .6992 | .6972 | .8181 | .9048 | .9063 |
| Odds Ratio | 2.63 | 2.75 | 4.96 | 8.86 | 12.5 |
| % Rejected | 0.62 | 15.69 | 39.38 | 54.46 | 66.76 |

In general, these results are better than the results for pat07.

A test program named adzcrf2.exe (see, Appendix II) was produced as a demo of this final training. This program permits the running of pat07 and CRFEL2 based on the value input in the ELISA field. A value of 0 in the field causes pat07 to be used.

The analysis of variable relationships was performed. Based on the analysis of the relationships, the variables which showed Endo Present as a contributing factor were compared to the variables used in predicting Endo. Results of training two networks (PATVARSA and PATVARS3) showed that in the case of Endo, relationships were not symmetric, as they are when using correlation. CRFVAR-SA.XLS was built from the sensitivity analysis results to summarize the results. These results show the nonlinear nature of the relationships. The importance of a variable is affected by the other variables in the training run. This suggests that a means of eliminating unimportant variables in an automated fashion may be required to increase the usefulness of this analysis.

Analysis of the variables relationship (CRFVAROO - CRFVAR64) showed that in most cases, the log of the ELISA 2 test had greater significance than the raw ELISA 2 value. In particular, the log value ranked higher for both predicting Endo Present and AFS Stage.

Conclusions

The ELISA 2 test adds to the predictive power of the neural network. The ELISA 2 test has eliminated the need for the original ELISA tests. Based on this result it is likely that results of the work with the Western Blot data will further improve the power of the neural network diagnostic test.

The effects of increased training data could be clearly seen in the comparison of Run 3 to pat06. The difference in performance suggests that the performance of the neural network will increase substantially with an increase in training data. It appears from the comparison that doubling the data could improve the performance by 10-15%. With 8-10 times the data the performance might increase to 75-80%.

EXAMPLE 7
Patient History Stage/AFS Score Training Requirements

Using methods developed in the above Examples, identify relevant variables for either the stage of the disease or the AFS Score. The selection of the target output variable to be used will be determined by a comparison of test set performance from a training run using the phase 1 list of important patient history variables. Once the list of important variables are selected, a consensus of 8 neural networks will be trained on the 510 patient database.

Methodology Used

Training examples were built for the Stage desired output and the AFS score desired output. There were 7 patients missing Stage information and 28 patients missing Score information. For the stage variable, the average value of 2.09 was used where the data was missing. For score, the missing data was replaced with a value depending on the value of the stage variable. For stage 1, a score of 3 was used. From stage 2, 10.5 was used. For stage 3, 28 was used and for stage 4 the value 55 was used.

Stage and score were reprocessed so that the desired output would fall in the range of 0.0 to 1.0. Stage was translated linearly. Two methods were used for score. The first was the square root of the score divided by 12.5. The second was the log of score+1 divided by the log of 150.

The holdout method was used to train networks on stage, square root score and log of score. These networks were trained using 45 variables. The results were compared to determine which variable and processing would be used for the remainder of the Example. The log of score was chosen.

At this point the procedure for isolating the set of important variables was begun. Eight networks were trained on the full training example and the consensus sensitivity analysis was generated to produce the first ranking of the variables. Then the Chi Square contingency table was generated to produce the second ranking of the variables. The procedure for isolating important variables was started manually, but was found to be too time consuming. The procedure was implemented as a computer program and was run on a computer for about one week before completing.

From the results of the variable selection, a set of eight networks were trained on the full training example. The consensus results were analyzed and compared to the Endo present results.

Results

The sensitivity analysis of all 45 variables gave the following ranking of variables:

| Name | Input # |
|---|---|
| Past history of Endo | 33 |
| Hist of Pelvic Surgery | 34 |
| Dysmenorrhea | 40 |
| #Birth | 11 |
| age(preproc) | 1 |
| Medication History | 35 |
| #Preg | 10 |
| Ectopic Pregnancy | 26 |
| Pelvic Pain | 37 |
| Adnnexal msses/Thickening | 43 |
| #Abort | 12 |
| Current Exod. Hormones | 36 |
| Hormone induced | 18 |
| Other history | 32 |
| Infertility | 42 |
| Packs/Day | 8 |
| Uterine/Tubal Anomalies | 24 |
| Dyspaarunia | 41 |
| Anovulatory | 15 |
| Hist of Infert | 13 |
| Unknown | 16 |
| Menstrual Abnormalities | 39 |
| Gyn Cancer | 31 |
| Abnormal PAP/Dysplasia | 30 |
| Other Symptoms | 45 |
| Herpes | 19 |
| Ovulatory | 14 |
| Genital Warts | 20 |
| Fibroids | 25 |
| Ovarian Cysts | 28 |
| Drug Use | 9 |
| Dysfunctional Uterine Bld. | 27 |
| PID | 23 |
| Hypertension | 4 |
| Vag Infections | 22 |
| Undetermined | 44 |
| Other STD | 21 |
| Preg HTM | 5 |
| Autoimmune Disease | 6 |
| Abdominal Pain | 38 |
| Preg Induced DM | 3 |
| Oligoovulatory | 17 |
| Diabetes | 2 |

-continued

| Name | Input # |
| --- | --- |
| Polycystic Ovarian Snyd | 29 |
| Transplant | 7 |

The Chi Square analysis gave the following ranking of variables:

| Name | Input # |
| --- | --- |
| Past history of Endo | 33 |
| #Preg | 10 |
| #Birth | 11 |
| Packs/Day | 8 |
| Dysmenorrhea | 40 |
| Pelvic Pain | 37 |
| Preg HTM | 5 |
| Hist of Infert | 13 |
| Abnormal PAP/Dysplasia | 30 |
| Infertility | 42 |
| Diabetes | 2 |
| Herpes | 19 |
| Hist Of Pelvic Surgery | 34 |
| #Abort | 12 |
| Other Symptoms | 45 |
| Medication History | 35 |
| Undetermined | 44 |
| Dysfunctional Uterine Bld. | 27 |
| Gyn Cancer | 31 |
| Uterine/Tubal Anomalies | 24 |
| Polycystic Ovarian Synd | 29 |
| Dyspaarunia | 41 |
| Genital Warts | 20 |
| Adnnexal masses/Thickening | 43 |
| Oligoovulatory | 17 |
| Autoimmune Disease | 6 |
| Abdominal Pain | 38 |
| Unknown | 16 |
| Ectopic Pregnancy | 26 |
| Ovulatory | 14 |
| Fibroids | 25 |
| Current Exod Hormones | 36 |
| Ovarian Cyst | 28 |
| Drug Use | 9 |
| Vag Infections | 22 |
| Preg Induced DM | 3 |
| PID | 23 |
| age(preproc) | 1 |
| Hormone induced | 18 |
| Anovulatory | 15 |
| Menstrual Abnormalities | 39 |
| Hypertension | 4 |
| Other STD | 21 |
| Transplant | 7 |
| Other history | 32 |

The variables chosen in the variable selection procedure were as follows, showing the ranking from the final sensitivity analysis:

| Name | Input # |
| --- | --- |
| Past history of Endo | 33 |
| #Preg | 10 |
| Hist of Pelvic Surgery | 34 |
| age(proproc) | 1 |
| Dysmenorrhea | 40 |
| Ectopic Preg. | 26 |
| Oligoovulatory | 17 |

The comparison of the score network to the Endo present network can be performed by forcing a threshold on the desired score output to produce an Endo present comparison. The results for the score and the pat07 networks are shown below.

| NETWORK | PAT07 | SCR07 |
| --- | --- | --- |
| Sensitivity | .828179 | .679525 |
| Specificity | .598174 | .647399 |
| PPV | .732523 | .789655 |
| NPV | .723757 | .509091 |
| Odds Ratio | 2.695 | 2.017751 |

Conclusions

The set of variables identified in this Example appear to be reasonable.

The automated variable selection methodology appears to function properly. The choice of variables is well predicted by the sensitivity analysis.

Now that there are two methods for predicting the disease, the Endo present network and the Score network could be combined to improve the reliability of the prediction.

EXAMPLE 8

Patient History Adhesions Training Requirements

Using methods as outlined in EXAMPLE 7, identify relevant variables for Adhesions target output variable. This target output variable will be run using the phase 1 list of important patient history variables. This will also permit a comparison of the new outputs to the Endo present target variable used in phase 1. Once the list of important variables are selected, a consensus of 8 neural networks will be trained on the 510 patient database.

Methodology Used

Training data for the adhesions variable was generated in the same manner as for EXAMPLE 7. The adhesions variable generated two output variables in a manner similar to that used for Endo present. At this point the procedure for isolating the set of important variables was begun. Eight networks were trained on the full training example and the consensus sensitivity analysis was generated to produce the first ranking of the variables. Then the Chi Square contingency table was generated to produce the second ranking of the variables. The procedure for isolating important variables was started manually, but was found to be too time consuming. The procedure was implemented as a computer program and was run on a computer for about one week before completing.

From the results of the variable selection, a set of eight networks were trained on the full training example. The consensus results were analyzed and compared to the Endo present results.

Results

The sensitivity analysis of all 45 variables gave the following ranking of variables:

| Name | Input # |
| --- | --- |
| Hist of Infert | 13 |
| Medication History | 35 |
| Ectopic Pregnancy | 26 |
| Packs/Day | 8 |
| Hist of Pelvic Surgery | 34 |
| Infertility | 42 |
| #Birth | 11 |
| Dyspaarunia | 41 |

-continued

| Name | Input # |
|---|---|
| Hormone Induced | 18 |
| Past history of Endo | 33 |
| Herpes | 19 |
| #Preg | 10 |
| Current Exod. Hormones | 36 |
| age(preproc) | 1 |
| Dysmenorrhea | 40 |
| Uterine/Tubal Anomalies | 24 |
| Anovulatory | 15 |
| Other history | 32 |
| Ovarian Cyst | 28 |
| Pelvic Pain | 37 |
| Gyn Cancer | 31 |
| Ovulatory | 14 |
| Menstrual Abnormalities | 39 |
| #Abort | 12 |
| Unknown | 16 |
| Abnormal PAP/Dysplasia | 30 |
| Abdominal Pain | 38 |
| Adnnexal masses/Thickening | 43 |
| Fibroids | 25 |
| Pelivic inflammatory disease (PID) | 23 |
| Dysfunctional Uterine Bld | 27 |
| Vag Infections | 22 |
| Drug Use | 9 |
| Other Symptoms | 45 |
| Genital Warts | 20 |
| Autoimmune Disease | 6 |
| Hypertension | 4 |
| Other STD | 21 |
| Preg Induced DM | 3 |
| Preg HTM | 5 |
| Polycystic Ovarian Synd | 29 |
| Oligoovulatory | 17 |
| Diabetes | 2 |
| Undetermined | 44 |
| Transplant | 7 |

The Chi Square analysis gave the following ranking of variables:

| Name | Input # |
|---|---|
| Hist of Infert | 13 |
| Infertility | 42 |
| Medication History | 35 |
| Herpes | 19 |
| Ovulatory | 14 |
| Dysmenorrhea | 40 |
| Dyspaarunia | 41 |
| Packs/Day | 8 |
| Ectopic Preg. | 26 |
| Current Exod. Hormones | 36 |
| Menstrual Abnormalities | 39 |
| Anovulatory | 15 |
| Past history of Endo | 33 |
| Fibroids | 25 |
| Hormone induced | 18 |
| #Preg | 10 |
| Gyn Cancer | 31 |
| Hist of Pelvic Surgery | 34 |
| PID | 23 |
| Uterine/Tubal Anomalies | 24 |
| #Abort | 12 |
| #Birth | 11 |
| Other STD | 21 |
| Abdominal Pain | 38 |
| Unknown | 16 |
| Vag Infections | 22 |
| Abnormal PAP/Dysplasia | 30 |
| Dysfunctional Uterine Bld | 27 |
| Oligoovulatory | 17 |

-continued

| Name | Input # |
|---|---|
| Polycystic Ovarian Synd | 29 |
| Autoimmune Disease | 6 |
| Genital Warts | 20 |
| Other Symptoms | 45 |
| Ovarian Cyst | 28 |
| Other history | 32 |
| Pelvic Pain | 37 |
| age(preproc) | 1 |
| Preg Induced DM | 3 |
| Preg HTM | 5 |
| Adnnexal masses/Thickening | 43 |
| Undetermined | 44 |
| Diabetes | 2 |
| Drug Use | 9 |
| Hypertension | 4 |
| Transplant | 7 |

The variables chosen in the variable selection procedure were as follows, showing the ranking from the final sensitivity analysis:

| Name | Input # |
|---|---|
| Hist of Infert | 13 |
| Dyspaarunia | 41 |
| Ectopic Preg | 26 |
| Packs/Day | 8 |
| Hist of Pelvic Surgery | 34 |
| Medication History | 35 |
| Ovulatory | 14 |
| Menstrual Abnormalities | 39 |
| Oligoovulatory | 17 |

The comparison of the Score network to the Endo present network can be performed by forcing a threshold on the desired score output to produce an Endo present comparison. The results for the score and the pat07 networks are shown below.

| NETWORK | PAT07 | ADH07 |
|---|---|---|
| Sensitivity | .828179 | .825083 |
| Specificity | .598174 | .473430 |
| PPV | .732523 | .696379 |
| NPV | .723757 | .649007 |
| Odds Ratio | 2.695 | 2.148148 |

Conclusions

The set of variables identified in this Example appear to be reasonable. The automated variable selection methodology appears to function properly. The choice of variables is well predicted by the sensitivity analysis.

EXAMPLE 9

This example shows the reproducibility of the process provided herein.

Methodology Used

Software used for the selection of important variables for Adhesions and Score was modified to operate with the Endo present desired output. The software was further modified to allow it to be run in the general case instead of needing to be recompiled for each specific test.

The run was made on the Endo Present variable in the same fashion as the runs for Adhesion and score. This included using a consensus of 4 networks during the variable selection process. The training data was partitioned into five partitions during the training process, generating a total of 20 networks for each evaluation of the current set of variables being tested.

The results of runs with different random number seeds indicated that the number of networks in the consensus might need to be increased.

Two additional variable selection runs were made with a consensus of 10 networks used during the process. In this case, a total of 50 networks were trained to evaluate a single combination of variables. Two separate runs were made in this fashion with only the random starting seed changing.

From these final two variable selection runs, a set of eight networks were trained for each of the sets of variables (pat08, pat09), to allow their performance to be evaluated on new data (not included in the original 510 record database). Statistics on the performance of these networks were generated so that they could be compared to the original pat07 consensus nets.

Results

In each case where different random number seeds were used, the variable selection process found a different set of important variables. When the number of networks in the consensus was increased to 10, the variables common in the different runs increased.

Many of the original 14 variables used for pat07 were confirmed as being important in the variable selection runs using 10 consensus nets. The final runs made on the selected variables were named pat08 and pat09.

The variables used in pat08 and pat09 consensus networks are shown below along with their sensitivity analysis rankings:

| INPUT | PAT08 Variable Name | Average |
|---|---|---|
| 10: | Past HX of Endo | 1.525819 |
| 05: | #Birth | 1.489470 |
| 14: | Dysmenorrhea | 1.302913 |
| 12: | Medication History | 1.263276 |
| 11: | Hist of Pelvic Surgery | 1.235421 |
| 13: | Pelvic Pain | 1.192193 |
| 01: | Age(preproc) | 1.178076 |
| 04: | Packs/Day | 1.063709 |
| 06: | Hist of Infert | 0.943830 |
| 07: | Hormone Induced | 0.925489 |
| 16: | Other Symptoms | 0.879384 |
| 15: | Infertility | 0.873955 |
| 09: | Abnormal PAP/Dysplasia | 0.7061778 |
| 03: | Preg HTN | 0.576799 |
| 08: | Herpes | 0.441410 |
| 02: | Diabetes | 0.402080 |
| 06: | Past HX of Endo | 1.420401 |
| 04: | #Birth | 1.353489 |
| 01: | age(preproc) | 1.187359 |
| 09: | Pelvic Pain | 1.183929 |
| 10: | Dysmenorrhea | 1.141531 |
| 07: | Hist of Pelvic Surgery | 1.064250 |
| 03: | Packs/Day | 1.042488 |
| 11: | Other Symptoms | 0.780530 |
| 05: | Herpes | 0.699654 |
| 08: | Medication History | 0.623505 |
| 02: | Preg HTN | 0.502863 |

Conclusions

The variable selection process appears works well and has produced two alternative networks that work as well or better than the pat07 nets. The reason for this conclusion is that the performance statistics generated only on the training data appear slightly better for the pat07 then pat08 and pat09. Since the variable selection process carefully picks variables based on test set performance, the associated networks are not likely to have been overtrained. As a network becomes overtrained the typical characteristic is that the training example performance increases and the test set performance decreases. Thus the higher performance of pat07 may be the result of slight overtraining.

While the variable selection process appears to have produced two alternative selections on the same training data, the performance of the two selections appears to be very similar. This is based on the test set performance of the final variable selections for the two runs. It has become clear that when two variables are closer in their relative performance, then random factors can influence their relative ranking. The random factors in the variable selection runs included the random starting points and the use of added noise on the inputs during training. The random noise has been shown to aid in producing better generalization (translation: test set performance). As the number of networks in the consensus increases, the effects of the random influences are decreased.

The determination of a set of variables that produces a high quality network seems to be addressed by the variable selection process. As more combinations of variables that work successfully are enumerated, it is evident that certain variables or combinations of variables are essential to good performance.

EXAMPLE 10

Evaluation of the Elimination of Past History of Endometriosis and History of Pelvic Surgery on Diagnostic Performance.

The purpose of this Example was to determine the importance of 'Past history of endometriosis' and 'Past history of pelvic surgery' variables in evaluating a patient's risk of having endometriosis, and to provide an alternative means (different from sensitivity analysis) to measure the importance of any given variable in predicting the outcome.

Tasks:

1. Apply the variable selection process excluding the 'Past history of endometriosis.

2. Repeat task (1) using different random seed variables for the variable selection process.

3. For both sets of 'endometriosis relevant variables' identified in tasks (1) and (2) above, complete the consensus network training process.

4. Repeat the above tasks (1), (2) and (3) excluding the 'Past history of Pelvic surgery' variable from the Endometriosis database.

5. Repeat the above tasks (1), (2), and (3) excluding both the 'Past history of endometriosis' and the 'Past history of endometriosis' variables from the Endometriosis database.

Methodology Used

The variable selection software developed in Example 9 was used as the basis to generate results for each of Example 10. The software was modified so that the user could identify variables that would be excluded from consideration based on the requirements of Example 10. This software was also modified to allow the reporting of classification performance for each of the sets of variables tested so that the effect of an eliminated variable could be more easily understood.

For each variable selection run that was made, parameters for the variable selection process were set as follows:

| Number of partitions: | 5 |
| Consensus networks: | 10 |
| Training example size: | 510 |
| Number of passes: | 999 |

The ordering of database variables in the variable selection process was based on the sensitivity analysis and Chi square analysis. This ordering was the same as used in pat08 and pat09.

The networks trained for this Example are identified as follows (the two nets have different random seeds);

| Past Hist. of Endo eliminated: | pat10, pat11. |
| Hist. of Pelvic Surgery eliminated: | pat12, pat13. |
| Both variables eliminated: | pat14, pat15. |

Once the variable selection process was completed for each of the combinations of variables and random seeds, a set of eight networks were trained using the selected variables identified. Each of these networks was trained on the complete 510 record database. From these training runs, a consensus of the outputs was generated in an Excel spreadsheet so that the performance of each of the networks could be evaluated.

Results

The typical performance of a consensus of networks was estimated using the holdout method with a partition of 5. When all variables were available, as in pat08 and pat09, the classification performance was estimated to be 65.23%.

When the past history of endometriosis variable was eliminated from consideration (pat10 and pat11), the performance was estimated at 62.47%. This represents a drop of 2.76%.

When the history of pelvic surgery variable was eliminated from consideration (pat12 and pat13), the performance was estimated at 64.52%. This represents a drop of only 0.72%.

When both variables were eliminated from consideration (pat14 and pat15), the performance was estimated to be 62.43%. This represents a drop of 2.80%. This is only slightly worse than just eliminating past history of endometriosis and appears to be consistent with other results based on the assumption that the variables are independent (are not correlated).

Conclusions

While history of pelvic surgery was used by the neural networks when it was available, the effect of eliminating this variable was minimal. The neural networks appear to be able to compensate for the elimination of this variable by using other information.

The removal of Past history of Endometriosis was significant. This variable was always at the top of the list in any sensitivity analysis. Its elimination caused about a 2.76% drop in performance over the average when all variables were available for use. Given that the average performance is estimated at 65.23%, and 50% can be achieved by chance, this represents an effective drop in performance of 18.12%.

When both variables were eliminated, there does not appear to be any significant drop in performance, which indicates there was no interaction between these two variables. This process of eliminating a variable and running the variable selection process appears to be a good approach to determining the true value of a given variable. It should be noted that there are two variables that are important to the diagnosis, but are highly correlated, the elimination of only one would have little effect since the network would compensate by using the other. It is only when both were eliminated that their value becomes clear.

EXAMPLE 11

Evaluation of the Elimination of Pelvic Pain and dysmenorrhea on Diagnostic Performance Requirements Goals:
1. To determine the importance of 'Pelvic Pain' and "Dysmenorrhea' variables in evaluating a patient's risk of having endometriosis.
2. To provide a separate mechanism (different from sensitivity analysis) to measure the importance of any given variable in predicting the outcome.

Tasks:
1. Apply the variable selection process described herein.
2. Repeat task (1) using different random seed variables for the variable selection process.
3. For both sets of 'endometriosis relevant variables' identified in tasks (1) and (2) above, and complete the consensus network training process.
4. Repeat the above tasks (1), (2) and (3) excluding the 'Dysmenorrhea' variable from the Endometriosis database.
5. Repeat the above tasks (1), (2), and (3) excluding both the 'Pelvic Pain' and the 'Dysmenorrhea' variables from the Endometriosis database.

Methodology Used

The variable selection software developed in Example 9 was used as the basis to generate results for each of these tasks. For each variable selection run that was made, parameters for the variable selection process were sat as follows;

| Number of partitions: | 5 |
| Consensus networks: | 10 |
| Training example size: | 510 |
| Number of passes: | 999 |

The ordering of database variables in the variable selection process was based on the sensitivity analysis and Chi square analysis. This ordering was the same as used in pat08 and pat09. The networks trained for this task are identified as follows (the two nets have different random seeds);

| Pelvic Pain eliminated: | pat16, pat17, pat17A |
| Dysmenorrhea eliminated: | pat18, pat19. |
| Both variables eliminated: | pat20, pat21. |
| Four variables (EXs. 11 and 12): | pat22, pat23, and pat23A |

Once the variable selection process was completed for each of the combinations of variables and random seeds, a set of eight networks were trained using the selected variables identified. Each of these networks was trained on the complete 510 record database. From these training runs, a consensus of the outputs was generated in an Excel spreadsheet so that the performance of each of the networks could be evaluated.

Results

The typical performance of a consensus of networks was estimated using the holdout method with a partition of 5.

When all variables were available, as in pat08 and pat09, the Classification performance was estimated to be 65.23%.

When the pelvic pain variable was eliminated from consideration (pat16 and pat17), the performance was estimated at 61.03%. This represents a drop of 4.20%.

When the dysmenorrhea variable was eliminated from consideration (pat18 and pat19), the performance was estimated at 63.44%. This represents a drop of only 1.79%.

When both variables were eliminated from consideration (pat20 and pat21), the performance was estimated to be 61.22%. This represents a drop of 4.00%. This is better than when pelvic pain was eliminated only. This suggests that the performance drop for pelvic pain is overstated. The best performing network that did not include pelvic pain had a performance of 62.29%, which gives a drop of 2.94%. This would be more reasonable an estimate given the performance when both were eliminated.

Conclusions

With the four variables tested, the ranking of the variables in order of importance is as follows:

| | |
|---|---|
| Pelvic pain | 2.94%–4.20% drop |
| Past hist. of endo | 2.76% drop |
| Dysmenorrhea | 1.79% drop |
| Hist. of pelvic surg | 0.72% drop |

This process of eliminating a variable and running the variable selection process is a good approach to determining the value of a given variable. It should be noted that if there were two variables that were important to the diagnosis, but were highly correlated, the elimination of only one would have little effect since the network would compensate by using the other. It is only when both were eliminated that their true value would become clear.

EXAMPLE 12

Training of Neural Network to Differentiate Mild Versus Severe Endometriosis

Goals:
1. To train a consensus of networks which differentiates between minimal/mild versus moderate/severe endometriosis.

Task:
1. Train networks to AFS score as follows:
   positive=Endo Stage III or IV
   negative=No Endo, Endo Stage I or II
2. Apply the variable selection process described in Method for Developing Medical and Biochemical Tests Using Neural Networks of the Endometriosis database.
3. Repeat task (2) using different random seed variables for the variable selection process.
4. Compare variables selected in (2) and (3) above before proceeding. If selected set of variables differ widely, repeat task (2) using different random seed weights.
5. Train final consensus networks for variables selected in (2) and (3) above.
6. Repeat steps (2) through (5) using only the subset of the endometriosis database for which Endo was present in the patient.

Methodology Used

The variable selection software developed in EXAMPLE 10 and modified in EXAMPLE 11, was used as the basis to generate results for each of the tasks in this example.

For each variable selection run that was made, parameters for the variable selection process were set as follows;

| | |
|---|---|
| Number of partitions: | 5 |
| Consensus networks: | 20 |
| Training example size: | 510 (290 for step (6)) |
| Number of passes: | 999 |

The ordering of database variables in the variable selection process was based on the sensitivity analysis an chi square analysis run specifically for the new target output described in Example 1. The networks trained for this Example are identified as follows (the two nets have different random seeds);

Nets trained on full database: AFS01 and AFS02

Nets trained on Endo present subset: AFSEP1 and AFSEP2.

Once the variable selection process was completed for each of the combinations of variables and random seeds, a set of eight networks were trained using the selected variables identified. Each of these networks for AFS01 and AFS02 variables were trained on the complete 510 record database. Each of the networks for AFSEP1 and AFSEP2 variables were trained on the 291 records for which the endo present variable was positive. From these training runs, a consensus of the outputs was generated in an Excel spreadsheet so that the performance of each of the networks could be evaluated.

Results

The count of variables found in the reduced subset run was smaller that for the runs on the full training example. The typical performance of a consensus of networks was estimated using the holdout method with a partition of 5. The typical classification performance for the AFS run using the full training example was 77.22549%. The typical classification performance on the endo present subset was 63.008621 %. If all examples were classified as negative, the performance for the full training example would be 78.82% and 65.29% for the subset. By changing the cutoff values for positive and negative classification better performance than suggested by these numbers can be achieved.

Conclusions

The results of the variable selection runs for the full training example and the subset of endo present examples suggests that the size of the training example is of importance in the determination of the important variables. It is clear that as the size of the training example increases, more variables will be considered important. This result can also be interpreted as an indication that more training data will improve the variable selection process and also the overall performance of the consensus networks used in building the diagnostic test.

EXAMPLE 13

Variable Selection and development of neural nets for predicting pregnancy related events and improvement of the performance of tests for fetal fibronectin The Fetal Fibronectin Enzyme Immunoassay (fFN ELISA) detects the presence or absence of fetal fibronectin (fFN) in cervicovaginal secretions (see, U.S. Pat. No. 5,468, 619). Detection of fFN in cervicovaginal secretions of symptomatic pregnant women between 24 and 34 completed weeks gestation is associated with preterm delivery. This test is used to predict impending delivery within 7 or 14 days of sampling. For prediction of delivery within 14 days for sampling of fFN, the negative result is greater than 99% accurate. The positive result is more difficult to interpret, and the positive predictive value is less than 20%.

Neural networks were trained to assess the risk of preterm delivery using over 700 examples of pregnant women who were symptomatic for preterm delivery. Each example contained a multitude of information about that patient, including symptoms, reproductive history and other factors. Neural networks were trained to recognize complex patterns of interactions between these factors that indicate when a woman is at risk for preterm delivery. These neural networks are contained in the Preterm Delivery Risk Assessment software, which augments the fFN ELISA test result by decreasing false positive observations.

A. Variables

The following are variables based on patient input data. Neural networks using all or selected subsets of these variables may be generated. Combinations of at least three of these variables may be used in conjunction with decision-support systems, particularly neural nets to predict risk of preterm delivery or impending delivery. The inputs for the variables are either yes, no, no answer, or a text input, such as age. The variables, listed by type are as follows:

1 Age

Ethnic origin variables:

2 EthOrg1: Caucasian;
3 EthOrg2: Black;
4 EthOrg3: Asian;
5 EthOrg4: Hispanic;
6 EthOrg5: Native American; and
7 EthOrg6: Other than the above.

Marital status variables:

8 MarSt1: Single;
9 MarSt2: Married;
10 MarSt3: Divorced/Separated;
11 MarSt4: Widowed;
12 MarSt5: Living with partner; or
13 MarSt6: Other than those listed above.

Education variables:

14 Edu0: Unknown;
15 Edu1: <High School;
16 Edu2: High School Graduate; or
17 Edu3: College/trade.

Patient complaint variables:

18 PATIENT COMPLAINT#1 Patient has Uterine Contractions with or without pain;
19 PATIENT COMPLAINT#2 Patient has intermittent lower abdominal pain, dull, low backache, pelvic pressure;
20 PATIENT COMPLAINT#3 Patient has bleeding during the second or third trimester;
21 PATIENT COMPLAINT#4 Patient has menstrual-like or Intestinal cramping;
22 PATIENT COMPLAINT#5 Patient has change in vaginal discharge or amount, color, or consistency; or
23 PATIENT COMPLAINT#6 Patient is not "feeling right".

Variables from physician tests and assessments:

24 Pooling refers to visual assessment to determine whether amniotic fluid has leaked into the vagina (see, e.g., Chapter 36, Section 18, p. 657 in *Maternal Fetal Medicine: Principle and Practice,* 2nd Edition, Creasy, R. F. et al., eds., W. B. Saunders & Co. (1989));
25 Ferning refers to the results of a test to detect the pattern formed when amniotic fluid is present in a cervical sample smeared on a clean slide and allowed to air dry (see, e.g., Chapter 36, Section 18, p. 657 in *Maternal Fetal Medicine: Principle and Practice,* 2nd Edition, Creasy, R. F. et al., eds., W. B. Saunders & Co. (1989));
26 Nitrazine refers to results from a known test used to measure the pH of amniotic fluid that has leaked into the vagina (see, e.g., Chapter 36, Section 18, p. 657 in *Maternal Fetal Medicine: Principle and Practice,* 2nd Edition, Creasy, R. F. et al., eds., W. B. Saunders & Co. (1989));
27 estimated gestational based (EGA) on last period (LMP);
28 EGA by sonogram (SONO);
29 EGA by Best-EGA is the best of the EGA by SONO and EGA by LMP determined as follows:
   if EGA by SONO is<13 weeks, then EGA best is EGA SONO;
   if the difference by EGA by LMP and EGA by SONO is>2 weeks, then EGA best is EGA by SONO;
   otherwise EGA best is EGA by LMP;
30 EGA at Sampling refers to the EGA when fFN sampled;
31 CD INTERP, which refers to cervical dilatation (interpreted values—i.e. based on physicians estimates) where the number will be between 0 and 10 cm and is determined from the physicians response;
32 Gravity, which refers to the number of time woman has been pregnant;
33 Parity-term, which refers to the number of term births;
34 Parity-preterm, which refers to the number of preterm births;
35 Parity-abortions, which refers to the number of pregnancies ending in spontaneous or elective abortions;
36 Parity-living, which refers to the number of living children;
37 Sex within 24 hrs prior to sampling for fFN;
38 Vaginal bleeding at time of sampling;
39 Cervical consistency at time of sampling; and
40 UC INTERP, which refers to uterine contractions per hour as interpreted by the physician.

Complications 41 0 COMP No previous pregnancies;
42 1 COMP have had at least one previous pregnancy without complications;
43 2nd comp at least one preterm delivery (delivery prior to 35 weeks);
44 3rd comp at least one previous pregnancy with a premature rupture of membrane (PROM);
45 4th comp at least one previous delivery with incompetent cervix;
46 5 COMP at least on previous pregnancy with pregnancy induced hypertension (PIH)/preeclampsia;
47 6 COMP at least one previous pregnancy with spontaneous abortion prior to 20 weeks;
48 OTHER COMP at least one previous pregnancy with a complication not listed above; and
49 RESULT—fFN ELISA qualitative test result (if positive value is 1, if negative value is 0).

The variable selection protocol has been applied to these variables for selected outcomes, and the results are set forth below. Exemplary neural nets are provided.

B. A first set of neural networks demonstrating that the methods herein can be used to predict pregnancy related events EGA1-EGA4

For these nets the preterm delivery defined as less than or equal to 34 weeks, 0 days. The other nets herein (described below) define preterm delivery as less than or equal 34 weeks, 6 days.

Data was collected from the over 700 test patients involved in a clinical trial of the assay described in U.S. Pat. No. 5,468,61 9. Variable selection was performed without fetal fibronectin (fFN) test data. The final networks, designate EGA1-EGA4 were trained with the variables set forth in the table below.

EGA1- EGA4 represent neural networks used for variable selection. For EGA1, the variable selection protocol was performed a network architecture with 8 inputs in the input layer, three processing elements in the hidden layer, and one output in the output layer. EGA2 is the same as EGA1, except that it is 9 inputs in the input layer.

EGA3 has 7 inputs in the input layer, three processing elements in the hidden layer, and one output in the output layer. EGA4 is the same as EGA1, except that it is 8 inputs in the input layer. The variables selected are as follows:

| EGA1 | EGA2 | EGA3 | EGA4 |
|---|---|---|---|
| — | fFN | — | fFN |
| Ethnic Origin 1 (Caucasian) | | Ethnic Origin 4 (Hispanic) | |
| EGA Sonogram | | Marital Status 5 (living with partner) | |
| EGA Best (physician's determination of estimated gestational age) | | Marital Status 6 (other) | |
| EGA Sampling | | EGA Best | |
| Cervical dilation interpretation | | Cervical dilation interpretation | |
| Vaginal bleeding (at time of sampling) | | Vaginal bleeding (at time of sampling) | |
| 1 complications (prev. preg w/o complications) | | Other complications (prev. preg. w complications) | |
| Other complications (prev. preg. w complications) | | | |

EGA = estimated gestational age

Final consensus network performance

| Net | TP | TN | FP | FN | SN | SP | PPV | NVP | OR |
|---|---|---|---|---|---|---|---|---|---|
| EGA1 | 35 | 619 | 92 | 17 | 67.3 | 87.0 | 27.6 | 97.3 | 6.0 |
| EGA2 | 37 | 640 | 71 | 15 | 71.2 | 90.0 | 34.3 | 97.7 | 7.9 |
| EGA3 | 36 | 602 | 109 | 16 | 69.2 | 84.7 | 24.8 | 97.4 | 5.1 |
| EGA4 | 32 | 654 | 57 | 20 | 61.5 | 92.0 | 36.0 | 87.0 | 8.9 |
| fFN | 31 | 592 | 119 | 21 | 59.6 | 83.3 | 20.7 | 96.6 | 7.3 |

EGA = estimated gestational age (less than 34 weeks); TP = true positives; TN = true negatives; FP = false positives; FN = false negative; SN = sensitivity; SP = specificity;, PPV = positive predictive value; NPV = negative predictive value; OR = odds ratio (total number correct/total number correct answers); and fFN = the results from the ELISA assay for fFN.

The results show that the network EGA4, the neural net that includes seven patient variables and includes the fFN ELISA assay and that predicts delivery at less than 34 weeks, has far fewer false positives than the fFN ELISA assay. In addition, the number of false positives was reduced by 50%. Thus, incorporation of the fFN test into a neural net improved the performance of the fFN ELISA assay. All of the neural nets performed better than the fFN test alone.

Thus, the methods herein, can be used to develop neural nets, as well as other decision-support systems, that can be used to predict pregnancy related events.

C. Neural network prediction of delivery before 35 completed weeks of gestation—EGA5 and EGA6

The fFN-NET database was used for all the experiments; organization of variables and order of variables was the same as described herein. Two variable selection runs were performed on the training data to determine the important variables to be used for the consensus runs. In each of the runs the hidden layer contained 5 processing elements. This choice was based on the use of the variable selection process to determine the best size of the hidden layer. Variable selection was run with different numbers of hidden units in the neural network. The performance of the final selection of variables was compared for each different hidden layer configuration. Five hidden units were found to give the best performance. Each run used a partition of 5 and a consensus of 10 networks. The top 10 variables were examined during the run before a variable was selected to be in the selection. During these runs the biochemical test variable, fFN result, was not included
in the possible variables for variable selection.

The resulting choices of variables were then re-evaluated using a consensus
of 20 networks so that the two separate runs could be compared on an equal
basis. Then the fFN result variable was added to the selected variables and
the selections were re-evaluated using a consensus of 20 networks. This allowed the effect of the biochemical test on the performance to be determined. The final consensus training runs, using 8 networks, were made using all available data for training and the best performing set of variables from the above evaluations with the fFN result variable included.

1. Variable selection

Using the same database described above for EGA1-EGA4, the variable selection protocol was applied as described above, except that the variable selection procedure was applied in the absence of the fFN test result. Since it is known that the results of this test are highly predictive of preterm or impending delivery, it was excluded from the variable selection procedure in order to eliminate its overriding influence, and to thereby select the important variables from among the other 48 variables.

Application of the variable selection procedure to the 48 variables resulted in selection of the following variables:
1. Ethnic Origin 1: Caucasian (i.e., yes or no);
2. Marital Status 5: living with partner (yes or no);
3. EGA by sonogram
4. EGA at sampling
5. estimated date of delivery by best
6. cervical dilatation (CM)
7. Parity-preterm
8. vaginal bleeding at time of sampling
9. cervical consistency at time of sampling; and
10. previous pregnancy without complication.

2. Neural nets

Using these variables two consensus networks were trained. One, designated EGA5, was trained without including the results of the fFN ELISA test result, and the other, designated EGA6, was trained with the results of the fFN ELISA test result.

Figure 17:
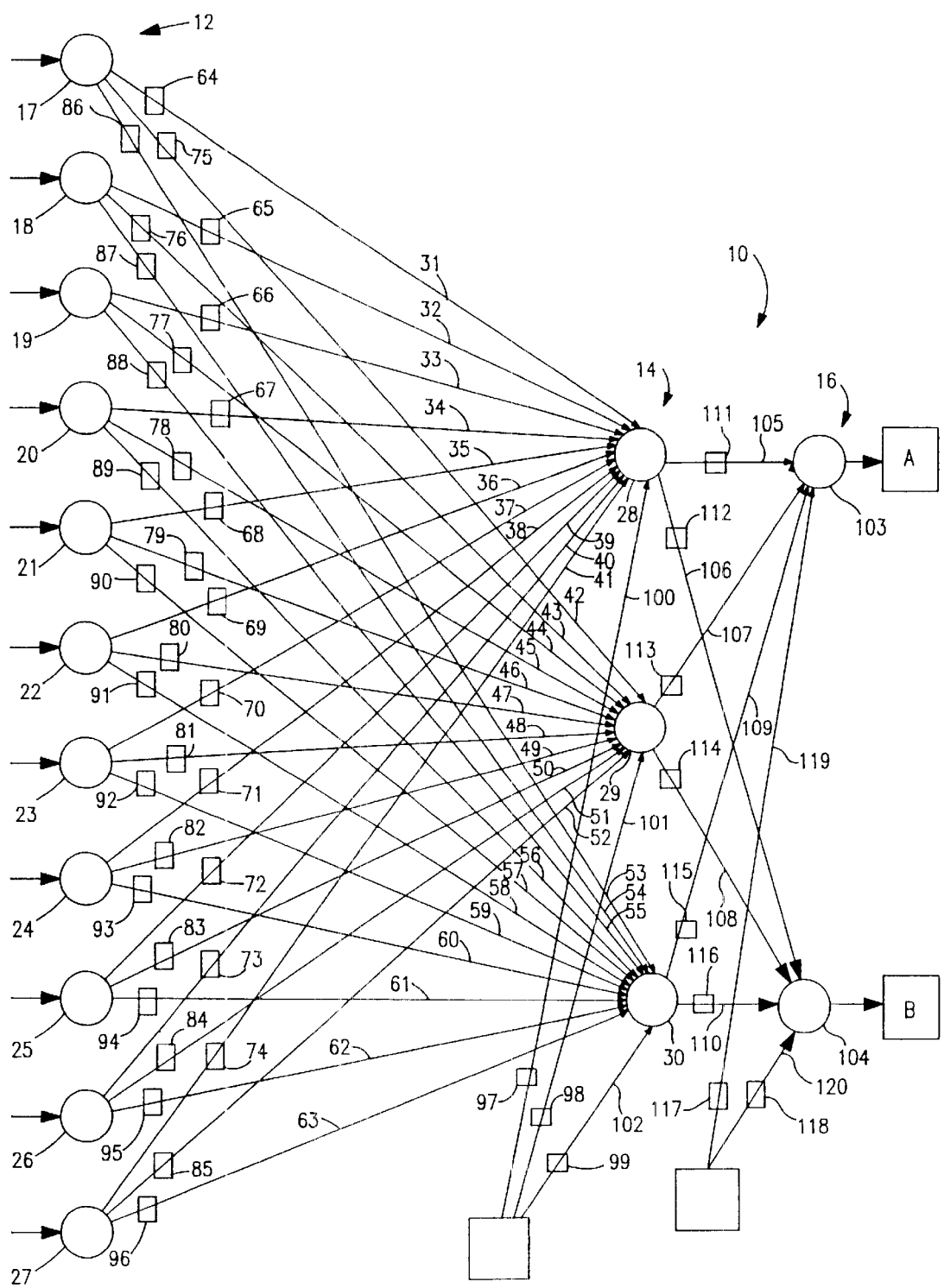
FIG. 17 is a schematic diagram of a neural network (EGA6) trained on clinical data of the form used for the consensus network of a plurality of neural networks.

FIG. 17, which represents EGA6, is a schematic diagram of an embodiment of one type of neural network 10 trained on clinical data of the form used for the consensus network (FIG. 10) of a plurality of neural networks. The structure is stored in digital form, along with weight values and data to be processed in a digital computer. This neural network 10 contains three layers, an input layer 12, a hidden layer 14 and an output layer 16. The input layer 12 has eleven input preprocessors 17–27, each of which is provided with a normalizer (not shown in the figure, see table below), which generates a mean and standard deviation value to weight the clinical factors and which are input into the input layer. The mean and standard deviation values are unique to the network training data. The input layer preprocessors 17–27 are each coupled to first and second and third processing elements 28, 29 and 30, of the hidden layer 14 via paths 31–41, 42–52 and 53–63 so that each hidden layer processing element 28, 29 and 30 receives a value or signal from each input preprocessor 17–27. Each path is provided with a unique weight based on the results of training on training data. The unique weights 64–74, 75–85, and 86–96 (see, also Table below) are non-linearly related to the output and are unique for each network structure and initial values of the training data. The final value of the weights are based on the initialized values assigned for network training. The combination of the weights that result from training constitute a functional apparatus whose description as expressed in weights produces a desired solution, or more specifically a risk assessment for preterm delivery before 35 weeks.

The hidden layer 14 is biased by bias weights 97, 98 and 99 provided via paths 100, 101, and 102 to the processing elements 28, 29 and 30. The output layer 16 contains two output processing elements 103, 104. The output layer 16 receives input from the hidden layer processing elements 28, 29 and 30 via paths 105–110. The output layer processing elements 103, 104 are weighted by weights 111–116. The output layer 16 is biased by bias weights 117, 118 provided via paths 119 and 120 to the processing elements 103 and 104.

The preliminary risk of delivery before 35 completed weeks of gestation is the output pair of values A and B from the two processing elements 103 and 104. The values are always positive between zero and One of the indicators is indicative of a risk of preterm delivery. The other is an indicator of the absence of such risk. While the output pair A, B provide generally valid indication of risk, a consensus network of trained neural networks provides a higher confidence index. EGA 6 contains 8 such trained neural networks.

The following tables set forth the values of the individual weights for each of the 8 consensus networks, designed EGA6_0 through EGA6_7.

EGA6_0

| Input layer node/ weight | hidden layer (nodes) | | | output layer (nodes) | |
|---|---|---|---|---|---|
| | 1st | 2nd | 3rd | 1st | 2nd |
| 0 | 0.412437 | −0.143143 | −1.885393 | −0.9598620 | 0.945025 |
| 1 | 2.041149 | −0.021533 | 0.162966 | −4.839373 | 4.875033 |
| 2 | 1.224530 | 0.971002 | −0.590964 | −2.524601 | 2.524054 |
| 3 | 0.575975 | −3.249891 | −2.814656 | 2.583483 | −2.561113 |
| 4 | 0.784864 | 0.600535 | −0.300794 | | |
| 5 | 1.075542 | 0.1601136 | 0.549237 | | |
| 6 | −1.047227 | 0.047396 | 0.905172 | | |
| 7 | −0.966051 | 0.163156 | 0.630888 | | |
| | −0.193761 | −0.149381 | 0.163185 | | |

-continued

EGA6_0

| Input layer node/ weight | hidden layer (nodes) | | | output layer (nodes) | |
|---|---|---|---|---|---|
| | 1st | 2nd | 3rd | 1st | 2nd |
| 9 | −0.680552 | −2.362585 | 1.365873 | | |
| 10 | 1.010706 | −3.633732 | −1.443890 | | |
| 11 | 1.728520 | −0.590057 | 0.878588 | | |

EGA6_1

| Input layer node/weight | hidden layer (nodes) | | | output layer (nodes) | |
|---|---|---|---|---|---|
| | 1st | 2nd | 3rd | 1st | 2nd |
| 0 | 2.675421 | −0.552641 | 0.673642 | 0.183663 | 0.197713 |
| 1 | −1.181347 | 0.284937 | 0.720041 | −3.170281 | 3.095180 |
| 2 | −0.178288 | −1.102137 | 0.655263 | 3.795940 | −3.747696 |
| 3 | 1.048956 | −0.941387 | −1.733601 | −6.612447 | 6.498429 |
| 4 | 0.033454 | 0.927974 | 2.987905 | | |
| 5 | −1.161823 | 1.217736 | 1.014796 | | |
| 6 | 6.168329 | 2.549298 | −1.321217 | | |
| 7 | −1.560728 | −1.637513 | −1.160331 | | |
| 8 | 1.671384 | 3.395848 | −0.117778 | | |
| 9 | 0.416004 | 1.452099 | −0.246268 | | |
| 10 | −2.228914 | 1.834281 | 0.748248 | | |
| 11 | −3.687070 | 1.693113 | −0.492244 | | |

EGA6_2

| Input layer node/weight | hidden layer (nodes) | | | output layer (nodes) | |
|---|---|---|---|---|---|
| | 1st | 2nd | 3rd | 1st | 2nd |
| 0 | −1.013347 | 1.392476 | 3.390216 | 1.093532 | −1.084186 |
| 1 | −3.020375 | 0.554074 | 2.172394 | −1.633913 | 1.632363 |
| 2 | −0.899928 | 1.928149 | 0.466793 | −3.099829 | 3.091530 |
| 3 | −8.108200 | 0.583508 | 0.030467 | −2.860816 | 2.845121 |
| 4 | 3.260629 | 9.249855 | 0.577971 | | |
| 5 | −0.567385 | 1.008019 | 0.196682 | | |
| 6 | −2.382355 | −2.942121 | 0.568323 | | |
| 7 | −1.996632 | −2.203792 | −0.852693 | | |
| 8 | 0.217054 | −0.230021 | −0.710703 | | |
| 9 | 0.380832 | −0.276078 | −1.551226 | | |
| 10 | 1.933148 | 0.603005 | −0.856832 | | |
| 11 | −1.922944 | −1.396864 | −2.356188 | | |

EGA6_3

| Input layer node/weight | hidden layer (nodes) | | | output layer (nodes) | |
|---|---|---|---|---|---|
| | 1st | 2nd | 3rd | 1st | 2nd |
| 0 | 1.493395 | −2.294246 | 2.173191 | −1.417536 | 1.413825 |
| 1 | 3.959154 | 0.635345 | 0.976585 | −2.381441 | 2.355649 |
| 2 | 0.396474 | −1.310699 | 0.708136 | 2.652994 | −2.638396 |
| 3 | −0.404996 | −0.906109 | 1.164319 | −3.176520 | 3.136459 |
| 4 | −0.113969 | −0.611193 | −0.896189 | | |
| 5 | 0.665321 | −1.422789 | 0.184973 | | |
| 6 | 1.628547 | 2.765793 | 0.315556 | | |
| 7 | −0.673276 | 1.645794 | −0.975604 | | |
| 8 | −2.422190 | 1.272992 | 0.612878 | | |
| 9 | −1.494859 | 2.990876 | 0.002188 | | |

-continued

EGA6_3

| Input layer | hidden layer (nodes) | | | output layer (nodes) | |
|---|---|---|---|---|---|
| node/weight | 1st | 2nd | 3rd | 1st | 2nd |
| 10 | −0.316486 | −0.614556 | −0.993159 | | |
| 11 | −3.208810 | −0.869353 | −3.219709 | | |

EGA6_4

| Input layer | hidden layer (nodes) | | | output layer (nodes) | |
|---|---|---|---|---|---|
| node/weight | 1st | 2nd | 3rd | 1st | 2nd |
| 0 | 1.595199 | −1.400935 | −1.254950 | −1.033706 | 1.017989 |
| 1 | 1.597543 | 1.434936 | −1.886380 | −3.899452 | 3.915186 |
| 2 | 0.424391 | −0.524230 | 0.974168 | 2.759211 | −2.750812 |
| 3 | 1.340851 | 0.063071 | −5.226755 | −2.077351 | 2.087066 |
| 4 | 0.145379 | −3.090206 | −1.188423 | | |
| 5 | 0.569193 | −1.556114 | −1.835809 | | |
| 6 | 0.380544 | 3.770102 | −1.193652 | | |
| 7 | −0.414611 | 2.391878 | −0.326348 | | |
| 8 | 0.082901 | 0.821397 | −2.173482 | | |
| 9 | −0.893175 | 0.099641 | −1.615205 | | |
| 10 | 0.312568 | −0.034908 | −1.900884 | | |
| 11 | 1.068789 | 1.023022 | −1.393905 | | |

EGA6_5

| Input layer | hidden layer (nodes) | | | output layer (nodes) | |
|---|---|---|---|---|---|
| node/weight | 1st | 2nd | 3rd | 1st | 2nd |
| 0 | 2.503198 | −2.428604 | −0.130730 | −2.186942 | 2.173897 |
| 1 | −2.192063 | −3.125744 | 3.638620 | −2.776665 | 2.660086 |
| 2 | 1.579702 | 0.833396 | 1.472541 | 2.737514 | −2.713886 |
| 3 | −0.067358 | 0.422544 | −1.196156 | −1.586596 | 1.647172 |
| 4 | 1.298254 | −3.568407 | −1.013145 | | |
| 5 | 1.992165 | −3.716873 | −0.868908 | | |
| 6 | −4.089348 | 2.595805 | 3.020147 | | |
| 7 | −2.734360 | 2.001578 | −0.018092 | | |
| 8 | −1.668519 | −0.383332 | −3.587072 | | |
| 9 | −1.886910 | 0.268403 | −0.229832 | | |
| 10 | −1.519840 | −1.147216 | 1.671855 | | |
| 11 | −1.200146 | 3.289453 | −4.163397 | | |

EGA6_6

| Input layer | hidden layer (nodes) | | | output layer (nodes) | |
|---|---|---|---|---|---|
| node/weight | 1st | 2nd | 3rd | 1st | 2nd |
| 0 | −1.443015 | 0.865813 | 0.382970 | −2.388151 | 2.408045 |
| 1 | −1.582839 | 0.593947 | 0.830775 | 4.015757 | −4.056962 |
| 2 | −1.119793 | −0.355416 | 0.803208 | −2.574057 | 2.594654 |
| 3 | 2.549989 | 0.295836 | 0.454763 | −3.381956 | 3.430132 |
| 4 | −3.080358 | −3.033361 | 1.023391 | | |
| 5 | −2.302934 | 0.508087 | −0.703378 | | |
| 6 | −0.040867 | −2.352165 | −1.982702 | | |
| 7 | 1.082370 | 3.718414 | −4.853944 | | |
| 8 | −0.564883 | −4.419714 | −2.375676 | | |
| 9 | 0.953993 | −2.047337 | −0.481060 | | |
| 10 | −1.062311 | 0.216755 | −2.037935 | | |
| 11 | 1.488106 | −3.616466 | −0.630520 | | |

EGA6_7

| Input layer | hidden layer (nodes) | | | output layer (nodes) | |
|---|---|---|---|---|---|
| node/weight | 1st | 2nd | 3rd | 1st | 2nd |
| 0 | 1.622433 | 1.633779 | −3.852473 | −0.748768 | 0.742163 |
| 1 | 0.043906 | −0.351661 | −2.431170 | −3.003003 | 2.983215 |
| 2 | 0.732213 | −0.661362 | −0.746753 | −2.218790 | 2.184970 |
| 3 | −2.027060 | 1.301339 | −1.768983 | 3.052581 | −3.004828 |
| 4 | 1.521622 | 1.790975 | −0.154270 | | |
| 5 | 1.677837 | −0.625462 | 0.730582 | | |
| 6 | −1.347791 | −4.165056 | −0.685942 | | |
| 7 | −1.774773 | 5.494371 | 1.034300 | | |
| 8 | −0.827799 | 1.789396 | 0.538103 | | |
| 9 | −0.509971 | −0.183482 | 1.543398 | | |
| 10 | 0.605369 | 2.345229 | 1.277570 | | |
| 11 | 0.691960 | −3.950886 | 2.871648 | | |

The EGA6 preprocessing information is the same for each of the 8 neural networks in the consensus. The input is preprocessed by subtracting the mean value and dividing by the standard deviation.

| Node | Mean | Standard Deviation |
|---|---|---|
| 1 | 0.399738 | 0.490166 |
| 2 | 0.011796 | 0.108036 |
| 3 | 30.593335 | 4.979660 |
| 4 | 30.709605 | 5.405745 |
| 5 | 30.278038 | 2.976036 |
| 6 | 0.490092 | 0.667659 |
| 7 | 0.178244 | 0.471996 |
| 8 | 0.198946 | 0.508406 |
| 9 | 1.823197 | 0.757205 |
| 10 | 0.399738 | 0.490166 |
| 11 | 0.195282 | 0.396677 |

EGA5 is a set of 8 consensus networks trained similarly to EGA6, except that the input variables did not include the variable representing the result of the fFN ELISA test. This network can be used as a point of care application to give immediate result to the clinician rather than the 24 to 48 hours required to process the fFN sample.

D. Neural network prediction of risk of delivery within 7 days—EGAD7 and EGAD7F

1. Variable selection

Using the same database described above for EGA1-EGA6, the variable selection protocol was applied to prediction of the risk for delivery within 7 days of sampling for the fFN test. As noted above for EGA5 and EGA6, the variable selection procedure was applied in the absence of the fFN test result. Application of the variable selection procedure to the 48 variables resulted in selection of the following variables:

1. Ethnic Origin 1: Caucasion (i.e., yes or no);
2. Uterine contractions with or without pain (i.e., yes or no);
3. Parity-abortions;
4. Vaginal bleeding at time of sampling;
5. Uterine contractions per hour;
6. No previous pregnancies.

2. Neural nets

Using these variables two consensus networks were trained. One, designated EGAD7 was trained without including the results of the fFN ELISA test result, and the other, designated EGAD7f, was trained with the results of the fFN ELISA test result.

Figure 18:
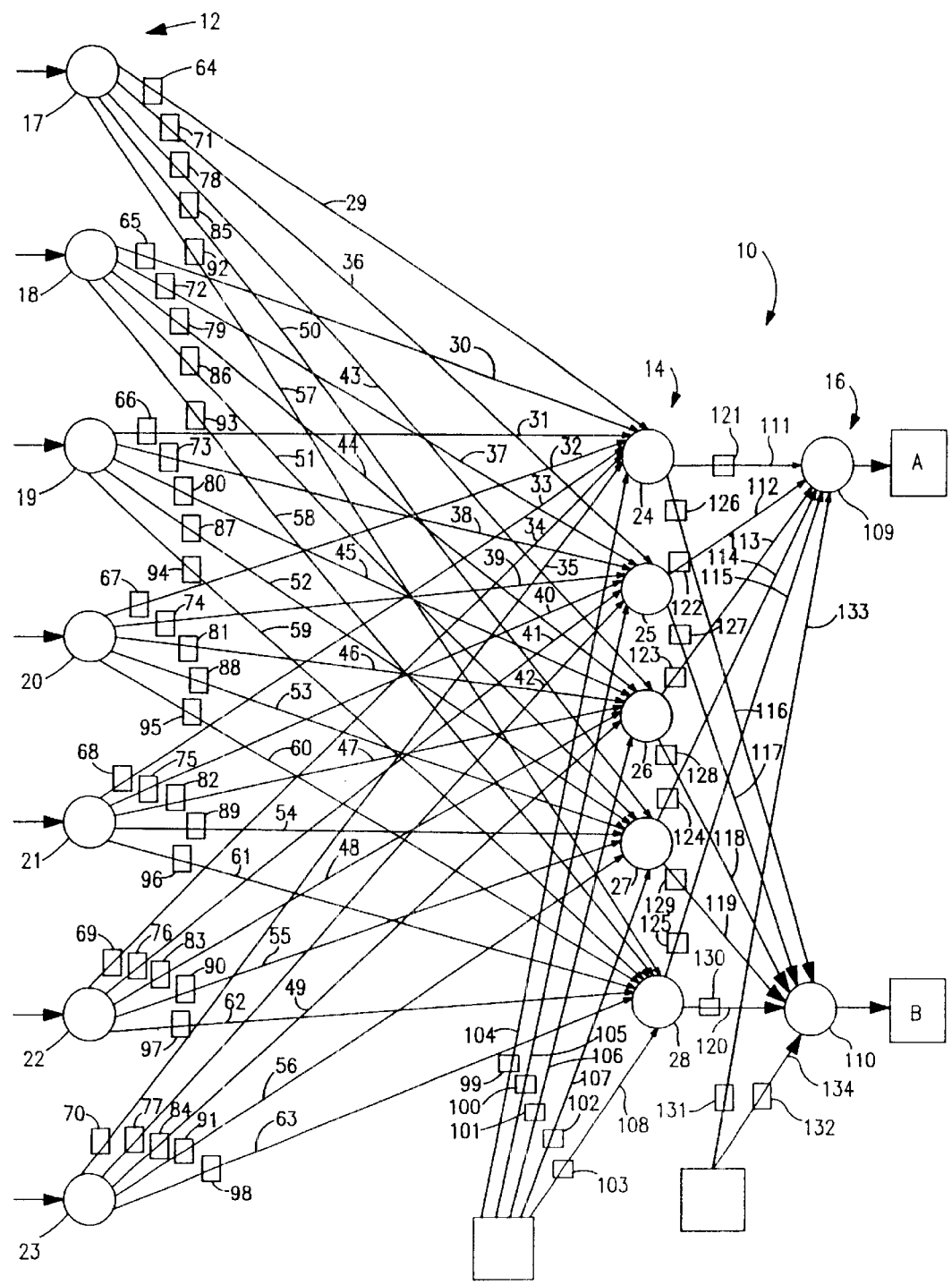
FIG. 18 is a schematic diagram of a neural network, such as EGAD7f and EGAD14f, trained on clinical data of the form used for the consensus network of a plurality of neural networks.

FIG. 18, which represents EGA7f, is a schematic diagram of an embodiment of the neural network 10 trained on clinical data of the form used for the consensus network (FIG. 10) of a plurality of neural networks. The structure is stored in digital form, along with weight values and data to be processed in a digital computer. This neural network 10 contains three layers, an input layer 12, a hidden layer 14 and an output layer 16. The input layer 12 has seven input preprocessors 17–23, each of which is provided with a normalizer (not shown in the figure, see table below) which generates a mean and standard deviation value to weight the clinical factors which are input into the input layer. The mean and standard deviation values are unique to the network training data. The input layer preprocessors 17–23 are each coupled to first, second, third, fourth and fifth processing elements 24–28, respectively, of the hidden layer 14 via paths 29–35, 36–42, 43–49, 50–56, and 57–63 so that each hidden layer processing element 24–28, receives a value or signal from each input preprocessor 17–23. Each path is provided with a unique weight based on the results of training on training data. The unique weights 64–70, 71–77, 78–84, 85–91 and 92–98 (see, also Table below) are non-linearly related to the output and are unique for each network structure and initial values of the training data. The final value of the weights are based on the initialized values assigned for network training. The combination of the weights that result from training constitute a functional apparatus whose description as expressed in weights produces a desired solution, or more specifically a risk assessment of delivery within 7 days of sampling for the fFN ELISA test.

The hidden layer 14 is biased by bias weights 99, 100, 101, 102 and 103 provided via paths 104, 105, 106, 107 and 108 to the processing elements 24, 25, 26, 27 and 28. The output layer 16 contains two output processing elements 109, 110. The output layer 16 receives input from the hidden layer processing elements 24–28 via paths 111–120. The output layer processing elements 109, 110 are weighted by weights 121–130. The output layer 16 is biased by bias weights 131, 132 provided via paths 133 and 134 to the processing elements 109 and 110.

The preliminary risk of delivery within 7 days from sampling for the fFN ELISA test is the output pair of values A and B from the two processing elements 109 and 110. The values are always positive between zero and one. One of the indicators is indicative of a risk of delivery within 7 days. The other is an indicator of the absence of such risk. While the output pair A, B provide generally valid indication of risk, a consensus network of trained neural networks provides a higher confidence index. EGAD7f contains 8 such trained neural networks.

The following tables set forth the values of the individual weights for each of the 8 consensus networks, designated EGAD7f0 through EGAD7f7:

| | EGAD7f0 | | | | | | |
|---|---|---|---|---|---|---|---|
| Input layer node/ | hidden layer (nodes) | | | | | output layer (nodes) | |
| weight | 1st | 2nd | 3rd | 4th | 5th | 1st | 2nd |
| 0 | −0.204716 | 1.533574 | 1.452831 | 0.129981 | −1.784807 | 0.854229 | −0.883808 |
| 1 | −1.843673 | 1.957059 | −2.668371 | −0.551016 | 1.505628 | −5.294533 | 5.303048 |
| 2 | −1.324609 | 0.258418 | −1.280479 | −0.476101 | 0.827188 | −7.468771 | 7.514580 |
| 3 | −1.281561 | 1.697443 | 6.865219 | 4.212538 | −1.953753 | −5.082050 | 5.003566 |
| 4 | −1.159086 | −0.345244 | −4.689749 | −0.406485 | 1.027280 | 4.014138 | −4.006929 |
| 5 | −2.042978 | 0.182091 | 2.612433 | 2.399196 | −1.397453 | −4.105859 | 4.105161 |
| 6 | −4.076656 | 1.416529 | 0.979842 | −2.589272 | 0.068466 | | |
| 7 | −0.499705 | −1.383732 | −2.411544 | 0.173131 | −1.919889 | | |

| | EGAD7f1 | | | | | | |
|---|---|---|---|---|---|---|---|
| Input layer node | hidden layer (nodes) | | | | | output layer (nodes) | |
| weight | 1st | 2nd | 3rd | 4th | 5th | 1st | 2nd |
| 0 | 1.522090 | 6.396365 | 1.750606 | 0.650769 | 0.673423 | 0.282480 | −0.222861 |
| 1 | 1.930314 | 0.027271 | 0.386927 | 1.602559 | 3.495371 | −5.126995 | 4.888618 |
| 2 | 1.578675 | −0.445222 | 0.352425 | 1.305894 | 1.703156 | −3.751147 | 3.752025 |
| 3 | 1.821893 | 6.258497 | 1.140159 | 1.363783 | −0.717021 | −5.496184 | 5.687717 |
| 4 | −4.599618 | 0.218248 | 0.385593 | 0.945824 | 0.644622 | 7.713794 | −8.054935 |
| 5 | −2.755846 | −1.799000 | 2.162089 | 1.730335 | −0.388646 | −3.429169 | 3.706028 |
| 6 | 0.524701 | 1.669467 | 1.741620 | 3.956515 | 4.717868 | | |
| 7 | −2.089663 | −0.190423 | −1.736970 | 0.085315 | −1.010295 | | |

EGAD7f2

| Input layer node weight | hidden layer (nodes) | | | | | output layer (nodes) | |
|---|---|---|---|---|---|---|---|
| | 1st | 2nd | 3rd | 4th | 5th | 1st | 2nd |
| 0 | 0.554749 | 4.029042 | 1.041783 | 0.687361 | 2.078268 | 0.718456 | −0.756554 |
| 1 | 0.314365 | −1.614025 | 4.560114 | −0.197290 | 2.352322 | 3.339842 | −3.185465 |
| 2 | −1.992577 | −1.810437 | 2.067243 | −0.021868 | 0.041441 | −5.596330 | 5.470991 |
| 3 | −4.762585 | −6.021220 | 3.627642 | 3.505088 | 1.221308 | 0.815486 | −0.906961 |
| 4 | 8.422636 | −1.088322 | −1.229308 | −2.513499 | 0.344056 | −4.076351 | 4.165072 |
| 5 | −0.547021 | −6.256763 | 1.108255 | 1.341978 | −0.074222 | −7.385492 | 7.372295 |
| 6 | 0.581056 | −2.916328 | 0.639607 | 0.894802 | 2.365492 | | |
| 7 | 1.260577 | −1.583044 | 0.882731 | −1.113407 | −1.657523 | | |

EGAD7f3

| Input layer node/ weight | hidden layer (nodes) | | | | | output layer (nodes) | |
|---|---|---|---|---|---|---|---|
| | 1st | 2nd | 3rd | 4th | 5th | 1st | 2nd |
| 0 | 1.258939 | 0.778115 | 1.117508 | −5.828234 | 3.275221 | −0.174440 | 0.260818 |
| 1 | 1.038074 | 0.395096 | −1.080656 | −0.580291 | −1.077984 | −6.546609 | 6.515666 |
| 2 | −2.174144 | 0.453939 | −0.677622 | −1.330231 | −0.383479 | −8.061748 | 8.067432 |
| 3 | 0.608410 | 2.262108 | 9.263388 | 4.024162 | 0.949009 | 4.938700 | −5.060233 |
| 4 | 1.443697 | −1.530076 | −0.812837 | 1.549062 | −1.594324 | 5.420476 | −5.517191 |
| 5 | −1.437676 | 0.749049 | 5.493512 | −2.797146 | −2.056666 | −5.085781 | 5.127757 |
| 6 | 0.778191 | 1.397835 | −3.635368 | 2.191902 | −2.403500 | | |
| 7 | −1.776540 | −0.675587 | 0.115710 | 0.388203 | −1.363938 | | |

EGAD7f4

| Input layer node/ weight | hidden layer (nodes) | | | | | output layer (nodes) | |
|---|---|---|---|---|---|---|---|
| | 1st | 2nd | 3rd | 4th | 5th | 1st | 2nd |
| 0 | −1.839879 | 0.255905 | 3.002103 | 0.886848 | −0.485949 | −1.461668 | 1.340040 |
| 1 | −1.335228 | −3.428058 | 0.665937 | −1.072765 | −0.372897 | −1.862627 | 1.815599 |
| 2 | 0.062547 | 0.489211 | 0.946443 | −3.642373 | 3.973801 | 5.835287 | −5.699555 |
| 3 | 1.888678 | 1.928167 | 4.900952 | 1.928106 | −1.866227 | −5.463729 | 5.463984 |
| 4 | −5.217631 | −1.441138 | −4.114171 | 0.629958 | −1.615146 | −5.726771 | 5.763464 |
| 5 | −0.631546 | 1.735842 | 1.158419 | 0.638580 | −3.276926 | −7.193156 | 7.177080 |
| 6 | −3.109977 | −0.377960 | 1.372646 | 2.625961 | −1.700064 | | |
| 7 | −0.070132 | 1.763962 | −2.234798 | −1.165563 | −1.845262 | | |

EGAD7f5

| Input layer node/ weight | hidden layer (nodes) | | | | | output layer (nodes) | |
|---|---|---|---|---|---|---|---|
| | 1st | 2nd | 3rd | 4th | 5th | 1st | 2nd |
| 0 | −1.456277 | 1.321048 | 1.214385 | 0.069355 | −0.206125 | −1.581118 | 1.811097 |
| 1 | 1.988970 | −2.788917 | 1.700144 | −3.790842 | 0.760984 | −3.282460 | 2.842431 |
| 2 | −0.889522 | −1.748239 | 0.798888 | −0.481237 | 0.248333 | −6.391959 | 6.435954 |
| 3 | 15.258006 | 0.809204 | 4.071811 | −3.751193 | −6.873492 | −6.817300 | 6.829902 |
| 4 | −18.202002 | −2.000871 | 0.021785 | 0.812317 | 0.713510 | 6.157183 | −6.412641 |
| 5 | 0.440615 | −0.470067 | −1.578267 | −0.216803 | −3.315356 | −7.015062 | 6.902892 |

-continued

EGAD7f5

| Input layer node/ weight | hidden layer (nodes) | | | | | output layer (nodes) | |
| --- | --- | --- | --- | --- | --- | --- | --- |
| | 1st | 2nd | 3rd | 4th | 5th | 1st | 2nd |
| 6 | −1.931575 | 0.510900 | 1.162408 | −2.528233 | 1.405955 | | |
| 7 | −3.758462 | −0.570789 | −6.338710 | 0.877703 | −0.985724 | | |

EGAD7f6

| Input layer node/ weight | hidden layer (nodes) | | | | | output layer (nodes) | |
| --- | --- | --- | --- | --- | --- | --- | --- |
| | 1st | 2nd | 3rd | 4th | 5th | 1st | 2nd |
| 0 | 1.512437 | −0.333348 | −0.557454 | −0.790704 | 0.049061 | −0.918761 | 0.804829 |
| 1 | −0.704182 | −0.032274 | −3.201322 | −0.966885 | −0.213225 | −2.987857 | 2.999401 |
| 2 | 0.443652 | −0.736894 | −0.713164 | −0.709163 | −0.725865 | −5.682138 | 5.675150 |
| 3 | 2.734173 | 0.555570 | −2.071605 | 7.636067 | −7.109310 | 4.989255 | −4.851893 |
| 4 | −4.066469 | −0.039688 | 0.313027 | −0.265136 | 0.152398 | −4.107172 | 4.101486 |
| 5 | 0.943337 | −0.658673 | −0.079748 | 3.091015 | −5.459067 | −5.247225 | 5.231175 |
| 6 | −0.211375 | 0.247671 | −2.400778 | 2.663087 | −1.717437 | | |
| 7 | −1.291067 | −4.507938 | 1.526173 | −0.139780 | −0.451653 | | |

EGAD7f7

| Input layer node/ weight | hidden layer (nodes) | | | | | output layer (nodes) | |
| --- | --- | --- | --- | --- | --- | --- | --- |
| | 1st | 2nd | 3rd | 4th | 5th | 1st | 2nd |
| 0 | 0.580523 | 0.319374 | −0.660897 | 1.072931 | −0.522045 | −0.833235 | 1.016355 |
| 1 | 0.432923 | 3.916608 | 0.386343 | −1.324510 | −1.566712 | −4.472839 | 4.433871 |
| 2 | −0.312324 | 3.099275 | 0.344633 | −3.254393 | −1.081114 | −4.873536 | 4.919722 |
| 3 | 4.019378 | −5.440501 | −9.105190 | 1.955846 | −2.152612 | 4.971172 | −5.215318 |
| 4 | −0.355344 | 0.495595 | 0.543102 | −2.001959 | −0.989721 | −3.436097 | 3.478752 |
| 5 | −1.585942 | −3.885213 | −2.778485 | 1.068593 | −1.697807 | −4.098137 | 4.165162 |
| 6 | −0.209687 | −0.646458 | −2.399903 | 0.177487 | 2.339257 | | |
| 7 | −8.951553 | −1.471208 | 0.725651 | −2.732204 | 1.538870 | | |

| Node | Mean | Standard Deviation |
| --- | --- | --- |
| 1 | 0.399738 | 0.490166 |
| 2 | 0.517693 | 0.500015 |
| 3 | 0.621232 | 1.030720 |
| 4 | 0.198946 | 0.508406 |
| 5 | 2.144928 | 2.291734 |
| 6 | 0.281782 | 0.450163 |
| 7 | 0.195282 | 0.396677 |

EGAD7 is a set of 8 consensus networks trained similarly to EGAD7f, except that the input variables did not include the variable representing the result of the fFN ELISA test. This network can be used as a point of care application to give immediate result to the clinician rather than the 24 to 48 hours required to process the fFN sample.

E. Neural network prediction of risk of delivery within 14 days—EGAD14f and EGAD14

1. Variable selection

Using the same database described above for EGA1-EGAD7, the variable selection protocol was applied to prediction of the risk for delivery within 14 days of sampling for the fFN test. As noted above for EGA5, EGA6 and EGAD7, the variable selection procedure was applied in the absence of the fFN test result. Application of the variable selection procedure to the 48 variables resulted in selection of the following variables:

1. Ethnic Origin 4: Hispanic (i.e., yes or no);
2. Marital Status 5: living with partner;
3. Uterine contractions with or without pain (i.e., yes or no);
4. Cervical dilatation;

5. Uterine contractions per hour;
6. No previous pregnancies.

2. Neural nets

Using these variables two consensus networks were trained. One, designated EGAD14 was trained without including the results of the fFN ELISA test result, and the other, designated EGAD14f, was trained with the results of the fFN ELISA test result.

FIG. 18, which represents EGAD14f (as well as EGAD7f), is a schematic diagram of an embodiment of the neural network 10 trained on clinical data of the form used for the consensus network (FIG. 10) of a plurality of neural networks. The structure is stored in digital form, along with weight values and data to be processed in a digital computer. This neural network 10 contains three layers, an input layer 12, a hidden layer 14 and an output layer 16. The input layer 12 has seven input preprocessors 17–23, each of which is provided with a normalizer (not shown in the figure, see Table, below) which generates a mean and standard deviation value to weight the clinical factors which are input into the input layer. The mean and standard deviation values are unique to the network training data. The input layer preprocessors 17–23 are each coupled to first, second, third, fourth and fifth processing elements 24–28, respectively, of the hidden layer 14 via paths 29–35, 36–42, 43–49, 50–56, and 57–63 so that each hidden layer processing element 24–28, receives a value or signal from each input preprocessor 17–23. Each path is provided with a unique weight based on the results of training on training data. The unique weights 64–70, 71–77, 78–84, 85–91 and b 92–98 (see, also Table below) are non-linearly related to the output and are unique for each network structure and initial values of the training data. The final value of the weights are based on the initialized values assigned for network training. The combination of the weights that result from training constitute a functional apparatus whose description as expressed in weights produces a desired solution, or more specifically a risk assessment of delivery within 14 days of sampling for the fFN ELISA test.

The hidden layer 14 is biased by bias weights 99, 100, 101, 102 and 103 provided via paths 104, 105, 106, 107 and 108 to the processing elements 24, 25, 26, 27 and 28. The output layer 16 contains two output processing elements 109, 110. The output layer 16 receives input from the hidden layer processing elements 24–28 via paths 111–120. The output layer processing elements 109, 110 are weighted by weights 121–130. The output layer 16 is biased by bias weights 131, 132 provided via paths 133 and 134 to the processing elements 109 and 110.

The preliminary risk of delivery within 14 days from sampling for the fFN ELISA test is the output pair of values A and B from the two processing elements 109 and 110. The values are always positive between zero and one. One of the indicators is indicative of a risk of delivery within 14 days. The other is an indicator of the absence of such risk. While the output pair A, B provide generally valid indication of risk, a consensus network of trained neural networks provides a higher confidence index. EGAD14f contains 8 such trained neural networks.

The following tables set forth the values of the individual weights for each of the 8 consensus networks, designed EGAD14f0 through EGAD14f7.

| Input layer node/weight | hidden layer (nodes) | | | | | output layer (nodes) | |
|---|---|---|---|---|---|---|---|
| | 1st | 2nd | 3rd | 4th | 5th | 1st | 2nd |

EGAD14f0

| | 1st | 2nd | 3rd | 4th | 5th | 1st | 2nd |
|---|---|---|---|---|---|---|---|
| 0 | −0.191126 | 1.174059 | 0.810632 | 0.148573 | −2.437188 | 0.106355 | −0.108766 |
| 1 | −2.921661 | −0.713076 | 1.312931 | 10.427816 | 1.824513 | −2.220130 | 2.198498 |
| 2 | −0.848702 | 1.614504 | 2.640692 | −0.445807 | 1.218097 | −2.016395 | 2.005455 |
| 3 | −1.008667 | 0.138305 | 1.372127 | 0.788516 | −3.114650 | −4.365818 | 4.349520 |
| 4 | −1.422990 | −1.517308 | −1.632533 | −3.146550 | 0.256047 | 2.291882 | −2.293527 |
| 5 | −2.588523 | −0.733381 | 0.992748 | 1.482687 | 1.197727 | −4.864353 | 4.861522 |
| 6 | −3.611756 | −2.669159 | 3.364100 | −1.806442 | 0.833890 | | |
| 7 | −0.516151 | −2.104245 | −2.052761 | −0.615030 | −1.621589 | | |

EGAD14f1

| | 1st | 2nd | 3rd | 4th | 5th | 1st | 2nd |
|---|---|---|---|---|---|---|---|
| 0 | 0.396502 | 2.426709 | 0.752911 | 1.549394 | −0.064008 | −0.285667 | 0.714618 |
| 1 | 1.248711 | 2.179334 | −0.016570 | −0.040113 | 2.457661 | −3.745954 | 3.884410 |
| 2 | 1.912210 | 0.937177 | −1.742286 | −2.094312 | −1.165847 | −4.912591 | 4.966647 |
| 3 | −1.018760 | −1.087528 | −0.344108 | 0.384237 | −1.077692 | −7.433263 | 7.309962 |
| 4 | 1.090578 | −2.229295 | −0.890326 | −1.334206 | 0.822185 | 2.080292 | −2.595363 |
| 5 | 1.399831 | −5.077936 | −0.600345 | 4.128439 | −1.715393 | 5.481619 | −5.611861 |
| 6 | 2.241531 | −4.673233 | −0.209741 | 2.954158 | −4.565109 | | |
| 7 | 0.077090 | −0.194145 | −4.391311 | 3.250038 | −2.360049 | | |

EGAD14f2

| Input layer node/weight | hidden layer (nodes) | | | | | output layer (nodes) | |
|---|---|---|---|---|---|---|---|
| | 1st | 2nd | 3rd | 4th | 5th | 1st | 2nd |
| 0 | 0.286926 | 1.855804 | 0.103985 | −2.590399 | 2.265841 | 1.54065 | −1.592696 |
| 1 | 1.928731 | 0.410516 | −2.015740 | 1.017801 | 2.088775 | 2.433105 | −2.545955 |
| 2 | −0.666312 | −1.178337 | 1.227737 | −1.471309 | 1.922938 | −4.736276 | 4.903823 |
| 3 | −2.716156 | −2.328632 | −0.566546 | 0.854688 | −0.448565 | −2.220462 | 2.268171 |
| 4 | 0.654814 | −0.197945 | −2.256156 | −0.410249 | −0.792705 | −4.049918 | 4.142265 |
| 5 | −2.004537 | −3.451720 | 3.311102 | 1.787226 | −0.682330 | −3.930044 | 4.036821 |
| 6 | −0.947058 | −1.898302 | −0.131517 | 4.187262 | 2.272720 | | |
| 7 | 0.485620 | −0.138471 | 1.038285 | −1.245135 | −6.442445 | | |

EGAD14f3

| Input layer node/weight | hidden layer (nodes) | | | | | output layer (nodes) | |
|---|---|---|---|---|---|---|---|
| | 1st | 2nd | 3rd | 4th | 5th | 1st | 2nd |
| 0 | 1.199346 | 1.135219 | 2.839737 | −4.673778 | 2.903983 | −0.702760 | 0.935822 |
| 1 | −1.274101 | 1.559637 | 1.386395 | −0.042351 | −0.874145 | −3.244763 | 3.144603 |
| 2 | −0.353335 | 0.325171 | −1.677620 | −0.793429 | 0.788584 | −4.933673 | 4.849451 |
| 3 | −0.678281 | −2.157454 | −3.084480 | 1.009661 | 0.327746 | 3.306738 | −3.432135 |
| 4 | 1.116566 | 0.128203 | −2.188180 | 2.315793 | −1.815446 | 4.993960 | −5.098751 |
| 5 | −1.277371 | −0.415757 | −0.080374 | −0.694424 | −1.022831 | −4.266839 | 4.064770 |
| 6 | −4.836841 | 3.738553 | −0.703345 | 0.271620 | −0.626113 | | |
| 7 | −0.953257 | −0.463343 | 1.314770 | −0.196871 | −2.372877 | | |

EGAD14f4

| Input layer node/weight | hidden layer (nodes) | | | | | output layer (nodes) | |
|---|---|---|---|---|---|---|---|
| | 1st | 2nd | 3rd | 4th | 5th | 1st | 2nd |
| 0 | −1.810913 | −0.014885 | 0.167362 | −2.605120 | −0.205378 | −0.681096 | 0.709641 |
| 1 | 5.080080 | 1.259709 | 0.430446 | 0.680130 | −3.098744 | −3.611765 | 3.644697 |
| 2 | −0.414857 | −0.328851 | −0.335724 | 5.756228 | 1.904646 | 4.377642 | −4.419249 |
| 3 | 0.525909 | 1.767786 | −0.375093 | 1.041263 | −0.566611 | −6.720907 | 6.647904 |
| 4 | −7.166096 | −0.912267 | −1.948366 | −1.117219 | −1.237101 | −2.355787 | 2.337121 |
| 5 | −4.340267 | −0.345630 | −0.077869 | 3.853568 | −2.550077 | −2.249878 | 2.171079 |
| 6 | −2.586306 | −3.315458 | 0.378838 | 5.812339 | −3.619375 | | |
| 7 | 0.213139 | −1.546969 | −10.991954 | −1.186517 | −0.502957 | | |

EGAD14f5

| Input layer node/weight | hidden layer (nodes) | | | | | output layer (nodes) | |
|---|---|---|---|---|---|---|---|
| | 1st | 2nd | 3rd | 4th | 5th | 1st | 2nd |
| 0 | −2.439228 | 0.954525 | 1.242215 | −27.696498 | 0.322283 | −2.017057 | 2.095211 |
| 1 | 1.998281 | 1.928331 | 0.638520 | −1.415280 | 1.871968 | 6.487561 | −6.308325 |
| 2 | −0.869648 | −0.994059 | 0.768856 | 0.368344 | 1.457719 | −4.867902 | 4.744858 |
| 3 | 0.295868 | −0.257773 | 1.422994 | 0.033843 | −4.658167 | −2.392888 | 2.192236 |
| 4 | −1.800394 | −2.612705 | −1.668799 | 51.649234 | −0.537556 | 1.222661 | −1.270161 |
| 5 | 0.992302 | −0.938952 | 1.104910 | 3.731820 | 1.651959 | −1.649461 | 1.594009 |
| 6 | −1.787379 | −1.045545 | 2.711432 | 0.288323 | −0.572490 | | |
| 7 | −0.374909 | −0.877122 | −1.918442 | 214.812434 | −1.773228 | | |

EGAD14f6

| Input layer | hidden layer (nodes) | | | | | output layer (nodes) | |
|---|---|---|---|---|---|---|---|
| node/weight | 1st | 2nd | 3rd | 4th | 5th | 1st | 2nd |
| 0 | 3.984308 | −0.300188 | 6.132831 | 1.776838 | 1.182643 | −0.141300 | −0.062816 |
| 1 | −2.478863 | 0.891740 | −0.185527 | −0.442487 | 1.045499 | −5.041497 | 4.985260 |
| 2 | 0.389668 | 0.650328 | −289.318971 | 0.651142 | 0.169117 | −7.230831 | 7.280185 |
| 3 | 0.370846 | 0.503667 | 21.787679 | 1.820010 | −0.802930 | 2.464335 | −2.250474 |
| 4 | −0.950033 | −0.054657 | 0.942573 | −1.024688 | −1.842654 | 2.637713 | −2.636534 |
| 5 | 3.200645 | 0.464231 | 0.728644 | 1.784671 | −5.371345 | −3.675622 | 3.704625 |
| 6 | 0.647747 | 2.560388 | −0.798268 | 3.237414 | −4.493387 | | |
| 7 | −1.276096 | −1.593493 | 66.059880 | 0.493228 | −0.126844 | | |

EGAD14f7

| Input layer | hidden layer (nodes) | | | | | output layer (nodes) | |
|---|---|---|---|---|---|---|---|
| node/weight | 1st | 2nd | 3rd | 4th | 5th | 1st | 2nd |
| 0 | 0.888004 | 0.521346 | −0.513845 | 0.767983 | −0.956920 | −1.088033 | 1.265836 |
| 1 | 0.191409 | 1.634987 | −0.771837 | −2.402982 | −1.003714 | −4.407106 | 4.589468 |
| 2 | 2.233326 | 0.767802 | −10.205298 | 0.362276 | 0.797006 | −4.385751 | 4.466996 |
| 3 | −0.588252 | −5.586697 | 0.233547 | 0.586147 | 1.589040 | 5.286517 | −5.562157 |
| 4 | −1.544910 | −0.829764 | 0.624734 | −5.119879 | −0.276545 | −0.907527 | 0.809701 |
| 5 | −0.361805 | 0.397313 | −1.973167 | −2.953926 | −0.614287 | −5.146765 | 5.284392 |
| 6 | −0.136039 | −1.488352 | −3.541771 | 3.717852 | −1.091340 | | |
| 7 | −8.058644 | −1.997797 | 1.520159 | −0.638158 | 1.013775 | | |

The EGAD14F preprocessing information is the same for each of the 8 neural networks in the consensus. The input is preprocessed by subtracting the mean value and dividing by the standard deviation.

| Node | Mean | Standard Deviation |
|---|---|---|
| 1 | 0.152031 | 0.359287 |
| 2 | 0.91796 | 0.108036 |
| 3 | 0.517693 | 0.500015 |
| 4 | 0.490092 | 0.667659 |
| 5 | 2.144928 | 2.291734 |
| 6 | 0.281782 | 0.450163 |
| 7 | 0.195282 | 0.396677 |

EGAD14 is a set of 8 consensus networks trained similarly to EGAD14f, except that the input variables did not include the variable representing the result of the fFN ELISA test. This network can be used as a point of care application to give immediate result to the clinician rather than the 24 to 48 hours required to process the fFN sample.

EXAMPLE 14

Training of Consensus Neural Networks on Specific subsets of Pat07 Variables

The examples shows the results of a task designed to quantitate the contribution of pat07 variables to pat07 performance, and to develop endometriosis networks using minimal numbers of pat07 variables.

Tasks:
1. Train final consensus networks using the following combination of Pat07 variables:
   a. All 14 minus Hx Endo (13 variables total)
   b. All 14 minus pelvic pain (13 variables total)
   c. All 14 minus dysmenorrhea (13 variables total)
   d. All 14 minus pelvic surgery (13 variables total)
2. Train final consensus networks using other combinations of Pat07 variables.
   a. Hx Endo, pelvic pain, and dysmenorrhea
   b. Hx Endo, pelvic pain, dysmenorrhea and Hx pelvic surgery
3. Train final consensus networks using other combinations of pat07 variables as indicated from above results.

Methodology Used

Using the original patient database, training examples were generated for each of the combinations of variables to be evaluated. These training examples contained only the variables required for the given consensus run. TrainDos™ was used in batch mode to train a set of eight neural networks for each of the combinations of variables to be evaluated. The networks were trained using the same parameters as the Pat07 training runs. The only difference was the setting of the random number seeds for each network. Each network was trained on the full 510 record database.

From these training runs, a consensus of the outputs was generated in an Excel spreadsheet so that the performance of each of the networks could be evaluated.

Results

Since these runs were final training runs, the effects of eliminating variables could be seen but did not give as clear an indication as can be achieved by the holdout method.

Conclusions

The results of the variable selection runs on the full training example for the purposes of determining the contribution of a given set of .variables is not as good a method as the evaluation method used in the variable selection process. The "holdout" method for evaluation with a partition of 5 and 20 net consensus gives a substantially better statistic for comparison of variables.

EXAMPLE 15

METHOD AND APPARATUS FOR AIDING IN THE DIAGNOSIS OF ENDOMETRIOSIS USING A PLURALITY OF PARAMETERS SUITED FOR ANALYSIS THROUGH A NEURAL NETWORK (PAT07)

Figure 7:
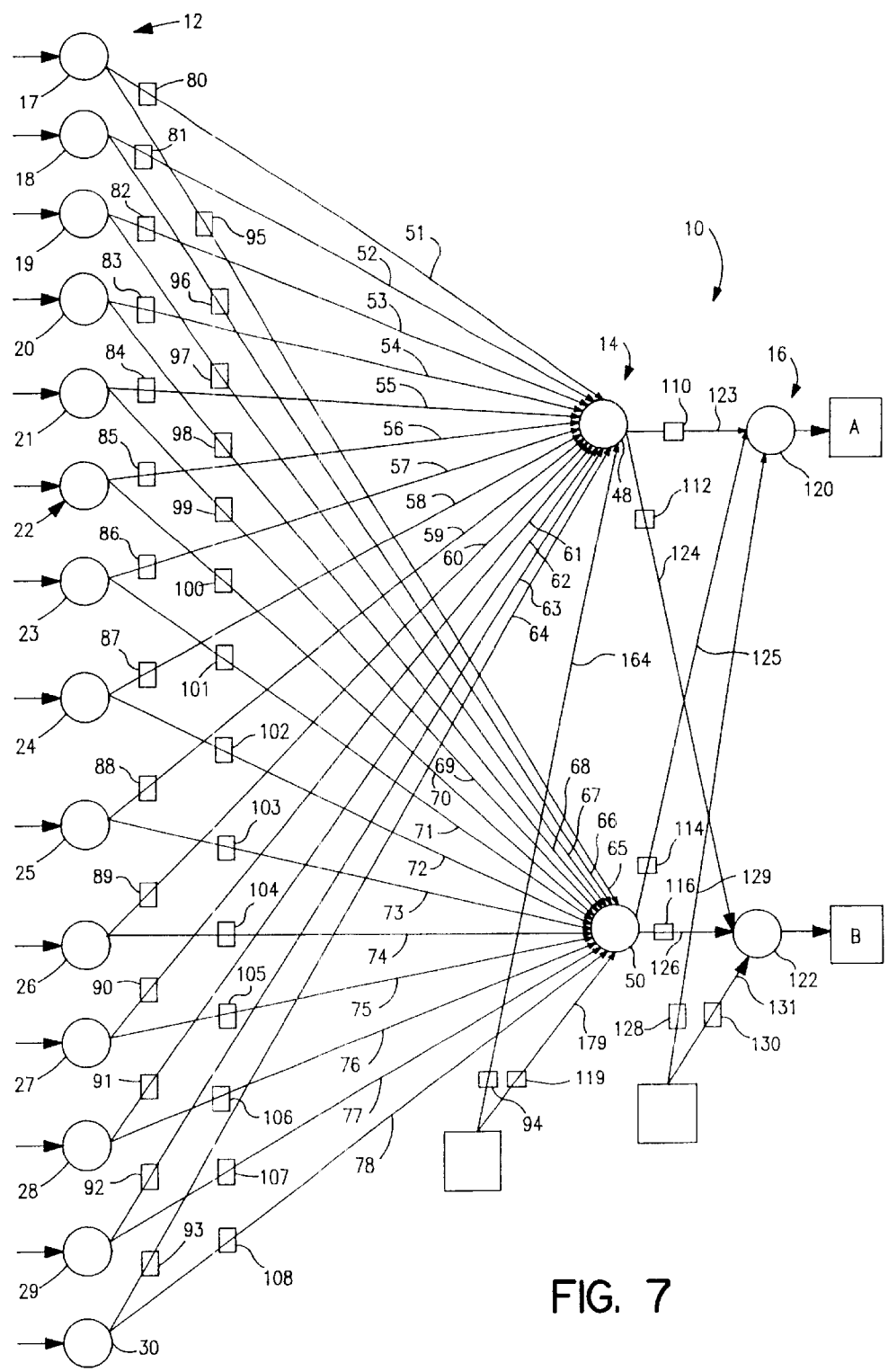
FIG. 7 is a schematic diagram of a neural network trained on clinical data of the form used for the consensus network of a plurality of neural networks.

FIG. 7 is a schematic diagram of an embodiment of one type of neural network 10 trained on clinical data of the form used for the consensus network (FIG. 10) of a plurality of neural networks. The structure is stored in digital form, along with weight values and data to be processed in a digital computer. This first type neural network 10 contains three layers, an input layer 12, a hidden layer 14 and an output layer 16. The input layer 12 has fourteen input preprocessors 17–30, each of which is provided with a normalizer (not shown) which generates a mean and standard deviation value to weight the clinical factors which are input into the input layer. The mean and standard deviation values are unique to the network training data. The input layer preprocessors 17–30 are each coupled to first and second processing elements 48, 50 of the hidden layer 14 via paths 51–64 and 65–78 so that each hidden layer processing element 48, 50 receives a value or signal from each input preprocessor 17–30. Each path is provided with a unique weight based on the results of training on training data. The unique weights 80–93 and 95–108 are non-linearly related to the output and are unique for each network structure and initial values of the training data. The final value of the weights are based on the initialized values assigned for network training. The combination of the weights that result from training comprise a functional apparatus whose description as expressed in weights produces a desired solution, or more specifically a preliminary indicator of a diagnosis for endometriosis.

For the endometriosis test provided herein, the factors used to train the neural network and upon which the output is based are the past history of the disease, number of births, dysmenorrhea, age, pelvic pain, history of pelvic surgery, smoking quantity per day, medication history, number of pregnancies, number of abortions, abnormal PAP/dysplasia, pregnancy hypertension, genital warts and diabetes. These fourteen factors have been determined to be a set of the most influential (greatest sensitivity) from the original set of over forty clinical factors. (Other sets of influential factors have been derived, see, EXAMPLES, above).

The hidden layer 14 is biased by bias weights 94, 119 provided via paths 164 and 179 to the processing elements 48 and 50. The output layer 16 contains two output processing elements 120, 122. The output layer 16 receives input from both hidden layer processing elements 48, 50 via paths 123, 124 and 125, 126. The output layer processing elements 120, 122 are weighted by weights 110, 112 and 114, 116. The output layer 16 is biased by bias weights 128, 130 provided via paths 129 and 131 to the processing elements 120 and 122.

The preliminary indication of the presence, absence or severity of endometriosis is the output pair of values A and B from the two processing elements 120, 122. The values are always positive between zero and one. One of the indicators is indicative that endometriosis is present. The other one of the indicators is indicative that endometriosis is absent. While the output pair A, B provide generally valid indication of the disease, a consensus network of trained neural networks provides a higher confidence index.

Figure 10:
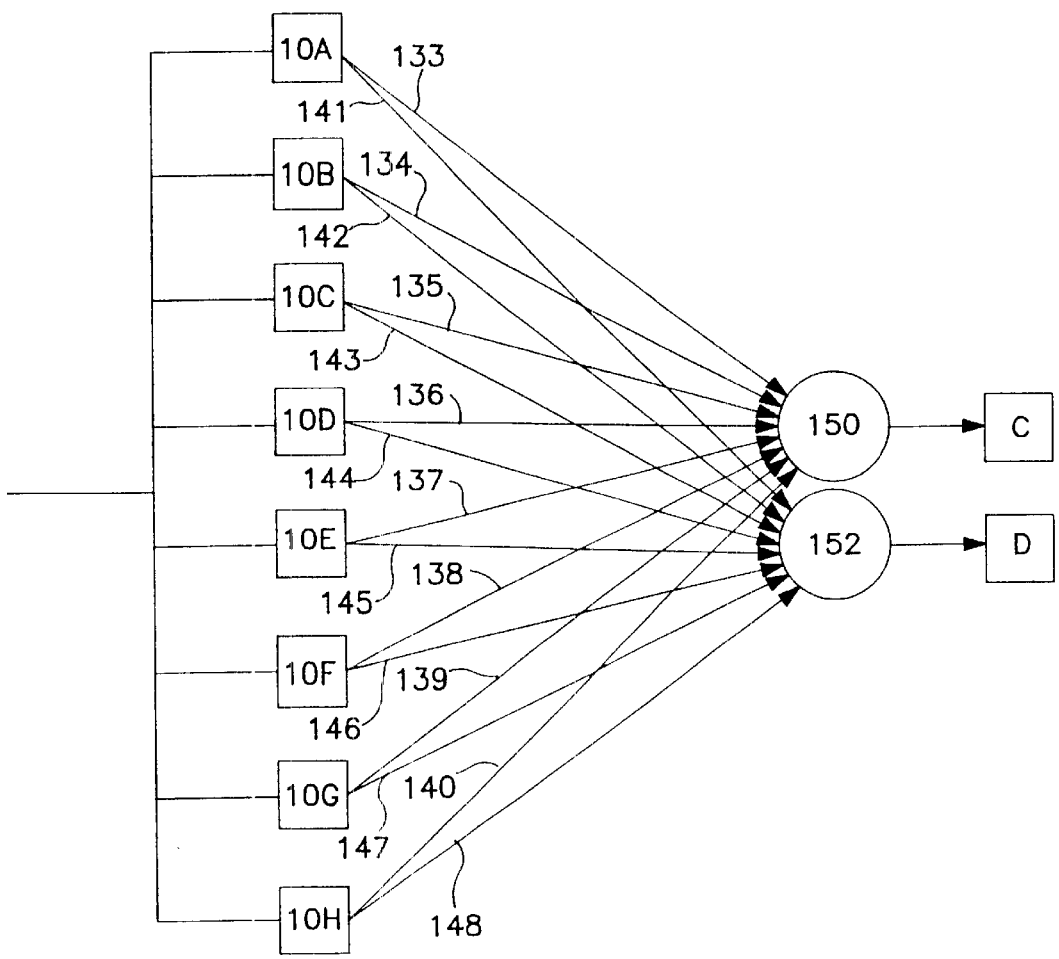
FIG. 10 is a schematic diagram of a consensus network of eight neural networks using either the first or second embodiment of the neural network.

Referring to FIG. 10, a final indicator pair C, D is based on an analysis of a consensus of preliminary indicator pairs from a plurality, specifically eight, trained neural networks 10A–10H (FIG. 10). Each preliminary indicator pair A, B is provided to one of two consensus processors 150, 152. via paths 133–140 and 141–148. The first consensus processor 150 processes all positive indicators. The second consensus processor 152 processes all negative indicators. Each consensus processor 150, 152 is an averager, i.e., it merely forms a linear combination, such as an average, of the collection of like preliminary indicator pairs A, B. The resultant confidence indicator pair is the desired result, where the inputs are the set of clinical factors for the patient under test.

Figure 9:
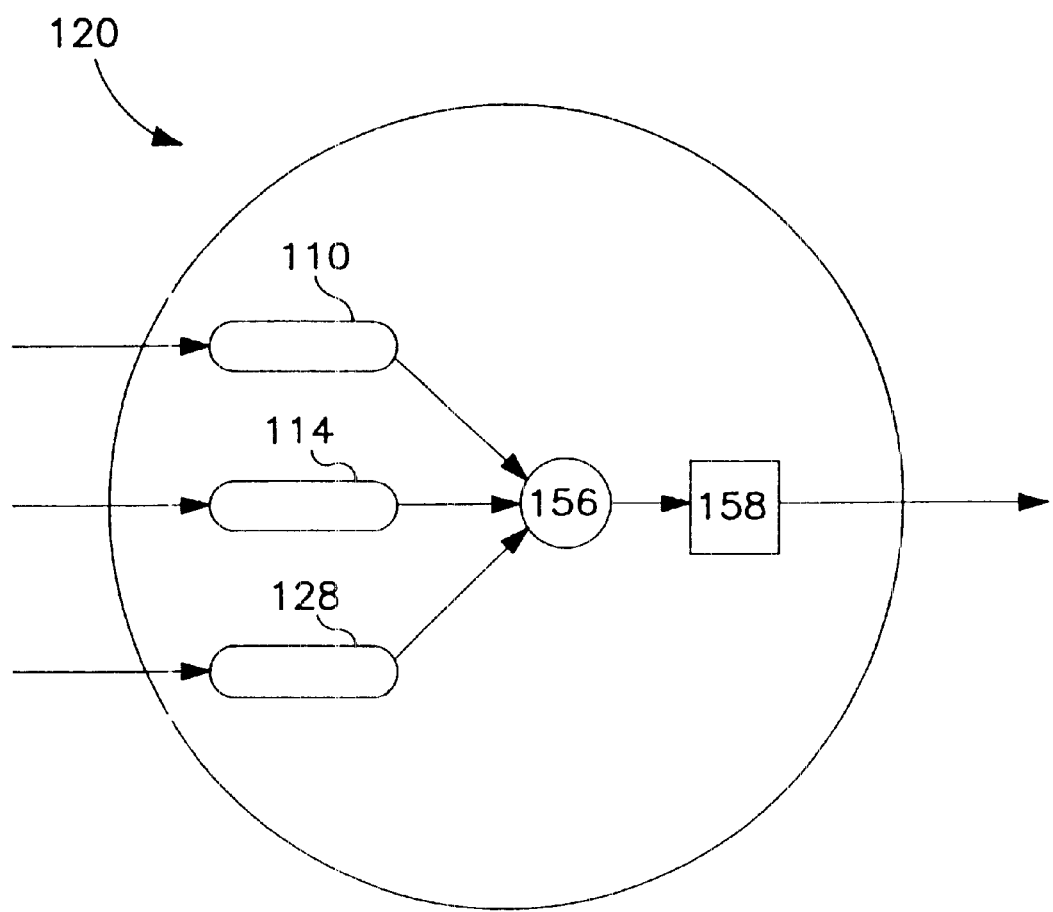
FIG. 9 is a schematic diagram of a processing element at each node of the neural network.

FIG. 9 illustrates a typical processor element 120. Similar processors 48 and 50 have more input elements, and processor element 122 is substantially identical. Typical processor element 120 comprises a plurality of weight multipliers 110, 114, 128 on respective input paths (numbering in total herein 15, 16 or 3 per element and shown herein as part of the processor element 120). The weighted values from the weight multipliers are coupled to a summer 156. The summer 156 output is coupled to an activation function 158, such as a sigmoid transfer function or an arctangent transfer function. The processor elements can be implemented as dedicated hardware or in a software function.

A sensitivity analysis can be performed to determine the relative importance of the clinical factors. The sensitivity analysis is performed on a digital computer as follows: A trained neural network is run in the forward mode (no training) for each training example (input data group for which true output is known or suspected). The output of the network for each training example is then recorded. Thereafter, the network is rerun with each input variable being replaced by the average value of that input variable over the entire training example. The difference in values for each output is then squared and summed (accumulated) to obtain individual sums.

This sensitivity analysis process is performed for each training example. Each of the resultant sums is then normalized according to conventional processes so that if all variables contributed equally to the single resultant output, the normalized value would be 1.0. From this information, the normalized value can be ranked in order of importance.

In analysis of clinical data, it was determined that the order of sensitivity of factors for this neural network system are the past history of the disease, number of births, dysmenorrhea, age, pelvic pain, history of pelvic surgery, smoking quantity per day, medication history, number of pregnancies, number of abortions, abnormal PAP/dysplasia, pregnancy hypertension, genital warts and diabetes.

A specific neural network system has been trained and has been found to be an effective diagnostic tool. The neural network system, as illustrated by FIGS. 7 and 10, is described as follows:

Weights, in order of identification and not in order of sensitivity:

0. Bias
1. Age

2. Diabetes
3. Pregnancy hypertension
4. Smoking Packs/Day
5. #Pregnancies
6. #Births
7. #Abortions
8. Genital Warts
9. Abnormal PAP/Dysplasia
10. History of Endometriosis
11. History of Pelvic Surgery
12. Medication History
13. Pelvic Pain
14. Dysmenorrhea are as follows for each of eight of the first type of neural networks 10:

First neural network A:

| Node\weight | 1st Hidden Layer | 2nd Hidden Layer | 1st Output Layer | 2nd Output Layer |
|---|---|---|---|---|
| 0 | 0.15 | 0.77 | −0.12 | 0.12 |
| 1 | −1.19 | 2.25 | −0.44 | 0.44 |
| 2 | −0.76 | −2.30 | 0.66 | −0.65 |
| 3 | 3.01 | −1.48 | | |
| 4 | 1.81 | −0.85 | | |
| 5 | 1.87 | 0.27 | | |
| 6 | 3.56 | −1.70 | | |
| 7 | −0.48 | −0.47 | | |
| 8 | 1.33 | 0.84 | | |
| 9 | −1.96 | −6.19 | | |
| 10 | −4.45 | 0.50 | | |
| 11 | 1.36 | −0.95 | | |
| 12 | −1.61 | 0.40 | | |
| 13 | −1.97 | 2.38 | | |
| 14 | −0.91 | 1.86 | | |

First Neural Network B:

| Node/Weight | 1st Hidden Layer | 2nd Hidden Layer | 1st Output Layer | 2nd Output Layer |
|---|---|---|---|---|
| 0 | −0.16 | −1.62 | 0.70 | −0.70 |
| 1 | −3.30 | 0.79 | −0.69 | 0.69 |
| 2 | 0.85 | 0.45 | −0.65 | 0.65 |
| 3 | 1.00 | 2.14 | | |
| 4 | 1.00 | 3.82 | | |
| 5 | −0.81 | 3.93 | | |
| 6 | 1.57 | 3.96 | | |
| 7 | −1.40 | 2.27 | | |
| 8 | 0.46 | −0.54 | | |
| 9 | 1.16 | 1.51 | | |
| 10 | −0.80 | −4.76 | | |
| 11 | −0.01 | 2.83 | | |
| 12 | −1.19 | 0.74 | | |
| 13 | −1.10 | −0.43 | | |
| 14 | −2.29 | −0.17 | | |

First Neural Network C

| Node\weight/ | 1st Hidden Layer | 2nd Hidden Layer | 1st Output Layer | 2nd Output Layer |
|---|---|---|---|---|
| 0 | 0.94 | 0.77 | 0.10 | −0.10 |
| 1 | 1.43 | 3.31 | −0.90 | 0.90 |
| 2 | 0.30 | −1.48 | 0.87 | −0.87 |
| 3 | 1.17 | −0.83 | | |
| 4 | 2.11 | 0.60 | | |
| 5 | −1.16 | −2.09 | | |
| 6 | 1.033 | −1.39 | | |
| 7 | −0.68 | −0.40 | | |
| 8 | −0.88 | −0.19 | | |
| 9 | 0.31 | −0.89 | | |
| 10 | −1.74 | 1.36 | | |
| 11 | 1.62 | 0.59 | | |
| 12 | −1.49 | −1.11 | | |
| 13 | −1.05 | 0.26 | | |
| 14 | −0.41 | 1.036 | | |

First Neural Network D

| Node\weight | 1st Hidden Layer | 2nd Hidden Layer | 1st Output Layer | 2nd Output Layer |
|---|---|---|---|---|
| 0 | 1.08 | −0.03 | −1.43 | 1.30 |
| 1 | 1.27 | −0.58 | 1.39 | 1.28 |
| 2 | −0.89 | −0.46 | 1.28 | 1.17 |
| 3 | −1.00 | −0.94 | | |
| 4 | −1.74 | 0.73 | | |
| 5 | −0.40 | 0.10 | | |
| 6 | −1.38 | 0.55 | | |
| 7 | 1.26 | −0.79 | | |
| 8 | 1.06 | −0.10 | | |
| 9 | 0.66 | −1.36 | | |
| 10 | 0.71 | 1.01 | | |
| 11 | −0.57 | 0.00 | | |
| 12 | 0.67 | −0.38 | | |
| 13 | 1.89 | −0.49 | | |
| 14 | −0.90 | 1.57 | | |

First Neural Network E

| Node\Weight | 1st Hidden Layer | 2nd Hidden Layer | 1st Output Layer | 2nd Output Layer |
|---|---|---|---|---|
| 0 | 0.14 | −3.93 | 0.46 | −0.46 |
| 1 | −2.12 | −1.07 | −0.52 | 0.51 |
| 2 | 8.36 | 1.16 | −0.80 | 0.82 |
| 3 | 1.02 | 1.39 | | |
| 4 | 1.79 | 1.01 | | |
| 5 | 0.31 | −1.08 | | |
| 6 | 2.87 | 2.33 | | |
| 7 | 0.84 | 0.76 | | |
| 8 | −1.24 | −0.51 | | |
| 9 | −1.75 | −0.31 | | |
| 10 | −2.98 | −1.92 | | |
| 11 | 1.72 | 0.59 | | |
| 12 | −1.22 | 0.06 | | |

-continued

First Neural Network E

| Node\Weight | 1st Hidden Layer | 2nd Hidden Layer | 1st Output Layer | 2nd Output Layer |
|---|---|---|---|---|
| 13 | −2.47 | −0.76 | | |
| 14 | −1.14 | −1.44 | | |

First Neural Network F

| Node\weight | 1st Hidden Layer | 2nd Hidden Layer | 1st Output Layer | 2nd Output Layer |
|---|---|---|---|---|
| 0 | −1.19 | 0.82 | 0.68 | −0.68 |
| 1 | −2.93 | 0.19 | −0.67 | 0.67 |
| 2 | 1.19 | 0.72 | −0.58 | 0.59 |
| 3 | 6.85 | 0.83 | | |
| 4 | 1.08 | 0.59 | | |
| 5 | 0.66 | 0.07 | | |
| 6 | 1.65 | 1.06 | | |
| 7 | −0.28 | 0.51 | | |
| 8 | −1.63 | 1.04 | | |
| 9 | −1.15 | 1.47 | | |
| 10 | −0.80 | −1.97 | | |
| 11 | 0.43 | 0.97 | | |
| 12 | −0.13 | −0.91 | | |
| 13 | −3.10 | 0.15 | | |
| 14 | −2.27 | 0.09 | | |

First Neural Network G

| Node\weight | 1st Hidden Layer | 2nd Hidden Layer | 1st Output Layer | 2nd Output Layer |
|---|---|---|---|---|
| 0 | −1.18 | 1.08 | 0.69 | −0.69 |
| 1 | −2.55 | 1.11 | −0.70 | 0.70 |
| 2 | 0.48 | 0.52 | −0.50 | 0.50 |
| 3 | −1.40 | 1.41 | | |
| 4 | 1.11 | 0.55 | | |
| 5 | −0.28 | −0.48 | | |
| 6 | 2.33 | −0.23 | | |
| 7 | 0.33 | 0.44 | | |
| 8 | −1.92 | −1.23 | | |
| 9 | 0.99 | 0.77 | | |
| 10 | −1.41 | −2.96 | | |
| 11 | 0.68 | 1.40 | | |
| 12 | −0.28 | −0.28 | | |
| 13 | −1.66 | −0.64 | | |
| 14 | −0.79 | −2.38 | | |

First Neural Network H

| Node\weight | 1st Hidden Layer | 2nd Hidden Layer | 1st Output Layer | 2nd Output Layer |
|---|---|---|---|---|
| 0 | 15.74 | −2.48 | 0.017 | −0.75 |
| 1 | −0.76 | −2.49 | 0.41 | 0.34 |
| 2 | −0.91 | 0.99 | −0.84 | 0.85 |
| 3 | −1.13 | 1.97 | | |
| 4 | −0.75 | 2.41 | | |
| 5 | −0.66 | 1.51 | | |
| 6 | −0.83 | 1.01 | | |
| 7 | 1.03 | −0.26 | | |
| 8 | 0.75 | −0.76 | | |
| 9 | −0.48 | 2.00 | | |
| 10 | −0.48 | −5.03 | | |
| 11 | 2.01 | 1.77 | | |
| 12 | −0.015 | −0.77 | | |
| 13 | 0.25 | −2.29 | | |
| 14 | 1.11 | −2.01 | | |

Normalized Observation Value For First Type Neural Networks

| Mean | Standard Deviation |
|---|---|
| −0.000000 | 1.000000 |
| 0.01 | 0.08 |
| 0.01 | 0.09 |
| 0.16 | 0.37 |
| 1.09 | 1.39 |
| 0.55 | 0.94 |
| 0.54 | 0.93 |
| 0.01 | 0.10 |
| 0.03 | 0.17 |
| 0.23 | 0.42 |
| 0.65 | 0.48 |
| 0.39 | 0.49 |
| 0.19 | 0.39 |
| 0.72 | 0.45 |

Figure 8:
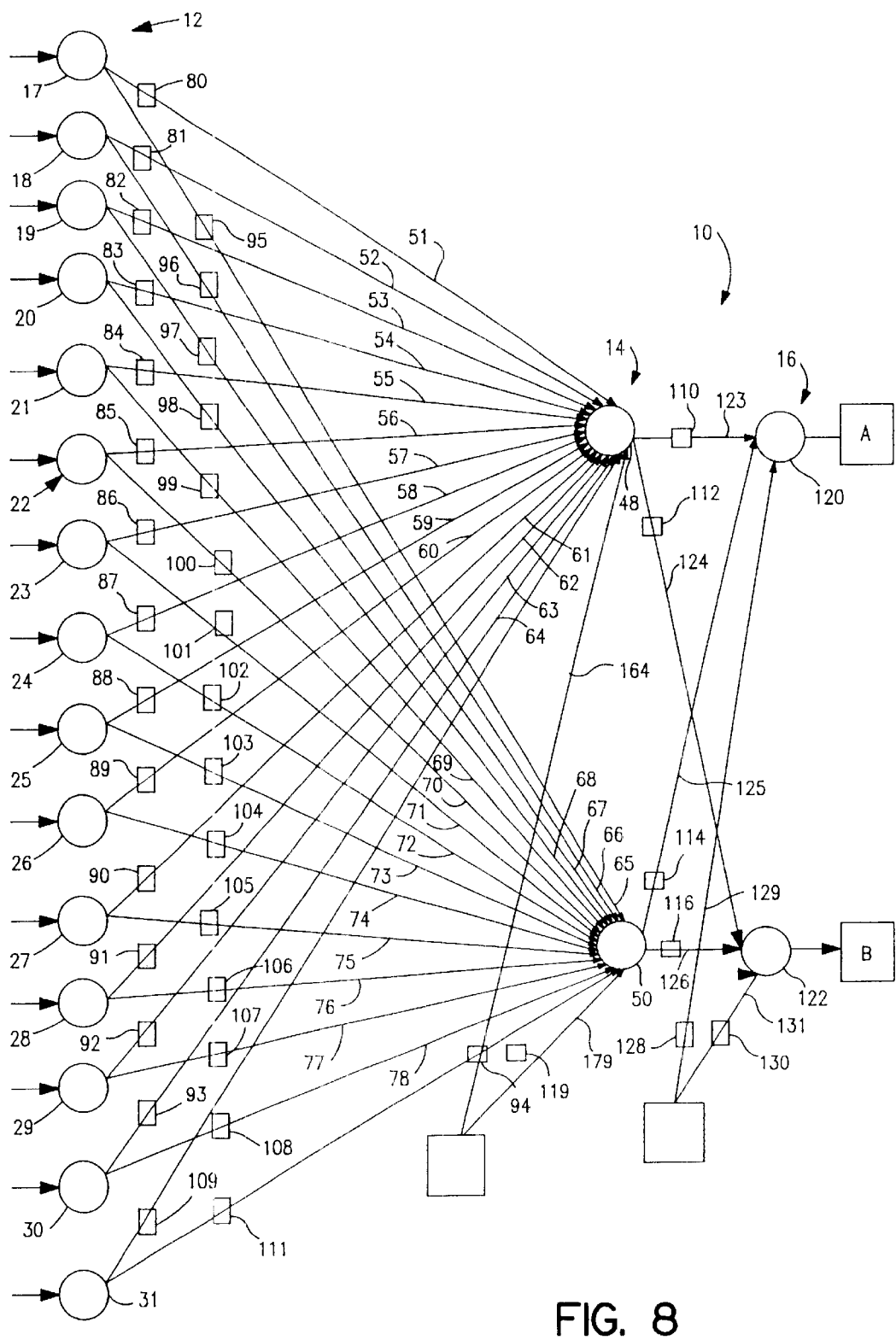
FIG. 8 is a schematic diagram of a second embodiment of a neural network trained on clinical data augmented by test results data of the form used for the consensus of eight neural networks.

Further, as provided herein, the results of biochemical tests, such as tests according to the ELISA format test, may be used to produce trained augmented neural network systems to produce a relatively higher confidence level in terms of sensitivity and specificity. These second type neural networks are illustrated in FIG. 8. The numbering is identical to FIG. 7, except for the addition of a node 31 in the input layer 12 and a pair of weights 109 and 111. All weights, however, in the network change upon training with the additional biochemical result. The exact weight set is dependent on the specific biochemical test training example.

The training system provided herein may be used. Alternative training techniques may also be used (see, e.g, Baxt, "Use of an Artificial Neural Network for the Diagnosis of Myocardial Infarction," *Annals of Internal Medicine* 115, p.843 (Dec. 1, 1991); "Improving the Accuracy of an Artificial Neural Network Using Multiple Differently Trained Networks," *Neural Computation* 4, p. 772 (1992)).

In evaluating the test results, it was noted that a high score correlated with presence of disease, a low score correlated with absence of the disease, and extreme scores raised confidence, while midrange scores reduced confidence. The presence of endometriosis was indicated by an output of 0.6 or above, and its absence by 0.4 or less. It was also noted that higher relative scores correlated with higher relative severity of the disease. The methods herein, minimize the number of patients that require further, often surgical, procedures to establish the presence, absence or severity of the disease condition.

Since modifications will be apparent to those of skill in this art, it is intended that this invention be limited only by the scope of the appended claims.

APPENDICES I–III

Copyright (c) 1997

Appendix I

```
/*      Copyright (c) 1991–1995 Duane DeSieno
/ ***************************** END TRAIN.C************************
void FindVariables ()
{
short x,n,i,k;
long nIn;
long NumPasses;
struct ddnet FAR *pnet;
float HHUGE *TrnData;
FILE *fLog;
FILE *fp;
FILE *fEnum;
    /* load the structures */
    ddget_struct (NetNum, &pnet);
    /* load the root network parameters *7
    sprintf (ParFileName, "%s.par", RootName);
    dd_read_parms (NetNum,ParFileName);
    sprintf (ParFileName, "%s.vsp",RootName);
    sprintf (TrnFileName, "%s.trn",RootName);
    sprintf (LogFileName, "%s.vsl",RootName);
    /* read the partameters for variable selection from .vsp file */
    fp = fopen(ParFileName,"r");
    if(fp == NULL) {
        printf("could not open variable selection parameters file! ");
        return;
    }
    fLog = fopen(LogFileName, "a");
    /* setup initial list */
    for(x=0; x<MaxVars; x++) Impvar[x] = EXCLUDE;
    nAvailVars = 0;
    /* nPartition = 5;          */
    fgets(str,256,fp);
    nPartition = (short)atoi(str);
    fprintf (fLog, "nPartitions = %d\n",nPartition);
    printf("nPartitions = %d\n",nPartition);
    /* nConsensus = 10;         */
    fgets(str,256,fp);
    nConsensus = (short)atoi(str);
    fprintf (fLog, "nConsensus = %d\n", nConsensus)
    printf("nConsensus = %d\n",nConsensus);
    /* nTop = 10;               */
    fgets(str,256,fp)
    nTop = (short)atoi(str);
    fprintf (fLog, "nTop = %d\n",nTop);
    printf("nTop = %d\n",nTop);
    /* pnet->Trainsize = 510; */
    fgets (str,256,fp);
    pnet->TrainSize = atoi(str);
    fprintf(fLog, "TrainSize = %ld\n",pnet->TrainSize);
    printf("TrainSize = %ld\n",pnet->TrainSize);
    /* pnet->Sigma[0] = (REAL)500; */
    fgets(str,256,fp);
    pnet->Sigma[0] = (REAL)atoi(str);
    fprintf (fLog, "report every %d passes\n", (int)pnet->Sigma[0];
    printf("report every %d passes\n", (int)pnet->Sigma[0];
    /* NumPasses = 999L; */
    fgets(str,256,fp)
    NumPasses = atoi(str);
    fprintf (fLog, "NumPasses = %ld\n",NumPasses);
    printf("NumPasses = %ld\n",NumPasses);
    /* setup the ChiSq and SA lists */
    nAvailVars = 0;
    for(n=0; n<pnet->MaxPEs[0]; n++) {
        fgets(str,256,fp);
        ChiSqList[n] = (short)atoi(str);
        /* add code for initial set of vars */
        if(ChiSqList[n] < 0)   {
            ChiSqList [n] = -ChiSqList [n];
            ImpVar[ChiSqList[n]- 1] = NORMUSE;
        }
        SAList[n] = (short)atoi(strchr(str,',')+1);
        /* add code to never use these vars */
        if(SAList[n] < 0)   {
```

-continued

Appendix I

```
            SAList[n] = -SAList [n];
            ImpVar[SAList[n] - 1] = NEVER;
        } else {
            nAvailVars += 1;
        }
        fprintf(fLog,"[%02d] ChiSq = %d SA =
%d\n",n,ChiSqList[n], SAList[n]);
        printf("[%02d] ChiSq = %d SA = %d\n",n,ChiSqList[n],SAList[n]);
    }
    fprintf(fLog, "Availaable Variables = %d\n", nAvailVars);
    for(n=0; n<nConsensus; n++)    {
        fgets(str,256,fp);
        Seeds[n] = atoi(str);
        fprintf(fLog, "[%02d] Seed = %ld\n",n,Seeds [n]);
        printf("[%02d] Seed = %ld\n",n,Seeds [n]);
    }
    fclose(fLog);
    fclose(fp);
    /* load in the training data */
    MaxVars = pnet->MaxPEs [0];
    ImpVarErr = (REAL) 9999.0;
    pnet->TestSize = pnet->TrainSize / (long)nPartition;
    pnet->LearnFlag = 1;
    dd_allocate_net (NetNum);
    /* set up special processing for inputs */
    dd_set_inputs_func(NetNum, partition_get_input_data)
    if( AllocTrn(NetNum, (short)1, (short)pnet->TrainSize+10) < 0) {
        printf("Error Allocating Training set!\n");
        exit (0)
    }
    dd_get_trn_array(NetNum, &TrnData);
    ReadTrnSet(NetNum, (short)1, (short)pnet->TrainSize, TrnFileName);
    pnet->TrainSize -= pnet->TestSize;
        /* copy ImpVar list to InputFunction list */
        fLog = fopen(LogFileName, "a");
        nIn = 0;
        for(x = 0; x < MaxVars; x++)    {
        if(ImpVar[x] == NORMUSE) {
            InputFunction [x] = NORMUSE;
            nIn++;
            printf("1");
            fprintf(fLog, "1");
        } else if(ImpVar[x] == NEVER) {
            InputFunction[x] = EXCLUDE;
            printf C".");
            fprintf(fLog,".");
        } else {
            InputFunction[x] = EXCLUDE;
            printf ("0");
            fprintf(fLog, "0")
        }
    }
    printf(" initial selection \n");
    fprintf(fLog," initial selection \n");
    fclose (fLog);
    if(nIn > 0) {
        /* train consensus of networks on the partitioned data */
        TrainSelection (0,nIn,NumPasses);
        ConsensusErr [0] /= (REAL)nConsensus;
        ConsensusClass[0] /= (REAL)nConsensus;
        printf("Initial Consensus Error %f Class %f \n",
            (float)ConsensusErr [0], (float)ConsensusClass [0]);
        fLog = fopen(LogFileName,"a")
        fprintf(fLog,"Initial Consensus Error %f Class %f \n",
            (float)ConsensusErr [0], (float)ConsensusClass [0]);
        fclose(fLog);
        ImpVarErr = ConsensusErr[0]
    }
/* open enumeration file for reading */
fEnum = fopen("Enum.1st","r");
if(fEnum != NULL) {
    while(fgets(str,256,fEnum) != 0) {
        /* generate the combination from the string */
        x = 0;
        for(k = 0; k < MaxVars; k++) {
            if(str[k] =='0') {
                InputFunction[k] = EXCLUDE;
```

Appendix I

```
                    printf("0")
            } else if(str[k] == '1') {
                InputFunction [k] = NORMUSE;
                printf("1");
                x++;
            } else {
                InputFunction [k] = EXCLUDE;
                printf("?")
            }
        }
        printf("\n");
        /* evaluate the combination */
        /* train consensus of networks on the partitioned data */
        TrainSelection (0, (long) (x) ,Numpasses);
        /* statistics */
        ConsensusErr [0] /= (REAL)nConsensus;
        ConsensusClass[0] /= (REAL) nConsensus;
        fLog = fopen(LogFileName, "a");
        for(i = 0; i < MaxVars; i++) {
            if(InputFunction[i] == NORMUSE) {
                printf("%2d,",(int) (i+1));
                fprintf(fLog, "%2d,", (int) (i+1));
            }
        }
            printf("Consensus Error %f Class %f \n",
                (float) ConsensusErr[0], (float) ConsensusClass [0]);
            fprintf(fLog,"Consensus Error %f Class %f \n",
                (float) ConsensusErr[0], (float) ConsensusClass [0]);
            fclose(fLog);
        }
        fclose(fEnum);
    }
#ifdef NOT
    for(x = 1; x <= nAvailVars; x++) {
        /* generate x at a time combinations */
        /* initialize the array */
        for (i = 0; i < x; i++) {
            NewVar[i]= i;
        }
        /* iterate through the combinations */
        do {
            /* set up InputFunction[] from NewVar[]*/
            n = 0;
            k = 0;
            for(i = 0; i < MaxVars; i++) {
                InputFunction[i] = NORMUSE; /* EXCLUDE; */
                if(ImpVar[i] == NEVER) {
                    InputFunction[i] = EXCLUDE;
                    continue;
                }
                if(k < x && NewVar[k] == n) {
                    InputFunction[i] EXCLUDE; /* NORMUSE; */
                    k += 1;
                }
                n += 1;
            }
            /* evaluate the combination */
            /* train consensus of networks on the partitioned data */
            TrainSelection(0, (long) (nAvailVars - x) ,Numpasses);
            /* statistics */
            ConsensusErr[0] /= (REAL)nConsensus;
            ConsensusClass[0] /= (REAL)nConsensus;
            fLog = fopen(LogFileName,"a");
            for(i = 0; i < MaxVars; i++)
                if(InputFunction[i] == NORMUSE) {
                    printf("%2d,", (int) (i+1));
                    fprintf(fLog, "%2d,",(int) (i+1));
                }
            }
            printf("Consensus Error %f Class %f \n",
                    (float)ConsensusErr [0], (float)ConsensusClass [0]);
            fprintf(fLog,"Consensus Error %f Class %f \n",
                    (float)ConsensusErr [0], (float)ConsensusClass [0]);
            fclose(fLog);
            /* geneerate next selection */
            for(i = x-1; i >=0; i--) {
                NewVar [i]++;
```

-continued

Appendix I

```
                    for(k = i+1; k < x; k++) {
                        NewVar[k] =NewVar[k-1] + 1;
                    }
                    if(NewVar[x-1] < nAvailVars) {
                        break;
                    }
                }
            } while (NewVar[x-1] < nAvailVars);
        }
else
        /* start the process of generating the important variables */
        do {
            /* training data contains all variables */
            /* use special array for getting inputs to network */
            /* determine the variables to use in the current run
            /* build list from ChiSq and SA */
            nNewVar = 0;
            for(x = 0; x < MaxVars; x++) {
                if(ImpVar[SAList[x]-1] == EXCLUDE) {
                    NewVar [nNewVar] = SAList [x] - (short) 1;
                    ImpVar[SAList[x] - 1] =USED;
                    nNewVar++;
                }
                if(ImpVar[ChiSqList[x] - 1] == EXCLUDE) {
                    NewVar[nNewVar] = ChiSqList [x] - (short) 1;
                    ImpVar[ChiSqList[x] - 1] = USED;
                    nNewVar++;
                }
                if(nNewVar >= nTop) break;
            }
            /* work through the list of new variables */
            f Log = fopen(LogFileName, "a");
            for(n = 0; n < nNewVar; n++)
                /* copy ImpVar list to InputFunction list */
                nIn = 0;
                for(x = 0; x < MaxVars; x++) {
                    if(ImpVar [x] == NORMUSE) {
                        InputFunction [x] = NORMUSE;
                        nIn++;
                        printf("1")
                        fprintf (fLog, "1");
                    } else if(ImpVar [x] == NEVER) {
                        InputFunction [x] = EXCLUDE;
                        printf(".");
                        fprintf(fLog, ".");
                    } else {
                        InputFunction [x] = EXCLUDE;
                        printf("0");
                        fprintf(fLog, "0");
                    }
                }
                InputFunction[NewVar[n]] = NORMUSE;
                nIn++;
            printf("...+ %d\n",NewVar[n] +1);
            fprintf (fLog, "...+ %d\n",NewVar[n] +1);
            fclose(fLog);
                /* train consensus of networks on the partitioned data */
                TrainSelection (n,nIn,NumPasses);
                ConsensusErr [n] /= (REAL)nConsensus;
                ConsensusClass [n]/= (REAL)nConsensus;
                printf("Var %d Consensus Error %f Class %f \n",
(int)NewVar [n] + 1,
                    (float) ConsensusErr [n], (float) ConsensusClass [n]);
                fLog = fopen(LogFileName, "a");
                fprintf(fLog,"Var %d Consensus Error %f Class %f \n",
(int)NewVar [n]+1,
                    (float) ConsensusErr [n], (float) ConsensusClass [n]);
                fclose (fLog)
            }
            /* Test of the list of variables is complete */
            /* Find the best variable based on error */
            BestErr = (REAL)999999.0;
            BestVar = -1;
            for(n=0; n< nNewVar; n++) {
                if(ConsensusErr [n] < BestErr) {
                    BestErr = ConsensusErr [n];
                    BestClass = ConsensusClass [n];
```

-continued

Appendix I

```
                BestVar = NewVar [n];
            }
        }
        /* Is there a variable that improved the ImpVar list Error */
        /* Add the variable to the list of important variables */
        if(BestErr < ImpVarErr) {
            ImpVar[BestVar] = NORMUSE;
            ImpVarErr = BestErr;
            printf("Added %d to Imp Var List Error = %f Class = %f\n",
                (int)BestVar+1, (float) BestErr, (float) BestClass);
            fLog = fopen(LogFileName, "a");
            fprintf(fLog,"Added %d to Imp Var List Error = %f Class =
%f\n",
                (int)BestVari+1, (float)BestErr, (float)BestClass);
            fclose(fLog);
            for(x=0; x<MaxVars; x++)
                /* cleanup from build of new variables list */
                if(ImpVar[x] == USED) ImpVar[x] = EXCLUDE;
            }
        }
    /* if no improvement or no variables remaining, stop */
    } while(BestVar != -1 && nNewVar < 0);
    /* report the list of Important Variables and the Network Error */
    fLog = fopen(LogFileName,"a");
    for(x=0; x<MaxVars; x++) {
        if(ImpVar[x] == NORMUSE) {
            printf("USE [%d]\n", (int)x+1);
            fprintf (fLog, "USE [%d]\n", (int)x+1);
        }
    }
#endif
    fclose(fLog);
    dd_free_net (NetNum);
    if(TrnData != NULL) {
        FreeTrn(NetNum);
        TrnData = NULL;
    }
}
```

Appendix II

Copyright (c) 1991–1995 Adeza Biomedical Corporation

FORM1.FRM - 1

' Neural Network Function Declarations
Declare Function LoadNet% Lib "TKSDLL.DLL" (ByVal Net%, ByVal NetName$)
Declare Function AllocNet% Lib "TKSDL.DLL" (ByVal Net%)
Declare Function FreeNet% Lib "TKSDLL.DLL" (ByVal Net%)
Declare Function Readweights% Lib "TKSDLL.DLL" (ByVal Net%, ByVal NetName$)
Declare Function LoadWeights% Lib "TKSDLL.DLL" (ByVal Net%, ByVal NetName$)
Declare Function ReadParms% Lib "TKSDLL.DLL" (ByVal Net%, ByVal NetName$)
Declare Function LoadParms% Lib "TKSDLL.DLL" (ByVal Met%, ByVal NetName$)
Declare Function WriteWeights% Lib "TKSDLL.DLL" (ByVal Net%, ByVal NetName$)
Declare Function SaveWeights% Lib "TKSDLL.DLL" (ByVal Net%, ByVal NetName$)
Declare Function WriteParms% Lib "TKSDLL.DLL" (ByVal Net%, ByVal NetName$)
Declare Function SaveParms% Lib "TKSDLL.DLL" (ByVal Net%, ByVal NetName$)
Declare Function PutInput# Lib "TKSDLL.DLL" (ByVal Net%, ByVal nIn%, pIn#)
Declare Function PutState# Lib "TKSDLL.DLL" (ByVal Net%, ByVal Layer%, ByVal nSt%, pSt#)
Declare Function PutOutput# Lib "TKSDLL.DLL" (ByVal Net%, ByVal nSt%, pSt#)
Declare Function PutTrn# Lib "TKSDLL.DLL" (ByVal Net%, ByVal nIn%, pIn#)
Declare Function PutWeight# Lib "TKSDLL.DLL" (ByVal Net%, ByVal Layer%, ByVal pe%, ByVal nWt%, pWt#)
Declare Function PutParm# Lib "TKSDLL.DLL" (ByVal Net%, ByVal ParmName$, ByVal Layer%, pWt#)
Declare Function GetInput# Lib "TKSDLL.DLL" (ByVal Net%, ByVal nIn%)
Declare Function GetState# Lib "TKSDLL.DLL" (ByVal Net%, ByVal Layer%, ByVal nSt%)
Declare Function GetOutput# Lib "TKSDLL.DLL" (ByVal Net%, ByVal nSt%)
Declare Function GetWeight# Lib "TKSDLL.DLL" (ByVal Net%, ByVal Layer%, ByVal pe -continued

```
%, ByVal nWt%)
Declare Function GetParm# Lib "TKSDLL.DLL" (ByVal Net%, ByVal ParmName$, ByVal L
ayer%)
Declare Function GetTrn# Lib "TKSDLL.DLL" (ByVal Net%, ByVal nIn%)
Declare Function GetNumInputs% Lib "TKSDLL.DLL" (ByVal Net%)
Declare Function GetNumOutputs% Lib "TKSDLL.DLL" (ByVal Net%)
Declare Function GetNumPEs% Lib "TKSDLL.DLL" (ByVal Net%, ByVal Layer%)
Declare Function GetNumLayers% Lib "TKSDLL.DLL" (ByVal Net%)
Declare Function InitializeWts% Lib "TKSDLL.DLL" (ByVal Net%)
Declare Function TrainNet% Lib "TKSDLL.DLL" (ByVal Net%)
Declare Function IterateNet% Lib "TKSDLL.DLL" (ByVal Net%)
Declare Function IsNetAvail% Lib "TKSDLL.DLL" (ByVal Net%)
Declare Function PutGrade% Lib "TKSDLL.DLL" (ByVal Net%, pGrade#)
Declare Function GetWtsGrade# Lib "TKSDLL.DLL" (ByVal Net%)
Declare Function AdjustWts% Lib "TKSDLL.DLL" (ByVal Net%)
Declare Function GetBestWts% Lib "TKSDLL.DLL" (ByVal Net%)
Declare Function AllocTrn% Lib "TKSDLL.DLL" (ByVal Net%, ByVal InclDesired%, ByV
al NumExamples%)
Declare Function FreeTrn% Lib "TKSDLL.DLL" (ByVal Net%)
Declare Function PutTrnData# Lib "TKSDLL.DLL" (ByVal Net%, ByVal InclDesired%, B
yVal Example%, ByVal Offset%, pVal#)
Declare Function GetTrnData# Lib "TKSDLL.DLL" (ByVal Net%, ByVal InclDesired%, B
yVal Example%, ByVal Offset%)
Declare Function ReadTrnSet% Lib "TKSDLL.DLL" (ByVal Net%, ByVal InclDesired%, B
yVal NumExamples%, ByVal NetName$)
Declare Function BatchTrain% Lib "TKSDLL.DLL" (ByVal Net%, ByVal MaxPasses%, pTa
rgetError#)
FORM1.FRM - 2

'Variables
Dim Age
Dim NetAge#
Dim NetPacks#
Dim NetBirth#
Dim NetPreg#
Dim NetAbort#
Dim NetDiabetes#
Dim NetPregHTN#
Dim NetHxEndo#
Dim NetDysmen#
Dim NetPelPain#
Dim NetPAP#
Dim NetHxPelSur#
Dim NetMedHx#
Dim NetGenWarts#
Dim NetElisa#
Sub RunNets ()
    Con1 = 0
    Con2 = 0
    If NetElisa# = 0# Then
        NetAge# = (Age - 32.07688) / 5.226876
        For i = 0 To 7
            a = PutInput(i, 1, NetAge#)
            a = PutInput(i, 2, NetDiabetes#)
            a = PutInput(i, 3, NetPregHTN#)
            a = PutInput(i, 4, NetPacks#)
            a = PutInput(i, 5, NetPreg#)
            a = PutInput(i, 6, NetBirth#)
            a = PutInput(i, 7, NetAbort#)
            a = PutInput(i, 8, NetGenWarts#)
            a = PutInput(i, 9, NetPAP#)
            a = PutInput(i, 10, NetHxEndo#)
            a = PutInput(i, 11, NetHxPelSur#)
            a = PutInput(i, 12, NetMedHx#)
            a = PutInput(i, 13, NetPelPain#)
            a = PutInput(i, 14, NetDysmen#)
            a = IterateNet(i)
            Con1 = Con1 + GetState(i, 3, 1)
            Con2 = Con2 + GetState(i, 3, 2)
        Next i
    Else
        NetAge# = Age
        For i = 8 To 15
            a = PutInput(i, 1, NetAge#)
            a = PutInput(i, 2, NetDiabetes#)
            a = PutInput(i, 3, NetPregHTN#)
            a = PutInput(i, 4, NetPacks#)
            a = PutInput(i, 5, NetPreg#)
            a = PutInput(i, 6, NetBirth#)
```

-continued

```
            a = PutInput(i, 7, NetAbort#)
            a = PutInput(i, 8, NetGenWarts#)
FORM1.FRM - 3 a = PutInput(i, 9, NetPAP#)
            a = PutInput(i, 10, NetHxEndo#)
            a = PutInput(i, 11, NetHxPelSur#)
            a = PutInput(i, 12, NetMedHx#)
            a = PutInput(i, 13, NetPelPain#)
            a = PutInput(i, 14, NetDysmen#)
            a = PutInput(i, 15, NetElisa#)
            a = IterateNet(i)
            Con1 = Con1 + GetState(i, 3, 1)
            Con2 = Con2 + GetState(i, 3, 2)
        Next i
    End If
    Con1 = Con1 / 8
    Con2 = Con2 / 8
    Text2.Text = Con1
    Text4.Text = Con2
    'Generate Score
    If NetElisa# = 0# Then
        Score = (Con1 − Con2) * 25
    Else
        Score = (Con1 − Con2) * 18
    End If
    Text8.Text = Score
End Sub
Sub Check1_Click ()
    NetDiabetes# = 1# - NetDiabetes#
    RunNets
End Sub
Sub Check2_Click ()
    NetDysmen# = 1# - NetDysmen#
    RunNets
End Sub
Sub Check3_Click ()
    NetPAP# = 1# - NetPAP#
    RunNets
End Sub
Sub Check4_Click ()
    NetPelPain# = 1# - NetPelPain#
    RunNets
End Sub
Sub Check5_Click ()
    NetHxPelSur# = 1# - NetHxPelSur#
    RunNets
End Sub
Sub Check6_Click ()
    NetMedHx# = 1# - NetMedHx#
    RunNets
FORM1.FRM - 4

End Sub
Sub Check7_Click ()
    NetGenWarts# = 1# - NetGenWarts#
    RunNets
End Sub
Sub Check8_Click ()
    NetPregHTN# 1# - NetPregHTN#
    RunNets
End Sub
Sub Check9_Click ()
    NetHxEndo# = 1# - NetHxEndo#
    RunNets
End Sub
Sub Command1_Click ()
    Age = 30
    Text1.Text = Age
    NetAge# = (Age - 32.07688) / 5.226876
    NetPacks# = 0#
    Text3.Text = NetPacks#
    Text2.Text = "Not Run"
    Text4.Text = "Not Run"
    NetPreg# = 0#
    Text5.Text = NetPreg#
    NetBirth#= 0#
    Text6.Text = NetBirth#
    NetAbort# = 0#
```

```
        Text7.Text = NetAbort#
        NetElisa# = 0#
        Text7.Text = NetElisa#
        NetDiabetes# = 0#
        Check1.Value = 0
        NetPregHTN# = 0#
        Check8.Value = 0
        NetHxEndo#= 0#
        Check9.Value = 0
        NetDysem# = 0#
        Check2.Value = 0
        NetPelPain# = 0#
        Check4.Value = 0
        NetPAP# = 0#
        Check3.Value = 0
        NetHxPelSur# = 0#
        Check5.Value = 0
        NetMedHx# = 0#
        Check6.Value = 0
        NetGenWarts# = 0#
        Check7.Value = 0
End Sub
FORM1.FRM - 5

Sub Command2_Click ()
    End
End Sub
Sub Form_Load ()
a = Load.Net(0, "pat07_0")
If a <> 0 Then GoTo mess
a = LoadNet(1, "pat07_1")
If a <> 1 Then GoTo mess
a = LoadNet(2, "pat07_2")
If a <> 2 Then GoTo mess
a = LoadNet(3, "pat07_3")
If a <> 3 Then GoTo mess
a = LoadNet(4, "pat07_4")
If a <> 4 Then GoTo mess
a = LoadNet(5, "pat07_5")
If a <> 5 Then GoTo mess
a = LoadNet(6, "pat07_6")
If a <> 6 Then GoTo mess
a = LoadNet(7, "pat07_7")
If a <> 7 Then GoTo mess
a = LoadNet(8, "crfe12_0")
If a <> 8 Then GoTo mess
a = LoadNet(9, "crfe12_1")
If a <> 9 Then GoTo mess
a = LoadNet(10, "crfe12_2")
If a <> 10 Then GoTo mess
a = LoadNet(11, "crfe12_3")
If a <> 11 Then GoTo mess
a = LoadNet (12, "crfe12_4")
If a <> 12 Then GoTo mess
a = LoadNet(13, "crfe12_5")
If a <> 13 Then GoTo mess
a = LoadNet(14, "crfe12_6")
If a <> 14 Then GoTo mess
a = LoadNet(15, "crfe12_7")
mess:
    If a <> 15 Then Text4.Text = a + "NO GOOD"
    'initialize variables
    Age = 30
    Text1.Text = Age
    NetAge# = (Age - 32.07688) / 5.226876
    NetPacks# = 0#
    Text3.Text = NetPacks4#
    Text2.Text = "Not Run"
    Text4.Text = "Not Run"
    NetPreg# = 0#
    Text5.Text = NextPreg#
    NetBirth# = 0#
    Text6.Text = NetBirth#
    NetAbort# = 0#
    Text7.Text = NetAbort#
    NetElisa# = 0#
    Text9.Text = NetElisa#
```

-continued

FORM1.FRM - 6

```
    NetDiabetes# = 0#
    NetPregHTN# = 0#
    NetHxEndo# = 0#
    NetDysmen# = 0#
    NetPelPain# = 0#
    NetHxPelSur# = 0#
    NetMedHx# = 0#
    NetGenWarts# = 0#
End Sub
Sub Text1_Change ()
    Age = Val(Text1.Text)
    RunNets
End Sub
Sub Text1_LostFocus ()
    RunNets
End Sub
Sub Text3_Change ()
    NetPacks# = Val(Text3.Text)
    RunNets
End Sub
Sub Text3_LostFocus ()
    RunNets
End Sub
Sub Text5_Change ()
    NetPreg# = Val(Text5.Text)
    RunNets
End Sub
Sub Text5_LostFocus ()
    RunNets
End Sub
Sub Text6_Change ()
    NetBirth# = Val(Text6.Text)
    RunNets
End Sub
Sub Text6_LostFocus ()
    RunNets
End Sub
Sub Text7_Change ()
    NetAbort# = Val(Text7.Text)
    RunNets
End Sub
Sub Text7_LostFocus ()
    RunNets
End Sub
```

FORM1.FRM - 7

```
Sub Text9_Change ()
    If Val(Text9.Text) <= 0# Then
        NetElisa# = 0#
    Else
        NetElisa# = Log(Val(Text9.Text))
    End If
    RunNets
End Sub
Sub Text9_LostFocus ()
    RunNets
End Sub
```

APPENDIX III

Copyright (c) 1997 Duane DeSieno

```
/***********************************************************************/
/*      aa_nets.h      revised 7/01/95                      */
/* Copyright (c) 1991–1995 Logical Designs Consulting Inc.  */
/***********************************************************************/
/* This include file works for both DLL and DOS environments */
/* The following define determines the floating point precision */
/* Do not change it unless you intend to all source files */
#define USE_DOUBLES
#ifdef USE_DOUBLES
```

-continued

```
#define REAL double
#define SIG_LIMIT 44.0
#else
#define REAL float
#define SIG_LIMIT 30.0
#endif
/* The following prevents multiple inclusion of this header file */
#ifndef __AA_NETS_H__
#define __AA_NETS_H__
/* The following prevents C++ compiler from mangling names */
#ifdef __cplusplus
extern "C" {
#endif /* __cplusplus */
#ifdef __WINDOWS
#include <windows.h>
#endif
#include <stdio.h>
#include <stdlib.h>
#include <math.h>
#include <string.h>
/* Uncomment the following to enable user messages */
#define AA_ENABLE_USER_MESSAGES
#ifdef __WINDOWS
#ifdef __WIN32
#define HUGE
#define EXPORT
#else
#define HUGE _huge
#define EXPORT _export
#endif
#else
typedef unsigned short HANDLE;
#define PASCAL
#ifdef MSC_APPL
#include <malloc.h>
#include <conio.h>
#define HUGE huge
#define FAR _far
#define EXPORT
#endif
#ifdef BC_APPL
#include <alloc.h>
#include <conio.h>
#define FAR
#define HUGE huge
#define EXPORT
#endif
#ifdef SC_APPL
#include <dos.h>
#include <conio.h>
#define FAR
#define HUGE _huge
#define EXPORT
#endif
#ifdef UNIX_APPL
#define FAR
#define HUGE
#define EXPORT
#endif
#ifdef WD32_APPL
#include <conio.h>
#define FAR
#define HUGE
#define EXPORT
#endif
#endif
#define MAX_LAYERS    5
#define NUM_NETS      32
struct ddnet {
    /* Network Description Parameters */
    long    NetArch;                  /* network interconnection arrangement */
    long    nLayers;                  /* The total number of layers in the net */
    long    MaxPEs[MAX_LAYERS];       /* max Processing Elements (for Mallocs) */
    long    nPEs[MAX_LAYERS];         /* number of hidden */
    long    PEFunc[MAX_LAYERS];       /* Processing Element Function */
    long    PETrans[MAX_LAYERS];      /* Processing Element Transfer Function */
    long    oIn[MAX_LAYERS];          /* Offset of Layer Inputs (init routine) */
    long    oWts[MAX_LAYERS];         /* Offset of Weights (from init routine) */
    long    oOut[MAX_LAYERS];         /* Offset of Layer Outputs (init routine) */
```

-continued

```
    long    nIn[MAX LAYERS];        /* count of Layer Inputs (init routine) */
    long    nWts[MAX_LAYERS];       /* total number of weights (init routine) */
    /* Network Training Parameters */
    long    LearnFlag;              /* 0=disable 1=enable */
    long    BatchSize;              /* parameter for batching */
    long    TrainSize;              /* parameter for preprocessing */
    long    TestSize;               /* parameter for preprocessing */
    long    InitWtsFlag;            /* 0=No 1=Initialize weights */
    long    RandSeed;               /* for random number generator */
    long    NetErrorType;           /* kind of error to minimize by net */
    REAL    ErrorTol;               /* Error Tolerance for training */
    REAL    InputNoise;             /* Error Tolerance for training */
    long    nTrialPEs;              /* for growing algorithm, number of trial units */
    long    RcrOpsPerIter;          /* ops per iteration for recurrent nets */
    long    TrnSequence;            /* Order of presentation of training set */
    long    TestWhileTrn; /* controls
            processing fro training and
            testing */
    long    classMethod;            /* Method used to to classification performance measurement
*/
    long        NetRule [MAX_LAYERS];   /* weight adjustment by layer */
    long        IterLimit[MAX_LAYERS];  /* for growing algorithms only */
    REAL        InitWtsVal[MAX_LAYERS]; /* multiplier for grand() */
    REAL        XferOfs[MAX_LAYERS];    /* offset for XferPrime */
    REAL        PESigma[MAX_LAYERS];    /* Initial Sigma for L1, L2, RBF */
    REAL        PEMu[MAX LAYERS];       /* Learning factor for PESigma */
    REAL        Alpha[MAX_LAYERS];      /* learning rule parameters */
    REAL        Beta[MAX_LAYERS];       /* Values dependent on learning rule used */
    REAL        Gamma[MAX_LAYERS];
    REAL        Delta[MAX_LAYERS]
    REAL        Epsilon[MAX_LAYERS];
    REAL        Theta[MAX_LAYERS];
    REAL        Lambda[MAX_LAYERS];
    REAL        Mu[MAX_LAYERS];
    REAL        Sigma[MAX_LAYERS];
    REAL        WtsDecay[MAX_LAYERS];
    /* Network pointers (not all are allocated for a given network) */
    REAL HUGE       *pCurWts;       /* pointer to current wieghts */
    REAL HUGE       *pBestWts;      /* pointer to best wieghts */
    REAL HUGE       *pGateWts;      /* pointer to spare weights */
    REAL HUGE       *pDirwts;       /* pointer to direction wieghts */
    REAL HUGE       *pBiasWts;      /* pointer to bias weights */
    REAL HUGE       *pTempWts;      /* pointer to spare weights */
    REAL HUGE       *pNetSts;       /* pointer to the weighted sums states */
    REAL HUGE       *pAsts;         /* pointer to the states for PE outputs */
    REAL HUGE       *pBSts;         /* pointer to the states for PE outputs */
    REAL HUGE       *pDelSts;       /* pointer to the states deltas */
    REAL HUGE       *pTrnSts;       /* pointer to the training states */
    REAL HUGE       *pErrSts;       /* pointer to the Error stats */
    REAL HUGE       *pPriorErrSts;  /* pointer to the Prior Error stats */
    REAL HUGE       *pErrSumSts;    /* pointer to the Error Sum stats */
    REAL HUGE       *pBiasSts;      /* pointer to the Bias stats */
    REAL HUGE       *pProbSts;      /* pointer to the Prop stats */
    REAL HUGE       *pCovMat;       /* pointer to covariance by output & trial unit */
    REAL HUGE       *pLastCovMat;   /* pointer to prior coy by output & trial unit */
    long HUGE       *poWts;         /* pointer to weights offsets by pe element */
    /* The following is to insure DLL compatibility */
    HANDLE      hCurWts;    /* HANDLE to current wieghts */
    HANDLE      hBestWts;   /* HANDLE to best wieghts */
    HANDLE      hGateWts;   /* HANDLE to spare weights */
    HANDLE      hDirWts;    /* HANDLE to direction wieghts */
    HANDLE      hBiasWts;   /* HANDLE to bias weights */
    HANDLE      hTempWts;   /* HANDLE to spare weights */
    HANDLE      hNetSts;    /* HANDLE to the weighted sums states */
    HANDLE      hASts;      /* HANDLE to the states for PE outputs */
    HANDLE      hBSts;      /* HANDLE to the states for PE outputs */
    HANDLE      hDelSts;    /* HANDLE to the states deltas */
    HANDLE      hTrnSts;    /* HANDLE to the training states */
    HANDLE      hErrSts;    /* HANDLE to the Error stats */
    HANDLE      hPriorErrSts;   /* HANDLE to the Prior Error stats */
    HANDLE      hErrSumSts; /* HANDLE to the Error Sum stats */
    HANDLE      hBiasSts;   /* HANDLE to the Bias stats */
    HANDLE      hProbSts;   /* HANDLE to the Prop stats */
    HANDLE      hCovMat;    /* HANDLE to covariance by output & trial unit */
    HANDLE      hLastCovMat;    /* HANDLE to prior coy by output & trial unit */
    HANDLE      hoWts;      /* HANDLE to weights offsets by pe element */
    /* Network Training Statistics and Globals*/
    long    Iteration;              /* iteration count */
    long    OperMode;
```

-continued

```
    long      TrialPick;
    long      CurCnt[MAX_LAYERS];
    long      TrainingMode;           /* In Training Testing or Sensitivity analysis */
    long      TrnMaxErrSample;        /* Training Example with Maximum Error */
    long      TrnClassCorrect;        /* Training set Correct count */
    long      TstMaxErrSample;        /* Test Example with Maximum Error */
    long      TstClassCorrect;        /* Training set Correct count */
    REAL      TrnError;               /* Training Set Error Statistic */
    REAL      TrnMaxError;            /* Training Set Error Statistic */
    REAL      TrnClassPercent;        /* Training Set Error Statistic */
    REAL      TstError;               /* Test Set Error Statistic */
    REAL      TstMaxError;            /* Test Set Error Statistic */
    REAL      TstClassPercent;        /* Test Set Error Statistic */
    REAL      PETempEMAX LAYERS];     /* Temperature for Hopfield MFA networks */
    REAL      LastVal[MAX_LAYERS];    /* current step size */
    REAL      CurTemp[MAX_LAYERS];
    REAL      CurErr[MAX_LAYERS];     /* to error function value */
    REAL      LastErr[MAX_LAYERS];    /* to error function value */
    REAL      BestErr[MAX_LAYERS];    /* best error value */
};
#ifndef max
#define max(a,b)    (((a)>(b))?(a):(b))
#define min(a,b)    (((a)<(b))?(a):(b))
#endif
#ifndef fabs
#define fabs(a)     (((a)>=0.0)?(a):(-a))
#endif
#ifndef ffsgn
#define ffsgn(a)    (((a)>0.0)?(1.0):(((a)==0.0)?(0.0):(-1.0)))
#endif
/* DEFINES for input layer preprocessing */
#define    NO_PREPROC       0
#define    MEAN_STD         1
#define    MAX_MIN          2
#define    SUM_1            3
#define    SUM_SQ_1         4
/* DEFINES for Network Error form */
#define    MEAN_SQ_ERR         1
#define    MEAN_ABS_ERR        2
#define    HYPER_SQ_ERR        3
#define    BI_HYPER_SQ_ERR     4
#define    MEAN_4PW_ERR        5
#define    CROSS_ENTROPY       6
#define    CLASS_ERR           7
#define    USER_DEFINED        8
/* DEFINES for Network Architecture */
#define    FEED_FORWARD     1
#define    FF_CON_PRIOR     2
#define    TOTAL_RCR        3
#define    PRIOR_RCR        4
#define    CASCADE          5
#define    CASCADE_RCR      6
#define    ELMAN_RCR        7
#define    JORDAN_RCR       8
/* DEFINES for the PE Functions */
#define    DOT_PROD      1
#define    L2_DIST       2
#define    L1_DIST       3
#define    QUAD_SUM      4
#define    RADIAL        5
#define    SIGMA_PI      6
#define    GRNN_SUM      7
#ifdef     AG_CUSTOM
#define    FUZZ_APP      8
#define    GEN_SIG_PI    9
#endif
/* DEFINES for Transfer Functions */
#define    SIGMOID              1
#define    BI_SIGMOID           2
#define    ATAN                 3
#define    BI_ATAN              4
#define    SIN                  5
#define    BI_SIN               6
#define    LINEAR               7
#define    THRES_LINEAR         8
#define    BI_THRES_LINEAR      9
#define    THRESHOLD           10
#define    BI_THRESHOLD        11
#define    GAUSS               12
```

-continued

```
#define     CAUCHY                  13
#define     WIN_TAKE_ALL            14
#define     PERIODIC_SIN            15
#define     STCH_THRES              16
#define     STCHBI_THRES            17
#define     MFA_THRES               18
#define     MFA_BI_THRES            19
/* DEFINES for Training set ordering */
#define     NORMAL                  0
#define     RANDOM                  1
#define     SHUFFLE                 2
#define     TD_REVERSE              3
/* DEFINES for Learning Rules for NetRule [layer] */
#define     NONE                    0
#define     BACK_PROP               1
#define     QUICK_PROP              2
#define     JACOBS_PROP             3
#define     KOHONEN_WTA             4
#define     SIM_ANNEAL              5
#define     RECURRENT_BP            6
#define     KOHONEN_LVQ             7
#define     CASCADE_CORR            8
#define     SW_RAND_OPT             9
#define     SIMPLEX_SA              10
#define     POWELL_OPT              11
#define     CONJ_GRAD               12
#define     PROB_NET                13
#define     GEN_REG_NET             14
#define     LEVEN_MARQ              15
#define     NUM_ALGO                16
/* DEFINES for CASCADE_CORR growing algorithms OperMode */
#define     TRIAL_ADJ               1
#define     OUTPUT_ADJ              2
#define     GLOBAL_ADJ              3
#define     MAX_CAPACITY            4
/* DEFINES for GRNN OperMode */
#define     LOAD_TRN                1
#define     SIGMA_ADJ               2
/* DEFINES for Classification Method */
#define     BEST_PICK               0
#define     WITHIN_TOL              1
/* The following is defined when error message displays should be shown */
#define     AA_SHOW_ERROR_MESSAGES
/* Error return codes */
#define     AA_ERROR_NONE                       0
#define     AA_ERROR_OPEN_FARMS_FILE            -1
#define     AA_ERROR_LOADING_PARMS              -2
#define     AA_ERROR_CREATE_PARMS_FILE          -3
#define     AA_ERROR_SAVING_FARMS               -4
#define     AA_ERROR_NO_EQUAL_IN_PARMS_LINE     -5
#define     AA_ERROR_IDENTIFIER_IN_PARMS        -6
#define     AA_ERROR_OPEN_WEIGHTS_FILE          -7
#define     AA_ERROR_LOADING_WEIGHTS            -8
#define     AA_ERROR_CREATE_WEIGHTS_FILE        -9
#define     AA_ERROR_SAVING_WEIGHTS             -10
#define     AA_ERROR_CREATE_WTS_LOG_FILE        -11
#define     AA_ERROR_SAVING_WTS_LOG             -12
#define     AA_ERROR_ALLOC                      -100
#define     AA_ERROR_ALLOC_poWts                ( AA_ERROR_ALLOC - 0 )
#define     AA_ERROR_ALLOC_pNetSts              ( AA_ERROR_ALLOC - 1 )
#define     AA_ERROR_ALLOC_pASts                ( AA_ERROR_ALLOC - 2 )
#define     AA_ERROR_ALLOC_pBSts                ( AA_ERROR_ALLOC - 3 )
#define     AA_ERROR_ALLOC_pDelSts              ( AA_ERROR_ALLOC - 4 )
#define     AA_ERROR_ALLOC_pTrnSts              ( AA_ERROR_ALLOC - 5 )
#define     AA_ERROR_ALLOC_pErrSts              ( AA_ERROR_ALLOC - 6 )
#define     AA_ERROR_ALLOC_pPriorErrSts         ( AA_ERROR_ALLOC - 7 )
#define     AA_ERROR_ALLOC_pErrSumSts           ( AA_ERROR_ALLOC - 8 )
#define     AA_ERROR_ALLOC_pBiasSts             ( AA_ERROR_ALLOC - 9 )
#define     AA_ERROR_ALLOC_pProbSts             ( AA_ERROR_ALLOC - 10 )
#define     AA_ERROR_ALLOC_pCovMat              ( AA_ERROR_ALLOC - 11 )
#define     AA_ERROR_ALLOC_pLastCovMat          ( AA_ERROR_ALLOC - 12 )
#define     AA_ERROR_ALLOC_pCurWts              ( AA_ERROR_ALLOC - 13 )
#define     AA_ERROR_ALLOC_pBestWts             ( AA_ERROR_ALLOC - 14 )
#define     AA_ERROR_ALLOC_pDirWts              ( AA_ERROR_ALLOC - 15 )
#define     AA_ERROR_ALLOC_pBiasWts             ( AA_ERROR_ALLOC - 16 )
#define     AA_ERROR_ALLOC_pGateWts             ( AA_ERROR_ALLOC - 17 )
#define     AA_ERROR_ALLOC_pTempWts             ( AA_ERROR_ALLOC - 18 )
/* function prototypes reference */
/* Visual Basic and Excel functions specific to the DLL library */
```

-continued

```
short    FAR PASCAL EXPORT    LoadNet(short NetNum, char FAR *pName);
short    FAR PASCAL EXPORT    LoadWeights(short NetNum, char FAR *pName);
short    FAR PASCAL EXPORT    ReadWeights(short NetNum, char FAR *pName);
short    FAR PASCAL EXPORT    LoadParms(short NetNum, char FAR *pName);
short    FAR PASCAL EXPORT    ReadParms(short NetNum, char FAR *pName);
short    FAR PASCAL EXPORT    AllocNet(short NetNum);
short    FAR PASCAL EXPORT    FreeNet(short NetNum);
short    FAR PASCAL EXPORT    SaveWeights(short NetNum, char FAR *pName);
short    FAR PASCAL EXPORT    WriteWeights(short NetNum, char FAR *pName);
short    FAR PASCAL EXPORT    SaveParms(short NetNum, char FAR *pName);
short    FAR PASCAL EXPORT    WriteParms(short NetNum, char FAR *pName);
double   FAR PASCAL EXPORT    PutInput(short NetNum, short nIn, double FAR *pIn );
double   FAR PASCAL EXPORT    PutState(short NetNum, short layer, short pe, double FAR *pSt);
double   FAR PASCAL EXPORT    PutOutput(short NetNum, short nSt, double FAR *pSt);
double   FAR PASCAL EXPORT    PutTrn(short NetNum, short nSt, double FAR *pSt);
double   FAR PASCAL EXPORT    PutWeight(short NetNum, short layer, short pe, short nWt, doubl
e FAR *pWt);
double   FAR PASCAL EXPORT    PutParm(short NetNum, char FAR *pName, short layer, double FAR
*pVal);
double   FAR PASCAL EXPORT    GetInput(short NetNum, short nIn);
double   FAR PASCAL EXPORT    GetState(short NetNum, short layer, short nSt);
double   FAR PASCAL EXPORT    GetOutput(short NetNum, short nSt);
double   FAR PASCAL EXPORT    GetTrn(short NetNum, short nSt);
double   FAR PASCAL EXPORT    GetWeight(short NetNum, short layer, short pe, short nWt);
double   FAR PASCAL EXPORT    GetParm(short NetNum, char FAR *pName, short layer);
short    FAR PASCAL EXPORT    GetNumInputs(short NetNum);
short    FAR PASCAL EXPORT    GetNumOutputs(short NetNum);
short    FAR PASCAL EXPORT    GetNumPEs(short NetNum, short layer);
short    FAR PASCAL EXPORT    GetNumLayers(short NetNum);
short    FAR PASCAL EXPORT    InitializeWts(short NetNum);
short    FAR PASCAL EXPORT    TrainNet(short NetNum);
short    FAR PASCAL EXPORT    IterateNet(short NetNum);
short    FAR PASCAL EXPORT    IsNetAVail(short NetNum);
short    FAR PASCAL EXPORT    PutGrade( short NetNum, double FAR *pVal);
double   FAR PASCAL EXPORT    GetWtsGrade( short NetNum);
short    FAR PASCAL EXPORT    AdjustWts(short NetNum);
short    FAR PASCAL EXPORT    GetBestWts(short NetNum);
short    FAR PASCAl EXPORT    AllocTrn(short NetNum, short InclDesired, short nExamples);
short    FAR PASCAL EXPORT    FreeTrn(short NetNum);
double   FAR PASCAL EXPORT    PutTrnData(short NetNum, short InclDesired, short example, shor
t offset, double FAR *pVal);
double   FAR PASCAL EXPORT    GetTrnData(short NetNum, short InclDesired, short example, shor
t offset);
short    FAR PASCAL EXPORT    ReadTrnSet(short NetNum, short InclDesired, short MaxTrn, char
FAR *pName );
short    FAR PASCAL EXPORT    BatchTrain( short NetNum, short MaxPasses, double FAR *TargetEr
ror );
/* user definable network evaluation function for graded and batched learning */
void FAR PASCAL EXPORT eval_net(short NetNum, REAL *pRMSError, REAL *pMaxError, REAL *pC
lassError);
void FAR PASCAL EXPORT dd_set_inputs_func(short NetNum, long (FAR PASCAL EXPORT *inputs_
fn) (short NetNum, long example));
void FAR PASCAL EXPORT dd_set_sample_func(short NetNum, void (FAR PASCAL EXPORT *sample
fn) (short NetNum, long example));
void FAR PASCAL EXPORT dd_set_pass_func(short NetNum, void (FAR PASCAL EXPORT *pass_fn)
short NetNum));
/* C language callable functions */
void FAR PASCAL dd_get_struct(short NetNum, struct ddnet FAR **pnet);
void FAR PASCAL dd_get tin array(short NetNum, float HUGE **ptrndata);
short FAR PASCAL dd_allocate_net(short NetNum);
void FAR PASCAL dd_initialize_wts(short NetNum);
void FAR PASCAL dd_free_net(short NetNum);
void FAR PASCAL dd_adjwts(short NetNum);
void FAR PASCAL dd_train_network(short NetNum, long MaxPasses, double TargetError );
void FAR PASCAL dd_train_sa(short NetNum, long MaxPasses, double TargetError);
void FAR PASCAL dd_train_swro(short NetNum, long MaxPasses, double TargetError);
void FAR PASCAL dd_train_meb(short NetNum, long MaxPasses, double TargetError);
void FAR PASCAL dd_train_pow(short NetNum, long MaxPasses, double TargetError);
void FAR PASCAL dd_train_cg(short NetNuin, long MaxPasses, double TargetError);
void FAR PASCAL dd_train_pnn(short NetNum, long MaxPasses, double TargetError);
void FAR PASCAL dd_train_grnn(short NetNum, long MaxPasses, double TargetError);
void FAR PASCAL dd_train_lm(short NetNum, long MaxPasses, double TargetError);
void FAR PASCAL dd_train_by_sample(short NetNum, long MaxPasses, double TargetError);
void FAR PASCAL dd_train( short NetNum );
void FAR PASCAL dd_iterate(short NetNum);
void FAR PASCAL dd_preproc(short NetNum);
void FAR PASCAL dd_gendir(short NetNum, short layer);
void FAR PASCAL dd_bstwts(short NetNum, short layer);
void FAR PASCAL dd_curwts(short NetNum, short layer);
```

-continued

```
void FAR PASCAL dd_otp_ff(short NetNum);
void FAR PASCAL dd_otp_ffcp(short NetNum);
void FAR PASCAL dd_otp_ti(short NetNum);
void FAR PASCAL dd_otp_pi(short NetNum);
void FAR PASCAL dd_otp_cas(short NetNum);
void FAR PASCAL dd_otp_cas_rcr(short NetNum);
void FAR PASCAL dd_otp_elm_rcr(short NetNum);
void FAR PASCAL dd_otp_jor_rcr(short NetNum);
void FAR PASCAL dd_grad(short NetNum);
void FAR PASCAL dd_grad_mse(short NetNum, short layer);
void FAR PASCAL dd_grad_mae(short NetNum, short layer);
void FAR PASCAL dd_grad_hse(short NetNum, short layer);
void FAR PASCAL dd_grad_bhse(short NetNum, short layer);
void FAR PASCAL dd_grad_m4pe(short NetNum, short layer);
void FAR PASCAL dd_grad_ce(short NetNum, short layer);
void FAR PASCAL dd_grad_y(short NetNum, short layer);
void FAR PASCAL dd_grad_ff(short NetNum, short layer);
void FAR PASCAL dd_grad_ffcp(short NetNum, short layer);
void FAR PASCAL dd_grad_t_rcr(short NetNum);
void FAR PASCAL dd_grad_cas(short NetNum, short layer);
void FAR PASCAL dd_grad_elm_rcr(short NetNum, short layer);
void FAR PASCAL dd_grad_jor_rcr(short NetNum, short layer);
void FAR PASCAL dd_adj_bpn(short NetNum, short layer);
void FAR PASCAL dd_adj_qp(short NetNum, short layer);
void FAR PASCAL dd_adj_jacob(short NetNum, short layer);
void FAR PASCAL dd_adj_koh(short NetNum, short layer);
void FAR PASCAL dd_adj_lvq(short NetNum, short layer);
void FAR PASCAL dd_adj_sa(short NetNum, short layer);
void FAR PASCAL dd_adj_swro(short NetNum, short layer);
void FAR PASCAL dd_grad_cascor(short NetNum);
void FAR PASCAL dd_adj_cascor(short NetNum);
void FAR PASCAL dd_adj_pnn(short NetNum);
void FAR PASCAL dd_adj_grnn(short NetNum);
void FAR PASCAL dd_adj_lm(short NetNum);
void FAR PASCAL dd_parms(short NetNum);
short FAR PASCAL dd_load_parms(short NetNum, char *name);
short FAR PASCAL dd_save_parms (short NetNum, char *name);
short FAR PASCAL dd_read_parms(short NetNum, char *name);
short FAR PASCAL dd_write_parms(short NetNum, char *name);
short FAR PASCAL dd_load_wts(short NetNum, char *name);
short FAR PASCAL dd_save_wts(short NetNum, char *name);
short FAR PASCAL dd_read_wts(short NetNum, char *name);
short FAR PASCAL dd_write_wts (short NetNum, char *name);
void FAR PASCAL dd_print_weights( short NetNum );
short FAR PASCAL dd_log_weights( short NetNum, char *fname );
void FAR PASCAL dd_add_pe(short NetNum,long layer);
void FAR PASCAL generate_offsets(short NetNum, long *pTotWts,long *pMaxWts);
void FAR PASCAL user_message( char *str );
char FAR *dd_getmem( HANDLE *pH, long len);
void FAR PASCAL dd_freemem(HANDLE *pH, char FAR *pM);
void FAR PASCAL add_wts(
          short NetNum,
          long layer,
          long Ofs,
          long cnt,
          double InitVal);
void FAR PASCAL XferFunc(
          REAL HUGE *pIn
          REAL HUGE *pOut,
          short  n,
          short  Type,
          REAL *Temp);
void FAR PASCAL Xferprime(
          REAL HUGE *pI,
          REAL HUGE *pN,
          REAL HUGE *pO,
          short  n,
          short  Type);
void FAR PASCAL PeFunc(
          REAL HUGE *pIn,
          REAL HUGE **ppWts,
          REAL HUGE *pOut,
          short  nIn,
          short  nOut,
          short  Type);
void FAR PASCAL PePrime(
REAL HUGE *pIn,
REAL HUGE *pErrIn
REAL HUGE *pWts
```

```
REAL HUGE *pDir,
REAL HUGE *pErrOut
REAL HUGE *pMu,
short    nIn,
short    nOut,
short    Type);
void FAR PASCAL vamul(
                REAL HUGE *pA,
                REAL HUGE *pvA,
                REAL HUGE *pB,
                REAL HUGE *pC,
                long n);
double FAR PASCAL crand(void);
double FAR PASCAL grand(void);
void FAR PASCAL surand(long idum);
double FAR PASCAL urand(void);
double FAR PASCAL xrand(void);
#ifdef__cplusplus
}
#endif
#endif /* __AA__NETS__H__*/
/***************************************************************/
// mainfrm.cpp implementation of the CMainFrame class
//
#include "stdafx.h"
#include "PTDinp.h"
#include "mainfrm.h"
#ifdef_DEBUG
#undef THIS__FILE
static char BASED__CODE THIS__FILE[] = FILE__;
#endif
///////////////////////////////////////////////////////////////////
// CMainFrame
IMPLEMENT__DYNCREATE(CMainFrame, CFrameWnd)
BEGIN__MESSAGE__MAP(CMainFrame, CFrameWnd)
    //{{AFX__MSG__MAP(CMainFrame)
        // NOTE - the ClassWizard will add and remove mapping macros here.
        //      DO NOT EDIT what you see in these blocks of generated code !
    ON__WM__CREATE ()
    //}}AFX__MSG__MAP
END__MESSAGE__MAP()
///////////////////////////////////////////////////////////////////
// arrays of IDs used to initialize control bars
// toolbar buttons - IDs are command buttons
static UINT BASED__CODE buttons [] =
{
    // same order as in the bitmap 'toolbar.bmp'
    ID__FILE__OPEN,
        ID__SEPARATOR,
    ID__REC__FIRST,
    ID__REC__PREV,
    ID__REC__NEXT,
    ID__REC__LAST,
        ID__SEPARATOR,
    ID__DATA__EDIT,
    ID__DATA__NEW
        ID__SEPARATOR,
    ID__REC GOTO,
        ID__SEPARATOR,
    ID__APP__ABOUT,
};
static UINT BASED__CODE indicators [] =
    ID__SEPARATOR,              // status line indicator
    ID__INDICATOR__CAPS,
    ID__INDICATOR__NUM,
    ID__INDICATOR__SCRL,
};
///////////////////////////////////////////////////////////////////
// CMainFrame construction/destruction
CMainFrame::CMainFrame ()
{
    // TODO: add member initialization code here
}
CMainFrame::~CMainFrame ()
{
int CMainFrame::OnCreate(LPCREATESTRUCT 1pCreatestruct)
{
    if (CFrameWnd::OnCreate(1pCreateStruct) == −1)
        return −1;
```

-continued

```
    if (!m_wndToolBar.Create(this) ||
        !m_wndToolBar.LoadBitmap(IDR_MAINFRAME)
        !m_wndToolBar.SetButtons (buttons,
            sizeof(buttons)/sizeof(UINT)))
    {
        TRACE("Failed to create toolbar\n");
        return -1;          // fail to create
    }
    if (!m_wndStatusBar.Create(this)    ||
        !m_wndStatusBar.SetIndicators(indicators,
            sizeof(indicators)/sizeof(UINT)))
    {
        TRACE("Failed to create status bar\n");
        return -1;          // fail to create
    }
    return 0;
}
/////////////////////////////////////////////////////////////////////////////
// CMainFrame diagnostics
#ifdef _DEBUG
void CMainFrame::AssertValid() const
{
    CFrameWnd::AssertValid();
}
void CMainFrame::Dump(CDumpContext& dc) const
{
    CFrameWnd::Dump(dc);
}
#endif //_DEBUG
/////////////////////////////////////////////////////////////////////////////
// CMainFrame message handlers
// mainfrm.h : interface of the CMainFrame class
//
/////////////////////////////////////////////////////////////////////////////
class CMainFrame public : CFrameWnd
{
protected: // create from serialization only
    CMainFrame ();
    DECLARE_DYNCREATE (CMainFrame)
// Attributes
public:
// Operations
public:
// Implementation
public:
    virtual ~CMainFrame ();
#ifdef _DEBUG
    virtual void AssertValid() const;
    virtual void Dump(CDumpContext& dc) const;
#endif
protected: // control bar embedded members
    CStatusBar m_wndStatusBar;
    CToolBar m_wndToolBar;
// Generated message map functions
protected:
    //{{AFX_MSG(CMainFrame)
    afx_msg int OnCreate(LPCREATESTRUCT lpCreateStruct);
        // NOTE - the ClassWizard will add and remove member functions here.
        // DO NOT EDIT what you see in these blocks of generated code!
    // }}AFX_MSG
    DECLARE_MESSAGE_MAP ()
/////////////////////////////////////////////////////////////////////////////
// PTDD1g1.cpp : Defines the class behaviors for the application.
//
#include "stdafx.h"
#include "PTDinp.h"
#include "PTDD1g1.h"
#ifdef _DEBUG
#define new DEBUG_NEW
#undef THIS_FILE
static char THIS_FILE[] = _FILE_;
#endif
/////////////////////////////////////////////////////////////////////////////
// CPTDInp dialog
CPTDInp::CPTDInp (CWnd* pParent /*=NULL*/)
    : CDialog(CPTDInp::IDD, pParent)
{
    //{{AFX_DATA_INIT(CPTDInp)
    m_DATE_OF_BIRTH ="";
```

-continued

```
    m_NAME_F = "";
    m_NAME_L = "";
    m_NAME_MI = "";
    m_1_COMP = FALSE;
    m_2_COMP = FALSE;
    m_3_COMP = FALSE;
    m_4_COMP = FALSE;
    m_5_COMP = FALSE;
    m_6_COMP = FALSE;
    m_ACOG_N = FALSE;
    m_ACOG_Y = FALSE;
    m_Antibiotics = FALSE;
    m_AntiHyper = FALSE;
    m_CervCerclage = FALSE;
    m_CervFirm = FALSE;
    m_CervMod = FALSE;
    m_CervSoft = FALSE;
    m_Corticosteroids = FALSE;
    m_Dilitation1_2 = FALSE;
    m_Dilitation2 = FALSE;
    m_Dilitation2_3 = FALSE;
    m_Dilitation3 = FALSE;
    m_DilitationGt3 = FALSE;
    m_Dilitation1 = FALSE;
    m_DilitationLt1 = FALSE;
    m_DilitationUkn = FALSE;
    m_EGAatSample = "";
    m_EGAbyLMP = "";
    m_EGAbySONO = "";
    m_EthnicOriginAsian = FALSE;
    m_EthnicOriginBlack = FALSE;
    m_EthnicOriginHispanic = FALSE;
    m_EthnicOriginNativeAmerican = FALSE;
    m_EthnicOriginOther = FALSE;
    m_EthnicOriginWhite = FALSE;
    m_FFN_Neg = FALSE;
    m_FFN_Pos = FALSE;
    m_GestationalDiabetes = FALSE;
    m_HypertensiveDisorders = FALSE;
    m_Insulin = FALSE;
    m_LadID = "";
    m_MedicationNone = FALSE;
    m_MedicationUnknown = FALSE;
    m_MultipleGestationQuads = FALSE;
    m_MultipleGestationTriplets = FALSE;
    m_MultipleGestationTwins = FALSE;
    m_MaritalStatusDivorced = FALSE;
    m_MaritalStatusLWP = FALSE;
    m_MaritalStatusMarried = FALSE;
    m_MaritalStatusOther = FALSE;
    m_MaritalStatusSingle = FALSE;
    m_MaritalStatusWidowed = FALSE;
    m_MultipleGestation = FALSE;
    m_PatientComp1 = FALSE;
    m_PatientComp2 = FALSE;
    m_PatientComp3 = FALSE;
    m_PatientComp4 = FALSE;
    m_PatientComp5 = FALSE;
    m_PatientComp6 = FALSE;
    m_Tocolytics = FALSE;
    m_UtCervAbnormal = FALSE;
    m_VaginalBleeding = FALSE;
    m_VaginalBleedingGross = FALSE;
    m_VaginalBleedingMed = FALSE;
    m_VaginalBleedingTrace = FALSE;
    m_2_COMP_1 = FALSE;
    m_2_COMP_2 = FALSE;
    m_2_COMP_3 = FALSE;
    m_ABORTIONS = "";
    m_PARITY = "";
    m_PatComp1_1_3 = FALSE;
    m_PatComp1_10_12 = FALSE;
    m_PatComp1_4_6 = FALSE;
    m_PatComp1_7_9 = FALSE;
    m_PatComp1_GT12 = FALSE;
    m_PatComp1_LT1 = FALSE;
    m_GRAVITY = "";
    //}}AFX_DATA_INIT
}
```

-continued

```
void CPTDInp::DoDataExchange(CDataExchange* pDX)
{
    CDialog::DoDataExchange(pDX);
    //{{AFX_DATA_MAP(CPTDInp)
    DDX_Text(pDX, IDC_DATE_OF_BIRTH, m_DATE_OF_BIRTH);
    DDX_Text(pDX, IDC_NAME_F, m_NAME_F);
    DDV_MaxChars(pDX, m_NAME_F, 24);
    DDX_Text(pDX, IDC_NAME_L, m_NAME_L);
    DDV_MaxChars(pDX, m_NAME_L, 24);
    DDX_Text(pDX, IDC_NAME_MI, m_NAME_MI);
    DDV_MaxChars(pDX, m_NAME_MI, 2);
    DDX_Check(pDX, IDC_1_COMP, m_1_COMP);
    DDX_Check(pDX, IDC_2_COMP, m_2_COMP);
    DDX_Check(pDX, IDC_3_COMP, m_3_COMP);
    DDX_Check(pDX, IDC_4_COMP, m_4_COMP);
    DDX_Check(pDX, IDC_5_COMP, m_5_COMP);
    DDX_Check(pDX, IDC_6_COMP, m_6_COMP);
    DDX_Check(pDX, IDC_ACOG_N, m_ACOG_N);
    DDX_Check(pDX, IDC_ACOG_Y, m_ACOG_Y);
    DDX_Check(pDX, IDC_ANTIBIOTICS, m_Antibiotics);
    DDX_CheckCpDX, IDC_ANTIHYPER, m_AntiHyper);
    DDX_Check(pDX, IDC_CERV_CERCLAGE, m_CervCerclage);
    DDX_Check(pDX, IDC_CERV_FIRM, m_CervFirm);
    DDX_Check(pDX, IDC_CERV_MOD, m_CervMod);
    DDX_Check(pDX, IDC_CERV_SOFT, m_CervSoft);
    DDX_Check(pDX, IDC_CORTICOSTEROIDS, m_Corticosteroids);
    DDX_Check(pDX, IDC_DILITATION_1_2, m_Dilitation1_2);
    DDX_Check(pDX, IDC_DILITATION_2, m_Dilitation2);
    DDX_Check(pDX, IDC_DILITATION_2_3, m_Dilitation2_3);
    DDX_Check(pDX, IDC_DILITATION_3, m_Dilitation3);
    DDX_Check(pDX, IDC_DILITATION_GT3, m_DilitationGt3);
    DDX_Check(pDX, IDC_DILITATION_1, m_Dilitation1);
    DDX_Check(pDX, IDC_DILITATION_LT1, m_DilitationLt1);
    DDX_Check(pDX, IDC_DILITATION_UKN, m_DilitationUkn);
    DDX_Text(pDX, IDC_EGA_AT_SAMP, m_EGAatSample);
    DDV_MaxChars(pDX, m_EGAatSample, 10);
    DDX_Text(pDX, IDC_EGA_BY_LMP, m_EGAbyLMP);
    DDX_Text(pDX, IDC_EGA_BY_SONO, m_EGAbySONO);
    DDX_Check(pDX, IDC_EO_ASIAN, m_EthnicOriginAsian);
    DDX_Check(pDX, IDC_EO_BLACK, m_EthnicOriginBlack);
    DDX_Check(pDX, IDC_EO_HISPANIC, m_EthnicOriginHispanic);
    DDX_Check(pDX, IDC_EO_NATIVE_AMERICAN, m_EthnicoriginNativeAmerican);
    DDX_Check(pDX, IDC_EO_OTHER, m_EthnicOriginOther);
    DDX_Check(pDX, IDC_EO_WHITE, m_EthnicOriginWhite);
    DDX_Check(pDX, IDC_FFN_NEG, m_FFN_Neg);
    DDX_Check(pDX, IDC_FFN_POS, m_FFN_Pos);
    DDX_Check(pDX, IDC_GEST_DIABETES, m_GestationalDiabetes);
    DDX_Check(pDX, IDC_HYPERTEN_DISORDERS, m_HypertensiveDisorders);
    DDX_Check(pDX, IDC_INSULIN, m_Insulin);
    DDX_Text(pDX, IDC_LAB_ID, m_LadID);
    DDX_Check(pDX, IDC_MED_NONE, m_MedicationNone);
    DDX_Check(pDX, IDC_MED_UKN, m_MedicationUnknown);
    DDX_Check(pDX, IDC_MG_QUADS, m_MultipleGestationQuads);
    DDX_Check(pDX, IDC_MG_TRIPLETS, m_MultipleGestationTriplets);
    DDX_Check(pDX, IDC_MG_TWINS, m_MultipleGestationTwins);
    DDX_Check(pDX, IDC_MS_DIVORCED, m_MaritalStatusDivorced);
    DDX_Check(pDX, IDC_MS_LWP, m_MaritalStatusLWP);
    DDX_Check(pDX, IDC_MS_MARRIED, m_MaritalStatusMarried);
    DDX_Check(pDX, IDC_MS_OTHER, m_MaritalStatusOther);
    DDX_Check(pDX, IDC_MS_SINGLE, m_MaritalstatusSingle);
    DDX_Check(pDX, IDC_MS_WIDOWED, m_MaritalStatusWidowed);
    DDX_Check(pDX, IDC_MULT_GEST, m_MultipleGestation);
    DDX_Check(pDX, IDC_PATIENT_COMP_1, m_PatientComp1);
    DDX_Check(pDX, IDC_PATIENT_COMP_2, m_PatientComp2);
    DDX_Check(pDX, IDC_PATIENT_COMP_3, m_PatientComp3);
    DDX_Check(pDX, IDC_PATIENT_COMP_4, m_PatientComp4);
    DDX_Check(pDX, IDC_PATIENT_COMP_5, m_PatientComp5);
    DDX_Check(pDX, IDC_PATIENT_COMP_6, m_PatientComp6);
    DDX_Check(pDX, IDC_TOCOLYTICS, m_Tocolytics);
    DDX_Check(pDX, IDC_UT_CWRV_ABNOBN, m_UtCervAbnormal);
    DDX_Check(pDX, IDC_VAGINAL_BLEEDING, m_VaginalBleeding);
    DDX_Check(pDX, IDC_VB_GROSS, m_VaginalBleedingGross);
    DDX_Check(pDX, IDC_VB_MED, m_VaginalBleedingMed);
    DDX_Check(pDX, IDC_VB_TRACE, m_VaginalBleedingTrace);
    DDX_Check(pDX, IDC_2_COMP_1, m_2_COMP_1);
    DDX_Check(pDX, IDC_2_COMP_2, m_2_COMP_2);
    DDX_Check(pDX, IDC_2_COMP_3, m_2_COMP_3);
    DDX_Text(pDX, IDC_ABORTIONS, m_ABORTIONS);
    DDV_MaxChars(pDX, m_ABORTIONS, 2);
```

```
        DDX_Text(pDX, IDC_PARITY, m_PARITY);
        DDV_MaxChars(pDX, m_PARITY, 2);
        DDX_Check(pDX, IDC_PC1_1_3, m_PatComp1_1_3);
        DDX_Check(pDX, IDC_PC1_10_12, m_PatComp1_10_12);
        DDX_Check(pDX, IDC_PC1_4_6, m_PatComp1_4_6);
        DDX_Check(pDX, IDC_PC1_7_9, m_PatComp1_7_9);
        DDX_Check(pDX, IDC_PC1_GT12, m_PatComp1_GT12);
        DDX_Check(pDX, IDC_PC1_LT1, m_PatComp1_LT1);
        DDX_Text(pDX, IDC_GRAVIDITY, m_GRAVITY);
        DDV_MaxChars(pDX, m_GRAVITY, 2);
        // }}AFX_DATA_MAP
}
BEGIN_MESSAGE_MAP(CPTDInp, CDialog)
        // {{AFX_MSG_MAP(CPTDInp)
        ON_WM_RBUTTONDOWN()
        ON_BN_CLICKED(IDC_ACOG_N, OnAcogN)
        ON_BN_CLICKED(IDC_ACOG_Y, OnAcogY)
        ON_BN_CLICKED(IDC_FFN_NEG, OnFfnNeg)
        ON_BN_CLICKED(IDC_FFN_POS, OnFfnPos)
        ON_BN_CLICKED(IDC_MG_QUADS, OnMgQuads)
        ON_BN_CLICKED(IDC_MG_TRIPLETS, OnMgTriplets)
        ON_BN_CLICKED(IDC_MG_TWINS, OnMgTwins)
        ON_BN_CLICKED(IDC_MULT_GEST, OnMultGest)
        ON_BN_CLICKED(IDC_DILITATION_1, OnDilitation1)
        ON_BN_CLICKED(IDC_DILITATION_1_2, OnDilitation12)
        ON_BN_CLICKED(IDC_DILITATION_2, OnDilitation2)
        ON_BN_CLICKED(IDC_DILITATION_2_3, OnDilitation23)
        ON_BN_CLICKED(IDC_DILITATION_3, OnDilitation3)
        ON_BN_CLICKED(IDC_DILITATION_GT3, OnDilitationGt3)
        ON_BN_CLICKED(IDC_DILITATION_LT1, OnDilitationLt1)
        ON_BN_CLICKED(IDC_DILITATION_UKN, OnDilitationUkn)
        ON_BN_CLICKED(IDC_CERV_FIRM, OnCervFirm)
        ON_BN_CLICKED(IDC_CERV_MOD, OnCervMod)
        ON_BN_CLICKED(IDC_CERV_SOFT, OnCervSoft)
        ON_BN_CLICKED(IDC_VAGINAL_BLEEDING, OnVaginalBleeding)
        ON_BN_CLICKED(IDC_VB_GROSS, OnVbGross)
        ON_BN_CLICKED(IDC_VB_MED, OnVbMed)
        ON_BN_CLICKED(IDC_VB_TRACE, OnVbTrace)
        ON_BN_CLICKED(IDC_2_COMP, On2Comp)
        ON_BN_CLICKED(IDC_2_COMP_1, On2Comp1)
        ON_BN_CLICKED(IDC_2_COMP_2, On2Comp2)
        ON_BN_CLICKED(IDC_2_COMP_3, On2Comp3)
        ON_BN_CLICKED(IDC_PATIENT_COMP 1, OnPatientComp1)
        ON_BN_CLICKED(IDC_PC1_1_3, OnPc113)
        ON_BN_CLICKED(IDC_PC1_10 12, OnPc11012)
        ON_BN_CLICKED(IDC_PC1_4_6, OnPc14E)
        ON_BN_CLICKED(IDC_PC1_7_9, OnPc179)
        ON_BN_CLICKED(IDC_PC1_GT12, OnPc1Gt12)
        ON_BN_CLICKED(IDC_PC1_LT1, OnPc1Lt1)
        ON_BN_CLICKED(IDC_EO_ASIAN, OnEoAsian)
        ON_BN_CLICKED(IDC_EO_BLACK, OnEoBlack)
        ON_BN_CLICKED(IDC_EO_HISPANIC, OnEoHispanic)
        ON_BN_CLICKED(IDC_EO_NATIVE_AMERICAN, OnEoNativeAmerican)
        ON_BN_CLICKED(IDC_EO_OTHER, OnEoOther)
        ON_BN_CLICKED(IDC_EO_WHITE, OnEoWhite)
        ON_BN_CLICKED(IDC_MS_DIVORCED, OnMsDivorced)
        ON_BN_CLICKED(IDC_MS_LWP, OnMsLwp)
        ON_BN_CLICKED(IDC_MS_MARRIED, OnMsMarried)
        ON_BN_CLICKED(IDC_MS_OTHER, OnMsOther)
        ON_BN_CLICKED(IDC_MS_SINGLE, OnMsSingle)
        ON_BN_CLICKED(IDC_MS_WIDOWED, OnMsWidowed)
        // }}AFX_MSG_MAP
END_MESSAGE_MAP()
/////////////////////////////////////////////////////////////////////////////
// CPTDInp message handlers
BOOL CPTDInp::OnInitDialog()
{
        CDialog::OnInitDialog();
        // TODO: Add extra initialization here
        //MoveWindow(0,-250,500,500);        // one way to handle large dialogs
        return TRUE; // return TRUE unless you set the focus to a control
}
Void CPTDInp::OnRButtonDown(UINT nFlags, CPoint point)
{
        // TODO: Add your message handler code here and/or call default
        CRect rect;
        GetWindowRect(&rect);
        CRect Desk;
        GetDesktopWindow( ) ->GetWindowRect(&Desk);
```

-continued

```
    //char str[256];
    //sprintf(str, "t %d 1 %d b %d r %d \n t %d 1 %d b %d r %d ",
    //    rect.top,rect.left,rect.bottom,rect.right,
    //    Desk.top,Desk.left,Desk.bottom,Desk.right)
    //AfxMessageBox(str);
    if(rect.top < 0 ) {
        rect.bottom = rect.bottom - rect.top;
        rect.top = 0;
        MoveWindow(rect);
    } else if (rect.bottom > Desk.bottom) {
        rect.top = Desk.bottom - 3 - (rect.bottom - rect.top);
        rect.bottom = Desk.bottom - 3;
        MoveWindow(rect);
    }
    CDialog::OnRButtonDown(nFlags, point);
}
void CPTDInp::OnAcogN()
{
    // get current values from dialog
    UpdateData (TRUE);
    if(m__ACOG__N) {
        m__ACOG__Y = FALSE;
    }
    // update dialog with new data
    UpdateData (FALSE);
}
void CPTDInp::OnAcogY()
{
    // get current values from dialog
    UpdateData (TRUE);
    if(m__ACOG__Y) {
        m__ACOG__N = FALSE;
    // update dialog with new data
    UpdateData (FALSE);
}
void CPTDInp::OnFfnNeg()
{
    // get current values from dialog
    UpdateData (TRUE);
    if(m__FFN__Neg)
        m__FFN__Pos = FALSE;
    }
    // update dialog with new data
    UpdateData (FALSE);
}
void CPTDInp::OnFfnPos()
{
    // get current values from dialog
    UpdateData (TRUE);
    if(m__FFN__Pos) {
        m__FFN__Neg = FALSE;
    }
    // update dialog with new data
    UpdateData (FALSE);
}
void CPTDInp::OnMgQuads ()
{
    // get current values from dialog
    UpdateData (TRUE);
    if(m__MultipleGestationQuads) {
        m__MultipleGestation = TRUE;
        m__MultipleGestationTwins = FALSE;
        m__MultipleGestationTriplets = FALSE;
    { else {
        if(m__MultipleGestationTwins == FALSE &&
          m__MultipleGestationTriplets == FALSE ) {
            m__MultipleGestation = FALSE;
        {
    {
    // update dialog with new data
    UpdateData (FALSE);
}
void CPTDInp::OnMgTriplets()
{
    // get current values from dialog
    UpdateData (TRUE);
    if(m__MultipleGestationTriplets) {
        m__MultipleGestation = TRUE;
        m__MultipleGestationQuads = FALSE;
```

-continued

```
            m_MultipleGestationTwins = FALSE;
        } else {
            if( m_MultipleGestationQuads == FALSE &&
                m_MultipleGestationTwins == FALSE) {
                m_MultipleGestation = FALSE;
            }
        }
    }
    // update dialog with new data
    UpdateData (FALSE);
}
void CPTDInp::OnMgTwins ()
{
    // get current values from dialog
    UpdateData (TRUE);
    if(m_MultipleGestationTwins) {
        m_MultipleGestation = TRUE;
        m_MultipleGestationQuads = FALSE;
        m_MultipleGestationTriplets = FALSE;
    } else {
        if(m_MultipleGestationQuads == FALSE &&
            m_MultipleGestationTriplets == FALSE
            m_MultipleGestation = FALSE;
        }
    }
    // update dialog with new data
    UpdateData (FALSE);
}
void CPTDInp::OnMultGest()
{
    // get current values from dialog
    UpdateData (TRUE);
    if(m_MultipleGestation) {
    } else {
        if((((CPTDinpApp*)AfxGetApp())->ClearSubfields)
            m_MultipleGestationQuads = FALSE;
            m_MultipleGestationTriplets = FALSE;
            m_MultipleGestationTwins = FALSE;
        }
    }
    // update dialog with new data
    UpdateData (FALSE);
}
void CPTDInp::OnDilitation1()
{
    // get current values from dialog
    UpdateData (TRUE);
    if(m_Dilitation1) {
        m_Dilitation1_2 = FALSE;
        m_Dilitation2 = FALSE;
        m_Dilitation2_3 = FALSE;
        m_Dilitation3 = FALSE;
        m_DilitationGt3 = FALSE;
        // m_Dilitation1 = FALSE;
        m_DilitationLt1 = FALSE;
        m_DilitationUkn = FALSE;
    }
    // update dialog with new data
    UpdateData (FALSE);
}
void CFTDInp::OnDilitation12()
{
    // get current values from dialog
    UpdateData (TRUE);
    if(m_Dilitation1_2) {
        //m_Dilitation1_2 = FALSE;
        m_Dilitation2 = FALSE;
        m_Dilitation2_3 = FALSE;
        m_Dilitation3 = FALSE;
        m_DilitationGt3 = FALSE;
        m_Dilitation1 = FALSE;
        m_DilitationLt1 = FALSE;
        m_DilitationUkn = FALSE;
    }
    // update dialog with new data
    UpdateData (FALSE);
}
void CPTDInp::OnDilitation2 ()
{
    // get current values from dialog
```

-continued

```
        UpdateData (TRUE);
        if(m_Dilitation2)
            m_Dilitation1_2 = FALSE;
            m_Dilitation2 = FALSE;
            m_Dilitation2_3 = FALSE;
            m_Dilitation3 = FALSE;
            m_DilitationGt3 = FALSE;
            m_Dilitation1 = FALSE;
            m_DilitationLt1 = FALSE;
            m_DilitationUkn = FALSE;
        }
        // update dialog with new data
        UpdateData (FALSE);
}
void CPTDInp::OnDilitation23 ()
{
        // get current values from dialog
        UpdateData (TRUE);
        if(m_Dilitation2_3)
            m_Dilitation1_2 = FALSE;
            m_Dilitation2 = FALSE;
            //m_Dilitation2_3 = FALSE;
            m_Dilitation3 = FALSE;
            m_DilitationGt3 = FALSE;
            m_Dilitation1 = FALSE;
            m_DilitationLt1 = FALSE;
            m_DilitationUkn = FALSE;
        }
        // update dialog with new data
        UpdateData (FALSE);
}
void CPTDInp::OnDilitation3 ()
{
        // get current values from dialog
        UpdateData (TRUE);
        if(m_Dilitation3) {
            m_Dilitation1_2 = FALSE;
            m_Dilitation2 = FALSE;
            m_Dilitation2_3 = FALSE;
            //m_Dilitation3 = FALSE;
            m_DilitationGt3 = FALSE;
            m_Dilitation1 = FALSE;
            m_DilitationLt1 = FALSE;
            m_DilitationUkn = FALSE;
        }
        // update dialog with new data
        UpdateData (FALSE);
}
void CPTDInp::OnDilitationGt3 ()
{
        // get current values from dialog
        UpdateData (TRUE);
        if(m_DilitationGt3) {
            m_Dilitation1_2 = FALSE;
            m_Dilitation2 = FALSE;
            m_Dilitation2_3 = FALSE;
            m_Dilitation3 = FALSE;
            //m_DilitationGt3 = FALSE;
            m_Dilitation1 = FALSE;
            m_DilitationLt1 = FALSE;
            m_DilitationUkn = FALSE;
        }
        // update dialog with new data
        UpdateData (FALSE);
}
void CPTDInp::OnDilitationLt1 ()
{
        // get current values from dialog
        UpdateData (TRUE);
        if(m_DilitationLt1) {
            m_Dilitation1_2 = FALSE;
            m_Dilitation2 = FALSE;
            m_Dilitation2_3 = FALSE;
            m_Dilitation3 = FALSE;
            m_DilitationGt3 = FALSE;
            m_Dilitation1 = FALSE;
            //m_DilitationLt1 = FALSE;
            m_DilitationUkn = FALSE;
        }
```

```
        // update dialog with new data
        UpdateData (FALSE);
}
void CPTDInp::OnDilitationUkn()
{
        // get current values from dialog
        UpdateData (TRUE);
        if(m_DilitationUkn) {
            m_Dilitation1_2 = FALSE;
            m_Dilitation2 = FALSE;
            m_Dilitation2_3 = FALSE;
            m_Dilitation3 = FALSE;
            m_DilitationGt3 = FALSE;
            m_Dilitation1 = FALSE;
            m_DilitationLt1 = FALSE;
            //m_DilitationUkn = FALSE;
        }
        // update dialog with new data
        UpdateData (FALSE);
}
void CFTDInp::OnCervFirm()
{
        // get current values from dialog
        UpdateData (TRUE);
        if(m CervFirm) {
            m_CervMod = FALSE;
            m_CervSoft = FALSE;
        }
        // update dialog with new data
        UpdateData (FALSE);
}
void CPTDInp::OnCervMod ()
{
        // get current values from dialog
        UpdateData (TRUE);
        if(m_CervMod) {
            m_CervFirm = FALSE;
            m_CervSoft = FALSE;
        }
        // update dialog with new data
        UpdateData (FALSE);
}
void CPTDInp::OnCervSoft()
{
        // get current values from dialog
        UpdateData (TRUE);
        if(m_CervSoft) {
            m_CervMod = FALSE;
            m_CervFirm = FALSE;
        {
        // update dialog with new data
        UpdateData (FALSE);
}
void CPTDInp::OnVaginalBleeding()
{
        // get current values from dialog
        UpdateData (TRUE);
        if (m_VaginalBleeding) {
        } else {
            if(((CPTDinpApp*)AfxGetApp())->ClearSubfields) {
                m_VaginalBleedingGross = FALSE;
                m_VaginalBleedingMed = FALSE;
                m_VaginalBleedingTrace = FALSE;
            }
        }
        // update dialog with new data
        UpdateData (FALSE);
}
void CPTDInp::OnVbGross()
{
        // get current values from dialog
        UpdateData (TRUE);
        if(m_VaginalBleedingGross) {
            m_VaginalBleeding = TRUE;
            m_VaginalBleedingMed = FALSE;
            m_VaginalBleedingTrace = FALSE;
        } else {
            if(m_vaginalBleedingMed == FALSE &&
              m_VaginalBleedingTrace == FALSE {
```

-continued

```
            m_vaginalBleeding = FALSE;
        }
    }
    // update dialog with new data
    UpdateData (FALSE);
}
void CPTDInp::OnVbMed()
{
    // get current values from dialog
    UpdateData (TRUE);
    if(m_VaginalBleedingMed) {
        m_VaginalBleedingGross = FALSE;
        m_VaginalBleeding = TRUE;
        m_VaginalBleedingTrace = FALSE;
    } else {
        if(m_VaginalBleedingGross == FALSE &&
          m_VaginalBleedingTrace == FALSE ) {
            m_VaginalBleeding = FALSE;
        }
    }
    // update dialog with new data
    UpdateData (FALSE);
}
void CPTDInp::OnVbTrace()
{
    // get current values from dialog
    UpdateData (TRUE);
    if(m_VaginalBleedingTrace) {
        m_VaginalBleedingGross = FALSE;
        m_VaginalBleedingMed = FALSE;
        m_VaginalBleeding = TRUE;
    } else {
        if(m_VaginalBleedingMed == FALSE &&
          m_VaginalBleedingGross == FALSE
            m_VaginalBleeding = FALSE;
        }
    }
    // update dialog with new data
    UpdateData (FALSE);
}
void CFTDInp::On2Comp()
{
    // get current values from dialog
    UpdateData (TRUE);
    if(m_2_COMP) {
    } else {
        if((((CPTDinpApp*)AfxGetApp()) ->ClearSubfields) {
            m_2_COMP_1 = FALSE;
            m_2_COMP_2 = FALSE;
            m_2_COMP_3 = FALSE;
        }
    }
    // update dialog with new data
    UpdateData (FALSE);
}
void CPTDInp::On2Comp1 ()
{
    // get current values from dialog
    UpdateData (TRUE);
    if(m_2_COMP_1)
        m_2_COMP = TRUE;
        m_2_COMP_2 = FALSE;
        m_2_COMP_3 = FALSE;
    } else {
        if(m_2_COMP_2 == FALSE &&
          m_2_COMP_3 == FALSE ) {
            m_2_COMP = FALSE;
        }
    }
    // update dialog with new data
    UpdateData (FALSE);
}
void CPTDInp::On2Comp2 ()
{
    // get current values from dialog
    UpdateData (TRUE);
    if(m_2_COMP_2)
    m_2_COMP = TRUE;
    m_2_COMP_1 = FALSE;
```

-continued

```
        m_2_COMP_3 = FALSE;
    } else {
        if(m_2_COMP_1 == FALSE &&
           m_2_COMP_3 == FALSE ) {
            m_2_COMP = FALSE;
        }
    }
    // update dialog with new data
    UpdateData (FALSE);
}
void CPTDInp::On2Comp3()
{
    // get current values from dialog
    UpdateData (TRUE);
    if(m_2_COMP_3)
        m_2_COMP = TRUE;
        m_2_COMP_2 = FALSE;
        m_2_COMP_1 = FALSE;
    } else {
        if(m_2 COMP 2 == FALSE &&
           m_2COMP 1 == FALSE ) {
            m_2_COMP = FALSE;
        }
    }
    // update dialog with new data
    UpdateData (FALSE);
}
void CPTDInp::OnPatientComp1()
{
    // get current values from dialog
    UpdateData (TRUE);
    if(m_PatientComp1) {
    } else {
        if((((CPTDinpApp*)AfxGetApp())->ClearSubfields) {
            m_PatComp1_LT1 = FALSE;
            m_PatComp1_1_3 = FALSE;
            m_PatComp1_4_6 = FALSE;
            m_PatComp1_7_9 = FALSE;
            m_PatComp1_10_12 = FALSE;
            m_PatComp1_GT12 = FALSE;
        }
    }
    // update dialog with new data
    UpdateData (FALSE);
}
void CPTDInp::OnPc113 ()
{
    // get current values from dialog
    UpdateData (TRUE);
    if(m_PatComp1_1_3) {
        m_PatComp1_LT1 = FALSE;
        m_PatientComp1 = TRUE;
        m_PatComp1_4_6 = FALSE;
        m_PatComp1_7_9 FALSE;
        m_PatComp1_10_12 = FALSE;
        m_PatComp1_GT12 = FALSE;
    } else {
        if(m_PatComp1_LT1 == FALSE &&
           m_PatComp1_1_3 == FALSE &&
           m_PatComp1_4_6 == FALSE &&
           m_PatComp1_7_9 == FALSE &&
           m_PatComp1_10_12 == FALSE &&
           m_PatComp1_GT12 == FALSE ) {
            m_PatientComp1 = FALSE;
        }
    }
    // update dialog with new data
    UpdateData (FALSE);
}
void CPTDInp::OnPc11012()
{
    // get current values from dialog
    UpdateData (TRUE);
    if(m_PatComp1_10_12) {
        m_PatComp1_LT1 = FALSE;
        m_PatComp1_1_3 = FALSE;
        m_PatComp1_4_6 = FALSE;
        m_PatComp1_7_9 = FALSE;
        m_PatientComp1 = TRUE;
```

-continued

```
            m_PatComp1_GT12 = FALSE;
        } else {
            if(m_PatComp1_LT1 == FALSE &&
                m_PatComp1_1_3 == FALSE &&
                m_PatComp1_4_6 == FALSE &&
                m_PatComp1_7_9 == FALSE &&
                m_PatComp1_10_12 == FALSE &&
                m_PatComp1_GT12 == FALSE ) {
                m_PatientComp1 = FALSE;
            }
        }
        // update dialog with new data
        UpdateData (FALSE);
    }
    void CPTDInp::OnPc146()
    {
        // get current values from dialog
        UpdateData (TRUE);
        if(m_PatComp1_4_6) {
            m_PatComp1_LT1 = FALSE;
            m_PatComp1_1_3 = FALSE;
            m_PatientComp1 = TRUE;
            m_PatComp1_7_9 = FALSE;
            m_PatComp1_10_12 = FALSE;
            m_PatComp1_GT12 = FALSE;
        } else {
            if(m_PatComp1_LT1 == FALSE &&
                m_PatComp1_1_3 == FALSE &&
                m_PatComp1_4_6 == FALSE &&
                m_PatComp1_7_9 == FALSE &&
                m_PatComp1_10_12 == FALSE &&
                m_PatComp1_GT12 == FALSE ) {
                m_PatientComp1 = FALSE;
            }
        }
        // update dialog with new data
        UpdateData (FALSE);
    }
    void CPTDInp::OnPc179()
    {
        // get current values from dialog
        UpdateData (TRUE);
        if(m_PatComp1_7_9) {
            m_PatComp1_LT1 = FALSE;
            m_PatComp1_1_3 = FALSE;
            m_PatComp1_4_6 = FALSE;
            m_PatientComp1 = TRUE;
            m_PatComp1_10_12 = FALSE;
            m_PatComp1_GT12 = FALSE;
        } else {
            if(m_PatComp1_LT1 == FALSE &&
                m_PatComp1_1_3 == FALSE &&
                m_PatComp1_4_6 == FALSE &&
                m_PatComp1_7_9 == FALSE &&
                m_PatComp1_10_12 == FALSE &&
                m_PatComp1_GT12 == FALSE ) {
                m_PatientComp1 = FALSE;
            }
        }
        // update dialog with new data
        UpdateData (FALSE);
    }
    void CPTDInp::OnPc1Gt12()
    {
        // get current values from dialog
        UpdateData (TRUE);
        if(m_PatComp1_GT12)
            m_PatComp1_LT1 = FALSE;
            m_PatComp1_1_3 = FALSE;
            m_PatComp1_4_6 = FALSE;
            m_PatComp1_7_9 = FALSE;
            m_PatComp1_10_12 = FALSE;
            m_PatientComp1 = TRUE;
        } else {
            if(m_PatComp1_LT1 == FALSE &&
                m_PatComp1_1_3 == FALSE &&
                m_PatComp1_4_6 == FALSE &&
                m_PatComp1_7_9 == FALSE &&
                m_PatComp1_10_12 == FALSE &&
```

-continued

```
                m_PatComp1_GT12 == FALSE ) {
               m_PatientComp1 = FALSE;
            }
        }
        // update dialog with new data
        UpdateData (FALSE);
}
void CPTDInp::OnPc1Lt1 ()
{
    // get current values from dialog
    UpdateData (TRUE);
    if(m_PatComp1_LT1)
            m_PatientComp1 = TRUE;
            m_PatComp1_1_3 = FALSE;
            m_PatComp1_4_6 = FALSE;
            m_PatComp1_7_9 = FALSE;
            m_PatComp1_10_12 = FALSE;
            m_PatComp1_GT12 = FALSE;
        } else {
            if(m_PatComp1_LT1 == FALSE &&
                m_PatComp1_1_3 == FALSE &&
                m_PatComp1_4_6 == FALSE &&
                m_PatComp1_7_9 == FALSE &&
                m_PatComp1_10_12 == FALSE &&
                m_PatComp1_GT12 == FALSE ) {
               m_PatientComp1 = FALSE;
            }
        }
        // update dialog with new data
        UpdateData (FALSE);
}
void CPTDInp::OnEoAsian()
{
#ifdef NOT
    // get current values from dialog
    UpdateData (TRUE);
    if(m_EthnicOriginAsian) {
        //m_EthnicOriginAsian = FALSE;
        m_EthnicOriginBlack = FALSE;
        m_EthnicOriginHispanic = FALSE;
        m_EthnicOriginNativeAmerican = FALSE;
        m_EthnicOriginOther = FALSE;
        m_EthnicOriginWhite = FALSE;
    }
    // update dialog with new data
    UpdateData (FALSE);
#endif
}
void CPTDInp::OnEoBlack()
{
#ifdef NOT
    // get current values from dialog
    UpdateData (TRUE);
    if(m_EthnicOriginBlack) {
        m_EthnicOriginAsian = FALSE;
        //m_EthnicOriginBlack = FALSE;
        m_EthnicOriginHispanic = FALSE;
        m_EthnicOriginNativeAmerican = FALSE;
        m_EthnicOriginOther = FALSE;
        m_EthnicOriginWhite = FALSE;
    }
    // update dialog with new data
    UpdateData (FALSE);
#endif
}
void CPTDInp::OnEoHispanic()
#ifdef NOT
    // get current values from dialog
    UpdateData (TRUE);
    if(m_EthnicOriginHispanic)
        m_EthnicOriginAsian = FALSE;
        m_EthnicOriginBlack = FALSE;
        //m_EthnicOriginHispanic = FALSE;
        m_EthnicOriginNativeAmerican = FALSE;
        m_EthnicOriginOther = FALSE;
        m_EthnicOriginWhite = FALSE;
    }
    // update dialog with new data
    UpdateData (FALSE);
```

-continued

```
#endif
}
void CPTDInp::OnEoNativeAmerican()
{
#ifdef NOT
    // get current values from dialog
    UpdateData (TRUE);
    if(m_EthnicOriginNativeAmerican) {
        m_EthnicOriginAsian = FALSE;
        m_EthnicOriginBlack = FALSE;
        m_EthnicOriginHispanic = FALSE;
        //m_EthnicOriginNativeAmerican = FALSE;
        m_EthnicOriginOther = FALSE;
        m_EthnicOriginWhite = FALSE;
    }
    // update dialog with new data
    UpdateData (FALSE);
#endif
}
void CPTDInp::OnEoOther()
{
#ifdef NOT
    // get current values from dialog
    UpdateData (TRUE);
    if(m_EthnicOriginOther) {
        m_EthnicOriginAsian = FALSE;
        m_EthnicOriginBlack = FALSE;
        m_EthnicOriginHispanic = FALSE;
        m_EthnicOriginNativeAmerican = FALSE;
        //m_EthnicOriginOther = FALSE;
        m_EthnicOriginWhite = FALSE;
    }
    // update dialog with new data
    UpdateData (FALSE);
#endif
}
void CPTDInp::OnEoWhite ()
{
#ifdef NOT
    // get current values from dialog
    UpdateData (TRUE);
    if(m_EthnicOriginWhite) {
        m_EthnicoriginAsian = FALSE;
        m_EthnicOriginBlack = FALSE;
        m_EthnicOriginHispanic = FALSE;
        m_EthnicOriginNativeAmerican = FALSE;
        m_EthnicOriginOther = FALSE;
        //m_EthnicOriginWhite = FALSE;
    }
    // update dialog with new data
    UpdateData (FALSE);
#endif
}
void CPTDInp::OnMsDivorced()
{
    // get current values from dialog
    UpdateData (TRUE);
    if(m_MaritalStatusDivorced) {
        //m_MaritalStatusDivorced = FALSE;
        m_MaritalStatusLWP = FALSE;
        m_MaritalStatusMarried = FALSE;
        m_MaritalStatusOther = FALSE;
        m_MaritalStatusSingle = FALSE;
        m_MaritalStatusWidowed = FALSE;
    }
    // update dialog with new data
    UpdateData (FALSE);
}
void CPTDInp::OnMsLwp()
{
    // get current values from dialog
    UpdateData (TRUE);
    if(m_MaritalStatusLWP) {
        m_MaritalStatusDiVorced = FALSE;
        //m_MaritalStatusLWP = FALSE;
        m_MaritalStatusMarried = FALSE;
        m_MaritalStatusOther FALSE;
        m_MaritalStatusSingle = FALSE;
        m_MaritalStatusWidowed = FALSE;
    }
```

-continued

```
        // update dialog with new data
        UpdateData (FALSE);
}
void CPTDInp::OnMsMarried()
{
        // get current values from dialog
        UpdateData (TRUE);
        if(m_MaritalStatusMarried)
                m_MaritalStatusDivorced = FALSE;
                m_MaritalStatusLWP = FALSE;
                //m_MaritalStatusMarried = FALSE;
                m_MaritalStatusOther = FALSE;
                m_MaritalStatusSingle = FALSE;
                m_MaritalStatusWidowed = FALSE;
        }
        // update dialog with new data
        UpdateData (FALSE);
}
void CPTDInp::OnMsOther()
{
        // get current values from dialog
        UpdateData (TRUE);
        if(m_MaritalStatusOther) {
                m_MaritalStatusDivorced = FALSE;
                m_MaritalStatusLWP = FALSE;
                m_MaritalStatusMarried = FALSE;
                //m_MaritalStatusOther = FALSE;
                m_MaritalStatusSingle = FALSE;
                m_MaritalStatusWidowed = FALSE;
        }
        // update dialog with new data
        UpdateData (FALSE);
}
        void CPTDInp::OnMsSingle()
        {
        // get current values from dialog
        UpdateData (TRUE);
        if(m_MaritalStatusSingle) {
                m_MaritalStatusDivorced = FALSE;
                m_MaritalStatusLWP = FALSE;
                m_MaritalStatusMarried = FALSE;
                m_MaritalStatusOther = FALSE;
                //m_MaritalStatusSingle = FALSE;
                m_MaritalStatusWidowed = FALSE;
        }
        // update dialog with new data
        UpdateData (FALSE);
}
void CPTDInp::OnMsWidowed ()
{
        // get current values from dialog
        UpdateData (TRUE);
        if(m_MaritalStatusWidowed) {
                m_MaritalStatusDivorced = FALSE;
                m_MaritalStatusLWP = FALSE;
                m_MaritalStatusMarried = FALSE;
                m_MaritalStatusOther = FALSE;
                m_MaritalStatusSingle = FALSE;
                //m_MaritalStatusWidowed = FALSE;
        }
        // update dialog with new data
        UpdateData (FALSE);
}
void CPTDInp::OnOK()
{
double val;
char str[32];
char *ps;
int m,d,y;
        UpdateData (TRUE);
        // Check the Date of Birth field
        // parse the data from mnm/dd/yyyy
        strcpy(str, m_DATE_OF_BIRTH);
        m = atoi(str);
        if( m < 1 || m > 12) {
                AfxMessageBox("Please enter date in mm/dd/yy format. Month out of range");
                return;
        }
        ps = strchr(str,'/');
```

```
        if( ps == NULL ) {
            AfxMessageBox("Please enter date in mm/dd/yy format.");
            return;
        } else {
        ps++;
        d = atoi(ps);
        if( d < 1 ||d > 31 ) {
            AfxMessageBox("Please enter date in mm/dd/yy format. Day out of range");
            return;
        }
    }
}
ps = strchr(ps,'/');
if( ps == NULL ) {
    AfxMessageBox("Please enter date in mm/dd/yy format.");
    return;
{ else }
ps++;
y = atoi(ps);
if( y < 30 ) y += 2000;
if( y < 99 ) y += 1900;
}
// Check all boxes that are used by the network
if(
    m_EthnicOriginAsian == FALSE &&
    m_EthnicOriginBlack == FALSE &&
    m_EthnicOriginHispanic == FALSE &&
    m_EthnicOriginNativeAxuerican == FALSE &&
    m_EthnicOriginOther == FALSE &&
    m_EthnicOriginWhite == FALSE
    ) {
    AfxMessageBox("Please make selection for Ethnic Origin");
    return;
}
if(
    m_MaritalStatusDivorced == FALSE &&
    m_MaritalStatusLWP == FALSE &&
    m_MaritalStatusMarried == FALSE &&
    m_MaritalStatusOther == FALSE &&
    m_MaritalStatusSingle == FALSE &&
    m_MaritalStatusWidowed == FALSE
    ) {
    AfxMessageBox("Please make selection for Marital Status");
    return;
}
if(
    m_CervFirm == FALSE &&
    m_CervMod == FALSE &&
    m_CervSoft == FALSE
    ) {
    // AfxMessageBox("Please make selection for Cervical Consistancy");
    //return;
}
if(
    m_Dilitation1_2 == FALSE &&
    m_Dilitation2 == FALSE &&
    m_Dilitation2_3 == FALSE &&
    m_Dilitation3 == FALSE &&
    m_DilitationGt3 == FALSE &&
    m_Dilitation1 == FALSE &&
    m_DilitationLt1 == FALSE &&
    m_DilitationUkn == FALSE
    ) {
    AfxMessageBox("Please make selection for Dilatation");
    return;
}
if(
    m_FFN_Neg == FALSE &&
    m_FFN_Pos == FALSE
    ) {
    AfxMessageBox("Please make selection for fFN Result");
    return;
}
val = (double)atof(m_EGAbySONO);
if( val == 0.0 ) {
    AfxMessageBox("Please enter value for EGA by SONO");
    return;
}
if( val < 24.0 || val > 45.0 ) {
    AfxMessageBox("Value for EGA by SONO must be between 24.0 and 45.0 weeks");
```

-continued

```
        return;
}
val = (double)atof(m_EGAbyLMP);
if( val == 0.0 ) {
    AfxNessageBox("Please enter value for EGA by LMP");
    return;
}
if( val < 24.0 || val > 45.0 ) {
    AfxMessageBox("Value for EGA by LMP must be between 24.0 and 45.0 weeks");
    return;
}
val = (double)atof(m_EGAatSample);
if( val == 0.0 ) {
    AfxMessageBox("Please enter value for EGA at Sample");
    return;
}
if( val < 24.0 val > 45.0 ) {
    AfxMessageBox("Value for EGA at Sample must be between 24.0 and 45.0 weeks");
    return;
}
strcpy(str,m_GRAVITY);
if( str[0] == 0 ) {
    AfxMessageBox("Please enter value for Gravity");
    return;
}
strcpy(str,m PARITY);
if( str[0] == 0 ) {
    AfxMessageBox("Please enter value for Parity");
    return;
}
strcpy(str,m_ABORTIONS);
if( str[0] == 0 ) {
    AfxMessageBox("Please enter value for Abortions");
    return;
}
if(m_2_COMP == TRUE &&
m_2_COMP_1 == FALSE &&
m_2_COMP_2 == FALSE &&
m_2_COMP_3 == FALSE ) {
    AfxMessageBox("Please make selection under History of Preterm Delivery");
    return;
}
if(m_VaginalBleedingMed == FALSE &&
m_VaginalBleedingGross == FALSE &&
m_VaginalBleeding == TRUE &&
m_VaginalBleedingTrace == FALSE ) {
AfxMessageBox("Please make selection under Vaginal Bleeding");
return;
}
if(m_MultipleGestation == TRUE &&
m_MultipleGestationQuads == FALSE &&
m_MultipleGestationTriplets == FALSE &&
m_MultipleGestationTwins == FALSE ) {
AfxMessageBox("Please make selection under Multiple Gestation");
return;
}
if(m_PatientComp1 == TRUE &&
    m_PatComp1_LT1 == FALSE &&
    m_PatComp1_1_3 == FALSE &&
    m_PatComp1_4_6 == FALSE &&
    m_Patcomp1_7_9 == FALSE &&
    m_PatComp1_10_12 == FALSE &&
    m_PatComp1_GT12 == FALSE ) {
    AfxMessageBox("Please select Number/hr under Uterine contractions");
    return;
    }
    CDialog::OnOK ();
}
// PTDDg//.h : header file
//
/////////////////////////////////////////////////////////////////////////
// CPTDInp dialog
class CPTDInp : public CDialog
{
// Construction
public:
    CPTDInp(CWnd* pParent = NULL); // standard constructor
// Dialog Data
    //{{AFX_DATA(CPTDInp)
```

-continued

```
enum { IDD = IDD_D_PTD_INP };
CString   m_DATE_OF_BIRTH;
CString   m_NAME_F;
CString   m_MAME_L;
CString   m_NAME_MI;
BOOL      m_1_COMP;
BOOL      m_2_COMP;
BOOL      m_3_COMP;
BOOL      m_4_COMP;
BOOL      m_5_COMP;
BOOL      m_6_COMP;
BOOL      m_ACOG_N;
BOOL      m_ACOG_Y;
BOOL      m_Antibiotics;
BOOL      m_AntiHyper;
BOOL      m_CervCerclage;
BOOL      m_CervFirm;
BOOL      m_CervMod;
BOOL      m_CervSoft;
BOOL      m_Corticosteroids;
BOOL      m_Dilitation1_2;
BOOL      m_Dilitation2;
BOOL      m_Dilitation2_3;
BOOL      m_Dilitation3;
BOOL      m_DilitationGt3;
BOOL      m_Dilitation1;
BOOL      m_DilitationLt1;
BOOL      m_DilitationUkn;
CString   m_EGAatSample;
CString   m_EGAbyLMP;
CString   m_EGAbySONO;
BOOL      m_EthnicOriginAsian;
BOOL      m_EthnicOriginBlack;
BOOL      m_EthnicOriginHispanic;
BOOL      m_EthnicOriginNativeAmerican;
BOOL      m_EthnicOriginOther;
BOOL      m_EthnicOriginWhite;
BOOL      m_FFN_Neg;
BOOL      m_FFN_Pos;
BOOL      m_GestationalDiabetes;
BOOL      m_HypertensiveDisorders;
BOOL      m_Insulin;
CString   m_LadID;
BOOL      m_MedicationNone;
BOOL      m_MedicationUnknown;
BOOL      m_MultipleGestationQuads;
BOOL      m_MultipleGestationTriplets;
BOOL      m_MultipleGestationTwins;
BOOL      m_MaritalStatusDivorced;
BOOL      m_MaritalStatusLWP;
BOOL      m_MaritalStatusMarried;
BOOL      m_MaritalStatusOther;
BOOL      m_MaritalStatusSingle;
BOOL      m_MaritalStatusWidowed;
BOOL      m_MultipleGestation;
BOOL      m_PatientComp1;
BOOL      m_PatientComp2;
BOOL      m_PatientComp3;
BOOL      m_PatientComp4;
BOOL      m_PatientComp5;
BOOL      m_PatientComp6;
BOOL      m_Tocolytics;
BOOL      m_UtCervAbnormal;
BOOL      m_VaginalBleeding;
BOOL      m_VaginalBleedingGross;
BOOL      m_VaginalBleedingMed;
BOOL      m_VaginalBleedingTrace;
BOOL      m_2_COMP_1;
BOOL      m_2_COMP_2;
BOOL      m_2_COMP_3;
CString   m_ABORTIONS;
CString   m_PARITY;
BOOL      m_PatComp1_1_3;
BOOL      m_PatComp1_10_12;
BOOL      m_PatComp1_4_6;
BOOL      m_PatComp1_7_9;
BOOL      m_PatComp1_GT12;
BOOL      m_PatComp1_LT1;
CString   m_GRAVITY;
```

-continued

```
    //}}AFX_DATA
// Implementation
protected:
    Virtual void DoDataExchange(CDataExchange* pDX); // DDX/DDV support
    // Generated message map functions
    //{{AFX_MSG(CPTDInp);
    virtual BOOL OnInitDialog();
    afx_msg void OnRButtonDown(UINT nFlags, CPoint point);
    afx_msg void OnAcogN();
    afx_msg void OnAcogY();
    afx_msg void OnFfnNeg();
    afx_msg void OnFfnPos();
    afx_msg void OnMgQuads();
    afx_msg void OnMgTriplets();
    afx_msg void OnMgTwins();
    afx_msg void OnMultGest();
    afx_msg void OnDilitation1();
    afx_msg void OnDilitation12();
    afx_msg void OnDilitation2();
    afx_msg void OnDilitation23();
    afx_msg void OnDilitation3();
    afx_msg void OnDilitationGt3();
    afx_msg void OnDilitationLt1();
    afx_msg void OnDilitationUkn();
    afx_msg void OnCervFirm();
    afx_msg void OnCervMod();
    afx_msg void OnCervSoft();
    afx_msg void OnVaginalBleeding();
    afx_msg void OnVbGross();
    afx_msg void OnVbMed();
    afx_msg void OnVbTrace();
    afx_msg void On2Comp();
    afx_msg void On2Comp1();
    afx_msg void On2Comp2();
    afx_msg void On2Comp3();
    afx_msg void OnPatientComp1();
    afx_msg void OnPc113();
    afx_msg void OnPc11012();
    afx_msg void OnPc146();
    afx_msg void OnPc179();
    afx_msg void OnPc1Gt12();
    afx_msg void OnPc1Lt1();
    virtual void OnOK();
    afx_msg void OnEoAsian();
    afx_msg void OnEoBlack();
    afx_msg void OnEoHispanic();
    afx_msg void OnEoNativeAmerican();
    afx_msg void OnEoOther();
    afx_msg void OnEoWhite();
    afx_msg void OnMsDivorced();
    afx_msg void OnMsLwp();
    afx_msg void OnMsMarried();
    afx_msg void OnMsOther();
    afx_msg void OnMsSingle();
    afx_msg void OnMsWidowed();
    //}}AFX_MSG
    DECLARE_MESSAGE_MAP ()
    // ptdgoto.cpp implementation file
    //
    #include "stdafx.h"
    #include "ptdinp.h"
    #include "ptdgoto.h"
    #ifdef _DEBUG
    #undef THIS_FILE
    static char BASED_CODE_THIS_FILE[] = _FILE_;
    #endif
    ////////////////////////////////////////////////////////////////////
    // CPtdGoto dialog
    CPtdGoto::CPtdGoto(CWnd* pParent /*=NULL*/)
    : CDialog(CPtdGoto::IDD, pparent)
{
    //{{AFX_DATA_INIT(CPtdGoto)
    m_IDStr = "";
    m_GotoMode = -1;
    m_RecNum = 0;
    //}}AFX_DATA_INIT
}
void CPtdGoto::DoDataExchange(CDataExchange* pDX)
{
```

```
        CDialog::DoDataExchange(pDX);
        //{{AFX_DATA_MAP(CPtdGoto)
        DDX_Text(pDX, IDC_E_GOTO_ID_NUM, m_IDStr);
        DDX_Radio(pDX, IDC_R_GOTO_SEL1, m_GotoMode);
        DDX_Text(pDX, IDC_E_GOTO_REC_NUM, m_RecNum);
        DDV_MinMaxLong(pDX, m_RecNum, 0, 100000);
        //}}AFX_DATA_MAP
}
BEGIN_MESSAGE_MAP (CPtdGoto, CDialog)
        //{{AFX_MSG_MAP(CPtdGoto)
                // NOTE: the ClassWizard will add message map macros here
        //}}AFX_MSG_MAP
END_MESSAGE_MAP()
/////////////////////////////////////////////////////////////////////////
// CPtdGoto message handlers
// ptdgoto.h : header file
//
/////////////////////////////////////////////////////////////////////////
// CPtdGoto dialog
class CPtdGoto : public CDialog
{
// Construction
public:
        CPtdGoto(CWnd* pParent = NULL); // standard constructor
// Dialog Data
        //{{AFX_DATA(CPtdGoto)
        enum { IDD = IDD_D_GOTO );
        CString m_IDStr;
        int     m_GotoMode;
        long    m_RecNum;
        //}}AFX_DATA
// Implementation
protected:
        virtual void DoDataExchange(CDataExchange* pDX);      // DDX/DDV support
        // Generated message map functions
        //{{AFX_MSG(CPtdGoto)
                // NOTE: the ClassWizard will add member functions here
        //}}AFX_MSG
        DECLARE_MESSAGE_MAP()
};
// PTDidoc.cpp : implementation of the CPTDinpDoc class
//
#include "stdafx.h"
#include "PTDinp.h"
#include "PTDidoc.h"
#include "PTDGoto.h"
#include "aa_nets.h"
#ifdef_DEBUG
#undef THIS_FILE
static char BASED_CODE_THIS_FILE[] = _FILE_;
#endif
/////////////////////////////////////////////////////////////////////////
// CPTDinpDoc
IMPLEMENT_DYNCREATE (CPTDinpDoc, CDocument)
BEGIN_MESSAGE_MAP(CPTDinpDoc, CDocument)
        //{{AFX_MSG_MAP(CPTDinpDoc)
        ON_COMMAND(ID_REC_FIRST, OnRecFirst)
        ON_COMMAND(ID_REC_LAST, OnRecLast)
        ON_COMMAND(ID_REC_NEXT, OnRecNext)
        ON_COMMAND(ID_REC_PREV, OnRecPrev)
        ON_COMMAND(ID_FILE_OPEN, OnFileOpen)
        ON_COMMAND(ID_BLD_NET_FILE, OnBidNetFile)
        ON_COMMAND(ID_REC_GOTO, OnRecGoto)
        ON_COMMAND(ID_FILE_MRU_FILE1, OnFileMruFile1)
        ON_COMMAND(ID_FILE_MRU_FILE2, OnFileMruFile2)
        ON_COMMAND(ID_FILE_MRU_FILE3, OnFileMruFile3)
        ON_COMMAND(ID_FILE_MAU_FILE4, OnFileMruFile4)
        //}}AFX_MEG_MAP
END_MESSAGE_MAP()
/////////////////////////////////////////////////////////////////////////
// CPTDinpDoc construction/destruction
CPTDinpDoc::CPTDinpDoc ()
{
    CurRecord = 0;
    NumRecords = 0;
    strcpy(PathName,"");
    IDStr = ""
    GotoMode = 0;
    InitializeRec();
```

```
    LoadNets();
    m_NetPos1 = 0.0;
    m_NetNeg1 = 0.0;
    m_NetPos2 = 0.0;
    m_NetNeg2 = 0.0;
    m_NetPos3 = 0.0;
    m_NetNeg3 = 0.0;
}
CPTDinpDoc::~CPTDinpDoc ()
{
    ((CPTDinpApp*)AfxGetApp())->m_pDoc = NULL;
    FreeNets ();
}
BOOL CPTDinpDoc::OnNewDocument()
{
    if (!CDocument::OnNewDocument())
        return FALSE;
    ((CPTDinpApp*)AfxGetApp())->m_pDoc = this;
    // TODO: add reinitialization code here
    // (SDI documents will reuse this document)
    return TRUE;
{
///////////////////////////////////////////////////////////
// CPTDinpDoc serialization
void CPTDinpDoc::Serialize (CArchive& ar)
    if (ar.IsStoring())
    {
        // TODO: add storing code here
    }
    else
    {
        // TODO: add loading code here
    }
}
///////////////////////////////////////////////////////////
// CPTDinpDoc diagnostics
#ifdef _DEBUG
void CPTDinpDoc::AssertValid() const
{
    CDocument::AssertValid();
}
void CPTDinpDoc::Dump(CDumpContext& dc) const
{
    CDocument::Dump (dc);
}
#endif //_DEBUG
///////////////////////////////////////////////////////////
// CPTDinpDoc commands
void CPTDinpDoc::OnRecFirst()
{
    CurRecord = 0;
    get_rec(Rec);
}
void CPTDinpDoc::OnRecLast()
{
    CurRecord = NumRecords - 1;
    get_rec (Rec);
}
void CPTDinpDoc::OnRecNext()
{
    CurRecord = min(CurRecord + 1, NumRecords - 1);
    get_rec(Rec);
}
void CPTDinpDoc::OnRecPrev()
{
    CurRecord = max(CurRecord - 1, 0);
    get_rec(Rec);
}
///////////////////////////////////////////////////////////
void CPTDinpDoc::get_rec( char* pRec )
{
FILE *fp;
char *stmp;
    fp = fopen(PathName, "rb");
    if(fp==NULL) {
    } else {
        fseek(fp, (long) ((REC_LENGTH + 2L)*CurRecord),SEEK_SET);
        fread(pRec,sizeof(char),(REC_LENGTH + 2L),fp);
        fclose(fp);
```

```
}
m_LAB_ID = get_fld(pRec,1,12);
m_NAME_L = get_fld(pRec,13,24);
m_NAME_F get_fld(pRec,37,24);
m_NAME_MI = get_fld(pRec,61,2);
m_DATE_OF_DATA_ENTRY = get_fld(pRec,63,10);     //time
m_PATIENT_AGE = (double)atof(get_fld(pRec,73,20));
m_DATE_OF_BIRTH = get_fld(pRec,93,10);
//stmp = get fld(pRec,103,2);
//if(stmp[0] == '1') m_ETHNIC_ORIGIN_WHITE = ("1"); else m_ETHNIC_ORIGIN_WHITE = ("0");
//if(stmp[0] == '2') m_ETHNIC_ORIGIN_BLACK = ("1"); else m_ETHNIC_ORIGIN_BLACK = ("0");
//if(stmp[0] == '3') m_ETHNIC_ORIGIN_ASIAN = ("1"); else m_ETHNIC_ORIGIN_ASIAN = ("0");
//if(stmp[0] == '4') m_ETHNIC_ORIGIN_HISPANIC = ("1"); else m_ETHNIC_ORIGIN_HISPANIC = ("0");
//if(stmp[0] == '5') m_ETHNIC_ORIGIN_NATIVE_AMERICAN = ("1"); else m_ETHNIC_ORIGIN_NATIVE_AMERICAN = ("0");
//if(stmp[0] == '6') m_ETHNIC_ORIGIN_OTHER = ("1"); else m_ETHNIC_ORIGIN_OTHER = ("0");
m_ETHNIC_ORIGIN_WHITE = get_fld(pRec,103,2);
m_ETHNIC_ORIGIN_BLACK = get_fld (pRec,105,2);
m_ETHNIC_ORIGIN_ASIAN = get_fld (pRec,107,2);
m_ETHNIC_ORIGIN_HISPANIC = get_fld(pRec,109,2);
m_ETHNIC_ORIGIN_NATIVE_AMERICAN = get_fld(pRec,111,2);
m_ETHNIC_ORIGIN_OTHER = get fid (pRec, 113,2);
stmp = get_fld(pRec,115,2);
if(stmp[0] == '1') m_MARITAL_STATUS_SINGLE = ("1"); else m_MARITAL_STATUS_SINGLE = ("0");
if(stmp[0] == '2') m_MARITAL_STATUS_MARRIED = ("1"); else m_MARITAL_STATUS_MARRIED = ("0");
if(stmp[0] == '3') m_MARITAL_STATUS_DIVORCED = ("1"); else m_MARITAL_STATUS_DIVORCED = ("0");
if(stmp[0] == '4') m_MARITAL_STATUS_WIDOWED = ("1"); else m_MARITAL_STATUS_WIDOWED = ("0");
if(stmp[0] == '5') m_MARITAL_STATUS_LWP = ("1"); else m_MARITAL_STATUS_LWP = ("0");
if(stmp[0] == '6') m_MARITAL_STATUS_OTHER = ("1"); else m_MARITAL_STATUS_OTHER = ("0");
m_ACOG_SYNPTOMS = get_fld(pRec,117,2);
stmp = get fld(pRec,119,2);
if(stmp[0] == '0') m_VAGINAL_BLEEDING = ("0"); else m_VAGINAL_BLEEDING = ("1");
if(stmp[0] == '1') m_VAGINAL_BLEEDING_TRACE = ("1"); else ci VAGINAL_BLEEDING_TRACE = ("0");
if(stmp[0] == '2') m_VAGINAL_BLEEDING_MEDIUM = ("1"); else m_VAGINAL_BLEEDING_MEDIUM = ("0");
if(stmp[0] == '3') m_VAGINAL_BLEEDING_GROSS = ("1"); else m_VAGINAL_BLEEDING_GROSS = ("0");
if(stmp[0] == 0) m_VAGINAL_BLEEDING ("0");
m_PATIENT_COMPLAINT_1 = get_fld(pRec,121,2);
m_PATIENT_COMPLAINT_2 = get_fld(pRec,123,2);
m_PATIENT_COMPLAINT_3 = get_fld(pRec,125,2);
m_PATIENT_COMPLAINT_4 = get_fld(pRec,127,2);
m_PATIENT_COMPLAINT_5 = get_fld(pRec,129,2);
m_PATIENT_COMPLAINT_6 = get_fld(pRec,131,2);
stmp = get_fld(pRec,133,2);
if(stmp[0] == '1') m_PATIENT_COMPLAINT_1_LT1 = ("1"); else m_PATIENT_COMPLAINT_1_LT1 = ("0");
if(stmp[0] == '2') m_PATIENT_COMPLAINT1_1_3 = ("1"); else m_PATIENT_COMPLAINT_1_1_3 = ("0");
if(stmp[0] == '3') m_PATIENT_COMPLAINT_1_4_6 = ("1"); else m_PATIENT_COMPLAINT_1_4_6 = ("0");
if(stmp[0] == '4') m_PATIENT_COMPLAINT_1_7_9 = ("1"); else m_PATIENT_COMPLAINT_1_7_9 = ("0");
if(stmp[0] == '5') m_PATIENT_COMPLAINT_1_10_12 = ("1"); else m_PATIENT_COMPLAINT_1_10_12 = ("0");
if(stmp[0] == '6') m_PATIENT_COMPLAINT_1_GT12 = ("1"); else m_PATIENT_COMPLAINT_1_GT12 = ("0");
m_EGA_BY_SONO = get_fld(pRec,135,8);
m_EGA_BY_LMP = get_fld(pRec,143,8);
m_EGA_AT_SAMPLING = get_fld(pRec,151,8);
m_GRAVITY = get_fld(pRec,159,2);
m_PARITY = get_fld(pRec,161,2);
m_ABORTIONS = get_fld(pRec,163,2);
stmp = get_fld(pRec,165,2);
if(stmp[0] == '1') m_2_COMP_1 = ("1"); else m_2_COMP_1 = ("0");
if(stmp[0] == '2') m_2_COMP_2 = ("1"); else m_2_COMP_2 = ("0");
if(stmp[0] == '3') m_2_COMP_3 = ("1"); else m_2_COMP_3 = ("0");
m_0 COMP = get_fld(pRec,167,2);
```

-continued

```
    m_1_COMP = get_fld(pRec,169,2);
    m_2_COMP = get_fld(pRec,171,2);
    m_3_COMP = get_fld(pRec,173,2);
    m_4_COMP = get_fld(pRec,175,2);
    m_5_COMP = get_fld(pRec,177,2);
    m_6_COMP = get_fld(pRec,179,2);
    stmp = get_fld(pRec,181,2);
    if(stmp[0] == '0') m_MULTIPLE_GESTATION = ("0"); else m_MULTIPLE_GESTATION = ("1");
    if(stmp[0] == '1') m_MULTIPLE_GESTATION_TWINS = ("1"); else m_MULTIPLE_GESTATION_TW
INS = ("0");
    if(stmp[0] == '2') m_MULTIPLE_GESTATION_TRIPLETS = ("1"); else m_MULTIPLE_GESTATION
TRIPLETS = ("0");
    if(stmp[0] == '3') m_MULTIPLE_GESTATION_QUADS = ("1"); else m_MULTIPLE_GESTATION_QU
ADS = ("0");
    if(stmp[0] == 0) m_MULTIPLE_GESTATION = ("0");
    m_UTCERV_ABNORMALITY = get_fld(pRec,183,2);
    m_CERVICAL_CERCLAGE = get_fld (pRec,185,2);
    m_GESTATIONAL_DIABETES = get_fld(pRec,187,2);
    m_HYPERTENSIVE_DISORDERS = get_fld(pRec,189,2);
    stmp = get_fld(pRec,191,2);
    if(stmp[0] == '0') m_DILITATION_UNKNOWN = ("1"); else m_DILITATION_UNKNOWN = ("0");
    if(stmp[0] == '1') m_DILITATION_LT1 = ("1"); else m_DILITATION_LT1= ("0");
    if(stmp[0] == '2') m_DILITATION_1 = ("1"); else m_DILITATION_1 = ("0");
    if(stmp[0] == '3') m_DILITATION1_2 = ("1"); else m_DILITATION_1_2 ("0");
    if(stmp[0] == '4') m_DILITATION_2 = ("1"); else m_DILITATION_2 = ("0");
    if(stmp[0] == '5') m_DILITATION_2_3 = ("1"); else m_DILITATION_2_3 = ("0");
    if(stmp[0] == '6') m_DILITATION_3 = ("1"); else m_DILITATION_3 = ("0");
    if(stmp[0] == '7') m_DILITATION_GT3 = ("1"); else m_DILITATION_GT3 = ("0");
    stmp = get_fld(pRec,193,2);
    if(stmp[0] == '1') m_CERVICAL_CONSISTANCY_FIRM = ("1"); else m_CERVICAL_CONSISTANCY
_FIRM = ("0");
    if(stmp[0] == '2') m_CERVICAL_CONSISTANCY_MOD = ("1"); else m_CERVICAL_CONSISTANCY_
MOD = ("0");
    if(stmp[0] == '3') m_CERVICAL_CONSISTANCY_SOFT = ("1"); else m_CERVICAL_CONSISTANCY
_SOFT = ("0");
    m_ANTIBIOTICS = get_fld(pRec,195,2);
    m_CORTICOSTEROIDS = get_fld(pRec,197,2);
    m_TOYOLYTICS = get_fld(pRec,199,2);
    m_INSULIN = get_fld(pRec,201,2);
    m_ANTIHYPERTENSIVES = get_fld (pRec,203,2);
    m_MEDICATIONS_NONE = get_fld(pRec,205,2);
    m_MEDICATIONS_UNKNOWN = get_fld(pRec,207,2);
    m_FFN_RESULT = get_fld(pRec,209,2);
    m_NetPos1 = (double)atof(get_fld(pRec, 211, 20));
    m_NetNeg1 = (double)atof(get_fld(pRec, 231, 20));
    m_NetPos2 = (double)atof(get_fld(pRec, 251, 20));
    m_NetNeg2 = (double)atof(get_fld(pRec, 271, 20));
    m_NetPos3 = (double)atof(get_fld(pRec, 291, 20));
    m_NetNeg3 = (double)atof(get_fld(pRec, 311, 20));
    UpdateAllViews (NULL);
}
char* CPTDinpDoc::get_fld(char* pRec, int ofs, int len)
{
int i;
    for( i = 0; i < len; i++)
        fld[i] = pRec[ofs-1+i];
    }
    fld[len] = 0;
    for( i = len-1; i >= 0; i--) {
        fld[i] == ' ') {
            fld[i] = 0;
        } else {
            break;
        }
    }
    return fld;
}
CTime& CPTDinpDoc::get_time_fld(char* pRec, int iofs, int len)
{
int i;
int m,d,y;
int ofs;
    for( i = 0; 1 < len; i++)
    fld[i] = pRec[iofs-1+i];
    }
    for( i = len-1; i > 0; i--)
        if(fld[i] == ' ') {
            fld[i] = 0;
        } else {
```

-continued

```
            break;
        }
    }
    strcpy(tstr,fld);
    m = d = y = 0;
    ofs = 0;
    while(tstr[ofs] == ' ') ofs++; // skip spaces;
    m = atoi(&tstr[ofs]);
    while(tstr[ofs] >= '0' && tstr[ofs] <= '9') ofs++; // skip number
    while(tstr[ofs] == '/' || tstr[ofs] == '-') ofs++; // skip delimiter
    d = atoi(&tstr[ofs]);
    if(d == 0) d = 1;
    while(tstr[ofs] >= '0' && tstr[ofs] <= '9') ofs++; // skip number
    while(tstr[ofs] == '/' // tstr[ofs] == '-') ofs++; // skip delimiter
    y = atoi(&tstr[ofs]);
    if(y<100) y += 1900;
    CTime t(y,m,d,0,0,0);
    tim = t;
    return(tim);
}
void CPTDinpDoc::put_rec(char* pRec)
{
FILE *fp;
CString stmp;
    put_fld(pRec, m_LAB_ID ,1,12);
    put_fld(pRec, m_NAME_L ,13,24);
    put_fld(pRec, m_NAME_F ,37,24);
    put_fld(pRec, m_NAIVE_MI ,61,2);
    put_fld(pRec, m_DATE_OF_DATA_ENTRY ,63,10);        //time
    put_dbl_fld(pRec, m_PATIENT_AGE ,73,20);
    put_fld(pRec, m_DATE_OF_BIRTH ,93,10);
    //stmp = " "
    //if( m_ETHNIC_ORIGIN_WHITE == "1") stmp = "1";
    //if( m_ETHNIC_ORIGIN_BLACK == "1") stmp = "2";
    //if( m_ETHNIC_ORIGIN_ASIAN == "1") stmp = "3";
    //if( m_ETHNIC_ORIGIN_HISPANIC == "1") stmp = "4";
    //if( m_ETHNIC_ORIGIN_NATIVE_AMERICAN == "1") stmp = "5";
    //if( m_ETHNIC_ORIGIN_OTHER == "1") stmp = "6";
    //put_fld(pRec, stmp,103,2);
    put_fld(pRec, m_ETHNIC_ORIGIN_WHITE ,103,2);
    put_fld(pRec, m_ETHNIC_ORIGIN_BLACK ,105,2);
    put_fld(pRee, m_ETHNIC_ORIGIN_ASIAN 407,2);
    put_fld(pRec, m_ETHNIC_ORIGIN_HISPANIC ,109,2);
    put_fld(pReC, m_ETHNIC_ORIGIN_NATIVE_AMERICAN ,111,2);
    put_fld(pRec, m_ETHNIC_ORIGIN_OTHER , 113,2);
    stmp= " ";
    if( m_MARITAL_STATUS_SINGLE == "1") stmp = "1";
    if( m_MARITAL_STATUS_MARRIED == "1") stmp = "2";
    if( m_MARITAL_STATUS_DIVORCED == "1") stmp = "3";
    if( m_MARITAL_STATUS_WIDOWED == "1") stmp = "4";
    if( m_MARITAL_STATUS_LWP == "1") stmp = "5";
    if( m_MARITAL_STATUS_OTHER == "1") stmp = "6";
    put_fld(pRec, stmp,115,2);
    put_fld(pRec, m_ACOG_SYNPTOMS ,117,2);
    stmp = " ";
    if( m_VAGINAL_BLEEDING == "0") stmp = "0";
    if( m_VAGINAL_BLEEDING_TRACE == "1") stmp = "1";
    if( m_VAGINAL_BLEEDING_IMEDIUM == "1") stmp = "2";
    if( m_VAGINAL_BLEEDING_GROSS == "1") stmp = "3";
    put_fld(pRec, stmp,119,2);
    put_fld(pRec, m_PATIENT_COMPLAINT_1 ,121,2);
    put_fld(pRec, m_PATIENT_COMPLAINT_2 ,123,2);
    put_fld(pRec, m_PATIENT_COMPLAINT_3 ,125,2);
    put_fld(pRec, m_PATIENT_COMPLAINT_4 ,127,2);
    put_fld(pRec, m_PATIENT_COMPLAINT_5 ,129,2);
    put_fld(pRec, m_PATIENT_COMPLAINT_6 ,131,2);
    stmp = " ";
    if( m_PATIENT_COMPLAINT_1_LT1 == "1") stmp "1";
    if( m_PATIENT_COMPLAINT_1_1_3 == "1") stmp = "2";
    if( m_PATIENT_COMPLAINT_1_4_6 == "1") stmp = "3";
    if( m_PATIENT_COMPLAINT_1_7_9 == "1") stmp = "4";
    if( m_PATIENT_COMPLAINT_1_10_12 == "1") stmp = "5";
    if( m_PATIENT_COMPLAINT_1_GT12 == "1") stmp = "6";
    put_fld(pRec, stmp,133,2);
    put_fld(pRec, m_EGA_BY_SONO ,135,8);
    put_fld(pRec, m_EGA_BY_LMP ,143,8);
    put_fldCpRec, m_EGA_AT_SAMPLING ,151,8);
    put_fld(pRec, m_GRAVITY ,159,2);
    put_fld(pRec, m_PARITY, 161,2);
```

-continued

```
        put_fld(pRec, m_ABORTIONS, 163,2);
        stmp = " ";
        if( m_2_COMP_1 == "1") stmp = "1";
        if( m_2_COMP_2 == "1") stmp = "2";
        if( m_2_COMP_3 == "1") stmp = "3";
        put_fld(pRec, stmp,165,2);
        put_fld(pRec, m_0_COMP ,167,2);
        put_fld(pRec, m_1_COMP ,169,2);
        put_fld(pRec, m_2_COMP ,171,2);
        put_fld(pRec, m_3_COMP ,173,2);
        put_fld(pRec, m_4_COMP ,175,2);
        put_fld(pRec, m_5_COMP ,177,2);
        put_fld(pRec, m_6_COMP ,179,2);
        stmp = " ";
        if( m_MULTIPLE_GESTATION == "0") stmp = "0";
        if( m_MULTIPLE_GESTATION_TWINS == "1") stmp = "1";
        if( m_MULTIPLE_GESTATION_TRIPLETS == "1") stmp = "2";
        if( m_MULTIPLE_GESTATION_QUADS == "1") stmp = "3";
        put_fld(pRec, stanp,181,2);
        put_fld(pRec, m_UTCERV_ABNORMALITY ,183,2);
        put_fld(pRec, m_CERVICAL_CERCLAGE ,185,2);
        put_fld(pRec, m_GESTATIONAL_DIABETES ,187,2);
        put_fld(pRec, m_HYPERTENSIVE_DISORDERS ,189,2);
        stmp = " ";
        if( m_DILITATION_UNKNOWN == "1") stmp = "0";
        if( m_DILITATION_LT1 == "1") stmp = "1";
        if( m_DILITATION_1 == "1") stmp = "2";
        if( m_DILITATION_1_2 == "1") stmp = "3";
        if( m_DILITATION_2 == "1") stmp = "4";
        if( m_DILITATION_2_3 == "1") stmp = "5";
        if( m_DILITATION_3 == "1") stmp = "6";
        if( m_DILITATION_GT3 == "1") stmp "7";
        put_fld(pRec, stmp,191,2);
        stmp = " ";
        if( m_CERVICAL_CONSISTANCY_FIRM == "1") stmp = "1";
        if( m_CERVICAL_CONSISTANCY_MOD == "1") stmp = "2";
        if( m_CERVICAL_CONSISTANCY_SOFT == "1") stmp = "3";
        put_fld(pRec, stmp,193,2);
        put_fld(pRec, m_ANTIBIOTICS ,195,2);
        put_fld(pRec, m_CORTICOSTEROIDS ,197,2);
        put_fld(pRec, m_TOYOLYTICS ,199,2);
        put_fld(pRec, m_INSULIN ,201,2);
        put_fld(pRec, m_ANTIHYPERTENSIVES ,203,2);
        put_fld(pRec, m_MEDICATIONS_NONE ,205,2);
        put_fld(pRec, m_MEDICATIONS_UNKNOWN ,207,2);
        put_fld(pRec, m_FFN_RESULT ,209,2);
        put_net_fld(pRec, m_Netpos1,211, 20);
        put_net_fld(pRec, m_&etNeg1,231, 20);
        put_net_fld(pRec, m_NetPos2,251, 20);
        put_net_fld(pRec, m_NetNeg2,271, 20);
        put_net_fld(pRec, m_NetPos3,291, 20);
        put_net_fld(pRec, m_NetNeg3,311, 20);
        fp = fopen(PathName,"r+b");
        if(fp==NULL) {
            fp = fopen(PathName,"wb");
            if(fp!=NULL)
                fwrite(Rec, sizeof(char), (REC_LENGTH+2L) , fp);
                fflush(fp);
                fclose(fp);
            }
        } else {
            fseek(fp, (long) ((REC_LENGTH+2L) *CurRecord) ,SEEK_SET);
            fwrite(pRec,sizeof(char), (REC_LENGTH+2L),fp);
            fflush(fp);
            fclose(fp);
        }
        UpdateAllViews (NULL);
}
void CPTDinpDoc::put_fld(char* pRec, CString& dat, int ofs, int len)
int i;
int fill;
        strcpy(fld,dat);
        fill = 0;
        for( i = 0; i < len; i++)
            if(fld[i] == 0) fill = 1;
            if(fill==0) {
                pRec[ofs-1+i] = fld[i];
            } else {
                pRec[ofs-1+i] = (char)' ';
```

```
        }
    }
}
void CPTDinpDoc::put_dbl_fld(char* pRec, double dat, int ofs, int len)
int i;
    sprintf(fld,"%20.41f",dat);
    for( i = 0; i < len; i++) {
            pRec[ofs-1+i] = fld[i];
    }
}
void CPTDinpDoc::put_net_fld(char* pRec, double dat, int ofs, int len)
{
int i;
    sprintf(fld,"%20.16lf",dat);
    for( i = 0; i < len; i++) {
            pRec[ofs-1+i] fld[i];
    }
}
void CPTDinpDoc::put_time_fld(char* pRec, CTime& dat, int ofs, int len)
{
int i;
char *pfld;
    pfld = time2str(dat);
    strcat(pfld,"           ");
    for( i = 0; i < len; i++)
        pRec[ofs-1+i] = pfld[i];
    }
}
void CPTDinpDoc::OnBldNetFile()
{
FILE *fp;
    // Get the File Name
    CFileDialog Dlg (FALSE, "ndb", NULL, OFN_OVERWRITEPROMPT,
        "NDB iles (*.nbd) |*.ndb||");
    Dlg.m_ofn.1pstrTitle = "Open fixed length Network DataBase file";
    if( Dlg.DoModal() == IDOK ) {
    strcpy (NetName,Dlg.GetPathName ());
    // open the new file
    fp = fopen(NetName,"wb");
    if(fp == NULL) {
        AfxMessageBox("Could not open the neural network output file!");
    } else {
        // build the record
        CurRecord = 0;
        HCURSOR hcurSave;
        hcurSave = SetCursor(LoadCursor(NULL, IDC_WAIT));
        while( CurRecord < NumRecords ( {
            // read the PTD record
            get_rec(Rec);
            // run the networks
            RunNets (CurRecord);
            // build the output record
            put_fld(NetRec, m_LAB_ID, 1, 12);
            put_net_fld(NetRec, m_NetPos1, 13, 20);
            put_net_fld(NetRec, m_NetNeg1, 33, 20);
            put_net_fld(NetRec, m_NetPos2, 53, 20);
            put_net_fld(NetRec, m_NetNeg2, 73, 20);
            put_net_fld(NetRec, m_NetPos3, 93, 20);
            put_net_fld(NetRec, m_NetNeg3, 113, 20);
            NetRec[132] = (char)0x0d;
            NetRec[133] = (char)0x0a;
            // write the output record
            fwrite(NetRec,sizeof(char) ,134, fp);
            // increment to the next PTD record
            CurRecord += 1;
        }
        // close the new file
        fclose(fp);
        SetCursor(hcurSave);
    }
    }
}
void CPTDinpDoc::InitializeRec()
{
    // add one-time construction code here
    for(int i = 0; i < REC_LENGTH; i++) Rec[i] = (char)' ';
    Rec[REC LENGTH]= (char)0x0d;
    Rec[REC_LENGTH + 1L] = (char)0x0a
    //CTime Dtime(1900,1,1,0,0,0);
```

```
char* Dtime = "min/dd/yy";
m_LAB_ID = ("");
m_NAME_L = ("");;
m_NAME_F = ("");;
m_NAME_MI = ("");;
m_DATE_OF DATA_ENTRY = time2str(CTime::GetCurrentTime());
m_PATIENT_AGE = 0.0;
m_DATE_OF_BIRTH = Dtime;
m_ETHNIC_ORIGIN_WHITE = ("");
m_ETHNIC_ORIGIN_BLACK = ("");
m_ETHNIC_ORIGIN_ASIAN = ("");
m_ETHNIC_ORIGIN_HISPANIC = ("");
m_ETHNIC_ORIGIN_NATIVE_AMERICAN = ("");
m_ETHNIC_ORIGIN_OTHER = ("");
m_MARITAL_STATUS_SINGLE = ("");
m_MARITAL_STATUS_MARRIED = ("");
m_MARITAL_STATUS_DIVORCED = ("");
m_MARITAL_STATUS_WIDOWED = ("");
m_MARITAL_STATUS_LWP = ("");
m_MARITAL_STATUS_OTHER = ("");
m_ACOG_SYNPTOMS = ("");
m_PATIENT_COMPLAINT_1 = ("");
m_PATIENT_COMPLAINT_1_1_3 = ("");
m_PATIENT_COMPLAINT_1_1_0 12 = ("");
m_PATIENT_COMPLAINT_1_4_6 = ("");
m_PATIENT_COMPLAINT_1_7_9 = ("");
m_PATIENT_COMPLAINT_1_GT12 = ("");
m_PATIENT_COMPLAINT_1_LT1 = ("");
m_VAGINAL_BLEEDING = ("");
m_VAGINAL_BLEEDING_TRACE = ("");
m_VAGINAL_BLEEDING_MEDIUM = ("");
m_VAGINAL_BLEEDING_GROSS = ("");
m_PATIENT_COMPLAINT_6 = ("");
m_PATIENT_COMPLAINT_3 = ("");
m_PATIENT_COMPLAINT_2 = ("");
m_PATIENT_COMPLAINT_5 = ("");
m_PATIENT_COMPLAINT_4 = ("");
m_EGA_BY_SONO = ("");
m_EGA_BYL_MP = ("");
m_EGA_AT_SAMPLING = ("");
m_0_COMP = ("");
m_1_COMP = ("");
m_2_COMP = ("");
m_3_COMP = ("");
m_4_COMP = ("");
m_5_COMP = ("");
m_6_COMP = ("");
m_2_COMP_1 = ("");
m_2_COMP_2 = ("");
m_2_COMP_3 = ("");
m_GRAVITY = ("");
m_PARITY = ("");
m_ABORTIONS = ("");
m_MULTIPLE_GESTATION = ("");
m_MULTIPLE_GESTATION_TWINS = ("");
m_MULTIPLE_GESTATION_TRIPLETS = ("");
m_MULTIPLE_GESTATION_QUADS = ("");
m_UTCERV_ABNORMALITY = ("");
m_CERVICAL_CERCLAGE = ("");
m_GESTATIONAL_DIABETES = ("");
m_HYPERTENSIVE_DISORDERS = ("");
m_DILITATION_LT1 = ("");
m_DILITATION_1 = ("");
m_DILITATION_1_2 = ("");
m_DILITATION_2 = ("");
m_DILITATION_2_3 = ("");
m_DILITATION_3 = ("");
m_DILITATION_GT3 = ("");
m_DILITATION_UNKNOWN = ("");
m_CERVICAL_CONSISTANCY_FIRM = ("");
m_CERVICAL_CONSISTANCY_MOD = ("");
m_CERVICAL_CONSISTANCY_SOFT = ("");
m_ANTIBIOTICS = ("");
m_CORTICOSTEROIDS = ("");
m_TOYOLYTICS = ("");
m_INSULIN = ("");
m_ANTIHYPERTENSIVES = ("");
m_MEDICATIONS_NONE = ("");
m_MEDICATIONS_UNKNOWN = ("");
```

-continued

```
        m_FFN_RESULT = ("");
}
void CPTDinpDoc::LoadNets ()
{
        // load eight networks for each consensus 1-8
        if(LoadNet(1,"ega6_0") != 1) {
                AfxMessageBox("Could not load ega6_0");
        }
        if(LoadNet(2,"ega6_1") != 2) {
                AfxMessageBox("Could not load ega6_1");
        }
        if(LoadNet(3,"ega6_2") != 3) {
                AfxMessageBox("Could not load ega6_2");
        }
        if(LoadNet(4,"ega6_3") != 4) {
                AfxMessageBox("Could not load ega6_3");
        }
        if(LoadNet(5,"ega6_4") != 5) {
                AfxMessageBox("Could not load ega6_4");
        if(LoadNet(6,"ega6_5") != 6) {
                AfxMessageBox("Could not load ega6_5");
        if(LoadNet(7,"ega6_6") != 7) {
                AfxMessageBox("Could not load ega6_6");
        }
        if(LoadNet(8,"ega6_7") != 8) {
                AfxMessageBox("Could not load ega6_7");
        // load eight networks for each consensus 9-16
        if(LoadNet(9,"egad7f0") != 9) {
                AfxMessageBox("Could not load egad7f0");
        }
        if(LoadNet(10,"egad7f1") != 10) {
                AfxMessageBox ("Could not load egad7f1");
        }
        if(LoadNet(11,"egad7f2") != 11) {
                AfxMessageBox("Could not load egad7f2");
        }
        if(LoadNet(12,"egad7f3") != 12) {
                AfxMessageBox("Could not load egad7f3");
        }
        if(LoadNet(13,"egad7f4") != 13) {
                AfxMessageBox("Could not load egad7f4");
        }
        if(LoadNet(14,"egad7f5") != 14) {
                AfxMessageBox("Could not load egad7f5");
        }
        if(LoadNet(15,"egad7f6") != 15) {
                AfxMessageBox("Could not load egad7f6");
        }
        if(LoadNet(16,"egad7f7") != 16) {
                AfxMessageBox("Could not load egad7f7");
        }
        // load eight networks for each consensus 17-24
        if(LoadNet(17,"egad14f0") != 17) {
                AfxMessageBox("Could not load egad14f");
        }
        if(LoadNet(18,"egad14f1") != 18) {
                AfxMessageBox ("Could not load egad14f1");
        }
        if(LoadNet(19,"egad14f2") != 19) {
                AfxMessageBox("Could not load egad14f2");
        }
        if(LoadNet(20,"egad14f3") != 20) {
                AfxMessageBox("Could not load egad14f3");
        }
        if(LoadNet(21,"egad14f4") != 21) {
                AfxMessageBox("Could not load egad14f4");
        }
        if(LoadNet(22,"egad14f5") != 22) {
                AfxMessageBox("Could not load egad14f5");
        }
        if(LoadNet(23,"egad14f6") != 23) {
                AfxMessageBox("Could not load egad14f6");
        }
        if(LoadNet(24,"egad14f7") != 24) {
                AfxMessageBox("Could not load egad14f7");
        }
}
void CPTDinpDoc::FreeNets()
{
```

-continued

```
        for (int = 1; i <= 24; i++) FreeNet(i);
}
void CPTDinpDoc::RunNets(long n)
{
double Val, Val1, frac;
// Run first ega6 nets
m_NetPos1 = 0.0;
m_NetNeg1 = 0.0;
for(int i = 1; i <=8; i++) {
    // build inputs from record
    Val = ((m_ETHNIC_ORIGIN_WHITE =="1")?1.0:0.0);
    PutInput(i,1,&Val);
    Val = ((m_MARITAL_STATUS_LWP =="1")?1.0:0.0);
    PutInput(i,2,&Val);
    Val = (double)atof(m_EGA_BY_SONO);
    frac = Val - floor(Val);
    Val = floor(Val) + (frac / 0.7);
    PutInput(i,3,&Val);
    //Val = (double)atof(m_EGA_BY_BEST);
    Val = (double)atof(m_EGA_BY_LMP);
    frac = Val - floor(Val);
    Val = floor(Val) + (frac / 0.7);
    Val1 = (double)atof(m_EGA_BY_SONO);
    frac = Val1 - floor(Val1);
    Val1 = floor(Val1) + (frac / 0.7);
    if (Val1 <= 13.0) {
        Val = Val1;
    } else {
        if(fabs(Val - Val1) > 2.0) {
        } else {
            Val = Val1;
        }
    }
    PutInput(i,4,&Val);
    Val = (double)atof(m_EGA_AT_SAMPLING);
    frac = Val - floor(Val);
    Val = floor(Val) + (frac / 0.7);
    PutInput(i,5,&Val);
    Val = 0.0; // CD_INTERP
    if( m_DILITATION_LT1 == "1" ) Val = 0.0;
    if( m_DILITATION_1 == "1" ) Val = 1.0;
    if( m_DILITATION_1_2 == "1" ) Val = 1.5;
    if( m_DILITATION_2 == "1" ) Val = 2.0;
    if( m_DILITATION_2_3 == "1" ) Val = 2.0;
    if( m_DILITATION_3 == "1" ) Val = 3.0;
    if( m_DILITATION_GT3 == "1" ) Val = 3.0;
    PutInput(i,6,&Val);
    Val = 0.0; // Parity-PreTerm
    if( m_2_COMP_1 == "1" ) Val = 1.0;
    if( m_2_COMP_2 == "1" ) Val = 2.0;
    if( m_2_COMP_3 == "1" ) Val = 3.0;
    PutInput (i,7,&Val);
    Val = ((m_VAGINAL_BLEEDING =="1")?1.0:0.0);
    PutInput(i,8,&Val);
    Val = 1.823197; // CERVICAL_CONSISTANCY
    if( m_CERVICAL_CONSISTANCY_FIRM == "1" ) Val = 1.0;
    if( m_CERVICAL_CONSISTANCY_MOD == "1" ) Val = 2.0;
    if( m_CERVICAL_CONSISTANCY_SOFT == "1" ) Val = 3.0;
    PutInput(i,9,&Val);
    Val = ((m_1_COMP =="1")?1.0:0.0);
    PutInput(i,10,&Val);
    Val = ((m_FFN_RESULT =="1")?1.0:0.0);
    PutInput(i,11,&Val);
    // iterate network
    IterateNet(i);
    // build consensus result
    m_NetPos1 += GetState(i,3,1) / 8.0;
    m_NetNeg1 += GetState(i,3,2) / 8.0;
}
m_NetVal1 = 25.0 * (m_NetPos1 - m_NetNeg1);
// Run first egad7f nets
m_NetPos2 = 0.0;
m_NetNeg2 = 0.0;
for(i = 9; i <=16; i++) {
    // build inputs from record
    Val = ((m_ETHNIC_ORIGIN_WHITE =="1")?1.0:0.0);
    PutInput (i,1,&Val);
    Val = ((m_PATIENT_COMPLAINT_1 == "1")?21.0:0.0);
    PutInput(i,2,&Val);
```

-continued

```
    Val = (double)atof(m_ABORTIONS);
    PutInput(i,3,&Val);
    Val = ((m_VAGINAL_BLEEDING =="1")?1.0:0.0);
    PutInput(i,4,&Val);
    Val = 0.0; //UC INTERP
    if( m_PATIENT_COMPLAINT_1_LT1 == "1") Val = 1.0;
    if( m_PATIENT_COMPLAINT_1_1_3 == "1" ) Val = 2.0;
    if( m_PATIENT_COMPLAINT_1_4_6 == "1" ) Val = 3.0;
    if( m_PATIENT_COMPLAINT_1_7_9 == "1" ) Val = 4.0;
    if( m_PATIENT_COMPLAINT_1_10_12 == "1" ) Val = 5.0;
    if( m_PATIENT_COMPLAINT_1_GT12 == "1" ) Val = 6.0;
    PutInput(i,5,&Val);
    Val = ((m_0_COMP "1")?1.0:0.0);
    PutInput(i,6,&Val);
    Val = ((m_FFN_RESULT =="1")?1.0:0.0);
    PutInput(i,7,&Val);
    // iterate network
    IterateNet(i);
    // build consensus result
    m_NetPos2 += GetState(i,3,1) / 8.0;
    m_NetNeg2 += GetState(i,3,2) / 8.0;
}
m_NetVal2 = 25.0 * (m_NetPos2-m_NetNeg2);
// Run first egad14f nets
m_NetPos3 = 0.0;
m_NetNeg3 = 0.0;
for(i = 17; i <=24; i++) {
    // build inputs from record
    Val = ((m_ETHNIC_ORIGIN_NATIVE_AMERICAN =="1")?1.0:0.0);
    PutInput(i,1,&Val);
    Val = ((m_MARITAL_STATUS_LWP =="1")?1.0:0.0);
    PutInput(i,2,&Val);
    Val = ((m_PATIENT_COMPLAINT_1 =="1")?1.0:0.0);
    PutInput(i,3,&Val);
    Val = 0.0;      //CD_INTERP
    if( m_DILITATION_LT1 == "1" ) Val = 0.0;
    if( m_DILITATION_1 == "1" ) Val = 1.0;
    if( m_DILITATION_1_2 == "1" ) Val = 1.5;
    if( m_DILITATION_2 == "1" ) Val = 2.0;
    if( m_DILITATION_2_3 == "1" ) Val = 2.0;
    if( m_DILITATION_3 == "1" ) Val = 3.0;
    if( m_DILITATION_GT3 == "1" ) Val = 3.0;
    PutInput(i,4,&Val);
    Val = 0.0; //UC INTERP
    if( m_PATIENT_COMPLAINT_1 LT1 == "1" ) Val = 1.0;
    if( m_PATIENT_COMPLAINT_1_1_3 == "1" ) Val = 2.0;
    if( m_PATIENT_COMPLAINT_1_4_6 == "1" ) Val = 3.0;
    if( m_PATIENT_COMPLAINT_1_7_9 == "1" ) Val = 4.0;
    if( m_PATIENT_COMPLAINT_1_10_12 == "1" ) Val = 5.0;
    if( m_PATIENT_COMPLAINT_1_GT12 == "1" ) Val = 6.0;
    PutInput(i,5,&Val);
    Val = ((m_0_COMP =="1")?1.0:0.0);
    PutInput(i,6,&Val);
    Val = ((m_FFN_RESULT =="1")?1.0:0.0);
    PutInput(i,7,&Val);
    // iterate network
    IterateNet(i);
    // build consensus result
    m_NetPos3 += GetState(i,3,1) / 8.0;
    m_NetNeg3 += GetState(i,3,2) / 8.0;
}
m_NetVal3 = 25.0 * (m_NetPos3-m_NetNeg3);
}
char* CPTDinpDoc::time2str( const CTime& tm )
{
    sprintf(tstr,"%d/%d/%d",tm.GetMonth(),tm.GetDay(), (tm.GetYear()-1900));
    return tstr;
}
CTime& CPTDinpDoc::str2time( CString& str
{
    int m,d,y;
    int ofs;
    strcpy(tstr, str);
    m = d = y = 0;
    ofs = 0;
    while(tstr[ofs] == ' ') ofs++; // skip spaces;
    m = atoi(&tstr[ofs]);
    while(tstr[ofs] >= '0' && tstr[ofs] <= '9') ofs++; // skip number
    while(tstr[ofs] == '/' || tstr[ofs] '-' ) ofs++; // skip delimiter
```

-continued

```
        d = atoi(&tstr[ofs]);
        while(tstr[ofs] >= '0' && tstr[ofs] <= '9') ofs++; // skip number
        while(tstr[ofs] == '/' || tstr[ofs] == '-') ofs++; // skip delimiter
        y = atoi(&tstr[ofs]);
        if(y<100) y += 1900;
        tim = CTime(y,m,d,0,0,0);
        return (tim);
}
void CPTDinpDoc::OnRecGoto()
{
        CPtdGoto dlg;
        int i;
        // Define and run a dialog to select the search mode and rec number etc.
        dlg.m_IDStr = IDStr;
        dlg.m_RecNum = curRecord + 1;
        dlg.m_GotoMode = GotoMode;
        if(dlg.DoModal() == IDOK) {
                GotoMode = dlg.m_GotoMode;
                switch (GotoMode) {
                    case 0:
                        // record number
                        CurRecord = dlg.m_RecNum - 1;
                        if (CurRecord < 0) CurRecord = 0;
                        if (CurRecord > NumRecords - 1 ) CurRecord = NumRecords - 1;
                        get_rec (Rec);
                        break;
                    case 1:
                        // ID string
                        IDStr = dlg.m_IDStr;
                        for (i = 0; i < NumRecords; i++) {
                                CurRecord = i;
                                get_rec(Rec);
                                if ( IDStr == m_LAB_ID ) break;
                        }
                        break;
                    default:
                        // Do nothing
                        break;
                }
        }
}
void CPTDinpDoc::OnFileMruFile1()
{
        GetPrivateProfileString    ("Recent File List",      //1pszSection
                                    "Fuel",                   //1pszEntry
                                    "untitled",               //1pszDefault
                                    PathName,                 // IpszReturnBuffer
                                    128,                      // cbReturnBuffer
                                    "ptdinp.ini");            // 1pszFilename
        get_file();
}
void CPTDinpDoc::OnFileMruFile2()
{
        GetPrivateProfileString    ("Recent File List",      //1pszSection
        "File2",                    //1pszEntry
        "untitled",                 // 1pszDefault
        PathName,                   // 1pszReturnBuffer
        128,                        // cbReturnBuffer
        "ptdinp.ini");              // 1pszFilename
        get_file();
}
void CPTDinpDoc::OnFileMruFile3()
{
        GetPrivateProfileString    ("Recent File List",      //1pszSection
        "File3",                    //1pszEntry
        "untitled",                 // 1pszDefault
        PathName,                   // 1pszReturnBuffer
        128,                        // cbReturnBuffer
        "ptdinp.ini");              // 1pszFilename
        get_file();
}
void CPTDinpDoc::OnFileMruFile4()
{
        GetPrivateProfileString    ("Recent File List",      //1pszSection
        "File4",                    //1pszEntry
        "untitled",                 // 1pszDefault
        PathName,                   // 1pszReturnBuffer
        128,                        // cbReturnBuffer
        "ptdinp.ini");              // 1pszFilename
```

```
        get_file();
}
void CPTDinpDoc::OnFileOpen()
{
//FILE *fp;
    // Get the File Name
    CFileDialog Dlg (TRUE, "fdb", NULL, OFN_OVERWRITEPROMPT
        "FDB iles (*fbd)|*f.fdb||");
    Dlg.m_ofn.1pstrTitle = "Open Fixed length DataBase file";
    if( Dlg.DoModal() == IDOK ) {
        strcpy(PathName,Dlg.GetPathName());
        AfxGetApp () ->AddToRecentFileList (PathName);
        get_file ();
#ifdef NOT
        CurRecord = 0;
        fp = fopen(PathName,"rb");
        if(fp==NULL) {
            fp = fopen(PathName,"wb");
            if(fp!=NULL) {
                fwrite(Rec,sizeof(char), (REC_LENGTH+2L),fp);
                fclose(fp);
            }
            NumRecords = 1;
            CurRecord = 0;
            InitializeRec();
            put_rec (Rec);
            get_rec (Rec);
        } else {
            CurRecord = 0;
            if(fread(Rec,sizeof(char), (REC_LENGTH+2L),fp)==(REC_LENGTH+2L)) {
                get_rec(Rec);
            }
            fseek (fp,0L,SEEK_END);
            NumRecords = ftell(fp) / (REC_LENGTH+2L);
            fclose(fp);
        }
#endif
    }
}
void CPTDinpDoc::get_file()
{
FILE *fp;
        CurRecord = 0;
        fp = fopen(PathName,"rb");
        if(fp==NULL) {
            fp = fopen(PathName,"wb");
            if(fp!=NULL) {
                fwrite(Rec,sizeof(char),(REC_LENGTH+2L),fp);
                fclose(fp);
            }
            NumRecords = 1;
            CurRecord = 0;
            InitializeRec();
            put_rec (Rec);
            get_rec (Rec);
        } else {
            CurRecord = 0;
            if(fread(Rec,sizeof(char), (REC_LENGTH+2L) , fp) ==(REC_LENGTH+2L)) {
                get_rec(Rec);
            {
            fseek(fp,0L,SEEK_END);
            NumRecords = ftell(fp) / (REC_LENGTH+2L);
            fclose(fp);
        }
    ((CPTDinpApp*)AfxGetApp())->SaveMRU();
}
// PTDinp.cpp : Defines the class behaviors for the application.
//
#include "stdafx.h"
#include "PTDinp.h"
#include "mainfrm.h"
#include "PTDidoc.h"
#include "PTDivw.h"
#ifdef_DEBUG
#undef THIS_FILE
static char BASED_CODE THIS_FILE[] = _FILE_;
#endif
/////////////////////////////////////////////////////////////////////
// CPTDinpApp
```

-continued

```
BEGIN_MESSAGE_MAP(CPTDinpApp, CWinApp)
    //{{AFX_MSG_MAP(CPTDinpApp)
    ON_COMMAND(ID_APP_ABOUT, OnAppAbout)
    ON_COMMAND(ID_CLR_SUBFIELDS, OnClrSubfields)
    ON_COMMAND(ID_EDIT_MODE, OnEditMode)
    //}}AFX_MSG_MAP
    // Standard file based document commands
    ON_COMMAND(ID_FILE_NEW, CWinApp::OnFileNew)
    ON_COMMAND(ID_FILE_OPEN, CWinApp::OnFileOpen)
    //Standard print setup command
    ON_COMMAND(ID_FILE_PRINT_SETUP, CWinApp::OnFilePrintSetup)
END_MESSAGE_MAP ()
/////////////////////////////////////////////////////////////////////////////
// CPTDinpApp construction
CPTDinpApp::CPTDinpApp()
{
    // TODO: add construction code here,
    // Place all significant initialization in InitInstance
    m_pDoc = NULL;
    EditMode = FALSE;
    ClearSubfields = FALSE;
}
/////////////////////////////////////////////////////////////////////////////
// The one and only CPTDinpApp object
CPTDinpApp NEAR theApp;
/////////////////////////////////////////////////////////////////////////////
// CPTDinpApp initialization
BOOL CPTDinpApp::InitInstance()
{
    // Standard initialization
    // If you are not using these features and wish to reduce the size
    // of your final executable, you should remove from the following
    // the specific initialization routines you do not need.
    SetDialogBkColor();           // Set dialog background color to gray
    LoadStdProfileSettings();     // Load standard INI file options (including MRU)
    // Register the application's document templates. Document templates
    // serve as the connection between documents, frame windows and views.
    CSingleDocTemplate* pDocTemplate;
    pDocTemplate = new CSingleDocTemplate(
        IDR_MAINFRAME,
        RUNTIME_CLASS (CPTDinpDoc),
        RUNTIME_CLASS (CMainFrame),         // main SDI frame window
        RUNTIME_CLASS (CPTDinpView));
    AddDocTemplate (pDocTemplate);
    // create a new (empty) document
    OnFileNew();
    if (m_1pCmdLine[0] != '\0')
    {
        // TODD: add command line processing here
    }
        ClearSubfields = TRUE;
        // check the menu item
        CMenu* pMenu = AfxGetApp () ->m_pMainWnd->GetMenu();
        pMenu->CheckMenuItem (ID_CLR_SUBFIELDS, MF_CHECKED);
    return TRUE;
}
/////////////////////////////////////////////////////////////////////////////
// CAboutDlg dialog used for App About
class CAboutDlg public CDialog
{
public:
    CAboutDlg();
// Dialog Data
    //{{AFX_DATA(CAboutDlg)
    enum {IDD = IDD_ABOUTBOX };
    //}}AFX_DATA
// Implementation
protected:
    virtual void DoDataExchange(CDataExchange* pDX);    // DDX/DDV support
    //{{AFX_MSG(CAboutDlg)
        // No message handlers
    //}}AFX_MSG
    DECLARE_MESSAGE_MAP()
};
CAboutDlg::CAboutDlg () : CDialog (CAboutDlg::IDD)
{
    //{{AFX_DATA_INIT(CAboutDlg)
    //}}AFX_DATA_INIT
}
```

-continued

```
void CAboutDlg::DoDataExchange(CDataExchange* pDX)
{
    CDialog::DoDataExchange(pDX);
    //{{AFX_DATA_MAP(CAboutDlg)
    //}}AFX_DATA_MAP
}
BEGIN_MESSAGE_MAP(CAboutDlg, CDialog)
    //{{AFX_MSG_MAP(CAboutDlg)
        // No message handlers
    //}}AFX_MSG_MAP
END_MESSAGE_MAP()
// App command to run the dialog
void CPTDinpApp::OnAppAbout()
{
    CAboutDlg aboutDlg;
    aboutDlg.DoModal();
}
/////////////////////////////////////////////////////////////////
//CPTDinpApp commands
void CPTDinpApp::OnClrSubfields()
{
    if (ClearSubfields) {
        ClearSubfields = FALSE;
        // uncheck the menu item
        CMenu* pMenu = AfxGetApp()->m_MainWnd->GetMenu();
        pMenu->CheckMenuItem(ID_CLR_SUBFIELDS,MF_UNCHECKED);
    } else {
        ClearSubfields = TRUE;
        // check the menu item
        CMenu* pMenu = AfxGetApp()->m_pMainWnd->GetMenu();
        pMenu->CheckMenuItem(ID_CLR_SUBFIELDS,MF_CHECKED);
    }
}
{
void CPTDinpApp::OnEditMode()
{
    if (EditMode) {
        EditMode = FALSE;
        // uncheck the menu item
        CMenu* pMenu = AfxGetApp()->m_pMainWnd->GetMenu();
        pMenu->CheckMenuItem(ID_EDIT_MODE,MF_UNCHECKED);
    } else {
        EditMode = TRUE;
        // check the menu item
        CMenu* pMenu = AfxGetApp()->m_pMainWnd->GetMenu();
        pMenu->CheckMenuItem(ID_EDIT_MODE,MF_CHECKED);
    }
}
void CPTDinpApp::SaveMRU()
{
    SaveStdProfileSettings();
}
; endoinp.def : Declares the module parameters for the application.
NAME            ENDOINP
DESCRIPTION     'ENDOINP Windows Application'
EXETYPE         WINDOWS
CODE            PRELOAD MOVEABLE DISCARDABLE
DATA            PRELOAD MOVEABLE MULTIPLE
HEAPSIZE        1024 ; initial heap size
; Stack size is passed
as argument to link-
er's /STACK option
// PTDinp.h : main-
header file for the
PTDINP application
//
#ifndef _AFXWIN_
H_
    #error include 'stdafx.h' before including this file for PCH
#endif
#include "resource.h"          // mainsymbols
/////////////////////////////////////////////////////////////////
// CPTDinpApp:
// See PTDinp.cpp for the implementation of this class
//
#include "PTDidoc.h"
class CPTDinpApp : public CwinApp
{
public:
    CPTDinpApp();
```

-continued

```
    CPTDinpDoc *m_pDoc;
    int NextDlgPage;
    int LastDlgPage;
    BOOL EditMode;
    BOOL ClearSubfields;
    CPTDinpDoc *GetDoc() {
        return m_pDoc;
    }
    void SaveMRU( void );
// Overrides
    virtual BOOL InitInstance();
// Implementation
//{{AFX_MSG(CPTDinpApp)
afx_msg void OnAppAbout();
afx_msg void OnClrSubfields();
afx_msg void OnEditMode();
//}}AFX_MSG
DECLARE_MESSAGE_MAP ()
};
/////////////////////////////////////////////////////////////////////////
// PTDivw.cpp : implementation of the CPTDinpView class
//
#include "stdafx.h"
#include "PTDinp.h"
#include "PTDidoc.h"
#include "PTDivw.h"
#include "PTDdlg.h"
#ifdef _DEBUG
#undef THIS_FILE
static char BASED_CODE THIS_FILE[] = _FILE_;
#endif
/////////////////////////////////////////////////////////////////////////
// CPTDinpView
IMPLEMENT_DYNCREATE (CPTDinpView, CView)
BEGIN_MESSAGE_MAP (CPTDinpView, CView)
    //{{AFX_MSG_MAP(CPTDinpView)
    ON_COMMAND(ID_DATA_EDIT, OnDataEdit)
    ON_COMMAND(ID_DATA_NEW, OnDataNew)
    //}}AFX_MSG_MAP
    // Standard printing commands
    ON_COMMAND(ID_FILE_PRINT, CView::OnFilePrint)
    ON_COMMAND(ID_FILE_PRINT_PREVIEW, CView::OnFilePrintPreview)
END_MESSAGE_MAP()
/////////////////////////////////////////////////////////////////////////
// CPTDinpView construction/destruction
CPTDinpView::CPTDinpView()
{
    // TODO: add construction code here
    ShowPrt = FALSE;
}
CPTDinpView::~CPTDinpView()
{
}
/////////////////////////////////////////////////////////////////////////
// CPTDinpView drawing
void CheckOut(CDC* pDC, char *str, int xpos, int ypos, int val)
{
    pDC->TextOut( xpos, ypos, str, strlen(str) );
    pDC->Rectangle(CRect( xpos - 6*29, ypos - 2*29, xpos - 2*29, ypos - 6*29));
    if(val) {
        CBrush brush(RGB(0,0,0));
        pDC->FillRect(CRect( xpos - 6*29, ypos - 2*29, xpos - 2*29, ypos - 6*29),&brush)
;
//        pDC->MoveTo(xpos - 6*29, ypos - 2*29);
//        pDC->LineTo( xpos - 2*29, ypos - 6*29);
//        pDC->MoveTo(xpos - 6*29, ypos - 6*29);
//        pDC->LineTo( xpos - 2*29, ypos - 2*29);
    }
}
void CPTDinpView::OnDraw(CDC* pDC)
{
    CPTDinpDoc* pDoc = GetDocument();
    CPTDinpApp* pApp = ((CPTDinpApp*)AfxGetApp());
    ASSERT_VALID(pDoc);
    CFont font10, font12;
    TEXTMETRIC tm;
    int nHeight;
    int i;
    // TODO: add draw code for native data here
```

-continued

```
    pDC->SetMapMode (MM_TWIPS);
    font12.CreateFont(-240,0,0,0,500, FALSE, FALSE, 0, ANSI_CHARSET,
            OUT_DEFAULT_PRECIS, CLIP_DEFAULT_PRECIS,
            DEFAULT_QUALITY, DEFAULT_PITCH | FF_ROMAN, "Times New Roman");
    CFont* pOldFont = (CFont*) pDC->SelectObject(&font12);
    pDC->GetTextMetrics (&tm);
    nHeight = tm.tmHeight + tm.tmExternalLeading;
char str[256]
char name[64];
    //pDC->Rectangle(CRect(0,0,11505,-15105)); // FULL PAGE RECT
    if(ShowPrt) {
        if(!pApp->EditMode) {
            sprintf(str,"           ADEZA DIAGNOSTIC SERVICES");
            pDC->TextOut( 2440, ((-1 * nHeight) - 720), str, strlen(str) );
            sprintf(str, "Pre-Term Delivery Risk Assessment Software:");
            pDC->TextOut( 2440, ((-2 * nHeight) - 720), str, strlen(str) );
            sprintf(str,"              Test Report Form ");
            pDC->TextOut( 2440, ((-3 * nHeight) - 720), str, strlen(str) );
        }
    } else {
        sprintf(str, "File: %s          ",pDoc->PathName);
        pDC->TextOut( 720, ((-1 * nHeight) - 720), str, strlen(str) );
        sprintf (str, "Current record: %1d       ", pDoc->CurRecord+1);
        pDC->TextOut( 720, ((-2 * nHeight) - 720), str, strlen(str) );
        sprintf (str, "Number of records: %1d ",pDoc->NumRecords);
        pDC->TextOut( 720, ((3 * nHeight) - 720), str, strlen(str) );
    }
    if((ShowPrt && !pApp->EditMode) || (!Showprt)) }
        sprintf(str,"Lab ID #:");
        pDC->TextOut( 720, ((-5 * nHeight) - 720), str, strlen(str) );
        sprintf(str,"%s         ",pDoc->m_LAB_ID);
        pDC->TextOut( 4320, ((-5 * nHeight) - 720), str, strlen(str) );
        strcpy( name, pDoc->m_NAME_F);
        strcat( name, " ");
        strcat( name, pDoc->m_NAME_MI);
        strcat( name, " ");
        strcat( name, pDoc->m_NAME_L);
        sprintf(str," Patient Name: ");
        pDC->TextOut( 720, ((-6 * nHeight) - 720), str, strlen(str) );
        sprintf(str," %s ",name);
        pDC->TextOut( 4320, ((-6 * nHeight) - 720), str, strlen(str) );
        pDoc->RunNets (pDoc->CurRecord);
        sprintf(str,"Pre-term Delivery Risk <34.6wks: ");
        pDC->Textout( 720, ((-7 * nHeight) - 720), str, strlen(str) );
        sprintf(str," %lf ",pDoc->m NetPos1);
        pDC->TextOut( 4320, ((-7 * nHeight) - 720), str, strlen(str) );
        sprintf(str," Pre-term Delivery Risk <7 days: ");
        pDC->TextOut( 720, ((-8 * nHeight) - 720), str, strlen(str) );
        sprintf(str," %1f ",pDoc->m NetPos2);
        pDC->TextOut( 4320, ((-8 * nHeight) - 720), str, strlen(str) );
        sprintf(str," Pre-term Delivery Risk <14 days: ");
        pDC->TextOut( 720, ((-9 * nHeight) - 720), str, strlen(str) );
        sprintf(str," %1f ",pDoc->m_NetPos3);
        pDC->TextOut( 4320, ((-9 * nHeight) - 720), str, strlen(str) );
        //if (pDoc->m_ACOG_SYMPTOMS == "0") {
        //     sprintf(str,"DISCLAIMER APPLIES:");
        //     pDC->TextOut( 720, ((-12 * nHeight) - 720), str, strlen(str) );
        //}
        for( i = 5; i <= 10; i++) {
            pDC->MoveTo(700,((-i * nHeight) - 720));
            pDC->LineTo(8640,((-i * nHeight) - 720));
        }
        pDC->MoveTo(700,((-5 * nHeight) - 720));
        pDC->LineTo(700,((-10 * nHeight) - 720));
        pDC->MoveTo(4320,((-5 * nHeight) - 720));
        pDC->LineTo(4320,((-10 * nHeight) - 720));
        pDC->MoveTo(8640,((-5 * nHeight) - 720));
        pDC->LineTo(8640,((-10 * nHeight) - 720));
    } else {
    font10.CreateFont(-200,0,0,0,500, FALSE, FALSE, 0, ANSI_CHARSET,
            OUT_DEFAULT_PRECIS, CLIP_DEFAULT_PRECIS,
            DEFAULT_QUALITY, DEFAULT_PITCH | FF_RONAN, "Times New Roman");
        pDC->SelectObject (&font10);
        //pDC->Rectangle(CRect( 0,0,11505,-15105));
        pDC->Rectangle(CRect( 1*29,-4*29,397*29,-22*29));
        pDC->Rectangle(CRect( 1*29,-24*29,397*29,-42*29));
        pDC->Rectangle(CRect( 1*29,-44*29,187*29,-95*29));
        pDC->Rectangle(CRect( 187*29,-44*29,397*29,-95*29));
        pDC->Rectangle(CRect( 1*29,-97*29,397*29,-114*29));
```

-continued

```
        pDC->Rectangle(CRect( 1*29,-116*29,397*29,-218*29));
        pDC->Rectangle(CRect( 1*29,-220*29,397*29,-240*29));
        pDC->Rectangle(CRect( 1*29,-242*29,187*29,-348*29));
        pDC->Rectangle(CRect( 187*29,-242*29,397*29,-348*29));
        pDC->Rectangle(CRect( 1*29,-350*29,397*29,-375*29));
        pDC->ReCtangle(CRect( 1*29,-377*29,397*29,-404*29));
        pDC->Rectangle(CRect( 1*29,-406*29,397*29,-425*29));
        pDC->ReCtangle(CRect( 1*29,-427*29,397*29,-470*29));
        sprintf(str,"ADEZA Pre-Term Delivery Risk Assessment ");
        pDC->TextOut( 7*29,-10*29, str, strlen(str) );
        sprintf(str,"Lab ID #: %s", pDoc->m_LAB_ID);
        pDC->TextOut( 267*29,-10*29, str, strlen(str) );
        sprintf(str, "PATIENT INFORMATION");
        pDC->TextOut( 159*29,-29*29, str, strlen(str) );
        strCpy( name, pDoc->m_NAME_L);
        sprintf(str, "Name(last)    %s", name);
        pDC->TextOut( 7*29,-57*29, str, strlen(str) );
        strcpy( name, pDoc->m_NAME_F);
        sprintf(str,"First %s", name);
        pDC->TextOut( 99*29,-51*29, str, strlen(str) );
        strcpy( name, pDoc->m_NAME_MI);
        sprintf(str,"M %s", name);
        pDC->TextOut( 160*29,-51*29, str, strlen(str) );
        sprintf(str,"DOB %s", pDoc->m_DATE_OF_BIRTH);
        pDC->TextOut( 7*29,-69*29, str, strlen(str) );
        sprintf(str, "Ethnic origin:");
        pDC->TextOut( 192*29,-48*29, str, strlen(str) );
        CheckOut(pDC, "Caucasian", 248*29,-48*29, (pDoc->m_ETHNIC_ORIGIN_WHITE == "1") );
        CheckOut(pDC,"African American", 298*29,-48*29, (pDoc->m_ETHNIC_ORIGIN_BLACK ==
"1") );
        CheckOut(pDC,"Asian", 368*29,-48*29, (pDoc->m_ETHNIC_ORIGIN_ASIAN == "1") );
        CheckOut(pDC, "Hispanic", 248*29,-59*29, (pDoc->m_ETHNIC_ORIGIN_HISPANIC == "1")
);
        CheckOut(pDC, "Native American", 298*29,-59*29, (pDoc->m_ETHNIC_ORIGIN_NATIVE_AME
RICAN == "1") );
        CheckOut(pDC,"Other", 368*29,-59*29, (pDoc->m_ETHNIC_ORIGIN_OTHER == "1") );
        sprintf(str, "Marital status:");
        pDC->TextOut( 192*29,-72*29, str, strlen(str) );
        CheckOut(pDC,"Married", 248*29,-72*29, (pDoc->m_MARITAL_STATUS_MARRIED == "1")
);
        CheckOut(pDC,"Single", 288*29,-72*29, (pDoc->m_MARITAL_STATUS_SINGLE == "1") );
        CheckOut (pDC, "Divorced/Separated", 322*29, -72*29, (pDoc->m_MARITAL_STATUS_DIVORC
ED == "1") ) ;
        CheckOut(pDC,"Widowed", 248*29,-83*29, (pDoc->m_MARITAL_STATUS_WIDOWED == "1") )
;
        CheckOut(pDC,"Living with partner", 293*29,-83*29, (pDoc->m_MARITAL_STATUS_LWP =
= "1") ) ;
        CheckOut(pDC,"Other", 368*29,-83*29, (pDoc->m_MARITAL_STATUS_OTHER == "1") );
        sprintf(str,"PATIENT HISTORY AND CLINICAL INFORMATION");
        pDC->TextOut( 117*29,-102*29, str, strlen(str) );
        sprintf(str,"At the time of sampling was the patient experiencing signs and symp
toms of possible preterm labor?");
        pDC->TextOut( 7*29,-119*29, str, strlen(str) );
        CheckOut(pDC,"Yes", 339*29,-119*29, (pDoc->m_ACOG_SYNPTOMS == "1") );
        CheckOut(pDC,"No", 370*29,119*29, (pDoc->m_ACOG_SYNPTOMS == "0") );
        sprintf(str,"If yes, please mark all that apply.");
        pDC->TextOut( 7*29,-134*29, str, strlen(str) );
        CheckOut(pDC,"Uterine contractions with or without pain", 19*29,-145*29, (pDoc->
m_PATIENT_COMPLAINT_1 == "1") );
        sprintf (str,"Number/hr");
        pDC->TextOut( 22*29,-158*29, str, strlen(str) );
        CheckOut(pDC,"<1", 73*29,-158*29, (pDoc->m_PATIENT_COMPLAINT_1_LT1 == "1") );
        CheckOut(pDC,"1-3", 105*29,-158*29, (pDoc->m_PATIENT_COMPLAINT_1_1_3 == "1") );
        CheckOut(pDC,"4-6", 137*29,-158*29, (pDoc->m_PATIENT_COMPLAINT_1_4_6 == "1") );
        CheckOut(pDC,"7-9", 73*29,-170*29, (pDoc->m_PATIENT_COMPLAINT_1_7_9 == "1") );
        CheckOut(pDC,"10-12", l05*29,-170*29, (pooc->m_PATIENT_COMPLAINT_1_10_12 == "1")
);
        CheckOut(pDC,">12", 137*29,-170*29, (pDoc->m_PATIENT_COMPLAINT_1_GT12 == "1") );
        CheckOut(pDC, "Vaginal bleeding", 19*29,-187*29, (pDoc->m_VAGINAL_BLEEDING == "1"
) );
        CheckOut(pDC,"Trace", 29*29,-194*29, (pDoc->m_VAGINAL_BLEEDING_TRACE == "1") );
        CheckOut(pDC,"Med", 64*29,-194*29, (pDoc->m_VAGINAL_BLEEDING_MEDIUM == "1") );
        CheckOut(pDC,"Gross", 94*29,-194*29, (pDoc->m_VAGINAL_BLEEDING_GROSS == "1") );
        CheckOut(pDC,"Patient is not '"feeling right"'", 19*29,-205*297 (pDoc->m_PATIENT
COMPLAINT_6 == "1") );
        CheckOut(pDC,"Bleeding during the second or third trimester", 167*29,-145*29, (p
Doc->m_PATIENT_COMPLAINT_3 == "1") );
        CheckOut(pDC,"Intermittent lower abdominal pain, dull, low backpain, pelvic pres
sure", 167*29,-157*29, (pDoc->m_PATIENT_COMPLAINT_2 == "1") );
```

-continued

```
        CheckOut(pDC,"Change in vaginal discharge -- amount, color, or consistency", 167
*29,-181*29, (pDoc->m_PATIENT_COMPLAINT_5 == "1") );
        CheckOut(pDC,"Menstrual-like cramping (with or without diarrhea)", 167*29,-193*2
9, (pDoc->m_PATIENT_COMPLAINT_4 == "1") );
        sprintf(str,"Gestational Age: EGA by first trimester sono %s", pDoc->m_EGA_BY_S
ONO);
        pDC->TextOut( 7*29,-225*29, str, strlen(str) );
        sprintf(str,"EGA by LMP %s", pDoc->m_EGA_BY_LMP);
        pDC->TextOut( 197*29,-225*29, str, strlen(str) );
        sprintf(str,"EGA at sampling %s",pDoc->m_EGA_AT_SAMPLING);
        pDC->TextOut( 287*29,-225*29, str, strlen(str) );
        sprintf(str,"Previous Pregnancy: Please mark all that apply.");
        pDC->TextOut( 7*29,-249*29, str, strlen(stry);
        CheckOut(pDC,"Previous pregnancy, no complications", 19*29,-260*29, (pDoc->m_1_C
OMP == "1") );
        CheckOut(pDC,"History of Preterm delivery", 19*29,-272*29, (pDoc->m_2_COMP == "1
") ) ;
        sprintf(str,"If Yes, how many?");
        pDC->TextOut( 22*29,-284*29, str, strlen(str) );
        CheckOut(pDC,"1", 97*29,-284*29, (pDoc->m_2_COMP_1 == "1") );
        Checkout(pDC,"2", 122*29,-284*29, (pDoc->m_2_COMP_2 == "1") );
        CheckOut(pDc,">2", 147*29,-284*29, (pDoc->m_2_COMP_3 == "1") );
        CheckOut(pDC,"History of Preterm PROM", 19*29,-296*29, (pDoc->m_3_COMP == "1") )
;
        CheckOut(pDc,"History of incompetent cervix", 19*29,-308*29, (pDoc->m_4_COMP ==
"1") ) ;
        CheckOut(pDC,"History of PIH/preeclampsia", 19*29,-320*29, (pDoc->m_5_COMP == "1
") );
        CheckOut(pDC,"History of SAB prior to 20 wks", 19*29,-332*29, (pDoc->m_6_COMP ==
"1") ) ;
        CheckOut(pDc, "Multiple Gestation:", 209*29, -272*29, (pDoc->m_MULTIPLE_GESTATION
== "1") )
        CheckOut(pDC,"Twins", 284*29,-272*29, (pDoc->m_MULTIPLE_GESTATION_TWINS == "1")
);
        Checkout(pDC,"Triplets", 317*29,-272*29, (pDoc->m_MULTIPLE_GESTATION_TRIPLETS ==
"1") ) ;
        Checkout(pDc,"Quads", 356*29,-272*29, (pDoc->m_MULTIPLE_GESTATION_QUADS == "1")
);
        CheckOut(pDc,"Uterine or cervical abnormality", 209*29,-284*29, (pDoc->m_UTCERV_
ABNORMALITY == "1") );
        CheckOut(pDC,"Cerclage", 209*29,--296*29, (pDoc->m_CERVICAL_CERCLAGE == "1") );
        Checkout (pDC, "Gestational Diabetes", 209*29, -308*29, (pDoc->m_GESTATIONAL_DIABET
ES == "1") );
        CheckOut(pDC,"Hypertensive Disorders", 209*29,-320*29, (pDoc->m_HYPERTENSIVE_DIS
ORDERS == "1") );
        sprintf(str,"Cervical Status immediately following sample collection:");
        pDC->TextOut( 7*29,-352*29, str, strlen(str) );
        sprintf(str, "Dilatation (cm)");
        pDC->TextOut( 9*29,-364*29, str, strlen(str) );
        CheckOut(pDC,"<1", 64*29,-364*29, (pDoc->m_DILITATION_LT1 == "1") );
        CheckOut(pDC,"1", 85*29,-364*29, (pDoc->m_DILITATION_1 == "1") );
        CheckOut(pDC,"1-2", 102*29,-364*29, (pDoc->m_DILITATION_1_2 == "1") );
        CheckOut(pDC,"2", 123*29,-364*29, (pDoc->m_DILITATION_2 == "1") );
        CheckOut(pDC,"2-3", 140*29,-364*29, (pDoc->m_DILITATION_2_3 == "1") );
        CheckOut(pDC,"3", 163*29,-364*29, (pDoc->m_DILITATION_3 == "1") );
        CheckOut(pDC,">3", 180*29,-364*29, (pDoc->m_DILITATION_GT3 == "1") );
        CheckOut(pDC,"Unknown", 201*29,-364*29, (pDoc->m_DILITATION_UNKNOWN == "1") );
        sprintf(str, "Cervical consistancy");
        pDC->TextOut( 249*29,-364*29, str, strlen(str) );
        CheckOut(pDC,"Firm", 324*29,-364*29, (pDoc->m_CERVICAL_CONSISTANCY_FIRM == "1")
);
        CheckOut(pDC,"Mod", 350*29,-364*29, (pDoc->m_CERVICAL_CONSISTANCY_MOD == "1") );
        CheckOut(pDC,"Soft", 376*29,-364*29, (pDoc->m_CERVICAL_CONSISTANCY_SOFT == "1")
);
        sprintf(str,"Medications at Time of Test (check all that apply)");
        pDC->TextOut( 7*29,-380*29, str, strlen(str) );
        CheckOut(pDC,"Antibiotics", 23*29,-392*29, (pDoc->m_ANTIBIOTICS == "1") );
        Checkout (pDC, "Corticosteroids", 76*29,-392*29, (pDoc->m_CORTICOSTEROIDS == "1")
);
        CheckOut(pDC,"Tocolytis", 144*29,-392*29, (pDoc->m_TOYOLYTICS == "1") );
        CheckOut(pDC,"Insulin", 193*29,-392*29, (pDoc->m_INSULIN == "1") );
        CheckOut(pDC, "Antihypertensives", 234*29, -392*29, (pDoc->m_ANTIHYPERTENSIVES ==
"1") );
        CheckOut(pDC,"None", 377*29,-392*29, (pDoc->m_MEDICATIONS_NONE == "1") );
        CheckOut(pDC,"Unknown", 348*29,-392*29, (pDoc->m_MEDICATIONS_UNKNOWN == "1") );
        sprintf(str,"Current Pregnancy: G: %s", pDoc->m_GRAVITY);
        pDC->TextOut( 195*29,-249*29, str, strlen(str) );
        sprintf(str,"P: %s", pDoc->m_PARITY);
        pDC->TextOut( 303*29,-249*29, str, strlen(str) );
```

-continued

```
        sprintf(str, "A: %s", pDoc->m_ABORTIONS);
        pDC->TextOut( 343*29,249*29, str, strlen(str) );
        sprintf(str, "Qualitative fFN Elisa Test Results:");
        pDC->TextOut( 7*29,-411*29, str, strlen(str) );
        CheckOut (pDC, "Positive", 144*29, -411*29, (pDoc->m_FFN_RESULT == "1") );
        CheckOut CpDC, "Negative", 234*29, -411*29, (pDoc->m_FFN_RESULT == "0") );
        sprintf(str,"Pre-term Delivery Risk <34.6wks: ");
        pDC->TextOut( 7*29,-432*29, str, strlen(str) );
        sprintf(str,"%1f ",pDoc->m_NetPos1);
        pDC->TextOut( 150*29,-432*29, str, strlen(str) );
        sprintf(str,"Pre-term Delivery Risk <7 days: ");
        pDC->TextOut( 7*29, -444*29, str, strlen(str) );
        sprintf(str,"%1f ",pDoc->m_NetPos2);
        pDC->TextOut( 150*29, -444*29, str, strlen(str) );
        sprintf(str,"Pre-term Delivery Risk <14 days: ");
        pDC->TextOut( 7*29, -456*29, str, strlen(str) );
        sprintf(str,"%1f ",pDoc->m_NetPos3);
        pDC->TextOut( 150*29, -456*29, str, strlen(str) );
        //if (pDoc->m_ACOG_SYNPTOMS == "0") {
        //      sprintf(str, "DISCLAIMER APPLIES:");
        //      pDC->TextOut( 7*29, -480*29, str, strlen(str) );
        //}
        }
    pDC->SelectObject (pOldFont);
}
/////////////////////////////////////////////////////////////////////////////
// CPTDinpView printing
BOOL CPTDinpView::OnPreparePrinting(CPrintInfo* pInfo)
{
    // default preparation
    return DoPreparePrinting(pInfo);
}
void CPTDinpView: :OnBeginPrinting(CDC* /*pDC*/, CPrintInfo* /*pInfo*/)
{
    // TODO: add extra initialization before printing
    ShowPrt = TRUE;
}
void CPTDinpView::OnEndPrinting(CDC* /*pDC*/, CPrintInfo* /*pInfo*/)
{
    // TODO: add cleanup after printing
    ShowPrt = FALSE;
    GetDocument()->UpdateAllViews(NULL);
}
/////////////////////////////////////////////////////////////////////////////
// CPTDinpView diagnostics
#ifdef _DEBUG
void CPTDinpView: :AssertValid() const
{
    CView::AssertValid();
}
void CPTDinpView::Dump(CDumpContext& dc) const
{
    CView::Dump(dc);
}
CPTDinpDoc* CPTDinpView::GetDocument() // non-debug version is inline
{
    ASSERT (m_pDocument->IsKindOf (RUNTIME_CLASS (CPTDinpDoc)));
    return (CPTDinpDoc* ) m_pDocument;
}
#endif //_DEBUG
/////////////////////////////////////////////////////////////////////////////
// CPTDinpView message handlers
void CPTDinpView: :Edit()
{
    CPTDInp dlg;
    int val;
    ((CPTDinpApp*)AfxGetApp() )->NextDlgPage = 1;
    m_pSet = GetDocument();
    // initialize all the variables in the record to allow smooth cancel
    //dlg.m_DATE_OF_DATA_ENTRY = m_pSet->m_DATE_OF_DATA_ENTRY;
    //dlg.m_PATIENT_AGE = m_pSet->m_PATIENT_AGE;
    //CString m_DATE_OF_BIRTH;
    dlg.m_DATE_OF_BIRTH = m_pSet->m_DATE_OF_BIRTH;
    //CString m_NAME_F;
    dlg.m_NAME_F = m_pSet->m_NAME_F;
    //CString m_NAME_L;
    dlg.m_NAME_L = m_pSet->m_NAME_L;
    //CString m_NAME_MI;
    dlg.m_NAME_MI = m_pSet->m_NAME_MI;
```

```
//BOOL      m_1_COMP;
dlg.m_1_COMP = (m_pSet->m_1_COMP == "1");
//BOOL      m_2_COMP;
dlg.m_2_COMP = (m_pSet->m_2_COMP == "1");
//BOOL      m_3_COMP;
dlg.m_3_COMP = (m_pSet->m_3_COMP == "1");
//BOOL      m_4_COMP;
dlg.m_4_COMP = (m_pSet->m_4_COMP == "1");
//BOOL      m_5_COMP;
dlg.m_5_COMP = (m_pSet->m_5_COMP =="1");
//BOOL      m_6_COMP;
dlg.m_6_COMP = (m_pSet->m_6_COMP =="1");
//BOOL      m_ACOG_N;
dlg.m_ACOG_N = (m_pSet->m_ACOG_SYNPTOMS =="1");
//BOOL      m_ACOG_Y;
dlg.m_ACOG_Y = (m_pSet->m_ACOG_SYNPTOMS == "1");
//BOOL      m_Antibiotics;
dlg.m_Antibiotics = (m_pSet->m_ANTIBIOTICS == "1");
//BOOL      m_AntiHyper;
dlg.m_AntiHyper = (m_pSet->m_ANTIHYPERTENSIVES == "1");
//BOOL      m_CervCerclage;
dlg.m_CervCerclage = (m_pSet->m_CERVICAL_CERCLAGE == "1");
//BOOL      m_CervFirm;
dlg.m_CervFirm = (m_pSet->m_CERVICAL_CONSISTANCY_FIRM =="1");
//BOOL      m_CervMod;
dlg.m_CervMod = (m_pSet->m_CERVICAL_CONSISTANCY_MOD == "1");
//BOOL      m_CervSoft;
dlg.m_CervSoft = (m_pSet->m_CERVICAL_CONSISTANCY_SOFT =="1");
//BOOL      m_Corticosteroids;
dlg.m_Corticosteroids = (m_pSet->m_CORTICOSTEROIDS == "1");
//BOOL      m_Dilitation1_2;
dlg.m_Dilitation1_2 = (m_pSet->m_DILITATION_1_2 =="1");
//BOOL      m_Dilitation2;
dlg.m_Dilitation2 = (m_pSet->m_DILITATION_2 == "1");
//BOOL      m Dilitation2_3;
dlg.m_Dilitation2_3 = (m_pSet->m_DILITATION_2_3 == "1");
//BOOL      m_Dilitation3;
dlg.m_Dilitation3 = (m_pSet->m_DILITATION_3 == "1");
//BOOL      m_DilitationGt3;
dlg.m_DilitationGt3 = (m_pSet->m_DILITATION_GT3 =="1");
//BOOL      m_Dilitation1;
dlg.m_Dilitation1 = (m_pSet->m_DILITATION_1 == "1");
//BOOL      m_DilitationLt1;
dlg.m_DilitationLt1 = (m_pSet->m_DILITATION_LT1 == "1");
//BOOL      m_DilitationUkn;
dlg.m_DilitationUkn = (m_pSet->m_DILITATION_UNKNOWN == "1");
//CString m_EGAatSample;
dlg.m_EGAatSample = m_pSet->m_EGA_AT_SAMPLING;
//CString m_EGAbyLMP;
dlg.m_EGAbyLMP = m_pSet->m_EGA_BY_LMP;
//CString m_EGAbySONO;
dlg.m_EGAbySONO = m_pSet->m_EGA_BY_SONO;
//BOOL      m_EthnicOriginAsian;
dlg.m_EthnicOriginAsian = (m_pSet->m_ETHNIC_ORIGIN_ASIAN == "1");
//BOOL      m_EthnicOriginBlack;
dlg.m_EthnicOriginBlack = (m_pSet->m_ETHNIC_ORIGIN_BLACK == "1");
//BOOL      m_EthnicOriginHispanic;
dlg.m_EthnicOriginHispanic = (m_pSet->m_ETHNIC_ORIGIN_HISPANIC == "1");
//BOOL      m_EthnicOriginNativeAmerican;
dlg.m_EthnicOriginNativeAmerican = (m_pSet->m_ETHNIC_ORIGIN_NATIVE_AMERICAN = "1");
//BOOL      m_EthnicOriginOther;
dlg.m_EthnicOriginOther = (m_pSet->m_ETHNIC_ORIGIN_OTHER == "1");
//BOOL      m_EthnicOriginWhite;
dlg.m_EthnicOriginWhite = (m_pSet->m_ETHNIC_ORIGIN_WHITE == "1");
//BOOL      m_FFN_Neg;
dlg.m_FFN_Neg = (m_pSet->m_FFN_RESULT == "0");
//BOOL      m_FFN_Pos;
dlg.m_FFN_Pos = (m_pSet->m_FFN_RESULT == "1");
//BOOL      m_GestationalDiabetes;
dlg.m_GestationalDiabetes = (m_pSet->m_GESTATIONAL_DIABETES =="1");
//BOOL      m_HypertensiveDisorders;
dlg.m_HypertensiveDisorders = (m_pSet->m_HYPERTENSIVE_DISORDERS == "1");
//BOOL      m_Insulin;
dlg.m_Insulin = (m_pSet->m_INSULIN == "1");
//CString m_LadID;
dlg.m_LadID = m_pSet->m_LAB_ID;
//BOOL      m_MedicationNone;
dlg.m_MedicationNone = (m_pSet->m_MEDICATIONS_NONE == "1");
//BOOL      m_MedicationUnknown;
```

-continued

```
dlg.m_MedicationUnknown = (m_pSet->m_MEDICATIONS_UNKNOWN == "1");
//BOOL     m_MultipleGestationQuads;
dlg.m_MultipleGestationQuads = (m_pSet->m_MULTIPLE_GESTATION_QUADS == "1");
//BOOL     m_MultipleGestationTriplets;
dlg.m_MultipleGestationTriplets = (m_pSet->m_MULTIPLE_GESTATION_TRIPLETS == "1");
//BOOL     m_MultipleGestationTwins;
dlg.m_MultipleGestationTwins = (m_pSet->m_MULTIPLE_GESTATION_TWINS == "1");
//BOOL     m_MaritalStatusDivorced;
dlg.m_MaritalStatusDivorced = (m_pSet->m_MARITAL_STATUS_DIVORCED == "1");
//BOOL     m_MaritalStatusLWP;
dlg.m_MaritalStatusLWP = (m_pSet->m_MARITAL_STATUS_LWP == "1");
//BOOL     m_MaritalStatusMarried;
dlg.m_MaritalStatusMarried = (m_pSet->m_MARITAL_STATUS_MARRIED == "1");
//BOOL     m_MaritalStatusOther;
dlg.m_MaritalStatusOther = (m_pSet->m_MARITAL_STATUS_OTHER == "1");
//BOOL     m_MaritalStatusSingle;
dlg.m_MaritalStatusSingle = (m_pSet->m_MARITAL_STATUS_SINGLE == "1");
//BOOL     m_MaritalStatusWidowed;
dlg.m_MaritalStatusWidowed = (m_pSet->m_MARITAL_STATUS_WIDOWED == "1");
//BOOL     m_MultipleGestation;
dlg.m_MultipleGestation = (m_pSet->m_MULTIPLE_GESTATION == "1");
//BOOL     m_PatientComp1;
dlg.m_PatientComp1 = (m_pSet->m_PATIENT_COMPLAINT_1 == "1");
//BOOL     m_PatientComp2;
dlg.m_PatientComp2 = (m_pSet->m_PATIENT_COMPLAINT_2 == "1");
//BOOL     m_PatientComp3;
dlg.m_PatientComp3 = (m_pSet->m_PATIENT_COMPLAINT_3 == "1");
//BOOL     m_PatientComp4;
dlg.m_PatientComp4 = (m_pSet->m_PATIENT_COMPLAINT_4 == "1");
//BOOL     m_PatientComp5;
dlg.m_PatientComp5 = (m_pSet->m_PATIENT_COMPLAINT_5 == "1");
//BOOL     m_PatientComp6;
dlg.m_PatientComp6 = (m_pSet->m_PATIENT_COMPLAINT_6 == "1");
//BOOL     m_Tocolytics;
dlg.m_Tocolytics = (m_pSet->m_TOYOLYTICS == "1");
//BOOL     m_UtCervAbnormal;
dlg.m_UtCervAbnormal = (m_pSet->m_UTCERV_ABNORMALITY == "1");
//BOOL     m_VaginalBleeding;
dlg.m_VaginalBleeding = (m_pSet->m_VAGINAL_BLEEDING == "1");
//BOOL     m_VaginalBleedingGross;
dlg.m_VaginalBleedingGross = (m_pSet->m_VAGINAL_BLEEDING_GROSS == "1");
//BOOL     m_VaginalBleedingMed;
dlg.m_VaginalBleedingMed = (m_pSet->m_VAGINAL_BLEEDING_MEDIUM == "1");
//BOOL     m_VaginalBleedingTrace;
dlg.m_VaginalBleedingTrace = (m_pSet->m_VAGINAL_BLEEDING_TRACE == "1");
//BOOL     m_2_COMP_1;
dlg.m_2_COMP_1 = (m_pSet->m_2_COMP_1 == "1");
//BOOL     m_2_COMP_2;
dlg.m_2_COMP_2 = (m_pSet->m_2_COMP_2 == "1");
//BOOL     m_2_COMP_3;
dlg.m_2_COMP_3 = (m_pSet->m_2_COMP_3 == "1");
//Cstring m_ABORTIONS;
dlg.m_ABORTIONS = m_pSet->m_ABORTIONS;
//CString m_GRAVITY;
dlg.m_GRAVITY = m_pSet->m_GRAVITY;
//CString m_PARITY;
dlg.m_PARITY = m_pSet->m_PARITY;
//BOOL     m_PatComp1_1_3;
dlg.m_PatComp1_1_3 = (m_pSet->m_PATIENT_COMPLAINT_1_1_3 = "1");
//BOOL     m_PatComp1_10_12;
dlg.m_PatComp1_10_12 = (m_pSet->m_PATIENT_COMPLAINT_1_10_12 == "1");
//BOOL     m_PatComp1_4_6;
dlg.m_PatComp1_4_6 = (m_pSet->m_PATIENT_COMPLAINT_1_4_6 == "1");
//BOOL     m_PatComp1_7_9;
dlg.m_PatComp1_7_9 = (m_pSet->m_PATIENT_COMPLAINT_1_7_9 == "1");
//BOOL     m_PatComp1_GT12;
dlg.m_PatComp1_GT12 = (m_pSet->m_PATIENT_COMPLAINT_1_GT12 == "1");
//BOOL     m_PatComp1_LT1;
dlg.m_PatComp1_LT1 = (m_pSet->m_PATIENT_COMPLAINT_1_LT1 == "1");
if(dlg.DoModal() == IDOK) {
    //dlg.m_DATE_OF_DATA_ENTRY = m_pSet->m_DATE_OF_DATA_ENTRY;
    //dlg.m_PATIENT_AGE = m_pSet->m_PATIENT_AGE;
    //CString m_DATE_OF_BIRTH;
    m_pSet->m_DATE_OF_BIRTH = dlg.m_DATE_OF_BIRTH;
    //CString m_NAME_F;
    m_pSet->m_NAME_F = dlg.m_NAME_F;
    //CString m_NAME_L;
    m_pSet->m_NAME_L = dlg.m_NAME_L;
    //CString m_NAME_MI;
```

-continued

```
        m_pSet->m_NAME_MI = dlg.m_NAME_MI;
//BOOL    m_1_COMP;
        m_pSet->m_1_COMP = (dlg.m_1_COMP?"1":"0");
//BOOL    m_2_COMP;
        m_pSet->m_2_COMP = (dlg.m_2_COMP?"1":"0");
//BOOL    m_3_COMP;
        m_pSet->m_3_COMP = (dlg.m_3_COMP?"1":"0");
//BOOL    m_4_COMP;
        m_pSet->m_4_COMP = (dlg.m_4_COMP?"1":"0");
//BOOL    m_5_COMP;
        m_pSet->m_5_COMP = (dlg.m_5_COMP?"1":"0");
//BOOL    m_6_COMP;
        m_pSet->m_6_COMP = (dlg.m_6_COMP?"1":"0");
//BOOL    m_ACOG_N;
        m_pSet->m_ACOG_SYNPTOMS = (dlg.m_ACOG_N?"0":" ");
//BOOL    m_AGOG_Y;
        m_pSet->m_ACOG_SYNPTOMS = (dlg.m_AGOG_Y?"1":m_pSet->m_AGOG_SYNPTOMS);
//BOOL    m_Antibiotics;
        m_pSet->m_ANTIBIOTICS = (dlg.m_Antibiotics?"1": "0");
//BOOL    m_AntiHyper;
        m_pSet->m_ANTIHYPERTENSIVES = (dlg.m_AntiHyper?"1": "0");
//BOOL    m_CervCerclage;
        m_pSet->m_CERVICAL_CERCLAGE = (dlg.m_CervCerclage?"1":"0");
//BOOL    m_CervFirm;
        m_pSet->m_CERVICAL_CONSISTANCY_FIRM = (dlg.m_CervFirm?"1":"0");
//BOOL    m_CervMod;
        m_pSet->m_CERVICAL_CONSISTANCY_MOD = (dlg.m_CervMod?"1":"0");
//BOOL    m_CervSoft;
        m_pSet->m_CERVICAL_CONSISTANCY_SOFT = (dlg.m_CervSoft?"1":"0");
//BOOL    m_Corticosteroids;
        m_pSet->m_CORTICOSTEROIDS = (dlg.m_Corticosteroids?"1":"0");
//BOOL    m_Dilitation1_2;
        m_pSet->m_DILITATION_1_2 = (dlg.m_Dilitation1_2?"1":"0");
//BOOL    m_Dilitation2;
        m_pSet->m_DILITATION_2 = (dlg.m_Dilitation2?"1":"0");
//BOOL    m_Dilitation2_3;
        m_pSet->m_DILITATION_2_3 = (dlg.m_Dilitation2_3?"1":"0");
//BOOL    m_Dilitation3;
        m_pSet->m_DILITATION_3 = (dlg.m_Dilitation3?"1":"0");
//BOOL    m_DilitationGt3;
        m_pSet->m_DILITATION_GT3 = (dlg.m_DilitationGt3?"1":"0");
//BOOL    m_Dilitation1;
        m_pSet->m_DILITATION_1 = (dlg.m_Dilitation1?"1":"0");
//BOOL    m_DilitationLt1;
        m_pSet->m_DILITATION_LT1 = (dlg.m_DilitationLt1?"1":"0")
//BOOL    m_DilitationUkn;
        m_pSet->m_DILITATION_UNKNOWN = (dlg.m_DilitatianUkn?"1":"0");
//CString m_EGAatSample;
        m_pSet->m_EGA_AT_SAMPLING = dlg.m_EGAatSample;
//CString m_EGAbyLMP;
        m_pSet->m_EGA_BY_LMP = dlg.m_EGAbyLMP;
//CString m_EGAbySONO;
        m_pSet->m_EGA_BY_SONO = dlg.m_EGAbySONO;
//BOOL    m_EthnicOriginAsian;
        m_pSet->m_ETHNIC_ORIGIN_ASIAN = (dlg.m_EthnicOriginAsian?"1":"0");
//BOOL    m_EthnicOriginBlack;
        m_pSet->m_ETHNIC_ORIGIN_BLACK = (dlg.m_EthnicOriginBlack?"1":"0");
//BOOL    m_EthnicOriginHispanic;
        m_pSet->m_ETHNIC_ORIGIN_HISPANIC = (dlg.m_EthnicOriginHispanic?"1":"0");
//BOOL    m_EthnicOriginNativeAmerican
        m_pSet->m_ETHNIC_ORIGIN_NATIVE_AMERICAN = (dlg.m_EthnicOriginNativeAmerican?"1":"0");
//BOOL    m_EthnicOriginOther;
        m_pSet->m_ETHNIC_ORIGIN_OTHER = (dlg.m_EthnicOriginOther?"1":"0");
//BOOL    m_EthnicOriginWhite;
        m_pSet->m_ETHNIC_ORIGIN_WHITE = (dlg.m_EthnicOriginWhite?"1":"0");
//BOOL    m_FFN_Neg;
        m_pSet->m_FFN_RESULT = (dlg.m_FFN_Neg?"0":" ");
//BOOL    m_FFN_Pos;
        m_pSet->m_FFN_RESULT = (dlg.m_FFN_Pos?"1":m_pSet->m_FFN_RESULT);
//BOOL    m_GestationalDiabetes;
        m_pSet->m_GESTATIONAL_DIABETES = (dlg.m_GestationalDiabetes?"1":"0");
//BOOL    m_HypertensiveDisorders
        m_pSet->m_HYPERTENSIVE_DISORDERS = (dlg.m_HypertensiveDisorders?"1":"0");
//BOOL    m_Insulin;
        m_pSet->m_INSULIN = (dlg.m_Insulin?"1":"0");
//CString m_LadID;
        m_pSet->m_LAB_ID = dlg.m_LadID;
//BOOL    m_MedicationNone;
```

-continued

```
m_pSet->m_MEDICATIONS_NONE = (dlg.m_MedicationNone?"1":"0");
//BOOL     m_MedicationUnknown;
m_pSet->m_MEDICATIONS_UNKNOWN = (dlg.m_MedicationUnknown?"1":"0");
//BOOL     m_MultipleGestationQuads;
m_pSet->m_MULTIPLE_GESTATION_QUADS = (dlg.m_MultipleGestationQuads?"1":"0");
//BOOL     m_MultipleGestationTriplets;
m_pSet->m_MULTIPLE_GESTATION_TRIPLETS (dlg.m_MultipleGestationTriplets?"1":"0"
//BOOL     m_MultipleGestationTwins;
m_pSet->m_MULTIPLE_GESTATION_TWINS = (dlg.m_MultipleGestationTwins?"1":"0");
//BOOL     m_MaritalStatusDivorced;
m_pSet->m_MARITAL_STATUS_DIVORCED = (dlg.m_MaritalStatusDivorced?"1":"0");
//BOOL     m_MaritalStatusLWP;
m_pSet->m_MARITAL_STATUS_LWP = (dlg.m_MaritalStatusLWP?"1":"0");
//BOOL     m_MaritalStatusMarried;
m_pSet->m_MARITAL_STATUS_MARRIED = (dlg.m_MaritalStatusMarried?"1":"0");
//BOOL     m_MaritalStatusOther;
m_pSet->m_MARITAL_STATUS_OTHER = (dlg.m_MaritalStatusOther?"1":"0");
//BOOL     m_MaritalStatusSingle;
m_pSet->m_MARITAL_STATUS_SINGLE = (dlg.m_MaritalStatusSingle?"1":"0");
//BOOL     m_MaritalStatusWidowed;
m_pSet->m_MARITAL_STATUS_WIDOWED = (dlg.m_MaritalStatusWidowed?"1":"0");
//BOOL     m_MultipleGestation;
m_pSet->m_MULTIPLE_GESTATION = (dlg.m_MultipleGestation?"1":"0");
//BOOL     m_PatientComp1;
m_pSet->m_PATIENT_COMPLAINT_1 = (dlg.m_PatientComp1?"1":"0");
//BOOL     m_PatientComp2;
m_pSet->m_PATIENT_COMPLAINT_2 = (dlg.m_PatientComp2?"1": "0");
//BOOL     m_PatientComp3;
m_pSet->m_PATIENT_COMPLAINT_3 = (dlg.m_PatientComp3?"1":"0");
//BOOL     m_PatientComp4;
m_pSet->m_PATIENT_COMPLAINT_4 = (dlg.m_PatientComp4?"1":"0");
//BOOL     m_PatientComp5;
m_pSet->m_PATIENT_COMPLAINT_5 = (dlg.m_PatientComp5?"1":"0");
//BOOL     m_PatientComp6;
m_pSet->m_PATIENT_COMPLAINT-6 = (dlg.m_PatientComp6?"1":"0");
//BOOL     m_Tocolytics;
m_pSet->m_TOYOLYTICS = (dlg.m_Tocolytics?"1":"0");
//BOOL     m_UtCervAbnormal;
m_pSet->m_UTCERV_ABNORMALITY = (dlg.m_UtCervAbnormal?"1":"0");
//BOOL     m_VaginalBleeding;
m_pSet->m_VAGINAL_BLEEDING = (dlg.m_VaginalBleeding?"1":"0");
//BOOL     m_VaginalBleedingGross;
m_pSet->m_VAGINAL_BLEEDING_GROSS = (dlg.m_VaginalBleedingGross?"1":"0");
//BOOL     m_VaginalBleedingMed;
m_pSet->m_VAGINAL_BLEEDING_MEDIUM (dlg.m_VaginalBleedingMed?"1":"0");
//BOOL     m_VaginalBleedingTrace;
m_pSet->m_VAGINAL_BLEEDING_TRACE = (dlg.m_VaginalBleedingTrace?"1":"0");
//BOOL     m_2_COMP_1;
m_pSet->m_2_COMP_1 = (dlg.m_2_COMP_1?"1":"0");
//BOOL     m_2_COMP_2;
m_pSet->m_2_COMP_2 = (dlg.m_2_COMP_2?"1":"0");
//BOOL     m_2_COMP_3;
m_pSet->m_2_COMP_3 = (dlg.m_2_COMP_3?"1":"0");
//CString m_ABORTIONS
m_pSet->m_ABORTIONS = dlg.m_ABORTIONS;
//Cstring m_GRAVITY;
m_pSet->m_GRAVITY = dlg.m_GRAVITY;
val = atoi(m_pSet->m_GRAVITY);
if(val ==0) {
    m_pSet->m_0_COMP = "1";
} else {
m_pSet->m_0_COMP = "0";
//CString m_PARITY;
m_pSet->m_PARITY = dlg.m_PARITY;
//BOOL     m_PatComp1_1_3;
m_pSet->m_PATIENT_COMPLAINT_1_1_3 (dlg.m_PatComp1_1_3?"1":"0");
//BOOL     m_PatComp1_10_12;
m_pSet->m_PATIENT_COMPLAINT1_10_12 = (dlg.m_PatComp1_10_12?"1":"0");
//BOOL     m_PatComp1_4_6;
m_pSet->m_PATIENT_COMPLAINT_1_4_6 = (dlg.m_PatComp1_4_6?"1":"0");
//BOOL     m_PatComp1_7_9;
m_pSet->m_PATIENT_COMPLAINT_1_7_9 = (dlg.m_PatComp1_7_9?"1":"0");
//BOOL     m_PatComp1_GT12;
m_pSet->m_PATIENT_COMPLAINT_1_GT12 = (dlg.m_PatComp1_GT12?"1":"0");
//BOOL     m_PatComp1_LT1;
m_pSet->m_PATIENT_COMPLAINT_1_LT1 = (dlg.m_PatComp1_LT1?"1":"0");
// generate the net fields
m_pSet->RunNets (m_pSet->CurRecord);
// write the record to the file
```

```
        m_pSet->put_rec(m_pSet->Rec);
    }
}
int CPTDinpView::str2int( CString& str )
{
    if(str == "0") return 2;
    if(str == "1") return 1;
    if(str == "2") return 0;
    return -1;
}
char* CPTDinpView::int2str( int val )
{
    if(val == 0) return "2";
    if(val == 1) return "1";
    if(val == 2) return "0";
    return "";
}
int CPTDinpView::yn2int( CString& str
{
    if(str == "0") return 1;
    if(str == "1") return 0;
    return -1;
}
char* CPTDinpView::int2yn( int val )
}
    if(val == 0) return "1";
    if(val == 1) return "0";
    return "";
}
void CPTDinpView::OnDataEdit()
{
    CPTDinpDoc* pDoc = GetDocument();
    FILE *fp;
    fp = fopen(pDoc->PathName,"rb");
    if(fp!=NULL) {
        fclose(fp);
    } else {
        CFileDialog Dlg(TRUE, "fdb",NULL, OFN_OVERWRTEPROMPT ,
            "FDB iles (*fbd)|*.fdb||");
        Dlg.m_ofn.1pstrTitle = "Open Fixed length DataBase file";
        if( Dlg.DoModal() == IDOK ) {
            strcpy (pDoc->PathName, Dlg.GetPathName ());
            fp = fopen(pDoc->PathName,"rb");
            if(fp==NULL)
                AfxMessageBox("Unable to open Database File!");
                return;
            }
            pDoc->CurRecord = 0;
            fseek ( fp, 0L, SEEK_END);
            pDoc->NumRecords = ftell(fp) / (REC_LENGTH+2L);
            fclose(fp);
        }
    }
    Edit -;
}
void CPTDinpView::OnDataNew()
{
FILE *fp;
    CPTDinpDoc* pDoc = GetDocument();
    // create a new record
        fp = fopen(pDoc->PathName,"ab");
        if(fp!=NULL)
            fwrite(pDoc->Rec,sizeof(char), (REC_LENGTH + 2L) , fp);
            fclose (fp);
        }
        pDoc->InitializeRec();
        pDoc->NumRecords += 1;
        pDoc->CurRecord = pDoc->NumRecords - 1;
        pDoc->put_rec (pDoc->Rec);
    // edit the new record
    pDoc->get_rec(pDoc->Rec);
    Edit ();
}
// PTDivw.h : interface of the CPTDinpView class
//
/////////////////////////////////////////////////////////////////
class CPTDinpView : public CView
{
protected: // create from serialization only
```

-continued

```
        CPTDinpView();
        DECLARE_DYNCREATE (CPTDinpView)
// Attributes
public:
        CPTDinpDoc* GetDocument ();
        BOOL ShowPrt;
        CPTDinpDoc* m_pSet;
        void Edit( void );
// Operations
public:
        // conversions for dialogs
        int str2int( CString& str );
        char* int2str( int val );
        int yn2int( CString& str );
        char* int2yn( int val );
// Implementation
public:
        virtual ~CPTDinpView();
        virtual void OnDraw(CDC* pDC; // overridden to draw this view
#ifdef_DEBUG
        virtual void AssertValid() const;
        virtual void Dump (CDumpContext& dc) const;
#endif
protected:
        // Printing support
        virtual BOOL OnPreparePrinting (CPrintInfo* pInfo);
        virtual void OnBeginPrinting(CDC* pDC, CprintInfo* pInfo);
        virtual void OnEndPrinting(CDC* pDC, CPrintInfo* pInfo);
// Generated message map functions
protected:
        //{{AFX_MSG(CPTDinpview)
        afx_msg void OnDataEdit();
        afx_msg void OnDataNew();
        //}}AFX_MSG
        DECLARE_MESSAGE_MAP()
};
#ifndef_DEBUG // debug version mPTDivw.cpp
inline CPTDinpDoc* CPTDinpView::GetDocument()
        { return (CPTDinpDoc*)m_pDocument;
#endif
///////////////////////////////////////////////////////////////
// stdafx.cpp : source file that includes just the standard includes
// stdafx.pch will be the pre-compiled header
// stdafx.obj will contain the pre-compiled type information
#include "stdafx.h"
// stdafx.h include file for standard system include files,
// or project specific include files that are used frequently, but
//      are changed infrequently
//
#include <afxwin.h>       // MFC core and standard components
#include <afxext.h>       // MFC extensions (including VB)
#include <afxdb.h>        // NEC database classes
//
// ENDOINP.RC2 -
resources App Studio does
not edit directly
//
#ifdef APSTUDIO_
INVOKED
        #error this file is not editable by App Studio
#endif //APSTUDIO_INVOKED
///////////////////////////////////////////////////////////////
// Version stamp for this .EXE
#include "ver.h"
VS_VERSION_INFO VERSIONINFO
        FILEVERSION           1,0,0,1
        PRODUCTVERSION        1,0,0,1
        FILEFLAGSMASK         VS_FF1_FILEFLAGSMASK
#ifdef_DEBUG
        FILEFLAGS             VS_FF_DEBUG|VS_FF_PRIVATEBUILD|VS_FF_PRERELEASE
#else
        FILEFLAGS             0 // final version
#endif
        FILEOS                VOS_DOS_WINDOWS16
        FILETYPE              VFT_APP
        FILESUBTYPE           0 // not used
BEGIN
        BLOCK "StringFileInfo"
        BEGIN
```

-continued

```
        BLOCK "040904E4"// Lang=US English, CharSet=Windows Multilingual
        BEGIN
            VALUE "CompanyName",       "\0"
            VALUE "FileDescription",   "ENDOINP MFC Application\0"
            VALUE "FileVersion",       "1.0.001\0"
            VALUE "InternalName",      "ENDOINP\0
            VALUE "LegalCopyright",    "\0"
            VALUE "LegalTrademarks",   "\0"
            VALUE "OriginalFilename",  "ENDOINP.EXE\0"
            VALUE "ProductName"        "ENDOINP\0"
            VALUE "ProductVersion",    "1.0.001\0"
        END
    END
    BLOCK "VarFileInfo"
    BEGIN
        VALUE "Translation", 0x409, 1252
            // English language (0x409) and the Windows ANSI codepage (1252)
    END
END
/////////////////////////////////////////////////////////////////////////////
// Add additional manually edited resources here...
/////////////////////////////////////////////////////////////////////////////
//{{NO_DEPENDENCIES}}
// App Studio generated include file.
// Used by PTDINP.RC
//
#define _APS_3D_CONTROLS                 1
#define IDD_ABOUTBOX                     100
#define IDD_ENDOIN_FORM                  101
#define IDD_ENDO_PG01                    102
#define IDD_ENDO_PG02                    103
#define IDD_ENDO_PG03                    104
#define IDD_ENDO_PG04                    105
#define IDD_ENDO_PG05                    106
#define IDD_ENDO_PG06                    107
#define IDD_ENDO_PG07                    108
#define IDD_ENDO_PG08                    109
#define IDD_ENDO_PG09                    110
#define IDD_ENDO_PG10                    111
#define IDD_ENDO_PG11                    112
#define IDD_ENDO_PG12                    113
#define IDD_ENDO_PG13                    114
#define IDD_ENDO_PG14                    115
#define IDD_ENDO_SP04A                   116
#define IDD_ENDO_SP04B                   117
#define IDD_ENDO_SP07A                   118
#define IDD_ENDO_SP08A                   119
#define IDD_ENDO_SP08B                   120
#define IDR_MAINFRAME                    128
#define IDR_ENDOINTYPE                   129
#define IDP_FAILED_OPEN_DATABASE         130
#define IDD__ENDO_SP08C                  131
#define IDD_ENDO_PG15                    132
#define IDD_ENDO_SP10A                   133
#define IDD_ENDO_SP08D                   134
#define IDD_ENDO_SP09A                   135
#define IDD_ENDO_SP08E                   136
#define IDD_ENDO_PG0                     137
#define IDD_ENDO_PG77                    138
#define IDD_D_PTD_INP                    139
#define IDD_D_GOTO                       140
#define IDB_BITMAP1                      141
#define IDC_E_DATE                       1000
#define IDC_E_ADEZA_ID                   1001
#define IDC_E_INST_ID                    1002
#define IDC_E_AGE_MENS2                  1002
#define IDC_E_ADEZA_ID2                  1002
#define IDC_E_TOTAL_POINTS               1002
#define IDC_E_PAT_BIRTHDATE              1003
#define IDC_E_PAT_ZIPCODE                1004
#define IDC_E_PAT_OCCUPATION             1005
#define IDC_C_PAT_WHITE                  1006
#define IDC_C_PAT_BLACK                  1007
#define IDC_C_PAT_HISPANIC               1008
#define IDC_C_PAT_ASIAN                  1009
#define IDC_C_PAT_OTHER                  1010
#define IDC_C_PAT_HIGHSCHOOL             1011
#define IDC_C_PAT_COLLEGE                1012
#define IDC_C_PAT_GRADUATE               1013
```

-continued

```
#define IDC_C_PAT_POSTGRAD        1014
#define IDC_C_MARRIED             1015
#define IDC_B_GOBACK              1016
#define IDC_C_SP_WHITE            1017
#define IDC_C_SP_BLACK            1018
#define IDC_C_SP_HISPANIC         1019
#define IDC_C_SP_ASIAN            1020
#define IDC_C_SP_OTHER            1021
#define IDC_C_SP_HIGHSCHOOL       1022
#define IDC_C_SP_COLLEGE          1023
#define IDC_C_SP_GRADUATE         1024
#define IDC_C_SP_POSTGRAD         1025
#define IDC_E_SP_OCCUPATION       1026
#define IDC_E_PAT_AGE             1027
#define IDC_C_PAT_FLAG            1028
#define IDC_R_DIAB_MELL1          1029
#define IDC_R_DIAB_MELL2          1030
#define IDC_R_DIAB_MELL3          1031
#define IDC_B_PREV_PG             1032
#define IDC_R_OTHER_STD1          1033
#define IDC_R_OTHER_STD2          1034
#define IDC_R_PI_DIAB1            1035
#define IDC_R_PI_DIAB2            1036
#define IDC_R_PI_DIAB3            1037
#define IDC_R_OTHER_STD3          1038
#define IDC_R_VAG_INF1            1039
#define IDC_R_VAG_INF2            1040
#define IDC_R_VAG_INF3            1041
#define IDC_R_GEN_WARTS1          1042
#define IDC_R_GEN_WARTS2          1043
#define IDC_R_GEN_WARTS3          1044
#define IDC_R_UT_TUB_ABNOR1       1045
#define IDC_R_UT_TUB_ABNOR2       1046
#define IDC_R_UT_TUB_ABNOR3       1047
#define IDC_R_DYS_UT_BLEED1       1048
#define IDC_R_DYS_UT_BLEED2       1049
#define IDC_R_HYPERTEN1           1050
#define IDC_R_DYS_UT_BLEED3       1050
#define IDC_R_HYPERTEN2           1051
#define IDC_R_SMOKING1            1051
#define IDC_R_HYPERTEN3           1052
#define IDC_R_SMOKING2            1052
#define IDC_R_PI_HYPERTEN1        1053
#define IDC_R_SMOKING3            1053
#define IDC_R_PI_HYPERTEN2        1054
#define IDC_R_DRUG_ABUSE1         1054
#define IDC_R_PI_HYPERTEN3        1055
#define IDC_R_DRUG_ABUSE2         1055
#define IDC_R_AUTO_IMMUNE1        1056
#define IDC_R_DRUG_ABUSE3         1056
#define IDC_R_AUTO_IMMUNE2        1057
#define IDC_R_PRES_MED1           1057
#define IDC_R_AUTO_IMMUNE3        1058
#define IDC_R_PRES_MED2           1058
#define IDC_R_PRES_MED3           1059
#define IDC_R_DYS_UT_BLEED4       1059
#define IDC_R_UNDETERMINED2       1060
#define IDC_R_OV_CYST1            1061
#define IDC_R_ORG_TRANS1          1062
#define IDC_R_OV_CYST2            1062
#define IDC_R_ORG_TRANS2          1063
#define IDC_R_OV_CYST3            1063
#define IDC_R_OTHER_CUR1          1063
#define IDC_R_ORG_TRANS3          1064
#define IDC_R_POLY_OV_SYND1       1064
#define IDC_R_OTHER_CUR2          1064
#define IDC_R_PEL_INFL_DIS1       1065
#define IDC_R_POLY_OV_SYND2       1065
#define IDC_R_PEL_INFL_DIS2       1066
#define IDC_R_POLY_OV_SYND3       1066
#define IDC_R_PEL_INFL_DTS3       1067
#define IDC_R_AB_PAP_DYSPL1       1067
#define IDC_R_HERPES1             1068
#define IDC_R_AB_PAP_DYSPL2       1068
#define IDC_R_HERPES2             1069
#define IDC_R_AB_PAP_DYSPL3       1069
#define IDC_R_HERPES3             1070
#define IDC_R_GYN_CANSER3         1070
#define IDC_R_GYN_CANSER2         1071
```

-continued

| | |
|---|---|
| #define IDC_R_GYN_CANSER1 | 1072 |
| #define IDC_R_FIBROIDS3 | 1073 |
| #define IDC_R_FIBROIDS2 | 1074 |
| #define IDC_R_FIBROIDS1 | 1075 |
| #define IDC_R_OTHER_HX3 | 1076 |
| #define IDC_R_OTHER_HX2 | 1077 |
| #define IDC_R_OTHER_HX1 | 1078 |
| #define IDC_R_PELVIC_PAIN1 | 1079 |
| #define IDC_R_ECTOPIC_PREG1 | 1079 |
| #define IDC_R_PELVIC_PAIN2 | 1080 |
| #define IDC_R_ECTOPIC_PREG2 | 1080 |
| #define IDC_R_ABDOM_PAIN1 | 1081 |
| #define IDC_R_ECTOPIC_PREG3 | 1081 |
| #define IDC_R_ABDOM_PAIN2 | 1082 |
| #define IDC_R_MENS_ABNORM1 | 1083 |
| #define IDC_R_MENS_ABNORM2 | 1084 |
| #define IDC_R_DYSMEN1 | 1085 |
| #define IDC_R_DYSMEN2 | 1086 |
| #define IDC_R_DISPAR1 | 1087 |
| #define IDC_R_DISPAR2 | 1088 |
| #define IDC_R_INFERTILITY1 | 1089 |
| #define IDC_R_INFERTILITY2 | 1090 |
| #define IDC_R_ADN_MAS_THICK1 | 1091 |
| #define IDC_R_ADN_MAS_THICK2 | 1092 |
| #define IDC_R_OVARIAN_CYST1 | 1093 |
| #define IDC_R_OVARIAN_CYST2 | 1094 |
| #define IDC_R_UNDETERMINED1 | 1095 |
| #define IDC_E_CUR_SYM_OTHER | 1096 |
| #define IDC_R_MENST_REG1 | 1097 |
| #define IDC_R_MENST_REG2 | 1098 |
| #define IDC_E_LAST_PERIOD | 1099 |
| #define IDC_E_RECENT_PART | 1100 |
| #define IDC_E_GRAVIDITY | 1101 |
| #define IDC_E_PARITY | 1102 |
| #define IDC_R_HX_INFERT1 | 1103 |
| #define IDC_R_HX_INFERT2 | 1104 |
| #define IDC_R_OV_STAT_KNOWN1 | 1105 |
| #define IDC_R_OV_STAT_KNOWN2 | 1106 |
| #define IDC_E_SPONT_ABORT | 1107 |
| #define IDC_R_MENS_FLOW1 | 1107 |
| #define IDC_E_ELECT_ABORT | 1108 |
| #define IDC_R_MENS_FLOW2 | 1108 |
| #define IDC_R_MENS_FLOW3 | 1109 |
| #define IDC_R_HX_OF_ENDO1 | 1110 |
| #define IDC_R_HX_OF_ENDO2 | 1111 |
| #define IDC_R_HX_PEL_SURG1 | 1112 |
| #define IDC_R_HX_PEL_SURG2 | 1113 |
| #define IDC_R_HORMONE_MED1 | 1114 |
| #define IDC_R_HORMONE_MED2 | 1115 |
| #define IDC_E_CUR_SURG_DATE | 1116 |
| #define IDC_E_CUR_SURG_REASON2 | 1117 |
| #define IDC_C_DIAG_LAPAR | 1118 |
| #define IDC_CLASER_OBLIT | 1119 |
| #define IDC_C_SURG_EXCISION | 1120 |
| #define IDC_C_BI_SAL_OOPH | 1121 |
| #define IDC_C_UNIL_OOPH | 1122 |
| #define IDC_C_EXC_OV_CYST | 1123 |
| #define IDC_C_OLULA | 1124 |
| #define IDC_C_HYSTERECTOMY | 1125 |
| #define IDC_C_HYSTEROSCOPY | 1126 |
| #define IDC_C_D_AND_C | 1127 |
| #define IDC_C_CUR_SURG_OTHER | 1128 |
| #define IDC_C_NORM_PEL | 1129 |
| #define IDC_E_NDO_PRESENT | 1130 |
| #define IDC_C_ADHESONS_PRES | 1131 |
| #define IDC_C_FIBROIDS_PRES | 1132 |
| #define IDC_C_PELV_INF_DISEASE | 1133 |
| #define IDC_C_GYN_CANCER | 1134 |
| #define IDC_C_OTHER_GYN_DIS | 1135 |
| #define IDC_R_AFS_STG1 | 1136 |
| #define IDC_R_AFS_STG2 | 1137 |
| #define IDC_R_AFS_STG3 | 1138 |
| #define IDC_R_AFS_STG4 | 1139 |
| #define IDC_C_BLUE_BK_LESIONS | 1141 |
| #define IDC_C_RED_LESIONS | 1142 |
| #define IDC_C_WHITE_LESIONS | 1143 |
| #define IDC_R_PEL_ADH_PRES1 | 1144 |
| #define IDC_R_PEL_ADH_PRES2 | 1145 |
| #define IDC_R_ENDO_CONF_BIOPSY1 | 1146 |

-continued

```
#define IDC_R_ENDO_CONF_BIOPSY2       1147
#define IDC_C_OVERIES_EST             1148
#define IDC_C_OVERIES_ADH             1149
#define IDC_C_FALLOP_EST              1150
#define IDC_C_FALLOP_ADH              1151
#define IDC_C_UT_LIG_EST              1152
#define IDC_C_-UT_LIG_ADH             1153
#define IDC_C_CULDESAC_EST            1154
#define IDC_C_CULDESAC_ADH            1155
#define IDC_C_BROAD_LIG_EST           1156
#define IDC_C_BROAD_LIG_ADE           1157
#define IDC_C_PEL_SIDE_EST            1158
#define IDC_C_PEL_SIDE_ADH            1159
#define IDC_C_VESIC_EST               1160
#define IDC_C_VESIC_ADH               1161
#define IDC_C_OTHER_EST               1162
#define IDC_C_OTHER_ADH               1163
#define IDC_E_PID_DATE                1164
#define IDC_R_HAVE_PID1               1165
#define IDC_E_PID_LOC_SPECIFY         1165
#define IDC_E_ADDL_PID                1165
#define IDC_R_HAVE_PID2               1166
#define IDC_E_PID_LOC_SPECIFY2        1166
#define IDC_C_PID_C_LAPS              1167
#define IDC_C_PID_C_LAPT              1168
#define IDC_C_PID_C_DIFF_DIAG         1169
#define IDC_C_PID_C_UNDET             1170
#define IDC_E_PID_DD_SPECIFY          1171
#define IDC_R_PID_CONF_SURG1          1172
#define IDC_R_GC_HISTOLOGY1           1172
#define IDC_R_PID_CONF_SURG2          1173
#define IDC_R_GC_HISTOLOGY2           1173
#define IDC_C_PID_M_ORG_UNKNOWN       1174
#define IDC_C_PID_ORG_NEISS           1175
#define IDC_C_PID_M_ORG_CH_TR         1176
#define IDC_C_PID_M_ORG_GM            1177
#define IDC_C_PID_M_ORG_OTHER         1178
#define IDC_C_PID_M_LOC_VAGINA        1179
#define IDC_C_PID_LOC_CERVIX          1180
#define IDC_C_PID_LOC_OVARIES         1181
#define IDC_C_PID_LOC_FALLOP          1182
#define IDC_C_PID_LOC_OTHER           1183
#define IDC_E_PID_ORG_SPECIFY         1184
#define IDC_R_GC_PRIMARY1             1185
#define IDC_R_GC_PRIMARY2             1186
#define IDC_R_GC_PRIMARY3             1187
#define IDC_R_GC_PRIMARY4             1188
#define IDC_R_GC_GRADE1               1189
#define IDC_R_GC_STAGE2               1190
#define IDC_R_GC_STAGE3               1191
#define IDC_R_GC_STAGE4               1192
#define IDC_R_GC_STAGE5               1193
#define IDC_R_GC_GRADE2               1194
#define IDC_R_GC_GRADE3               1195
#define IDC_R_GC_STAGE1               1196
#define IDC_E_GC_TUMOR_TYPE           1197
#define IDC_E_GC SITES SPECIFY        1198
#define IDC_E_GO_ADD INFO             1199
#define IDC_E_PKS PER DAY             1200
#define IDC_E_OTHER_STD_SPECIFY       1201
#define IDC_E_PRES_MED_DRUG1          1202
#define IDC_E_PRES_MED_DATE1          1203
#define IDC_E_PRES_MED_DRUG2          1204
#define IDC_E_OTHER_HX_SPECIFY        1204
#define IDC_E_PRES_MED_DATE2          1205
#define IDC_E_INFERT_PRI              1205
#define IDC_E_PRIMARY_LEN             1206
#define IDC_C_INFERT_SEC              1207
#define IDC_C_HOR_MED1                1207
#define IDC_E_SECONDARY_LEN           1208
#define IDC_E_HOR_MED_DOSE1           1208
#define IDC_E_HOR_MED_DATE1           1209
#define IDC_E_PEL_SURG_TYPE1          1209
#define IDC_E_HOR_MED_PURP1           1210
#define IDC_E_PEL_SURG_DATE1          1210
#define IDC_C_HOR_MED2                1211
#define IDC_E_PEL_SURG_DATE2          1211
#define IDC_R_OVUL_STAT1              1211
#define IDC_E_HOR_MED_DOSE2           1212
```

-continued

| | |
|---|---|
| #define IDC_E_PEL_SURG_TYPE2 | 1212 |
| #define IDC_R_OVUL_STAT2 | 1212 |
| #define IDC_E_HOR_MED_DATE2 | 1213 |
| #define IDC_E_PEL_SURG_DATE3 | 1213 |
| #define IDC_R_OVUL_STAT3 | 1213 |
| #define IDC_E_HOR_MED_PURP2 | 1214 |
| #define IDC_E_PEL_SURG_TYPE3 | 1214 |
| #define IDC_E_ST_OTHER_SPECIFY | 1214 |
| #define IDC_C_HOR_MED3 | 1215 |
| #define IDC_E_PEL_SURG_DATE4 | 1215 |
| #define IDC_E_ADH_OTHER_SPECIFY | 1215 |
| #define IDC_E_HOR_MED_DOSE3 | 1216 |
| #define IDC_E_PEL_SURG_TYPE4 | 1216 |
| #define IDC_C_MENST_HORM_INDUCED | 1216 |
| #define IDC_E_HOR_MED_DATE3 | 1217 |
| #define IDC_E_TYP_CYC_LEN | 1217 |
| #define IDC_E_HOR_MED_PURP3 | 1218 |
| #define IDC_E_TYP_PERIOD_LEN | 1218 |
| #define IDC_C_HOR_MED4 | 1219 |
| #define IDC_E_FREQUENCY | 1219 |
| #define IDC_E_HOR_MED_DOSE4 | 1220 |
| #define IDC_E_OTH_SURG_PROC_SPECIFY | 1220 |
| #define IDC_E_HOR_MED_DATE4 | 1221 |
| #define IDC_E_OTHER_GYN_SPECIFY | 1221 |
| #define IDC_E_HOR_MED_PURP4 | 1222 |
| #define IDC_C_CONFIRMED_BY_LAPAROSCOPY | 1222 |
| #define IDC_C_CONFIRMED_BY_LAPAROTOMY | 1223 |
| #define IDC_C_CONFIRMED_BY_BIOPSY | 1224 |
| #define IDC_E_LAPAROSCOPY_DATE | 1225 |
| #define IDC_E_LAPAROTOMY_DATE | 1226 |
| #define IDC_E_BIOPSY_DATE | 1227 |
| #define IDC_E_RECORD_COUNT | 1230 |
| #define IDC_R_HORMONE_INDUCED | 1232 |
| #define IDC_R_HORMONE_INDUCED2 | 1233 |
| #define IDC_EO_WHITE | 1247 |
| #define IDC_EO_BLACK | 1248 |
| #define IDC_EO_ASIAN | 1249 |
| #define IDC_EO_HISPANIC | 1250 |
| #define IDC_EO_NATIVE_AMERICAN | 1251 |
| #define IDC_EO_OTHER | 1252 |
| #define IDC_MS_MARRIED | 1253 |
| #define IDC_MS_SINGLE | 1254 |
| #define IDC_MS_WIDOWED | 1255 |
| #define IDC_MS_LWP | 1256 |
| #define IDC_MS_OTHER | 1257 |
| #define IDC_ACOG_Y | 1258 |
| #define IDC_ACOG_N | 1259 |
| #define IDC_MS_DIVORCED | 1260 |
| #define IDC_ANTIBIOTICS | 1261 |
| #define IDC_FFN_POS | 1262 |
| #define IDC_CORTICOSTEROIDS | 1263 |
| #define IDC_TOCOLYTICS | 1264 |
| #define IDC_INSULIN | 1265 |
| #define IDC_ANTIHYPER | 1266 |
| #define IDC_FFN_NEG | 1267 |
| #define IDC_MED_NONE | 1268 |
| #define IDC_MED_UKN | 1269 |
| #define IDC_PATIENT_COMP_1 | 1270 |
| #define IDC_PATIENT_COMP_3 | 1271 |
| #define IDC_PC1_LT1 | 1272 |
| #define IDC_PC1_1_3 | 1273 |
| #define IDC_PC1_4_6 | 1274 |
| #define IDC_PATIENT_COMP_2 | 1275 |
| #define IDC_VAGINAL_BLEEDING | 1276 |
| #define IDC_VB_TRACE | 1277 |
| #define IDC_VB_MED | 1278 |
| #define IDC_VB_GROSS | 1279 |
| #define IDC_PATIENT_COMP_6 | 1280 |
| #define IDC_PATIENT_COMP_5 | 1281 |
| #define IDC_PATIENT_COMP_4 | 1282 |
| #define IDC_EGA_BY_SONO | 1283 |
| #define IDC_EGA_BY_LMP | 1284 |
| #define IDC_EGA_AT_SAMP | 1285 |
| #define IDC_DILITATION_LT1 | 1286 |
| #define IDC_DILITATON_1 | 1287 |
| #define IDC_DILITATION_1_2 | 1288 |
| #define IDC_DILITATION_2 | 1289 |

-continued

```
#define IDC_DILITATION_2_3           1290
#define IDC_DILITATION_3             1291
#define IDC_DILITATION_GT3           1292
#define IDC_CERV_FIRM                1293
#define IDC_CERV_MOD                 1294
#define IDC_CERV_SOFT                1295
#define IDC_1_COMP                   1298
#define IDC_2_COMP                   1299
#define IDC_3_COMP                   1300
#define IDC_4_COMP                   1301
#define IDC_5_COMP                   1302
#define IDC_6_COMP                   1303
#define IDC_MULT_GEST                1304
#define IDC_UT_CERV_ABNORM           1305
#define IDC_CERV_CERCLAGE            1306
#define IDC_GEST_DIABETES            1307
#define IDC_HYPERTEN_DISORDERS       1308
#define IDC_MG_TWINS                 1309
#define IDC_MG_TRIPLETS              1310
#define IDC_MG_QUADS                 1311
#define IDC_NAME_L                   1313
#define IDC_NAME_F                   1314
#define IDC_NAME_MI                  1315
#define IDC_DATE_OF_BIRTH            1316
#define IDC_LAB_ID                   1317
#define IDC_DILITATION_UKN           1318
#define IDC_GRAVIDITY                1319
#define IDC_PARITY                   1320
#define IDC_ABORTIONS                1321
#define IDC_PC1_7_9                  1322
#define IDC_PC1_10_12                1323
#define IDC_PC1_GT12                 1324
#define IDC_2_COMP_1                 1325
#define IDC_2_COMP_2                 1326
#define IDC_2_COMP_3                 1327
#define IDC_R_GOTO_SEL1              1329
#define IDC_R_GOTO_SEL2              1330
#define IDC_E_GOTO_REC_NUM           1331
#define IDC_E_GOTO_ID_NUM            1332
#define IDD_DATA_NEW                 32771
#define ID_DATA_NEW                  32772
#define ID_DATA_EDIT                 32773
#define ID_REC_FIRST                 32774
#define ID_REC_NEXT                  32775
#define ID_REC_PREV                  32776
#define ID_REC_LAST                  32777
#define ID_BLD_NET_FILE              32778
#define ID_EDIT_MODE                 32779
#define IDC_LR_SUBFIELDS             32780
#define ID_REC_GOTO                  32781
// Next default values for new objects
//
#ifdef APSTUDIO_INVOKED
#ifndef APSTUDIO_READONLY_SYMBOLS
#define _APS_NEXT_RESOURCE_VALUE     142
#define _APS_NEXT_COMMAND_VALUE      32782
#define _APS_NEXT_CONTROL_VALUE      1333
#define _APS_NEXT_SYMED_VALUE        101
#endif
#endif
//Microsoft App Studio generated resource script.
//
#include "resource.h"
#define APSTUDIO_READONLY_SYMBOLS
/////////////////////////////////////////////////////////////////
//
// Generated from the TEXTINCLUDE 2 resource.
//
#include "afxres.h"
/////////////////////////////////////////////////////////////////
#undef APSTUDIO_READONLY_SYMBOLS
#ifdef APSTUDIO_INVOKED
/////////////////////////////////////////////////////////////////
//
// TEXTINCLUDE
//
1 TEXTINCLUDE DISCARDABLE
BEGIN
    "resource.h\0"
```

-continued

```
END
2 TEXTINCLUDE DISCARDABLE
BEGIN
    "#include ""afxres .h""""\r\n"
    "\0 "
END
3 TEXTINCLUDE DISCARDABLE
BEGIN
    "#include ""res\\PTDinp.rc2""""// non-App Studio edited resources\r\n"
    "\r\n"
    "#include ""afxres.rc""""\01/// Standard components\r\n"
    "#include ""afxprint.rc""""\011// printing/print preview resources\r\n"
    "#include ""afxdb.rc""""\011\011// Database resources\r\n"
    "\0"
END
/////////////////////////////////////////////////////////////////////
#endif       // APSTUDIO_INVOKED
/////////////////////////////////////////////////////////////////////
//
// Icon
//
IDR_MAINFRAME      ICON    DISCARDABLE       "RES\\PTDINP.ICO"
/////////////////////////////////////////////////////////////////////
//
// Bitmap
//
IDR_MAINFRAME              BITMAP   MOVEABLE PURE   "RES\\TOOLBAR.BMP"
IDB_BITMAP1                BITMAP   DISCARDABLE     "RES\\BITMAP1.BMP"
/////////////////////////////////////////////////////////////////////
//
// Menu
//
IDR_MAINFRAME MENU
PRELOAD DISCARDABLE
BEGIN
    POPUP "&File"
    BEGIN
        MENUITEM "&Open...\tCtrl+O",         ID_FILE_OPEN
        MENUITEM SEPARATOR
        MENUITEM "&Print",                   ID_FILE_PRINT
        MENUITEM "Print &Setup",             ID_FILE_PRINT_SETUP
        MENUITEM "Print Pre&view",           ID_FILE_PRINT_PREVIEW
        MENUITEM SEPARATOR
        MENUITEM "File1",                    ID_FILE_MRU_FILE1, GRAYED
        MENUITEM "File2",                    ID_FILE_MRU_FILE2, GRAYED
        MENUITEM "File3",                    ID_FILE_MRU_FILE3, GRAYED
        MENUITEM "File4",                    ID_FILE_MRU_FILE4, GRAYED
        MENUITEM SEPARATOR
        MENUITEM "E&xit",                    ID_APP_EXIT
    END
    POPUP "&Record"
    BEGIN
        MENUITEM "&First Record",            ID_REC FIRST
        MENUITEM "&Prev Record",             ID_RECPREV
        MENUITEM "&Next Record",             ID_REC NEXT
        MENUITEM "&Last Record",             ID_REC_LAST
        MENUITEM SEPARATOR
        MENUITEM "&Go to Record",            ID_REC_GOTO
        MENUITEM SEPARATOR
        MENUITEM "&Edit Record",             ID_DATA_EDIT
        MENUITEM "&New Record",              ID_DATA_NEW
        MENUITEM SEPARATOR
        MENUITEM "Neural &Data",             ID_BLD_NET_FILE
    END
    POPUP "&Options"
    BEGIN
        MENUITEM "&Print Full Form",         ID_EDIT_MODE
        MENUITEM "&Clear Subfields",         ID_CLR_SUBFIELDS
    END
    POPUP "&View"
    BEGIN
        MENUITEM "&Toolbar",                 ID_VIEW TOOLBAR
        MENUITEM "&Status Bar",              ID VIEW STATUS BAR
    END
    POPUP "&Help"
    BEGIN
        MENUITEM "&About PTDinp...",         ID_APP_ABOUT
    END
END
```

-continued

```
////////////////////////////////////////////////////////////////
//
// Accelerator
//
IDR_MAINFRAME ACCELERATORS PRELOAD MOVEABLE PURE
BEGIN
    "N",            ID_FILE_NEW,        VIRTKEY, CONTROL
    "O",            ID_FILE_OPEN,       VIRTKEY, CONTROL
    "S",            ID_FILE_SAVE,       VIRTKEY, CONTROL
    "P",            ID_FILE_PRINT,      VIRTKEY, CONTROL
    "Z",            ID_EDIT_UNDO,       VIRTKEY, CONTROL
    "X",            ID_EDIT_CUT,        VIRTKEY, CONTROL
    "C",            ID_EDIT_COPY,       VIRTKEY, CONTROL
    "V",            ID_EDIT_PASTE,      VIRTKEY, CONTROL
    VK_BACK,        ID_EDIT_UNDO,       VIRTKEY, ALT
    VK_DELETE,      ID_EDIT_CUT,        VIRTKEY, SHIFT
    VK_INSERT,      ID_EDIT_COPY,       VIRTKEY, CONTROL
    VK_INSERT,      ID_EDIT_PASTE,      VIRTKEY, SHIFT
    VK_F6,          ID_NEXT_PANE,       VIRTKEY
    VK_F6,          ID_PREV_PANE,       VIRTKEY, SHIFT
END
////////////////////////////////////////////////////////////////
// Dialog
//
IDD_ABOUTBOX DIALOG DISCARDABLE 34, 22, 217, 55
STYLE DS_MODALFRAME | WS_POPUP | WS_CAPTION | WS_SYSMENU
CAPTION "About PTDinp"
FONT 8, "MS Sans Serif"
BEGIN
    ICON            IDR_MAINFRAME,IDC_STATIC,11,17,18,20
    LTEXT           "Pre Term Delivery Application Version 1.0", IDC___STATIC,
                    40,10,139,8
    LTEXT           "Copyright \251 1997 ",IDC_STATIC,40,25,119,8
    DEFPUSHBUTTON   "OK", IDOK,175,32,32,14,WS_GROUP
END
IDD_D_PTD_INP DIALOG DISCARDABLE 0, 0, 399, 447
STYLE DS_MODALFRAME | WS_POPUP | WS_VISIBLE | WS_CAPTION | WS_SYSMENU
CAPTION "Pre-Term Delivery Risk Assessment Software: Data Entry Screen"
FONT 8, "MS Sans Serif"
BEGIN
    EDITTEXT        IDC_LAB_ID,305,8,68,12,ES_AUTOHSCROLL
    EDITTEXT        IDC_NAME_L,46,48,50,13,ES_AUTOHSCROLL
    EDITTEXT        IDC_NAME_F,117,48,40,13,ES_AUTOHSCROLL
    EDITTEXT        IDC_NAME_MI,170,48,12,13,ES_AUTOHSCROLL
    EDITTEXT        IDC_DATE_OF_BIRTH,28,66,59,12,ES_AUTOHSCROLL
    CONTROL         "Caucasian",IDC_EO_WHITE,"Button",BS_AUTOCHECKBOX |
                    WS_TABSTOP,242,48,45,10
    CONTROL         "African American",IDC_EO_BLACK,"Button",BS_AUTOCHECKBOX |
                    WS_TABSTOP,292,48,66,10
    CONTROL         "Asian",IDC_EO_ASIAN,"Button",BS_AUTOCHECKBOX |
                    WS_TABSTOP,362,48,29,10
    CONTROL         "Hispanic",IDC_EO_HISPANIC,"Button",BS_AUTOCHECKBOX |
                    WS_TABSTOP,242,59,40,10
    CONTROL         "Native American",IDC_EO_NATIVE_AMERICAN,"Button",
                    BS_AUTOCHECKBOX | WS_TABSTOP,292,59,65,10
    CONTROL         "Other",IDC_EO_OTHER,"Button",BS_AUTOCHECKBOX |
                    WS_TABSTOP,362,59,29,10
    CONTROL         "Married",IDC_MS_MARRIED,"Button",BS_AUTOCHECKBOX |
                    WS_TABSTOP,242,72,36,10
    CONTROL         "Single",IDC_MS_SINGLE,"Button",BS_AUTOCHECKBOX |
                    WS_TABSTOP,282,72,34,10
    CONTROL         "Divorced/Separated", IDC_MS_DIVORCED, "Button",
                    BS_AUTOCHECKBOX | WS_TABSTOP,316,72,77,10
    CONTROL         "Widowed",IDC_MS_WIDOWED,"Button",BS_AUTOCHECKBOX |
                    WS_TABSTOP,242,83,41,10
    CONTROL         "Living with partner",IDC_MS_LWP,"Button",
                    BS_AUTOCHECKBOX | WS_TABSTOP,287,83,73,10
    CONTROL         "Other",IDC_MS_OTHER,"Button",BS_AUTOCHECKBOX |
                    WS_TABSTOP,362,83,29,10
    CONTROL         "Yes",IDC_ACOG_Y,"Button",BS_AUTOCHECKBOX | WS_TABSTOP,
                    333,119,24,10
    CONTROL         "No",IDC_ACOG_N,"Button",BS_AUTOCHECKBOX | WS_TABSTOP,
                    364,119,21,10
    CONTROL         "Uterine contractions with or without pain",
                    IDC_PATIENT_COMP_1,"Button",BS_AUTOCHECKBOX | WS_TABSTOP,
                    13,145,143,10
    CONTROL         "<1",IDC_PC1_LT1,"Button",BS_AUTOCHECKBOX | WS_TABSTOP,
                    67,158,20,10
```

-continued

| | |
|---|---|
| CONTROL | "1–3",IDC_PC1_1_3,"Button",BS_AUTOCHECKBOX \| WS_TABSTOP, 99,158,22,10 |
| CONTROL | "4–6",IDC_PC1_4_6,"Button",BS_AUTOCHECKBOX \| WS_TABSTOP, 131,158,22,10 |
| CONTROL | "7–9",IDC_PC1_7_9,"Button",BS_AUTOCHECKBOX \| WS_TABSTOP, 67,170,22,10 |
| CONTROL | "10–12",IDC_PC1_10_12, "Button",BS_AUTOCHECKBOX \| WS_TABSTOP,99,170,30,10 |
| CONTROL | ">12", IDC_PC1_GT12, "Button", BS_AUTOCHECKBOX \| WS_TABSTOP, 131,170,24,10 |
| CONTROL | "Vaginal bleeding",IDC_VAGINAL_BLEEDING,"Button", BS_AUTOCHECKBOX \| WS_TABSTOP,13,181,65,10 |
| CONTROL | "Trace", IDC_VB_TRACE, "Button", BS_AUTOCHECKBOX \| WS_TABSTOP,23,194,30,10 |
| CONTROL | "Med", IDC_VB_MED, "Button", BS_AUTOCHECKBOX \| WS_TABSTOP, 58,194,25,10 |
| CONTROL | "Gross",IDC_VB_GROSS,"Button",BS_AUTOCHECKBOX \| WS_TABSTOP,88,194,30,10 |
| CONTROL | "Patient is not ""feeling right""",IDC_PATIENT_COMP_6, "Button",BS_AUTOCHECKBOX \| WS_TABSTOP,13,205,102,10 |
| CONTROL | "Bleeding during the second or third trimester", IDC_PATIENT_COMP_3,"Button",BS_AUTOCHECKBOX \| WS_TABSTOP, 161,145,155,10 |
| CONTROL ure", | "Intermittent lower abdominal pain, dull, low backpain, pelvic press |
| | IDC_PATIENT_COMP_2,"Button",BS_AUTOCHECKBOX \| WS_TABSTOP, 161,157,233,10 |
| CONTROL | "Change in vaginal discharge -- amount, color, or consistency", IDC_PATIENT_COMP_5,"Button",BS_AUTOCHECKBOX \| WS_TABSTOP, 161,181,208,10 |
| CONTROL | "Menstrual-like cramping (with or without diarrhea)", IDC_PATIENT_COMP_4,"Button",BS_AUTOCHECKBOX \| WS_TABSTOP, 161,193,171,10 |
| EDITTEXT | IDC_EGA_BY_SONO,155,224,37,12,BS_AUTOHSCROLL |
| EDITTEXT | IDC_EGA_BY_LMP,245,224,37,12,BS_AUTOHSCROLL |
| EDITTEXT | IDC_EGA_AT_SAMP,350,224,37,12,BS_AUTOHSCROLL |
| CONTROL | "Previous pregnancy, no complications",IDC_1_COMP, "Button",BS_AUTOCHECKBOX \| WS_TABSTOP,13,260,134,10 |
| CONTROL | "History of Preterm delivery",IDC_2_COMP,"Button", BS_AUTOCHECKBOX \| WS_TABSTOP,13,272,134, 10 |
| CONTROL | "1",IDC_2_COMP_1,"Button",BS_AUTOCHECKBOX \| WS TABSTOP, 91,284,19,10 |
| CONTROL | "2",IDC_2_COMP_2,"Button",BS_AUTOCHECKBOX \| WS_TABSTOP, 116,284,19,10 |
| CONTROL | ">2",IDC_2_COMP_3,"Button",BS_AUTOCHECKBOX \| WS_TABSTOP, 141,284,21,10 |
| CONTROL | "History of Preterm PROM",IDC_3_COMP,"Button", BS_AUTOCHECKBOX \| WS_TABSTOP,13,296,92,10 |
| CONTROL | "History of incompetent cervix",IDC_4_COMP,"Button", BS_AUTOCHECKBOX \| WS_TABSTOP,13,308,106,10 |
| CONTROL | "History of PIH/preeclampsia",IDC_5_COMP,"Button", BS_AUTOCHECKBOX \| WS_TABSTOP,13,320,102,10 |
| CONTROL | "History of SAB prior to 20 wks",IDC_6_COMP,"Button", BS_AUTOCHECKBOX \| WS_TABSTOP,13,332,109,10 |
| EDITTEXT | IDC_GRAVIDITY,277,246,20,12,ES_AUTOHSCROLL |
| EDITTEXT | IDC_PARITY,317,246,20,12,ES_AUTOHSCROLL |
| EDITTEXT | IDC_ABORTIONS,357,246,20,12,ES_AUTOHSCROLL |
| CONTROL | "Multiple Gestation:", IDC_MULT_GEST, "Button", BS_AUTOCHECKBOX \| WS_TABSTOP,203,272,72,10 |
| CONTROL | "Twins",IDC_MG_TWINS,"Button",BS_AUTOCHECKBOX \| WS_TABSTOP,278,272,30,10 |
| CONTROL | "Triplets", IDC_MG_TRIPLETS,"Button",BS_AUTOCHECKBOX \| WS_TABSTOP,311,272,36,10 |
| CONTROL | "Quads", IDC_MG_QUADS, "Button", BS_AUTOCHECKBOX \| WS_TABSTOP,350,272,32,10 |
| CONTROL | "Uterine or cervical abnormality",IDC_UT_CERV_ABNORM, "Button",BS_AUTOCHECKBOX \| WS_TABSTOP,203,284,110,10 |
| CONTROL | "Cerclage",IDC_CERV_CERCLAGE,"Button",BS_AUTOCHECKBOX \| WS_TABSTOP,203,296,40,10 |
| CONTROL | "Gestational Diabetes",IDC_GEST_DIABETES,"Button", BS_AUTOCHECKBOX \| WS_TABSTOP,203,308,79,10 |
| CONTROL | "Hypertensive Disorders", IDC_HYPERTEN_DISORDERS, "Button", BS_AUTOCHECKBOX \| WS_TABSTOP,203,320,86,10 |
| CONTROL | "<1 ",IDC_DILITATION_LT1,"Button",BS_AUTOCHECKBOX \| WS_TABSTOP,58,364,22,10 |
| CONTROL | "1 ",IDC_DILITATION_1,"Button",BS_AUTOCHECKBOX WS_TABSTOP,81,364,18,10 |
| CONTROL | "1–2 ",IDC_DILITATION_1_2,"Button",BS_AUTOCHECKBOX \| WS_TABSTOP,101,364,24,10 |

-continued

| | |
|---|---|
| CONTROL | "2 ",IDC_DILITATION_2,"Button",BS_AUTOCHECKBOX \| WS_TABSTOP,127,364,18,10 |
| CONTROL | "2–3 ",IDC_DILITATION_2_3,"Button",BS_AUTOCHECKBOX \| WS_TABSTOP,147,364,24,10 |
| CONTROL | "3 ",IDC_DILITATION_3,"Button",BS_AUTOCHECKBOX \| WS_TABSTOP,173,364,18,10 |
| CONTROL | ">3 ",IDC_DILITATION_GT3,"Button",BS_AUTOCHECKBOX \| WS_TABSTOP,193,364,22,10 |
| CONTROL | "Unk. ",IDC_DILITATION_UKN,"Button",BS_AUTOCHECKBOX \| WS_TABSTOP,217,364,29,10 |
| CONTROL | "Firm",IDC_CERV_FIRM,"Button",BS_AUTOCHECKBOX \| WS_TABSTOP,318,364,25,10 |
| CONTROL | "Mod",IDC_CERV_MOD,"Button",BS_AUTOCHECKBOX \| WS_TABSTOP, 344,364,25,10 |
| CONTROL | "Soft",IDC_CERV_SOFT,"Button",BS_AUTOCHECKBOX \| WS_TABSTOP,370,364,25,10 |
| CONTROL | "Antibiotics",IDC_ANTIBIOTICS,"Button",BS_AUTOCHECKBOX \| WS_TABSTOP,17,392,45,10 |
| CONTROL | "Corticosteroids",IDC_CORTICOSTEROIDS, "Button", BS_AUTOCHECKBOX \| WS_TABSTOP,70,392,60,10 |
| CONTROL | "Tocolytis", IDC_TOCOLYTICS, "Button", BS_AUTOCHECKBOX \| WS_TABSTOP,138,392,41,10 |
| CONTROL | "Insulin",IDC_INSULIN,"Button",BS_AUTOCHECKBOX \| WS_TABSTOP,187,392,33,10 |
| CONTROL | "Antihypertensives", IDC_ANTIHYPER, "Button", BS_AUTOCHECKBOX \| WS_TABSTOP,228,392,69,10 |
| CONTROL | "None", IDC_MED_NONE, "Button", ES_AUTOCHECKBOX \| WS_TABSTOP,305,392,29,10 |
| CONTROL | "Unknown", IDC_MED_UKN, BS_AUTOCHECKBOX \| WS_TABSTOP,342,392,42,10 |
| CONTROL | "Positive",IDC_FFN_POS,"Button",BS_AUTOCHECKBOX \| 115_TABSTOP,138,411,37,10 |
| CONTROL | "Negative",IDC_FFN_NEG,"Button",BS_AUTOCHECKBOX \| 115_TABSTOP,228,411,41,10 |
| DEFPUSHBUTTON | "Calculate Risk", IDOK, 270,429,62,14 |
| PUSHBUTTON | "Cancel",IDCANCEL,340,429,53,14 |
| LTEXT | "Cervical consistancy",IDC_STATIC,249,365,68,8 |
| LTEXT | "M",IDC_STATIC,160,51,7,8 |
| LTEXT | "Lab ID #:",IDC_STATIC,267,10,34,8 |
| LTEXT | "PATIENT INFORMATION", IDC_STATIC, 159,29,83,8 |
| LTEXT | "Name(last)",IDC_STATIC,7,51,36,8 |
| LTEXT | "First", IDC_STATIC, 99,51,15,8 |
| GROUPBOX | "",IDC_STATIC,1,40,187,56 |
| GROUPBOX | "",IDC_STATIC,187,40,210,56 |
| LTEXT | "Ethnic origin:",IDC_STATIC, 192,48,44,8 |
| LTEXT | "Marital status:", IDC_STATIC, 192,72,47,8 |
| LTEXT | "DOB", IDC_STATIC,7,69,16,8 |
| LTEXT | "PATIENT HISTORY AND CLINICAL INFORMATION",IDC_STATIC, 117,102,168,8 |
| GROUPBOX | "", IDC_STATIC, 1,112,396,107 |
| LTEXT | "At the time of sampling was the patient experiencing signs and sysptoms of possible preterm_labor?", IDC_STATIC,7,119,321,8 |
| LTEXT | "If yes, please mark all that apply.",IDC_STATIC,7,134, 109,8 |
| GROUPBOX | "", IDC_STATIC, 1,373,396,32 |
| LTEXT | "Qualitative fFN Elisa Test Results:",IDC_STATIC, 7,411, 118.8 |
| GROUPBOX | "",IDC_STATIC,1,402,396,24 |
| LTEXT | "Medications at Time of Test (check all that apply)", IDC_STATIC,7,380,163,8 |
| LTEXT | "Number/hr", IDC_STATIC,22,158,36,8 |
| GROUPBOX | "", IDC_STATIC, 1,216,396,25 |
| LTEXT | "Gestational Age: EGA by first trimester sono", IDC_STATIC,7,225,143,8 |
| LTEXT | "EGA by LMP",IDC_STATIC,197,225,42,8 |
| LTEXT | "EGA at sampling",IDC_STATIC, 287,225,55,8 |
| GROUPBOX | "", IDC_STATIC, 1,346,396,30 |
| LTEXT | "Cervical Status immediately following sample collection:", IDC_STATIC,7,352,182,8 |
| LTEXT | "Dilatation (cm) ", IDC_STATIC,9,364,48,8 |
| GROUPBOX | "",IDC_STATIC,1,238,187,111 |
| GROUPBOX | "",IDC_STATIC,187,238,210,111 |
| CONTROL | "Previous Pregnancy: Please mark all that apply.", IDC_STATIC, "Static",SS_LEFTNOWORDWRAP \| WS_GROUP,7,249, 159,8 |
| LTEXT | "Current Pregnancy: G:",IDC_STATIC,195,249,76,8 |
| GROUPBOX | "",IDC_STATIC,1,93,396,22 |
| GROUPBOX | "",IDC_STATIC,1,1,396,22 |

-continued

```
GROUPBOX                "",IDC_STATIC,1,20,396,23
LTEXT                   "P:",IDC_STATIC,303,249,8,8
LTEXT                   "A:",IDC_STATIC,343,249,8,8
LTEXT                   "If Yes, how many?",IDC_STATIC,22,284,61,8
END
IDD_D_GOTO DIALOG DISCARDABLE 0, 0, 163, 95
STYLE DS_MODALFRAME | WS_POPUP | WS_VISIBLE | WS_CAPTION | WS_SYSMENU
CAPTION "Go To Record..."
FONT 8, "MS Sans Serif"
BEGIN
    CONTROL             "Record Number",IDC_R_GOTO_SEL1,"Button",
                        BS_AUTORADIOBUTTON | WS_GROUP, 10, 16, 62,10
    CONTROL             "ID Number",IDC_R_GOTO_SEL2,"Button",BS_AUTORADIOBUTTON,
                        10, 40, 46, 10
    EDITTEXT            IDC_E_GOTO_REC_NUM,90,12,60,12,ES_AUTOHSCROLL
    EDITTEXT            IDC_E_GOTO_ID_NUM,90,36,60,12,ES_AUTOHSCROLL
    DEFPUSHBUTTON       "OK", IDOK, 40,76,50,14
    PUSHBUTTON          "Cancel", IDCANCEL,100,76,50,14
END
/////////////////////////////////////////////////////////////////////////////
//
// String Table
//
STRINGTABLE PRELOAD DISCARDABLE
BEGIN
    IDR_MAINFRAME              "PTDinp Windows Application\nPTDin\nPTDin Document\n\n\nPTDi
n.Document\nPTDinDocument"
END
STRINGTABLE PRELOAD DISCARDABLE
BEGIN
    AFX_IDS_APP_TITLE          "PTDinp Windows Application"
    AFX_IDS_IDLE_MESSAGE       "Ready"
END
STRINGTABLE DISCARDABLE
BEGIN
    ID_INDICATOR_EXT           "EXT"
    ID_INDICATOR_CAPS          "CAP"
    ID_INDICATOR_NUN           "NUN"
    ID_INDICATOR_SCRL          "SCRL"
    ID_INDICATOR_OVR           "OVR"
    ID_INDICATOR_REC           "REC"
END
STRINGTABLE DISCARDABLE
BEGIN
    ID_FILE_NEW                "Create a new document"
    ID_FILE_OPEN               "Open an existing document"
    ID_FILE_CLOSE              "Close the active document"
    ID_FILE_SAVE               "Save the active document"
    ID_FILE_SAVE_AS            "Save the active document with a new name"
    ID_FILE_PAGE_SETUP         "Change the printing options"
    ID_FILE_PRINT_SETUP        "Change the printer and printing options"
    ID_FILE_PRINT              "Print the active document"
    ID_FILE_PRINT_PREVIEW      "Display full pages"
END
STRINGTABLE DISCARDABLE
BEGIN
    ID_APP_ABOUT "Display program information, version number and copyright"
    ID_APP_EXIT "Quit the application; prompts to save documents"
END
STRINGTABLE DISCARDABLE
BEGIN
    ID_FILE_MRU_FILE1          "Open this document"
    ID_FILE_MRU_FILE2          "Open this document"
    ID_FILE_MRU_FILE3          "Open this document"
    ID_FILE_MRU_FILE4          "Open this document"
END
STRINGTABLE DISCARDABLE
BEGIN
    ID_NEXT_PANE               "Switch to the next window pane"
    ID_PREV_PANE               "Switch back to the previous window pane"
END
STRINGTABLE DISCARDABLE
BEGIN
    ID_EDIT_CLEAR              "Erase the selection"
    ID_EDIT_CLEAR_ALL          "Erase everything"
    ID_EDIT_COPY               "Copy the selection and put it on the Clipboard"
    ID_EDIT_CUT                "Cut the selection and put it on the Clipboard"
    ID_EDIT_FIND               "Find the specified text"
    ID_EDIT_PASTE              "Insert clipboard contents"
```

-continued

```
    ID_EDIT_REPEAT              "Repeat the last action"
    ID_EDIT_REPLACE             "Replace specific text with different text"
    ID_EDIT_SELECT_ALL          "Select the entire document"
    ID_EDIT_UNDO                "Undo the last action"
    ID_EDIT_REDO                "Redo the previously undone action"
END
STRINGTABLE DISCARDABLE
BEGIN
    ID_VIEW_TOOLBAR             "Show or hide the toolbar"
    ID_VIEW_STATUS_BAR          "Show or hide the status bar"
END
STRINGTABLE DISCARDABLE
BEGIN
    AFX_IDS_SCSIZE              "Change the window size"
    AFX_IDS_SCMOVE              "Change the window position"
    AFX_IDS_SCMINIMIZE          "Reduce the window to an icon"
    AFX_IDS_SCMAXIMIZE          "Enlarge the window to full size"
    AFX_IDS_SCNEXTWINDOW        "Switch to the next document window"
    AFX_IDS_SCPREVWINDOW        "Switch to the previous document window"
    AFX_IDS_SCCLOSE             "Close the active window and prompts to save the documents"
END
STRINGTABLE DISCARDABLE
BEGIN
    AFX_IDS_SCRESTORE           "Restore the window to normal size"
    AFX_IDS_SCTASKLIST          "Activate Task List"
END
STRINGTABLE DISCARDABLE
BEGIN
    IDD_DATA_NEW                "Starts data entry process for new record"
    ID_DATA_NEW                 "Create new record at end of file and edit."
    ID_DATA_EDIT                "Edit the currently selected record."
    ID_REC_FIRST                "Go to the first record in the file."
    ID_REC_NEXT                 "Go to the next record in the file."
    ID_REC_PREV                 "Go to the previous record in the file."
    ID_REC_LAST                 "Go to the last record inthe file."
    ID_BLD_NET_FILE             "Build file of neural data from currently opened database."
    ID_EDIT_MODE                "Print the full data form when checked or results only when
unchecked."
    ID_CLR_SUBFIELDS            "Clear subfields when item cleared."
    ID_REC_GOTO                 "Go to a specific record number or specific ID."
END
#ifndef APSTUDIO_INVOKED
/////////////////////////////////////////////////////////////////////////
//
// Generated from the TEXTINCLUDE 3 resource.
//
#include "res\PTDinp.rc2"    // non-App Studio edited resources
#include "afxres.rc"         // Standard components
#include "afxprint.rc"       // printing/print preview resources
#include "afxdb.rc"          // Database resources
/////////////////////////////////////////////////////////////////////////
#endif // not APSTUDIO_
INVOKED
#Microsoft Visual C++ generated
build script - Do not modify
PROJ = PTDINP
DEBUG = 0
PROGTYPE = 0
CALLER =
ARGS =
DLLS =
D_RCDEFINES = /d_DEBUG
R_RCDEFINES = /dNDEBUG
ORIGIN = MSVC
ORIGIN_VER = 1.00
PROJPATH = C:\DDD\AD97-
1\PTDINP\
USEMFC = 0
CC = cl
CPP = cl
CXX = cl
CCREATEPCHFLAG =
CPPCREATEPCHFLAG =
/YcSTDAFX.H
CUSEPCHFLAG =
CPPUSEPCHFLAG =
/YuSTDAFX.H
FIRSTC =
FIRSTCPP = STDAFX.CPP
```

-continued

```
RC = rc
CFLAGS_D_WEXE = /nologo
/G2 /W3 /Z7 /AL /0d /D
"_AFXDLL" /D "_DEBUG"
/FR /GA /GEf
CFLAGS_R_WEXE = /nologo
/Gs /G3 /W3 /AL /01 /D "NDE-
BUG" /D "_AFXDLL" /FR /GA
/GEf
LFLAGS_D_WEXE =
/NOLOGO /NOD /PACKC:61440
/STACK:10240 /ALIGN:16
/ONERROR:NOEXE /CO
LFLAGS_R_WEXE =
/NOLOGO INOD /PACKC:61440
/STACK:10240 /ALIGN:16
/ONERROR:NOEXE
LIBS_D_WEXE = mfc250d
oldnames libw llibcew mfcd250d
commdlg.lib shell.lib
LIBS_R_WEXE = mfc250 old-
names libw llibcew mfcd250
odbc commdlg.lib shell.lib
RCFLAGS = /nologo /z
RESFLAGS = /nologo /t /k
RUNFLAGS =
DEFFILE = PTDINP.DEF
OBJS_EXT =
LIBS_EXT = EVALNET.LIB
TKSDLL.LIB
!if "$(DEBUG)" == "1"
CFLAGS = $(CFLAGS_D_
WEXE)
LFLAGS = $(LFLAGS_D_
WEXE)
LIBS = $(LIBS_D_WEXE)
MAPFILE = nul
RCDEFINES = $(D_
RCDEFINES)
!else
CFLAGS = $(CFLAGS_R_
WEXE)
LFLAGS = $(LFLAGS_R_
WEXE)
LIBS = $(LIBS_R_WEXE)
MAPFILE = nul
RCDEFINES = $(R_
RCDEFINES)
!endif
!if [if exist MSVC.BND del
MSVC.BND]
!endif
SBRS =   STDAFX.SBR \
         PTDINP.SBR \
         MAINFRM.SBR \
         PTDIDOC.SBR \
         PTDIVW.SBR \
         PTDDLG1.SBR \
         PTDGOTO.SBR
EVALNET_DEP =
TKSDLL_DEP =
PTDINP_RCDEP = c:\ddd\ad97-1\ptdinp\res\ptdinp.ico \
    c:\ddd\ad97-1\ptdinp\res\ptdinp.rc2
STDAFX_DEP = c:\ddd\ad97-1\ptdinp\stdafx.h
PTDINP_DEP = c:\ddd\ad97-1\ptdinp\stdafx.h \
    c:\ddd\ad97-1\ptdinp\ptdinp.h \
    c: \ddd\ad97-1\ptdinp\ptdidoc.h \
    c: \ddd\ad97-1\ptdinp\mainfrm.h \
    c: \ddd\ad97-1\ptdinp\ptdivw.h
MAINFRM_DEP = c:\ddd\ad97-1\ptdinp\stdafx.h \
    c: \ddd\ad97-1\ptdinp\ptdinp.h \
    c: \ddd\ad97-1\ptdinp\ptdidoc.h \
    c: \ddd\ad97-1\ptdinp\mainfrm.h
PTDIDOC_DEP = c:\ddd\ad97-1\ptdinp\stdafx.h \
    c: \ddd\ad97-1\ptdinp\ptdinp.h \
    c: \ddd\ad97-1\ptdinp\ptdidoc.h \
    c: \ddd\ad97-1\ptdinp\aa_nets.h
PTDIVW_DEP = c:\ddd\ad97-1\ptdinp\stdafx.h \
    c: \ddd\ad97-1\ptdinp\ptdinp.h \
    c: \ddd\ad97-1\ptdinp\ptdidoc.h \
    c: \ddd\ad97-1\ptdinp\ptdivw.h \
```

```
    c: \ddd\ad97-1\ptdinp\ptddlgl.h
PTDDLG1_DEP = c:\ddd\ad97-1\ptdinp\stdafx.h \
    c: \ddd\ad97-1\ptdinp\ptdinp.h \
    c: \ddd\ad97-1\ptdinp\ptdidoc.h \
    c: \ddd\ad97-1\ptdinp\ptddlg.h
all: $(PROJ).EXE $(PROJ).BSC
PTDINP.RES: PTDINP.RC $(PTDINP_RCDEP)
    $(RC) $(RCFLAGS) $(RCDEFINES) -r PTDINP.RC
STDAFX.OBJ: STDAFX.CPP $(STDAFX DEP)
    $(CPP) $(CFLAGs) $(CPPCREATEPCHFLAG) /c STDAFX.CPP
PTDINP.OBJ: PTDINP.CPP $(PTDINP DEP)
    $(CPP) $(CFLAGS) $(CPPUSEPCHFLAG) /c PTDINP.CPP
MAINFRM.OBJ: MAINFRM.CPP $ (MAINFRM DEP)
    $(CPP) $(CFLAGS) $(CPPUSEPCHFLAG) /c MAINFRN.CPP
PTDIDOC.OBJ: PTDIDOC.CPP $(PTDIDOC_DEP)
    $(CPP) $(CFLAGS) $(CPPUSEPCHFLAG) /c PTDIDOC.CPP
PTDIVW.OBJ: PTDIVW.CPP $(PTDIVW DEP)
$(CPP) $(CFLAGS) $(CPPUSEPCHFLAG) /c PTDIVW.CPP
PTDDLG1.OBJ: PTDDLG1.CPP $ (PTDDLG1_DEP)
    $(CPP) $(CFLAGS) $ (CPPUSEPCHFLAG) /c PTDDLG1.CPP
PTDGOTO.OBJ: PTDGOTO.CPP $(PTDGOTO_DEP)
    $(CPP) $(CFLAGS) $(CPPUSEPCHFLAG) /c PTDGOTOCPP
$ (PROJ).EXE:: PTDINP.RES
$(PROJ).EXE:: STDAFX.OBJ PTDINP.OBJ MAINFRM.OBJ PTDIDOC.OBJ PTDIVW.OBJ PTDDLG1.OBJ \
    PTDGOTO.OBJ $(OBJS_EXT) $(DEFFILE)
    echo >NUL @<<$(PROJ).CRF
STDAFX.OBJ +
PTDINP.OBJ +
MAINFRM.OBJ +
PTDIDOC.OBJ +
PTDIVW.OBJ +
PTDDLG1.OBJ +
PTDGOTO.OBJ +
$(OBJS_EXT)
$(PROJ).EXE
$(MAPFILE)
c:\msvc\lib\+
c:\msvc\mfc\lib\+
EVALNET.LIB+
TKSDLL.LIB+
$ (LIBS)
$ (DEFFILE);
<<
    link $(LFLAGS) @$(PROJ).CRF
    $(RC) $(RESFLAGS) PTDINP.RES $@
    @copy $(PROJ).CRF MSVC.BND
$(PROJ).EXE:: PTDINP.RES
    if not exist MSVC.BND $(RC) $(RESFLAGS) PTDINP.RES $@
run: $(PROJ).EXE
    $(PROJ) $(RUNFLAGS)
$(PROJ).BSC: $(SBRS)
    bscmake @<<
/o$@$(SBRS)
<<
// PTDidoc.h : interface of the CPTDinpDoc class
//
/////////////////////////////////////////////////////////////////
#ifndef _PTDINPDOC_H
#define _PTDINPDOCH_
#define REC_LENGTH 330L
class CPTDinpDoc : public CDocument
{
protected: // create from serialization only
    CPTDinpDoc ();
    DECLARE_DYNCREATE(CPTDinpDoc)
// Attributes
public:
    CString m_LAB_ID;
    CString m_NAME_L;
    CString m_NAME_F;
    CString m_NAME_MI;
    CString m_DATE_OF_DATA_ENTRY;       //time
    double m_PATIENT_AGE;
    CString m_DATE_OF_BIRTH;
    CString m_ETHNIC_ORIGIN_WHITE;
    CString m_ETHNIC_ORIGIN_BLACK;
    CString m_ETHNIC_ORIGIN_ASIAN;
    CString m_ETHNIC_ORIGIN_HISPANIC;
    CString m_ETHNIC_ORIGIN_NATIVE_AMERICAN;
```

-continued

```
CString m_ETHNIC_ORIGIN_OTHER;
CString m_MARITAL_STATUS_SINGLE;
CString m_MARITAL_STATUS_MARRIED;
CString m_MARITAL_STATUS_DIVORCED;
CString m_MARITAL_STATUS_WIDOWED;
CString m_MARITAL_STATUS_LWP;
CString m_MARITAL_STATUS_OTHER;
CString m_ACOG_SYMPTOMS;
CString m_PATIENT_COMPLAINT_1;
CString m_PATIENT_COMPLAINT_1_1_3;
CString m_PATIENT_COMPLAINT_1_10_12;
CString m_PATIENT_COMPLAINT_1_4_6;
CString m_PATIENT_COMPLAINT_1_7_9;
CString m_PATIENT_COMPLAINT_1_GT12;
CString m_PATIENT_COMPLAINT_1_LT1;
CString m_VAGINAL_BLEEDING;
CString m_VAGINAL_BLEEDING_TRACE;
CString m_VAGINAL_BLEEDING_MEDIUM;
Cstring m_VAGINAL_BLEEDING_GROSS;
CString m_PATIENT_COMPLAINT_6;
CString m_PATIENT_COMPLAINT_3;
CString m_PATIENT_COMPLAINT_2;
CString m_PATIENT_COMPLAINT_5;
CString m_PATIENT_COMPLAINT_4;
CString m_EGA_BY_SONO;
CString m_EGA_BY_LMP;
CString m_EGA_AT_SAMPLING;
CString m_0_COMP;
CString m_1_COMP;
CString m_2_COMP;
CString m_3_COMP;
CString m_4_COMP;
CString m_5_COMP;
CString m_6_COMP;
CString m_2_COMP_1;
CString m_2_COMP_2;
CString m_2_COMP_3;
CString m_GRAVITY;
CString m_PARITY;
CString m_ABORTIONS;
CString m_MULTIPLE_GESTATION;
CString m_MULTIPLE_GESTATION_TWINS;
CString m_MULTIPLE_GESTATION_TRIPLETS;
CString m_MULTIPLE_GESTATION_QUADS;
CString m_UTCERV_ABNORMALITY;
CString m_CERVICAL_CERCLAGE;
CString m_GESTATIONAL_DIABETES;
CString m_HYPERTENSIVE_DISORDERS;
CString m_DILITATION_LT1;
CString m_DILITATION_1;
CString m_DILITATION_1_2;
CString m_DILITATION_2;
CString m_DILITATION_2_3;
CString m_DILITATION_3;
CString m_DILITATION_GT3;
CString m_DILITATION_UNKNOWN;
CString m_CERVICAL_CONSISTANCY_FIRM;
CString m_CERVICAL_CONSISTANCY_MOD;
CString m_CERVICAL_CONSISTANCY_SOFT;
CString m_ANTIBIOTICS;
CString m_CORTICOSTEROIDS;
CString m_TOYOLYTICS;
CString m_INSULIN;
Cstring m_ANTIHYPERTENSIVES;
CString m_MEDICATIONS_NONE;
Cstring m_MEDICATIONS_UNKNOWN;
CString m_FFN_RESULT;
char Rec[REC_LENGTH + 16];
char fld[256];
char PathName[128];
long CurRecord;
long NumRecords;
int GotoMode;
CString IDStr;
char tstr[256];
CTime tim;
char NetName[128];
char NetRec[1024];
double m_NetPos1;
```

```
        double m__NetNeg1;
        double m__NetVal1;
        double m__NetPos2;
        double m__NetNeg2;
        double m__NetVal2;
        double m__NetPos3;
        double m__NetNeg3;
        double m__NetVal3;
// Operations
public:
void get__rec( char* pRec );
char* get__fld(char* pRec, int ofs, int len);
CTime& get__time__fld(char* pRec, int ofs, int len);
void put__rec(char* pRec);
void put__fld(char* pRec, CString& dat, int ofs, int len);
void put__dbl__fld(char* pRec, double dat, int ofs, int len);
void put__net__fld(char* pRec, double dat, int ofs, int len);
void put__time__fld(char* pRec, CTime& dat, int ofs, int len);
void InitializeRec (void);
void LoadNets (void);
void FreeNets(void);
void RunNets(long n);
char* time2str( const CTimes& tm );
CTimes& str2time( CString& str );
void get__file( void );
// Implementation
public:
        virtual ~CPTDinpDoc();
        virtual void Serialize(CArchive& ar); // overridden for document i/o
#ifdef _DEBUG
        virtual void AssertValid() const;
        virtual void Dump(CDumpContext& dc) const;
#endif
protected:
        virtual BOOL OnNewDocument();
// Generated message map functions
protected:
        //{{AFX_MSG(CPTinpDoc)
        afx__msg void OnRecFirst();
        afx__msg void OnRecLast();
        afx__msg void OnRecNext();
        afx__msg void OnRecPrev();
        afx__msg void OnFileOpen();
        afx__msg void OnBldNetFile();
        afx__msg void OnRecGoto();
        afx__msg void OnFileMruFile1();
        afx__msg void OnFileMruFile2();
        afx__msg void OnFileMruFile3();
        afx__msg void OnFileMruFile4();
        //}}AFX_MSG
        DECLARE_MESSAGE_MAP()
};
#endif // _PTDINPDOC_H_
////////////////////////////////////////////////////////////
```

What is claimed:

1. A computer-based method for selecting variables for use in a computer-based system for prognosis, diagnosis and for predicting outcomes based upon a plurality of variables, comprising:

(a) obtaining a set of candidate variables based upon data obtained by observing or detecting an event or making physical or chemical observations or measurements or obtaining data resulting from tests, designating the candidate variables as a first set of candidate variables and entering them into a computer memory or computer-readable storage medium;

(b) providing a set of selected important variables and designating it the current set of selected important variables, wherein the set of selected important variables is initially empty;

(c) taking candidate variables from the set of candidate variables one at a time and evaluating each by training a computer-based decision-support system on that variable combined with the current set of selected important variables;

(d) selecting the best of the candidate variables, wherein the best variable is any one that gives the highest performance of the decision-support system, and if the best candidate variable improves performance compared to the performance of the selected important variables, adding it to the selected important variable set, removing it from the candidate set and continuing evaluating at step (c), wherein, when the best candidate variable does not improve performance, the process is completed;

(e) producing an output that comprises the resulting set of selected variables.

2. The method of claim 1, wherein in step (a) the candidate variables are obtained from patients and include historical data and/or biochemical data.

3. A method of diagnosis, comprising:

selecting a set of important selected variables according to the method of claim 1; and training a computer-based decision-support system using the selected final set of important selected variables to produce a test for diagnosis;

examining or querying a patient; and entering the resulting patient data into the trained decision-support system; and producing an output comprising a diagnostic indicator.

4. The method of claim 3, wherein the method of diagnosis assesses the likelihood that a medical condition or disorder is present, assesses the likelihood that a particular condition will develop or occur in the future, selects a course of treatment or determines the effectiveness of a treatment.

5. The method of claim 4, wherein the condition is a pregnancy-related condition or endometriosis.

6. The method of claim 5, wherein the pregnancy-related condition is preterm delivery or risk of delivery within a selected time period.

7. The method of claim 3, wherein the method of diagnosis assesses the presence, absence or severity of a medical condition or determines the likely outcome resulting of a course of treatment.

8. The method of claim 3, further comprising training a final decision-support system based on the completed set of selected important variables to produce a decision-support system based test for the condition.

9. The method of claim 3, wherein the condition is a gynecological condition.

10. The method of claim 9, wherein the condition is selected from among infertility, a pregnancy related event, and pre-eclampsia.

11. The method of claim 3, wherein the candidate variables include biochemical test data.

12. The method of claim 3, wherein the trained computer-based decision-support system includes a system selected from the group consisting of expert system, fuzzy logic systems, non-linear regression analysis system, multivariate analysis system, decision tree classifiers, Bayesian belief networks and neural networks.

13. The method of claim 3, wherein the trained computer-based decision-support system comprises a neural network or plurality of neural networks.

14. The method of claim 3, further comprising obtaining patient-data and entering such data into the trained decision-support system; and providing a diagnosis to the patient.

15. A computer-based diagnostic test produced by the method of claim 3.

16. A method of improving the effectiveness of a disnostic biochemical test, comprising:

selecting a set of important selected variable according to the method of claim 1 to identify a set of selected variable by collecting candidate variables from test subjects;

performing the biochemical test on test subjects to obtain test data, wherein the biochemical test is performed before, after or during the selecting step; and training a decision-support system using the selected final set of important selected varibales and the biochemical test data; and producing an output that is a test, wherein the output test is more effective than the biochemical test alone.

17. The method of claim 16, wherein the candidate variables are selected from the group consisting of:

Age;

Ethnic origin Caucasian;

Ethnic origin Black;

ethnic origin Asian;

ethnic origin Hispanic;

ethnic origin Native American;

ethnic origin other than the Native American, Hispanic, Asian, Black, or Caucasian;

martial status single;

martial status married;

martial status divorced or separated;

martial status widowed;

martial status living with partner;

martial status other than married, divorced/separated, widowed, or living with partner;

education unknown;

education less than high school;

education high school graduate;

education college or trade school;

patient has Uterine Contraction with or without pain;

patient has intermittent lower abdominal pain, dull, low backache pelvic pressure;

patient has bleeding during the second or third trimester;

patient has menstrual-like or intestinal cramping;

patient has change in vaginal discharge or amount, color, or consistency;

patient is not "feeling right";

pooling;

ferning;

nitrazine;

estimated gestational age (EGA) based on last menstrual period (LMP);

EGA by sonogram (SONO);

EGA by best, wherein EGA by best refers to the best of EGA by SONO and EGA by LMP determined as follows:

if EGA by SONO is <13 weeks, then EGA best is EGA SONO;

if the difference by EGA by LMP and EGA by SONO is >2 weeks, then EGA best is EGA by SONO; otherwise EGA best is EGA by LMP;

EGA at sampling;

cervical dilatation (CD);

gravity;

parity-term;

parity-preterm;

parity-abortions, wherein the number of abortions include spontaneous and elective abortions;

parity-living;

sex within 24 prior to sampling for fFN;

vaginal bleeding at time of sampling;

cervical consistency at time of sampling;

uterine contractions per hour as interpreted by the physician;

no previous pregnancies;

at least one previous pregnancy without complications;

at least one preterm delivery;

at least one previous pregnancy with a premature rupture of membrane (PROM);

at least one previous delivery with incompetent cervix;

at least on previous pregnancy with pregnancy induced hypertension (PIH)/preeclampsia;

at least one previous pregnancy with spontaneous abortion prior to 20 weeks; and at least one previous pregnancy with a complication not listed above.

18. The method of claim 17, wherein the biochemical test is a test that detects fetal fibronectin in cervico/vaginal samples.

19. A method of identifying a biochemical test that aids in diagnosis of a disorder or condition, comprising:
   (a) selecting a set of important selected variables according to the method of claim 1 by collecting candidate variables from test subjects by performing one or a plurality of biochemical tests to obtain biochemical test data from test subjects, wherein the biochemical test(s) is performed before, after or during the selecting step;
   (b) identifying a set of biochemical test data, and training a computer-based decision-support system using the selected final set of important selected variables combined with each member of the set of biochemical test data, and assessing the performance of the resulting system;
   (c) repeating the training and assessing with each member of the set of biochemical test data until all have been used in a training;
   (d) selecting the members of the set of biochemical data that results in a decision-support system that performs the best; and
   (e) producing a biochemical test that measures the selected biochemical data.

20. The method of claim 1 that is a computer-assisted method, wherein the set of n candidate variables and set of selected important variables are each stored in a computer.

21. The method of claim 1, wherein the computer-based decision-support system includes a system selected from the group consisting of expert systems, fuzzy logic systems, non-linear regression analysis systems, multivariate analysis systems, decision tree classifiers, Bayesian belief networks and neural networks.

22. The method of claim 1, wherein the computer-based decision-support system comprises a neural network or plurality of neural networks.

23. The method of claim 1 that is for generating variables for use in systems for diagnosing medical conditions or prognosticating medical conditions.

24. A computer system programmed with instructions for performing the method of claim 1.

25. A computer-readable medium, comprising instructions for performing the method of claim 1.

26. A computer-readable medium, comprising the set variables produced as the output of claim 1.

27. A method for variable selection, comprising:
   (a) collecting a first set of n candidate variable that correspond to measurements, the results of tests, queries or observations and a second set of selected important variables, wherein the second set is initially empty;
   (b) ranking all candidate variables, wherein the ranking is either arbitrary or ordered;
   (c) taking the highest m ranked variable one at a time, wherein m is from 1 up to n, and evaluating each by training a decision-support system on that variable combined with the current set of selected important variables;
   (d) selecting the best of the m variables, wherein the best variable is the one that gives the highest performance of the decision-support system, and if the best variable improves performance compared to the performance of the selected important variables, adding it to the selected important variable set, removing it from the candidate set and continuing evaluating at step (c), if the variable does not improve performance in comparison to the performance of the selected important variables, evaluating is continued at step (e);
   (e) determining if all variable on the candidate set have been evaluated, wherein if they have been evaluated, the process is complete and the set of selected important variables is a completed set, otherwise continuing by taking the next highest m ranked variables one at a time, and evaluating each by training a decision-support-system on that variable combined with the current set of important selected variables and performing step (d); and
   (f) producing an output comprising the set of important variables.

28. The method of claim 27, wherein the candidate variables include biochemical test data.

29. The method of claim 27, wherein ranking is based on an analysis comprising a sensitivity analysis or other decision-support system-based anaylsis.

30. The method of claim 27, wherein ranking is based on a process comprising a statistical analysis.

31. The method of claim 27, wherein ranking is based on a process comprising chi square, regression analysis or discriminant analysis.

32. The method of claim 27, wherein ranking is determined by a process that uses evaluation by an expert, a rule based system, a sensitivity analysis or combinations thereof.

33. The method of claim 27, wherein the sensitivity analysis, comprises:
   (i) determining an average observation value for each of the variables in the observation data set;
   (ii) selecting a training example, and running the example through a decision-support system to produce an output value, designated and stored as the normal output;
   (iii) selecting a first variable in the selected training example, replacing the observation value with the average observation value of the first variable, running the modified example in the decision-support system in the forward mode and recording the output as the modified output;
   (iv) squaring the difference between the normal output and the modified output and accumulating it as a total, wherein the total for each variable designated the selected variable total for each variable;
   (v) repeating steps (iii) and (iv) for each variable in the example;
   (vi) repeating steps (ii)–(v) for each example in the data set, wherein each total for the selected variable represents the relative contribution of each variable to the determination of the decision-support system output.

34. The method of claim 27, wherein the decision-support system includes a consensus of neural networks.

35. The method of claim 27, that is a computer-assisted method, wherein the set of n candidate variables and set of selected important variables are each stored in a computer.

36. The method of claim 27, further comprising training a final decision-support system based on the completed set of selected important variables to produce a decision-support system based test for the condition.

37. A method for variable selection, comprising:
   (a) providing a first set of n candidate variable and a second set of selected important variables, wherein the second set is initially empty;

(b) taking candidate variable one at a time evaluating each by training a computer-based decision-support system on that variable combined with the current set of selected important variables;

(c) selecting the best of the candidate variable, wherein the best variable is any one that gives the highest performance of the decision-support system, and if the best candidate variable improves performance compared to the performance of the selected important variables, adding it to the selected important variable set, removing it from the candidate set and continuing evaluating at step (b), wherein the best candidate variable does not improve performance, the process is completed, wherein the computer-based decision-support support system includes a consensus of neural networks; and (d) outputting the candidate variables onto a computer display or storing them on computer readable medium.

38. A method for developing a decision-support system-based test to aid in diagnosing a medical condition, disease or disorder in a patient, comprising:

(a) collecting observation by examining and querying a group of test patients in whom the medical condition is known;

(b) categorizing the observations into a set of candidate variable having observation values and storing the observation values as a observation data set in a computer;

(c) selecting a subset of selected important variables from the set of candidate variables by classifying the observation data set using a first decision-support system programmed into the computer system, whereby the subset of selected important variables includes the candidate variables substantially indicative of the medical condition; and (d) training a computer-based second decision-support system using the observation data corresponding to a subset of selected important variables, whereby the second decision-support system-based system constitutes a decision-support based diagnostic test for the condition, disease or disorder; and (e) storing the second decision-support system in a computer memory or on a computer-readable medium.

39. The method of claim 38, wherein the first decision-support system includes at least one neural network.

40. The method of claim 38, wherein the second decision-support system includes least one neural network.

41. The method of claim 38, wherein the step of selecting a subset of selected important variables includes:

(i) providing a first set of n candidate variables and a second set of selected important variable, wherein the second set is initially empty;

(ii) taking candidate variables one at a time and evaluating each by training a decision-support system on that variable combined with the current set of selected important variables;

(iii) selecting the best of the candidate variables, wherein the best variable is any one that gives the highest performance of the decision-support system, and if the best candidate variable improves performance compared to the performance of the selected important variables, adding it to the selected important variable set, removing it form the candidate set and continuing evaluating at step (ii), wherein the best candidate variable does not improve performance, the process is completed.

42. The method of claim 38, wherein the step of selecting a subset of selected important variable includes:

(i) providing a first set of n candidate variables and a second set of selected important varibales, wherein the second set is initially empty;

(ii) ranking all candidate variables, wherein the ranking is either arbitrary or ordered;

(iii) taking the highest m ranked variables one at a time, wherein m is from 1 up to n, and evaluating each by training a decision-support system on that variable combined with the current set of selected important variables;

(iv) selecting the best of the m variables, wherein the best variable is the one that gives the highest performance of the decision-support system, and if the best variable improves performance compared to the performance of the selected important variable, adding it to the selected important variable set, removing it from the candidate set and continuing evaluating at step (iii), if the variable does not improve performance in comparison to the performance of the selected important variables, evaluating is continued at step (v);

(v) determining if all variables on the candidate set have been evaluated, wherein if they have been evaluated, the process is complete and the set of selected important variables is a completed set, otherwise continuing by taking the next highest m ranked variables one at a time, and evaluating each by training a decision-support-system on that variable combined with the current set of important selected variables and performing step (iv).

43. The method of claim 42, wherein the candidate variables include biochemical test data.

44. The method of claim 42, wherein ranking is based on an analysis comprising a sensitivity analysis or other decision-support system-based analysis.

45. The method of claim 44, wherein the sensitivity analysis, comprises:

(i) determining an average observation value for each of the variables in the observation data set;

(ii) selecting a training example, and running the example through a decision-support system to produce and output value, designated and stored as the normal output;

(iii) selecting a first variable in the selected training example, replacing the observation value with the average observation value of the first variable, running the modified example in the decision-support system in the forward mode and recording the output as the modified output;

(iv) squaring the difference between the normal output and the modified output and accumulating it as a total, wherein the total for each variable designated the selected variable total for each variable;

(v) repeating steps (iii) and (iv) for each variable in the example;

(vi) repeating steps (ii)–(v) for each example in the data set, wherein each total for the selected variable represents the relative contribution of each variable to the determination of the decision-support system output.

46. The method of claim 42, wherein ranking is based on a process comprising a statistical analysis.

47. The method of claim 42, wherein ranking is based on a process comprising chi square, regression analysis or discriminant analysis.

48. The method of claim 42, wherein ranking is determined by a process that use evaluation by an expert, a rule based system, a sensitivity analysis or combinations thereof.

49. The method of claim 48, wherein the sensitivity analysis comprises:
   (i) determining an average observation value for each of the variables in the observation data set;
   (ii) selecting a training example, and running the example through a decision-support system to produce an output value, designated and stored as the normal output;
   (iii) selecting a first variable in the selected training example, replacing the observation value with the average observation value of the first variable, running the modified example in the decision-support system in the forward mode and recording the output as the modified output;
   (iv) squaring the difference between the normal output and the modified output and accumulating it as a total, wherein the total for each variable designated the selected variable total for each variable;
   (v) repeating steps (iii) and (iv) for each variable in the example;
   (vi) repeating steps (ii)–(v) for each example in the data set, wherein each total for the selected variable represents the relative contribution of each variable to the determination of the decision-support system output.

50. The method of claim 49, further comprising:
   (vii) ranking the variables according to their relative contribution to the determination of the decision-support system output.

51. The method of claim 38, wherein the step of training a second decision-support system includes a validating step wherein a previously-unused set of observation data is run through the second decision-support system after training to provide a performance estimate for indication of the medical condition, wherein the previously-unused set of observation data are collected from patients in whom the medical condition is known.

52. The method of claim 38, wherein the step of training a second decision-support system includes partitioning the observation data set into a plurality of partitions comprising at least one testing data partition and a plurality of training data partitions, wherein the second decision-support system is run using the plurality of training data partitions and the testing data partition is used to provide a final performance estimate for the second decision-support system after the training data partitions have been run.

53. The method of claim 52, wherein the second decision-support system comprises a plurality of neural networks, each neural network of the plurality having a unique set of starting weights and having a performance rating value.

54. The method of claim 53, wherein the final performance estimate is generated by averaging the performance rating values for the plurality of neural networks.

55. The method of claim 38, wherein the observation values are obtained from patient historical data results and/or biochemical test results.

56. The method of claim 55, wherein the pregnancy related condition is preterm delivery or risk of delivery within a selected time period.

57. The method of claim 38, wherein the condition is a pregnancy-related condition or endometriosis.

58. The method of claim 38, further comprising:
   (e) collecting additional observations from patients and categorizing them into a set of candidate variables, which are then added to first set of candidate variables; and then
   (f) repeating steps (c) and (d).

59. The method of claim 38, wherein the test assesses the presence, absence, severity or course of treatment of a disease, disorder or other medical condition or aids in determining the outcome resulting from a selected treatment.

60. The method of claim 38, further comprising, before, during or after collecting observations from a group of test patients and before training the second decision-support based system,
   performing biochemical tests on at least one test patient and collecting test results of a biochemical test from at least one or a portion of the test patients in whom the condition is known or suspected and categorizing them into a set of candidate variables, which are then added to first set of candidate variables; and then
   repeating steps (c) and (d).

61. The method of claim 60, wherein the test assesses the presence, absence, severity or course of treatment of a disease, disorder or other medical condition or aids in determining the outcome resulting from a selected treatment.

62. The method of claim 60, wherein the decision-support system includes a neural network and the final set constitutes a consensus of neural networks.

63. The method of claim 60, further comprising identifying any biochemical test data variable(s) that end up in the final subset of selected important variables, whereby the identified biochemical test data variable(s) serve as indicators of the disease, disorder or condition.

64. The method of claim 63, wherein the test assesses the presence, absence, severity or course of treatment of a disease, disorder or other medical condition or aids in determining the outcome resulting from a selected treatment.

65. The method of claim 63, wherein the decision-support system includes a neural network and the final set constitutes a consensus of neural networks.

66. The method of claim 63, wherein the first subset of relevant variables is identified using sensitivity analysis performed on the decision-support based system or consensus thereof.

67. The method of claim 63, wherein the first decision-support system includes at least one neural network.

68. The method of claim 63, wherein the second decision-support system includes at least one neural network.

69. The method of claim 63, wherein the step of selecting a subset of selected important variables includes:
   (i) providing a first set of n candidate variables and a second set of selected important variables, wherein the second set is initially empty;
   (ii) taking candidate variable one at a time and evaluating each by training a decision-support system on that variable combined with the current set of selected important variable;
   (iii) selecting the best of the candidate variables, wherein the best variable is any one that gives the highest performance of the decision-support system, and if the best candidate variable improves performance compared to the performance of the selected important variables, adding it to the selected important variable set, removing it from the candidate set and continuing evaluating at step (ii), wherein the best candidate variable does not improve performance, the process is completed.

70. The method of claim 63, wherein the step of selecting a subset of selected important variable includes:

(i) providing a first set of n candidate variable and a second set of selected important variables, wherein the second set is initially empty;

(ii) ranking all candidate variables, wherein the ranking is either arbitrary or ordered;

(iii) taking the highest m ranked variables one at a time, wherein m is from 1 up to n, and evaluating each by training a decision-support system on that variable combined with the current set of selected important variables;

(iv) selecting the best of the m variables, wherein the best variable is the one that gives the highest performance of the decision-support system, and if the best variable improves performance compared to the performance of the selected important variables, adding it to the selected important variable set, removing it from the candidate set and continuing evaluating at step (iii), if the variable does not improve performance in comparison to the performance of the selected important variables, evaluating is continued at step (v);

(v) determining if all variables on the candidate set have been evaluated, wherein if they have been evaluated, the process is complete and the set of selected important variables is a completed set, otherwise continuing by taking the next highest m ranked variables one at a time, and evaluating each by training a decision-support-system on that variable combined with the current set of important selected variables and performing step (iv).

71. The method of claim 70, wherein the candidate variables include biochemical test data.

72. The method of claim 70, wherein ranking is based on an analysis comprising a sensitivity analysis or other decision-support system-based analysis.

73. The method of claim 72, wherein the sensitivity analysis, comprises:

(i) determining an average observation value for each of the variables in the observation data set;

(ii) selecting a training example, and running the example through a decision-support system to produce an output value, designated and stored as the normal output;

(iii) selecting a first variable in the selected training example, replacing the observation value with the average observation value of the first variable, running the modified example in the decision-support system in the forward mode and recording the output as the modified output;

(iv) squaring the difference between the normal output and the modified output and accumulating it as a total, wherein the total for each variable designated the selected variable total for each variable;

(v) repeating steps (iii) and (iv) for each variable in the example;

(vi) repeating steps (ii)–(v) for each example in the data set, wherein each total for the selected variable represents the relative contribution of each variable to the determination of the decision-support system output.

74. The method of claim 70, wherein ranking is based on process comprising a statistical analysis.

75. The method of claim 70, wherein ranking is based on a process comprising chi square, regression analysis or discriminant analysis.

76. The method of claim 70, wherein ranking is determined by a process that uses evaluation by an expert, a rule based system, a sensitivity analysis or combinations thereof.

77. The method of claim 76, wherein the sensitivity analysis comprises:

(i) determining an average observation value for each of the variables in the observation data set;

(ii) selecting a training example, and running the example through a decision-support system to produce an output value, designated and stored as the normal output;

(iii) selecting a first variable in the selected training example, replacing the observation value with the average observation value of the first variable, running the modified example in the decision-support system in the forward mode and recording the output as the modified output;

(iv) squaring the difference between the normal output and the modified output and accumulating it as a total, wherein the total for each variable designated the selected variable total for each variable;

(v) repeating steps (iii) and (iv) for each variable in the example;

(vi) repeating steps (ii)–(v) for each example in the data set, wherein each total for the selected variable represents the relative contribution of each variable to the determination of the decision-support system output.

78. The method of claim 77, further comprising:

(vii) ranking the variables according to their relative contribution to the determination of the decision-support system output.

79. The method of claim 63, wherein the step of training a second decision-support system includes a validating step wherein a previously-unused set of observation data is run through the second decision-support system after training to provide a performance estimate for indication of the medical condition, wherein the previously-unused set of observation data are collected from patients in whom the medical condition is known.

80. The method of claim 63, wherein the step of training a second decision-support system includes partitioning the observation data set into a plurality of partitions comprising at least one testing data partition and a plurality of training data partitions, wherein the second decision-support system is run using the plurality of training data partitions and the testing data partition is used to provide a final performance estimate for the second decision-support system after the training data partitions have been run.

81. The method of claim 80, wherein the second decision-support system comprises a plurality of neural networks, each neural network of the plurality having a unique set of starting weights and having a performance rating value.

82. The method of claim 81, wherein the final performance estimate is generated by averaging the performance rating values for the plurality of neural networks.

83. The method of claim 63, wherein the observation values are obtained from patient historical data results and/or biochemical test results.

84. The method of claim 63, wherein the condition is a pregnancy-related condition or endometriosis.

85. The method of claim 63, further comprising:

(e) collecting additional observations from patients and categorizing them into a set of candidate variables, which are then added to first set of candidate variables; and then (f) repeating steps (c) and (d).

86. The method of claim 63, further comprising developing a diagnostic biochemical test for the identified biochemical test data variable(s).

87. A method for developing new biochemical tests or identifying new disease markers, comprising:

performing the method of claim 63, and identifying biochemcial data variables that are selected important variables;

and developing tests that detect the biochemical data or disease marker from which the variable is derived.

88. The method of claim 60, wherein the first subset of relevant variables is identified using sensitivity analysis performed on the decision-support based system or consensus thereof.

89. The method of claim 60, wherein the first decision-support system includes at least one neural network.

90. The method of claim 60, wherein the second decision-support system includes at least one neural network.

91. The method of claim 60, wherein the step of selecting a subset of selected important variable includes:
- (i) providing a first set of n candidate variables and a second set of selected important variables, wherein the second set is initially empty;
- (ii) taking candidate variables one at a time and evaluating each by training a decision-support system on that variable combined with the current set of selected important variables.
- (iii) selecting the best of the candidate variables, wherein the best variable is any one that gives the highest performance of the decision-support support system, and if the best candidate variable improves performance compared to the performance of the selected important variables, adding it to the selected important variable set, removing it from the candidate set and continuing evaluating at step (ii), wherein the best candidate variable does not imporive performance, the process is completed.

92. The method of claim 60, wherein the step of selecting a subset of selected important variables includes:
- (i) providing a first set of n candidate variables and a second set of selected important variables, wherein the second set is initially empty;
- (ii) ranking all candidate variables, wherein the ranking is either arbitrary or ordered;
- (iii) taking the highest m ranked variables one at a time, wherein m is from 1 up to n, and evaluating each by training a decision-support system on that variable combined with the current set of selected important variables;
- (iv) selecting the best of the m variables, wherein the best variable is the one that gives the highest performance of the decision-support system, and if the best variable improves performance compared to the performance of the selected important variables, adding it to the selected important variable set, removing it from the candidate set and continuing evaluating at step (iii), if the variable does not improve performance in comparsion to the performance of the selected important variables, evaluating is continued at step (v);
- (v) determining if all variables on the candidate set have been evaluated, wherein if they have been evaluated, the process is complete and the set of selected important variables is a completed set, otherwise continuing by taking the next highest m ranked variables one at a time, and evaluating each by training a decision-support-system on that variable combined with the current set of important selected variables and performing step (iv).

93. The method of claim 92, wherein the candidate variables include biochemical test data.

94. The method of claim 93, wherein ranking is determined by a process that uses evaluation by an expert, a rule based system, a sensitivity analysis or combinations thereof.

95. The method of claim 94, wherein the sensitivity analysis comprises:
- (i) determining an average observation value for each of the variables in the observation data set;
- (ii) selecting a training example, and running the example through a decision-support system to produce an output value, designated and stored as the normal output;
- (iii) selecting a first variable in the selected training example, replacing the observation value with the average observation value of the first variable, running the modified example in the decision-support system in the forward mode and recording the output as the modified output;
- (iv) squaring the difference between the normal output and the modified output and accumulating it as a total, wherein the total for each variable designated the selected variable total for each variable;
- (V) repeating steps (iii) and (iv) for each variable in the example;
- (vi) repeating steps (ii)–(v) for each example in the data set, wherein each total for the selected variables represents the relative contribution of each variable to the determination of the decision-support system output.

96. The method of claim 95, further comprising:
- (vii) ranking the variables according to their relative contribution to the determination of the decision-support system output.

97. The method of claim 92, wherein ranking is based on an analysis comprising a sensitivity analysis or other decision-support system-based analysis.

98. The method of claim 97, wherein the sensitivity analysis, comprises:
- (i) determining an average observation value for each of the variables in the observation data set;
- (ii) selecting a training example, and running the example through a decision-support system to produce an output value, designated and stored as the normal output;
- (iii) selecting a first variable in the selected training example, replacing the observation value with the average observation value of the first variable, running the modified example in the decision-support system in the forward mode and recording the output as the modified output;
- (iv) squaring the difference between the normal output and the modified output and accumulating it as a total, wherein the total for each variable designated the selected variable total for each variable;
- (v) repeating steps (iii) and (iv) for each variable in the example;
- (vi) repeating steps (ii)–(v) for each example in the data set, wherein each total for the selected variable represents the relative contribution of each variable to the determination of the decision-support system output.

99. The method of claim 92, wherein ranking is based on a process comprising a statistical analysis.

100. The method of claim 92, wherein ranking is based on a process comprising chi square, regression analysis or discriminant analysis.

101. The method of claim 60, wherein the step of training a second decision-support system includes a validating step wherein a previously-unused set of observation data is run through the second decision-support system after training to provide a performance estimate for indication of the medical condition, wherein the previously-unused set of observation data are collected from patients in whom the medical condition is known.

102. The method of claim 60, wherein the step of training a second decision-support system includes partitioning the observation data set into a pluarlity of partitions comprising at least one testing data partition and a plurality of training data partitions, wherein the second decision-support system is run using the plurality of training data partitions and the testing data partition is used to provide a final performance estimate for the second decision-support system after the training data partitions have been run.

103. The method of claim 102, wherein the second decision-support system comprises a plurality of neural networks, each neural network of the plurality having a unique set of starting weights and having a performance rating value.

104. The method of claim 103, wherein the final performance estimate is generated by averaging the performance rating values for the plurality of neural networks.

105. The method of claim 60, wherein the observation values are obtained from patient historical data results and/or biochemical test results.

106. The method of claim 60, wherein the condition is a pregnancy-related condition or endometriosis.

107. The method of claim 60, further comprising:
  (e) collecting additional observations from patients and categorizing them into a set of candidate variables, which are then added to first set of candidate variables; and then
  (f) repeating steps (c) and (d).

108. The method of claim 38, wherein the computer-based decision-support system includes a system selected from the group consisting of expert system, fuzzy logic systems, non-linear regression analysis systems, multivariate analysis systems, decision tree classifiers, Bayesian belief networks and neural networks.

109. The method of claim 38, wherein the computer-based decision-support system comprises a neural network or plurality of neural networks.

110. A computer-based diagnostic test produced by the method of claim 38.

111. A computer readable medium or computer memory, comprising a decision-support system produced by the method of claim 38.

112. A computer memory or on a computer-readable medium produced by the method of claim 38.

113. The method of claim 38, wherein the disorder is endometriosis and the candidate variables comprise at least four of the variables selected from:
  (i) past history of endometriosis, number of births, dysmenorrhea, age pelvic pain, history of pelvic surgery, smoking quantity per day, medication history, number of pregnancies, number of abortions, abnormal PAP/dysplasia, pregnancy hypertension, gential warts, and diabetes, or
  (ii) age, parity, gravidity, number of abortions, smoking quantity per day, past history of endometriosis, dysmenorrhea, pelvic pain, abnormal PAP, history of pelvic surgery, medication history, pregnancy hypertension, genital warts and diabetes.

114. The method of claim 113, wherein the decision-support system comprises a neural network or a consensus of neural networks.

115. The method of claim 113, wherein at least five variables are selected.

116. A method for analyzing effectiveness of a diagnostic test to aid in diagnosing the presence, absence or severity of a medical condition or for assessing a course of treatment or the effectiveness of a particular treatment in a patient comprising:
  (a) collecting observations from a group of test patients in whom the medical condition is known by querying and examining the test patients;
  (b) categorizing the observations into a set of candidate variables having observation values and storing the observation values as a observation data set in a computer;
  (c) selecting a subset of selected important variables from the set of candidate variables by classifying the observation data set using a first decision-support system programmed into the computer system; and
  (d) training a second decision-support system using the observation data corresponding to the subset of selected important variables;
  (e) performing the diagnostic test under analysis or treating test patients with the test treatment, wherein the test or treatment is performed before, during or after any of steps (a)–(d);
  (f) collecting results of the diagnostic test under analysis or collecting observation after or during treatment from same the group of test patients;
  (g) categorizing the observations into a second set of candidate variables having observation values, combining them with the observations from step (b), and storing the observation values as a observation data set in a computer;
  (h) selecting a second subset of selected important variables by classifying the observation data set using a first decision-support system programmed into the computer system;
  (i) training a third decision-support system using the observation data corresponding to a subset of selected important variables from step (g); and
  (j) comparing the performance of the second and third systems, thereby assessing the effectiveness of a disgnostic test to aid in diagnosing the presence, absence or severity of a medical condition or assessing the effectiveness of a course of treatment or the effectiveness of a particular treatment in treating a disease, disorder or condition.

117. The method of claim 116, wherein the method assesses the effectiveness of a diagnostic test in aiding in a diagnosis.

118. The method of claim 116, wherein the method assesses the presence, absence, severity or course of treatment of a disease, disorder or other medical condition or aids in determining the outcome resulting from a selected treatment.

119. The method of claim 116, wherein the decision-support system includes a neural network and the final set constitutes a consensus of neural networks.

120. The method of claim 116, wherein the first subset of relevant variables is identified using sensitivity analysis performed on the decision-support based system or consensus thereof.

121. The method of claim 116, wherein the first decision-support system includes at least one neural network.

122. The method of claim 116, wherein the second decision-support system includes at least one neural network.

123. The method of claim 116, wherein the third decision-support system includes at least one neural network.

124. The method of claim 116, wherein the step of selecting a subset of selected important variables includes:
  (i) providing a first set of n candidate variables and a second set of selected improtant variables, wherein the second set is initially empty;

(ii) taking candidate variables one at a time and evaluating each by training a decision-support system on that variable combined with the current set of selected important variables;

(iii) selecting the best of the candidate variables, wherein the best variable is any one that gives the highest performance of the decision-support system, and if the best candidate variable improves performance compared to the performance of the selected important variables, adding it to the selected important variable set, removing it from the candidate set and continuing evaluating at step (ii), wherein the best candidate variable does not improve performance, the process is completed.

125. The method of claim 116, wherein the step of selecting a subset of selected important variables includes:

(i) providing a first set of n candidate variables and a second set of selected important variables, wherein the second set is initially empty;

(ii) ranking all candidate variables, wherein the ranking is either arbitrary or ordered;

(iii) taking the highest m ranked variables one at a time, wherein m is from 1 up to n, and evaluating each by training a decision-support system on that variable combined with the current set of selected important variables;

(iv) selecting the best of the m variables, wherein the best variable is the one that gives the highest performance of the decision-support system, and if the best variable improves performance compared to the performance of the selected important variables, adding it to the selected important variable set, removing it from the candidate set and continuing evaluating at step (iii), if the variable does not improve performance in comparison to the performance of the selected important variables, evaluating is continued at step (v);

(v) determining if all variables on the candidate set have been evaluated, wherein if they have been evaluated, the process is complete and the set of selected important variables is a completed set, otherwise continuing by taking the next highest m ranked variables one at a time, and evaluating each by training a decision-support-system on that variable combined with the current set of important selected variables and performing step (iv).

126. The method of claim 125, wherein ranking is based on an analysis comprising a sensitivity analysis or other decision-support system-based analysis.

127. The method of claim 126, wherein ranking is determined by a process that uses evaluation by an expert, a rule based system, a sensitivity analysis or combinations thereof.

128. The method of claim 127, wherein the sensitivity analysis comprises:

(i) determining an average observation value for each of the variables in the observation data set;

(ii) selecting a training example, and running the example through a decision-support system to produce an output value, designated and stored as the normal output;

(iii) selecting a first variable in the selected training example, replacing the observation value with the average observation value of the first variable, running the modified example in the decision-support system in the forward mode and recording the output as the modified output;

(iv) squaring the difference between the normal output and the modified output and accumulating it as a total, wherein the total for each variable designated the selected variable total for each variable;

(v) repeating steps (iii) and (iv) for each variable in the example;

(vi) repeating steps (ii)–(v) for each example in the data set, wherein each total for the selected variable represents the relative contribution of each variable to the determination of the decision-support system output.

129. The method of claim 128, further comprising:

(vii) ranking the variables according to their relative contribution to the determination of the decision-support system output.

130. The method of claim 126, wherein the sentivity analysis, comprises:

(i) determining an average observation value for each of the variables in the observation data set;

(ii) selecting a training example, and running the example through a decision-support system to produce an output value, designated and stored as the normal output;

(iii) selecting a first variable in the selected training example, replacing the observation value with the average observation value of the first variable, running the modified example in the decision-support system in the forward mode and recording the output as the modified output;

(iv) squaring the difference between the normal output and the modified output and accumulating it as a total, wherein the total for each variable designated the selected variable total for each variable;

(v) repeating steps (iii) and (iv) for each variable in the example;

(vi) repeating steps (ii)–(v) for each example in the data set, wherein each total for the selected variable represents the relative contribution of each variable to the determination of the decision-support system output.

131. The method of claim 125, wherein ranking is based on process comprising a statistical analysis.

132. The method of claim 125, wherein ranking is based on a process comprising chi square, regression analysis or discriminant analysis.

133. The method of claim 116, wherein the step of training a second and/or third decision-support system includes a validating step wherein a previously-unused set of observation data is run through the second decision-support system after training to provide a performance estimate for indication of the medical condition, wherein the previously-unused set of observation data are collected from patients in whom the medical condition is known.

134. The method of claim 116, wherein the step of training a second and/or third decision-support system includes partitioning the observation data set into a plurality of partitions comprising at least one testing data partition and a plurality of training data partitions, wherein the second decision-support system is run using the plurlaity of training data partitions and the testing data partition is used to provide a final performance estimate for the second decision-support system after the training data partitions have been run.

135. The method of claim 134, wherein the each decision-support system comprises a plurality of neural networks, each neural network of the plurality having a unique set of weights and having a performance rating value.

136. The method of claim 135, wherein the final performance estimate is generated by averaging the performance rating values for the plurality of neural networks.

137. The method of claim 116, wherein the observation values are obtained from patient historical data results and/or biochemical test results.

138. The method of claim 116, wherein the condition is a pregnancy-related condition or endometriosis.

139. The method of claim 116, further comprising:
collecting additional observations from patients and categorizing them into a set of candidate variables, which are than added to first set of candidate variable at step (b); and then
(j) repeating steps (c)–(i).

140. A method for developing a condition-specific biochemical test to aid in diagnosing the presence, absence, or severity of a medical condition in a patient comprising:
(a) performing and collecting test results of a biochemcial test from a group of test patients in whom the condition is known or suspected;
(b) categorizing the test results and other observations into a set of candidate variables having observation values and storing the observation values as an observation data set in a computer;
(c) selecting a subject of selected important variables from a set of variables comprising the candidate variables by classifying the observation data set using a first decision-support system programmed into the computer system, whereby the subset of selected important variables includes the candidate variables substantially indicative of the medical condition; and
(d) identifying those variable(s) in the selected important variable set that correspond to biochemical data; and
(e) producing a biochemical test that assesses the data that corresponds to the identified variable(s).

141. The method of claim 140, wherein the decision-support system includes neural network or consensus thereof.

142. The method of claim 140, wherein the test assesses the presence, absence, severity or course of treatment of a disease, disorder or other medical condition or aids in determining the outcome resulting from a selected treatment.

143. The method of claim 140, wherein the decision-support system includes a neural network and the final set constitutes a consensus of neural networks.

144. The method of claim 140, wherein the first subset of relevant variables is identified using sensitivity analysis performed on the decision-support based system or consensus thereof.

145. The method of claim 140, wherein the first decision-support system includes at least one neural network.

146. The method of claim 140, wherein the second decision-support system includes at least one neural network.

147. The method of claim 140, wherein the step of selecting a subset of selected important variables includes:
(i) providing a first set of n candidate variables and a second set of selected important variables, wherein the second set is initially empty;
(ii) taking candidate variables one at a time and evaluating each by training a decision-support system on that variable combined with the current set of selected important variables;
(iii) selecting the best of the candidate variables, wherein the best variable is any one that gives the highest performance of the decision-support system, and if the best candidate variable improves performance compared to the performance of the selected important variables, adding it to the selected important variable set, removing ot from the candidate set and continuing evaluating at step (ii), wherein the best candidate variable does not improve performance, the process is completed.

148. The method of claim 140, wherein the step of selecting a subset of selected important variables includes:
(i) providing a first set of n candidate variables and a second set of selected important variables, wherein the second set is initially empty;
(ii) ranking all candidate variables, wherein the ranking is either arbitrary or ordered;
(iii) taking the highest m ranked variables one at a time, wherein m is from 1 up to n, and evaluating each by training a decision-support system on that variable combined with the current set of selected important variables;
(iv) selecting the best of the m variables, wherein the best variable is the one that gives the highest performance of the decision-support system, and if the best variable improves performance compared to the performance of the selected important variables, adding it to the selected important variable set, removing it from the candidate set and continuing evaluating at step (iii), if the variable does not improve performance in comparison to the performance of the selected important variables, evaluating is continued at step (v);
(v) determining if all variables on the candidate set have been evaluated, wherein if they have been evaluated, the process is completed and the set of selected important variables is a completed set, otherwise continuing by taking the next highest m ranked variables one at a time, and evaluating each by training a decision-support-system on that variable combined with the current set of important selected variables and performing step (iv).

149. The method of claim 148, wherein the candidate variables include biochemical test data.

150. The method of claim 149, wherein ranking is determined by a process that uses evaluation by an expert, a rule based system, a sensitivity analysis or combinations thereof.

151. The method of claim 150, wherein the sensitivity analysis comprises:
(i) determining an average observation value for each of the variable in the observation data set;
(ii) selecting a training example, and running the example through a decision-support system to produce an output value, designated and stored as the normal output;
(iii) selecting a first variable in the selected training example, replacing the observatio value with the average observation value of the first variable, running the modified example in the decision-support system in the forward mode and recording the output as the modified output;
(iv) squaring the difference between the normal output and the modified output and accumulating it as a total, wherein the total for each variable designated the selected variable total for each variable;
(v) repeating steps (iii) and (iv) for each variable in the example;
(vi) repeating steps (ii)–(v) for each example in the data set, wherein each total for the selected variable represents the relative contribution of each variable to the determination of the decision-support system output.

152. The method of claim 151, further comprising:
(vii) ranking the variables according to their relative contribution to the determination of the decision-support system output.

153. The method of claim 148, wherein ranking is based on an analysis comprising a sensitivity analysis or other decision-support system-based analysis.

154. The method of claim 153, wherein the sensitivity analysis, comprises:
(i) determining an average observation value for each of the variables in the observation data set;
(ii) selecting a training example, and running the example through a decision-support system to produce an output value, designated and stored as the normal output;
(iii) selecting a first variable in the selected training example, replacing the observation value with the average obseration value of the first variable, running the modified example in the decision-support system in the forward mode and recording the output as the modified output;
(iv) squaring the difference between the normal output and the modified output and accumulating it as a total, wherein the total for each variable designated the selected variable total for each variable;
(v) repeating steps (iii) and (iv) for each variable in the example;
(vi) repeating steps (ii)–(v) for each example in the data set, wherein each total for the selected variable represents the relative contribution of each variable to the determination of the decision-support system output.

155. The method of claim 148, wherein ranking is based on a process comprising a statistical analysis.

156. The method of claim 148, wherein ranking is based on a process comprising chi square, regression analysis or discriminant analysis.

157. The method of claim 140, wherein the step of training a second decision-support system includes a validating step wherein a previously-unused set of observation data is run through the second decision-support system after training to provide a performance estimate for indication of the medical condition, wherein the previously-unused set of observation data are collected from patients in whom the medical condition is known.

158. The method of claim 140, wherein the step of training a second decision-support system includes partitioning the observation data set into a plurality of partitions comprising at least one testing data partition and a plurality of training data partitions, wherein the second decision-support system is run using the plurality of training data partitions and the testing data partition is used to provide a final performance estimate for the second decision-support system after the training data partitions have been run.

159. The method of claim 158, wherein the second decision-support system comprises a plurality of neural networks, each neural network of the plurality having a unique set of starting weights and having a performance rating value.

160. The method of claim 159, wherein the final performance estimate is generated by averaging the performance rating values for the plurality of neural networks.

161. The method of claim 140, wherein the observation values are obtained from patient historical data results and/or biochemcial test results.

162. The method of claim 140, wherein the condition is a pregnancy-related condition or endometriosis.

163. The method of claim 140, further comprising:
(e) collecting additional observations from patients and categorizing them into a set of candidate variables, which are then added to first set of candidate variables; and then
(f) repeating steps (c) and (d).

164. A method for diagnosing endometriosis in a subject, comprising:
querying and examining the patient to assess at least three of the following variables:
Past history of endometriosis,
number of births,
dysmenorrhea,
age preprocessed to be normalized to a value between 1 and 0,
pelvic pain,
history of pelvic surgery,
smoking and if yes, the number of packs/day
medication history,
number of pregnancies,
number of abortions,
Abnormal PAP smear/dysplasia,
Pregnancy hyperplasia,
Genital Warts,
Diabetes,
entering the results of the queries and examination into a computer system that comprises a computer-based
decision-support system that has been trained to diagnose endometriosis; and
producing an output indicative of a diagnosis.

165. The method of claim 164, wherein the selected subset of these variables contains one or more of the following combinations of three variables set forth in sets (a)–(n):
a) number of births, history of endometriosis, history of pelvic surgery;
b) diabetes, pregnancy hypertension, smoking;
c) pregnancy hypertension, abnormal pap smear/dysplasia, history of endometriosis;
d) age, smoking, history of endometriosis;
e) smoking, history of endometriosis, dysmenorrhea;
f) age, diabetes, history of endometriosis;
g) pregnancy hypertension, number of births, history of endometriosis;
h) Smoking, number of births, history of endometriosis;
i) pregnancy hypertension, history endometriosis, history of pelvic surgery;
j) number of pregnancies, history of endometriosis, history of pelvic surgery;
k) number of births, abnormal PAP smear/dysplasia, history of endometriosis;
l) number of births, abnormal PAP smear/dysplasia, dysmenorrhea;
m) history of endometriosis, history of pelvic surgery, dysmenorrhea; and
n) number of pregnancies, history of endometriosis, dysmenorrhea.

166. The method of claim 165, wherein the decision support system is a neural network.

167. A method to aid in diagnosis of the presence, absence or severity of endometriosis in a patient comprising:
(a) querying and examining the patient to collect observation values reflecting presence and absence of specified clinical data factors and storing the observed clinical data factors in storage means of the computer system, the specified clinical data factors comprising at least four of the factors selected from:
(i) past history of endometriosis, number or births, dysmenorrhea, age, pelvic pain, history of pelvic surgery, smoking quantity per day, medication history, number of pregnancies, number of abortions, abnormal PAP/dysplasia, pregnancy hypertension, genital warts, and diabetes, or (ii) age, parity, gravidity, number of abortions, smoking quantity per day, past history of endometriosis, dysmenorrhea, pelvic pain, abnormal PAP, history of pelvic surgery, medication history, pregnancy hypertension, genital warts and diabetes;

(b) applying the observation values from the memory means to a first computer-based decision-support system trained on samples of the specified factors; and thereupon (c) extracting from the first decision-support system an output value, wherein the output value is a quantitative objective aid to enhance decision processes for a diagnosis of endometriosis.

168. The method of claim 167, wherein the decision-support system comprises a neural network.

169. The method of claim 167, wherein at least five factors are selected.

170. The method of claim 167, further comprising:

b1) applying said observation values from said memory means to a plurality of the first decision-support system, wherein each one of the first decision-support systems is trained on the samples of the specified factors with different starting weights for each training;

c1) extracting from the first decision-support system, output value pairs for each one of said first neural networks; and d) forming a linear combination of said first ones of said output value pairs and forming a linear combination of said second ones of said output value pairs, to obtain a confidence index pair, said confidence index pair being said quantitative objective aid.

171. The method of claim 170, wherein the first decision support system is a neural network that comprises a three-layer network containing an input layer, a hidden layer and an output layer, the input layer having fourteen input nodes, first and second hidden layer nodes, a hidden layer bias for each hidden layer node, first and second output layer nodes in the output layer, and an output layer bias for each output layer node.

172. The method of claim 170, wherein the first decision support system is a neural network and each of the plurality of first trained neural networks comprises a three-layer network comprising an input layer, a hidden layer and an output layer.

173. A decision support system is a neural network that comprises a three-layer neural network, comprising an input layer, a hidden layer and an output layer, the input layer having fourteen input nodes, first and second hidden layer nodes and a hidden layer bias for each hidden layer node and first and second output layer nodes in the output layer and an output layer bias for each output layer node, wherein weights, in order of identification as follows:
0. Bias
1. Age
2. Diabetes
3. Pregnancy hypertension
4. Smoking Packs/Day
5. Number of Pregnancies
6. Number of Births
7. Number of Abortions
8. Genital Warts
9. Abnormal PAP/Dysplasia
10. History of Endometriosis
11. History of Pelvic Surgery
12. Medication History
13. Pelvic Pain
14. Dysmenorrhea are as follows for each of eight neural networks of the first neural networks:

First neural network A
    to processing element at the first hidden layer node:
        0.15 −1.19 −0.76 3.01 1.81 1.87 3.56 −0.48 1.33 −1.96 −4.45 1.36 −1.61 −1.97 −0.91
    to processing element at the second hidden layer node:
        0.77 2.25 −2.30 −1.48 −0.85 0.27 −1.70 −0.47 0.84 −6.19 0.50 −0.95 0.40 2.38 1.86
    output layer weights (0 bias, first hidden layer weight, second hidden layer weight)
    to processing element at the first output layer node:
        −0.12 −0.44 0.66
    to processing element at the second output layer node:
        0.12 0.44 −0.65

First neural network B
    to processing element at the first hidden layer node:
        −0.16 −3.30 0.85 1.00 0.99 −0.81 1.57 −1.40 0.46 1.16 −0.80 −0.01 −1.19 −1.10 −2.29
    to processing element at the second hidden layer node:
        −1.62 0.79 0.45 2.14 3.82 3.93 3.96 2.27 −0.54 1.51 −4.76 2.83 0.74 −0.43 −0.17
    output layer weights (0 bias, first hidden layer weight, second hidden layer weight)
    to processing element at the first output layer node:
        0.70 −0.69 −0.65
    to processing element at the second output layer node:
        −0.70 0.69 0.65

First neural network C
    to processing element at the first hidden layer node:
        0.94 1.43 0.29 1.17 2.11 −1.16 1.033 −0.68 −0.88 0.31 −1.74 1.62 −1.49 −1.05 −0.41
    to processing element at the second hidden layer node:
        0.77 3.31 −1.48 −0.83 0.60 −2.09 −1.39 −0.40 −0.19 −0.89 1.36 0.59 −1.11 0.26 1.04
    output layer weights (0 bias, first hidden layer weight, second hidden layer weight)
    to processing element at the first output layer node:
        0.10 −0.90 0.87
    to processing element at the second output layer node:
        −0.10 0.90 −0.87

First neural network D
    to processing element at the first hidden layer node:
        1.08 1.27 −0.89 −1.00 −1.74 −0.40 −1.38 1.26 1.06 0.66 0.71 −0.57 0.67 1.89 −0.90
    to processing element at the second hidden layer node:
        −0.03 −0.58 −0.46 −0.94 0.73 0.10 0.55 −0.79 −0.098 −1.36 1.01 0.00 −0.38 −0.49 1.57
    output layer weights (0 bias, first hidden layer weight, second hidden layer weight)
    to processing element at the first output layer node:
        −1.43 1.39 1.28
    to processing element at the second output layer node:
        1.30 −1.28 −1.17

First neural network E
    to processing element at the first hidden layer node:
        0.14 −2.12 8.36 1.02 1.79 0.31 2.87 0.84 −1.24 −1.75 −2.98 1.72 −1.22 −2.47 −1.14 to processing element at the second hidden layer node:
-3.93 -1.07 1.16 1.39 1.01 -1.08 2.33 0.76 -0.51 -0.31 -1.92 0.59 0.06 -0.76 -1.44 output layer weights (0 bias, first hidden layer weight, second hidden layer weight)

to processing element at the first output layer node:
0.46 -0.52 -0.80 to processing element at the second output layer node:
-0.46 0.51 0.82

First neural network F to processing element at the first hidden layer node:
-1.19 -2.93 1.19 6.85 1.08 0.66 1.65 -0.28 -1.63 -1.15 -0.79 0.43 -0.13 -3.10 -2.27 to processing element at the second hidden layer node:
0.82 0.19 0.72 0.83 0.59 0.07 1.06 0.51 1.04 1.47 -1.97 0.97 -0.91 -0.15 0.09 output layer weights (0 bias, first hidden layer weight, second hidden layer weight)

to processing element at the first output layer node:
0.68 -0.67 -0.58 to processing element at the second output layer node:
-0.68 0.67 0.58

First neural network G to processing element at the first hidden layer node:
-1.18 -2.55 0.48 -1.40 1.11 -0.28 2.33 0.33 -1.92 0.99 -1.41 0.68 -0.28 -1.65 -0.79 to processing element at the second hidden layer node:
1.07 1.11 0.52 1.41 0.55 -0.48 -0.23 0.44 -1.23 0.77 -2.96 1.39 -0.28 -0.64 -2.38 output layer weights (0 bias, first hidden layer weight, second hidden layer weight)

to processing element at the first output layer node:
0.69 -0.70 -0.50 to processing element at the second output layer node:
-0.69 0.70 0.50

First neural network H to processing element at the first hidden layer node:
15.74 -0.76 -0.91 -1.13 -0.75 -0.66 -0.83 1.03 0.75 -0.48 -0.47 2.01 -0.02 0.25 1.11 to processing element at the second hidden layer node:
-2.48 -2.49 0.99 1.97 2.41 1.51 1.01 -0.26 -0.76 2.00 -5.03 1.77 -0.77 -2.29 -2.01 output layer weights (0 bias, first hidden layer weight, second hidden layer weight)

to processing element at the first output layer node:
0.02 0.41 -0.84 to processing element at the second output layer node:
-0.75 0.34 0.85.

174. The network of claim 173, wherein normalized observation values for each one of the first neural networks have the following mean and standard deviations, in order of the identification:
-0.00 1.00
0.01 0.08
0.01 0.09
0.16 0.37
1.09 1.39
0.55 0.94
0.54 0.93
0.01 0.10
0.03 0.17
0.23 0.42
0.65 0.48
0.39 0.49
0.19 0.39
0.72 0.45.

175. In a computer system, a method to aid in diagnosis of the presence, absence or severity of endometriosis in a patient comprising the steps of:

(a) collecting observation values reflecting presence and absence of specified factors and storing the observation factors in storage means of the computer system, the specified factors comprising: past history of the disease, number of births, dysmenorrhea, age, pelvic pain, history of pelvic surgery, smoking quantity per day, medication history, number of pregnancies, number of abortions, abnormal PAP/dysplasia, pregnancy hypertension, genital warts, and diabetes;

(b) obtaining results from the patient of a biochemical test relevant to endometriosis and storing in a computer memory or computer storage medium;

(c) applying the observation values and the relevant biochemical test results from the memory or storage medium to a neural network trained on samples of the specified factors and the test results; and thereupon (d) extracting from the trained neural network and output value pair, the output value pair being a preliminary indicator for the diagnosis of endometriosis.

176. The method of claim 175, further including the steps of:

(c1) applying the observation values and the relevant biochemical test results from the memory means to a plurality of the second neural networks, each one of the first neural networks being trained on the samples of the specified factors with starting weights for each training being randomly initialized;

(d1) extracting from each one of the first trained neural networks, output value pairs for each one of the first neural networks; and (e) forming a linear combination of the first ones of the output value pairs and forming a linear combination of the second ones of the output value pairs, to obtain a confidence index pair, the confidence index pair being a final indicator for the diagnosis of endometriosis.

177. The method of claim 176, wherein the plurality of the second trained neural networks each comprises a three-layer network containing an input layer, a hidden layer and an output layer, the input layer having fifteen input nodes, first and second hidden layer nodes and a hidden layer bias for each hidden layer node and first and second output layer nodes in the output layer and an output layer bias for each output layer node, wherein weights, in order of identification as follows:
0. Bias
1. Age
2. Diabetes
3. Pregnancy hypertension
4. Smoking Packs/Day
5. Number of Pregnancies
6. Number of Births
7. Number of Abortions
8. Genital Warts
9. Abnormal PAP/Dysplasia
10. History of Endometriosis
11. History of Pelvic Surgery
12. Medication History
13. Pelvic Pain 14. Dysmenorrhea
15. Biochemical test results.

178. The method of claim 175, wherein the first trained neural network comprises a three-layer network containing an input layer, a hidden layer and an output layer, the input layer having fifteen input nodes, first and second hidden layer nodes, a hidden layer bias for each hidden layer node, first and second output layer nodes in the output layer, and an output layer bias for each output layer node.

179. In a computer system, a neural network system to aid in diagnosis of the presence, absence or severity of endometriosis in a patient, the neural network system comprising:

a plurality of first trained neural networks each comprising a three-layer network containing an input layer, a hidden layer and an output layer, the input layer having fourteen input nodes, first and second hidden layer nodes, a hidden layer bias for each hidden layer node, first and second output layer nodes in the output layer, and an output layer bias for each output layer node, each trained neural network for generating a preliminary indicator for the diagnosis of endometriosis;

input means for observed values of clinical data factors;

storage means of the computer system for the observed values of the clinical data factors, the clinical data factors comprising:
      past history of the disease, number of births, dysmenorrhea, age, pelvic pain, history of pelvic surgery, smoking quantity per day, medication history, number of pregnancies, number of abortions, abnormal PAP/dysplasia, pregnancy hypertension, genital warts, and diabetes; and means for building a consensus from the output layer nodes, the consensus being a quantitative objective aid to enhance the decision process for the diagnosis of endometriosis.

180. The neural network system of claim 179, further including:

an input normalizer for normalizing the observation values from the memory means to a plurality of the first neural networks, each one of the first neural networks being trained on the samples of the specified factors with starting weights for each training being randomly initialized.

181. The neural network system of claim 179, wherein the consensus builder comprises a linear combiner of first ones of output value pairs and of second ones of output value pairs, to obtain a confidence index pair, the confidence index pair being the consensus and final indicator for the diagnosis of endometriosis.

182. The neural network system of claim 179, wherein weights, in order of identification as follows:
0. Bias
1. Age
2. Diabetes
3. Pregnancy hypertension
4. Smoking Packs/Day
5. Number of Pregnancies
6. Number of Births
7. Number of Abortions
8. Genital Warts
9. Abnormal PAP/Dysplasia
10. History of Endometriosis
11. History of Pelvic Surgery
12. Medication History
13. Pelvic Pain
14. Dysmenorrhea
are as follows for each of eight the first neural networks:
First neural network A
   to processing element at the first hidden layer node:
      0.15 −1.19 −0.76 3.01 1.81 1.87 3.56 −0.48 1.33 −1.96 −4.45 1.36 −1.61 −1.97 −0.91
   to processing element at the second hidden layer node:
      0.77 2.25 −2.30 −1.48 −0.85 0.27 −1.70 −0.47 0.84 −6.19 0.50 −0.95 0.40 2.38 1.86
   output layer weights (0 bias, first hidden layer weight, second hidden layer weight)
   to processing element at the first output layer node:
      −0.12 −0.44 0.66
   to processing element at the second output layer node:
      0.12 0.44 −0.65
First neural network B
   to processing element at the first hidden layer node:
      −0.16 −3.29 0.85 1.00 0.99 −0.81 1.57 −1.40 0.46 1.16 −0.80 −0.01 −1.19 −1.10 −2.29
   to processing element at the second hidden layer node:
      −1.62 0.79 0.45 2.14 3.82 3.93 3.96 2.27 −0.54 1.51 −4.76 2.83 0.74 −0.43 −0.17
   output layer weights (0 bias, first hidden layer weight, second hidden layer weight)
   to processing element at the first output layer node:
      0.70 −0.69 −0.65
   to processing element at the second output layer node:
      −0.70 0.69 0.65
First neural network C
   to processing element at the first hidden layer node:
      0.94 1.43 0.29 1.17 2.11 −1.16 1.03 −0.68 −0.88 0.31 −1.74 1.62 −1.49 −1.05 −0.41
   to processing elemept at the second hidden layer node:
      0.77 3.31 −1.48 −0.83 0.60 −2.09 −1.39 −0.40 −0.19 −0.89 1.36 0.59 −1.11 0.26 1.04
   output layer weights (0 bias, first hidden layer weight, second hidden layer weight)
   to processing element at the first output layer node:
      0.10 −0.90 0.87
   to processing element at the second output layer node:
      −0.10 0.90 −0.87
First neural network D
   to processing element at the first hidden layer node:
      1.08 1.27 −0.89 −1.00 −1.74 −0.40
      −1.38 1.26 1.06 0.66 0.71 −0.57 0.67 1.89 −0.90
   to processing element at the second hidden layer node:
      −0.03 −0.58 −0.46 −0.94 0.73 0.10 0.55 −0.79 −0.10 −1.36 1.01 0.00 −0.38 −0.49 1.57
   output layer weights (0 bias, first hidden layer weight, second hidden layer weight)
   to processing element at the first output layer node:
      −1.43 1.39 1.28
   to processing element at the second output layer node:
      1.30 −1.28 −1.17
First neural network E
   to processing element at the first hidden layer node:
      0.14 −2.12 8.36 1.02 1.79 0.31 2.87 0.84 −1.24 −1.75 −2.98 1.72 −1.22 −2.47 −1.14
   to processing element at the second hidden layer node:
      −3.93 −1.07 1.16 1.39 1.01 −1.08 2.33 0.76 −0.51 −0.31 −1.92 0.59 0.06 −0.76 −1.44
   output layer weights (0 bias, first hidden layer weight, second hidden layer weight)

to processing element at the first output layer node:
0.46 −0.52 −0.80 to processing element at the second output layer node:
−0.46 0.51 0.82

First neural network F to processing element at the first hidden layer node:
−1.19 −2.93 1.19 6.85 1.08 0.66 1.65 −0.28 −1.63 −1.15 −0.79 0.43 −0.13 −3.10 −2.27 to processing element at the second hidden layer node:
0.82 0.19 0.72 0.83 0.59 0.07 1.06 0.51 1.04 1.47 −1.97 0.97 −0.91 −0.15 0.09 output layer weights (0 bias, first hidden layer weight, second hidden layer weight)

to processing element at the first output layer node:
0.68 −0.67 −0.58 to processing element at the second output layer node:
−0.68 0.670.58

First neural network G to processing element at the first hidden layer node:
−1.18 −2.55 0.48 −1.40 1.11 −0.28 2.33 0.33 −1.92 0.99 −1.41 0.68 −0.28 −1.65 −0.79 to processing element at the second hidden layer node:
1.08 1.11 0.52 1.41 0.55 −0.48 −0.23 0.44 −1.23 0.77 −2.96 1.39 −0.28 −0.64 −2.38 output layer weights (0 bias, first hidden layer weight, second hidden layer weight)

to processing element at the first output layer node:
0.69 −0.70 −0.50 to processing element at the second output layer node:
−0.69 0.70 0.50

First neural network H to processing element at the first hidden layer node:
15.74 −0.76 −0.91 −1.13 −0.75 −0.66 −0.83 1.03 0.75 −0.48 −0.47 2.01 −0.02 0.25 1.11 to processing element at the second hidden layer node:
−2.48 −2.49 0.99 1.97 2.41 1.51 1.01 −0.26 −0.76 2.00 −5.03 1.77 −0.77 −2.29 −2.01 output layer weights (0 bias, first hidden layer weight, second hidden layer weight)

to processing element at the first output layer node:
0.017 0.41 −0.84 to processing element at the second output layer node:
−0.75 0.34 0.85.

183. The system of claim 182, wherein normalized observation values for each one of the first neural networks have the following mean and standard deviations, in order of the identification:

−0.00 1.00
0.01 0.08
0.01 0.09
0.16 0.37
1.09 1.39
0.55 0.94
0.54 0.93
0.01 0.10
0.03 0.17
0.23 0.42
0.65 0.48
0.39 0.49
0.19 0.39
0.72 0.45.

184. The system of claim 179, further comprising storage means for biochemical results, and wherein the plurality of networks have been trained to include biochemical test results.

185. A method for assessing the risk of delivery prior to completion of 35 weeks of gestation, comprising assessing a subset of variables containing at least three and up to all of the following variables:

Ethnic Origin Caucasian;
Marital Status living with partner;
EGA by sonogram;
EGA at sampling;
estimated date of delivery by best;
cervical dilatation (CM);
parity-preterm;
vaginal bleeding at time of sampling;
cervical consistency at time of sampling; and
previous pregnancy without complication, by querying and testing the subject;
entering the results of the queries and tests into a computer system that comprises a decision-support system that has been trained to assesses the risk of delivery prior to 35 weeks of gestation, and; and
producing an output that assesses the risk.

186. The method of claim 185, wherein the decision support system is a neural network.

187. The method of claim 185, wherein the decision-support system has been trained using a set of variables that do not include biochemical test data.

188. The method of claim 185, wherein the decision-support system has been trained using a set of variables that do not include the results of a test that detects fetal fibronectin in samples of mammalian body tissue and fluids.

189. The method of claim 185, wherein the set of variables further includes the result of a test that detects fetal fibronectin in cervico/vaginal samples.

190. In a computer system, a method for assessing the risk of delivery prior to completion of 35 weeks of gestation comprising:

(a) collecting observation values reflecting presence and absence of specified clinical data factors and storing the observed clinical data factors in storage means of the computer system, the specified clinical data factors comprising at least four up to all of the factors selected from the group consisting of:

Ethnic Origin Caucasian, Marital Status living with partner, EGA by sonogram, EGA at sampling, estimated date of delivery by best, cervical dilatation (CM), parity-preterm, vaginal bleeding at time of sampling, cervical consistency at time of sampling, and previous pregnancy without complication;

(b) applying the observation values from the memory means to a first decision-support system trained on samples of the specified factors; and thereupon (c) extracting from the first decision-support system an output value, wherein the output value is a quantitative objective aid to assess the risk of delivery prior to 35 weeks of gestation.

191. The method of claim 190, wherein the decision-support system comprises a neural network.

192. The method of claim 190, wherein at least five factors are selected.

193. The method of claim 190, wherein the clinical factors further comprise the result of a test that detects fetal fibronectin in cervico/vaginal samples.

194. The method of claim 193, wherein the selected factors include the result of the test.

195. The method of claim 194, further comprising:
b1) applying said observation values from said memory means to a plurality of the first decision-support system, wherein each one of the first decision-support systems is trained on the samples of the specified factors with different starting weights for each training;
c1) extracting from the first decision-support system, output value pairs for each one of said first neural networks; and
d) forming a linear combination of said first ones of said output value pairs and forming a linear combination of said second ones of said output value pairs, to obtain a confidence index pair, said confidence index pair being said quantitative objective aid.

196. The method of claim 195, wherein the first decision support system is a neural network that comprises a three-layer network containing an input layer, a hidden layer and an output layer, the input layer having eleven input nodes, first, second and third second hidden layer nodes, a hidden layer bias for each hidden layer node, first and second output layer nodes in the output layer, and an output layer bias for each output layer node.

197. The method of claim 195, wherein the first decision support system is a neural network and each of the plurality of first trained neural networks comprises a three-layer network comprising an input layer, a hidden layer and an output layer.

198. The method of claim 190, further comprising:
b1) applying said observation values from said memory means to a plurality of the first decision-support system, wherein each one of the first decision-support systems is trained on the samples of the specified factors with different starting weights for each training;
c1) extracting from the first decision-support system, output value pairs for each one of said first neural networks; and
d) forming a linear combination of said first ones of said output value pairs and forming a linear combination of said second ones of said output value pairs, to obtain a confidence index pair, said confidence index pair being said quantitative objective aid.

199. The method of claim 198, wherein the first decision support system is a neural network that comprises a three-layer network containing an input layer, a hidden layer and an output layer, the input layer having eleven input nodes, first, second and third second hidden layer nodes, a hidden layer bias for each hidden layer node, first and second output layer nodes in the output layer, and an output layer bias for each output layer node.

200. The method of claim 198, wherein the first decision support system is a neural network and each of the plurality of first trained neural networks comprises a three-layer network comprising an input layer, a hidden layer and an output layer.

201. The method of claim 190, wherein the clinical factors further comprise the result of a test that detects fetal fibronectin in mammalian body tissue and fluid samples.

202. A method for assessing the risk of delivery prior to completion of 35 weeks of gestation in a subject, comprising the steps of:
(a) collecting observation values reflecting presence and absence of specified factors and storing the observation factors in storage means of the computer system, the specified factors comprising: Ethnic Origin Caucasian, Marital Status living with partner, EGA by sonogram, EGA at sampling, estimated date of delivery by best, cervical dilatation (CM), parity-preterm, vaginal bleeding at time of sampling, cervical consistency at time of sampling, and previous pregnancy without complication;
(b) performing a test on the subject to obtain results of a test that detects fetal fibronectin (fFN) in mammalian body tissue and fluid samples;
(c) entering the observation values and the fFN test results into a neural network trained on samples of the specified factors and the test results; and thereupon
(d) producing from the trained neural network an output value pair, that is an indicator for the risk of delivery prior to 35 weeks of gestation.

203. The method of claim 202, further including the steps of:
(c1) applying the observation values and the relevant biochemical test results from the memory means to a plurality of the second neural networks, each one of the first neural networks being trained on the samples of the specified factors with starting weights for each training being randomly initialized;
(d1) extracting from each one of the first trained neural networks, output value pairs for each one of the first neural networks; and
(e) forming a linear combination of the first ones of the output value pairs and forming a linear combination of the second ones of the output value pairs, to obtain a confidence index pair, the confidence index pair being a final indicator for the risk of delivery prior to 35 weeks of gestation.

204. The method of claim 202, wherein the first trained neural network comprises a three-layer network containing an input layer, a hidden layer and an output layer, the input layer having eleven input nodes, first, second and third hidden layer nodes, a hidden layer bias for each hidden layer node, first and second output layer nodes in the output layer, and an output layer bias for each output layer node.

205. The method of claim 202, wherein the sample is a cervico/vaginal samples.

206. A method for assessing the risk for delivery in seven or fewer days in a pregnant subject, comprising assessing a subset of variables containing at least three up to all of the following variables:
Ethnic Origin Caucasian;
Uterine contractions with or without pain;
Parity-abortions;
vaginal bleeding at time of sampling;
uterine contractions per hour; and
No previous pregnancies, by querying and testing the subject;
entering the results of the queries and tests into a computer system that comprises a decision-support system that has been trained to assess the risk of delivery within seven days; and
producing an output that assesses the risk of delivery within seven days.

207. The method of claim 206, wherein:
the variables further include the results of a test to detect fetal fibronectin (fFN) in a cervico/vaginal sample;
the selected variables include the results of the test; and
the method measures the risk of delivery in 7 days or few days from the time of obtaining the sample for the fFN.

208. The method of claim 207, wherein the decision support system is a neural network.

209. The method of claim 207, wherein the decision-support system has been trained using a set of variables that do not include biochemical test data.

210. The method of claim 207, wherein the decision-support system has been trained using a set of variables that do not include the results of a test that detects fetal fibronectin in cervico/vaginal samples.

211. The method of claim 206, wherein:
the variables further include the results of a test for to detect fetal fibronectin (fFN) in mammalian body tissue and fluid samples;
the selected variables include the results of the test; and the method measures the risk of delivery in 7 days or few days from obtaining the sample for the fEN.

212. A method for assessing the risk for delivery in 7 days or fewer days, comprising:
(a) querying and examining test subjects to collect observation values reflecting presence and absence of specified clinical data factors and storing the observed clinical data factors in a storage medium of a computer system, the specified clinical data factors comprising at least four up to all of the factors selected from the group consisting of: Ethnic Origin Caucasian, Uterine contractions with or without pain, Parity-abortions, vaginal bleeding at time of sampling, uterine contractions per hour, prior to, and number of previous pregnancies;
(b) applying the observation values from the storage medium to a first computer-based decision-support system trained on samples of the specified factors;
(c) producing from the first decision-support system an output value, wherein the output value is a quantitative objective aid to assess the risk of delivery in less than or in 7 days; and
(d) assessing the risk of delivery within seven days based upon the output value.

213. The method of claim 212, wherein the decision-support system comprises a neural network.

214. The method of claim 212, wherein at least five factors are selected.

215. The method of claim 212, wherein the clinical factors further comprise the result of a test that detects fetal fibronectin in cervico/vaginal samples.

216. The method of claim 215, wherein the selected factors include the result of the test.

217. The method of claim 216, further comprising:
b1) applying said observation values from said memory means to a plurality of the first decision-support system, wherein each one of the first decision-support systems is trained on the samples of the specified factors with different starting weights for each training;
c1) extracting from the first decision-support system, output value pairs for each one of said first neural networks; and
d) forming a linear combination of said first ones of said output value pairs and forming a linear combination of said second ones of said output value pairs, to obtain a confidence index pair, said confidence index pair being said quantitative objective aid.

218. The method of claim 217, wherein the first decision support system is a neural network that comprises a three-layer network containing an input layer, a hidden layer and an output layer, the input layer having seven input nodes, first, second, third, forth and fifth second hidden layer nodes, a hidden layer bias for each hidden layer node, first and second output layer nodes in the output layer, and an output layer bias for each output layer node.

219. The method of claim 217, wherein the first decision support system is a neural network and each of the plurality of first trained neural networks comprises a three-layer network comprising an input layer, a hidden layer and an output layer.

220. The method of claim 212, further comprising:
b1) applying said observation values from said memory means to a plurality of the first decision-support system, wherein each one of the first decision-support systems is trained on the samples of the specified factors with different starting weights for each training;
c1) extracting from the first decision-support system, output value pairs for each one of said first neural networks; and
d) forming a linear combination of said first ones of said output value pairs and forming a linear combination of said second ones of said output value pairs, to obtain a confidence index pair, said confidence index pair being said quantitative objective aid.

221. The method of claim 212, wherein the first decision support system is a neural network that comprises a three-layer network containing an input layer, a hidden layer and an output layer, the input layer having six input nodes, first, second, third, forth and fifth second hidden layer nodes, a hidden layer bias for each hidden layer node, first and second output layer nodes in the output layer, and an output layer bias for each output layer node.

222. The method of claim 212, wherein the first decision support system is a neural network and each of the plurality of first trained neural networks comprises a three-layer network comprising an input layer, a hidden layer and an output layer.

223. The method of claim 212, wherein the clinical factors further comprise the result of a test that detects fetal fibronectin in mammalian body tissue and fluid samples.

224. A method for assessing the risk for delivery in 7 days or fewer days in a subject, comprising the steps of:
(a) querying and examining the subject to collect observation values reflecting presence and absence of specified factors and storing the observation factors in storage means of the computer system, the specified factors comprising: Ethnic Origin Caucasian, Uterine contractions with or without pain, Parity-abortions, vaginal bleeding at time of sampling, uterine contractions per hour, prior to and No previous pregnancies;
(b) performing and obtaining results from the patient of a test that detects fetal fibronectin (fFN) in mammalian body tissue and fluid samples, wherein the test is performed before, during or after the querying and examining step;
(c) applying the observation values and the fFN test results from the memory means to a neural network trained on samples of the specified factors and the test results; and thereupon
(d) obtaining from the neural network an output value pair that is an indicator for the risk of delivery in 7 days or few days from obtaining the cervico/vaginal sample.

225. The method of claim 224, further including the steps of:
(c1) applying the observation values and the relevant biochemical test results from the memory means to a plurality of the second neural networks, each one of the first neural networks being trained on the samples of the specified factors with starting weights for each training being randomly initialized;

(d1) extracting from each one of the first trained neural networks, output value pairs for each one of the first neural networks; and (e) forming a linear combination of the first ones of the output value pairs and forming a linear combination of the second ones of the output value pairs, to obtain a confidence index pair, the confidence index pair being the indicator of the risk for delivery in 7 days or fewer days.

226. The method of claim 224, wherein the first trained neural network comprises a three-layer network containing an input layer, a hidden layer and an output layer, the input layer having seven input nodes, first, second, third, fourth and fifth hidden layer nodes, a hidden layer bias for each hidden layer node, first and second output layer nodes in the output layer, and an output layer bias for each output layer node.

227. The method of claim 224, wherein the clinical factors further comprise the result of a test that detects fetal fibronectin in mammalian body tissue and fluid samples.

228. A method for assessing the risk for delivery in 14 or fewer days, comprising assessing a subset of variables containing at least three up to all of the following variables:
Ethnic Origin Hispanic;
Marital Status living with partner;
Uterine contractions with or without pain;
Cervical dilatation;
Uterine contractions per hour; and
No previous pregnancies, by querying and testing the subject; and
entering the results of the queries and tests into a computer system that comprises a decision-support system that has been trained to assess the risk of delivery within fourteen days; and
producing an output that assesses the risk for delivery in 14 or fewer days.

229. The method of claim 228, wherein:
the variables further include the results of a test for to detect fetal fibronectin (fFN) in a cervico/vaginal sample;
the selected variables include the results of the test; and
the method measures the risk of delivery in 14 days or few days from obtaining the sample for the fFN.

230. The method of claim 229, wherein the decision support system is a neural network.

231. The method of claim 229, wherein the decision-support system has been trained using a set of variables that do not include biochemical test data.

232. The method of claim 229, wherein the decision-support system has been trained using a set of variables that do not include the results of a test that detects fetal fibronectin in cervico/vaginal samples.

233. The method of claim 228, wherein:
the variables further include the results of a test that detects fetal fibronectin in mammalian body tissue and fluid samples;
the selected variables include the results of the test; and
the method measures the risk of delivery in 14 days or few days from obtaining the sample for the fFN.

234. A method for assessing the risk for delivery in 14 days or fewer days in a subject, comprising:

(a) querying and examining the subject to collect observation values reflecting presence and absence of specified clinical data factors and storing the observed clinical data factors in storage means of the computer system, the specified clinical data factors comprising at least four up to all of the factors selected from the group consisting of: Ethnic Origin Hispanic, Marital Status living with partner, Uterine contractions with or without pain, cervical dilatation, Uterine contractions per hour, and No previous pregnancies;

(b) applying the observation values from the memory means to a first computer-based decision-support system trained on samples of the specified factors; and thereupon (c) producing from the decision-support system an output value that is a quantitative objective aid to assess the risk of delivery in less than or in 14 days.

235. The method of claim 234, wherein the decision-support system comprises a neural network.

236. The method of claim 234, wherein at least five factors are selected.

237. The method of claim 234, wherein the clinical factors further comprise the result of a test that detects fetal fibronectin in cervico/vaginal samples.

238. The method of claim 234, wherein the selected factors include the result of the test.

239. The method of claim 238, further comprising:
b1) applying said observation values from said memory means to a plurality of the first decision-support system, wherein each one of the first decision-support systems is trained on the samples of the specified factors with different starting weights for each training;
c1) extracting from the first decision-support system, output value pairs for each one of said first neural networks; and
d) forming a linear combination of said first ones of said output value pairs and forming a linear combination of said second ones of said output value pairs, to obtain a confidence index pair, said confidence index pair being said quantitative objective aid.

240. The method of claim 238, wherein the first decision support system is a neural network that comprises a three-layer network containing an input layer, a hidden layer and an output layer, the input layer having seven input nodes, first, second, third, forth and fifth second hidden layer nodes, a hidden layer bias for each hidden layer node, first and second output layer nodes in the output layer, and an output layer bias for each output layer node.

241. The method of claim 238, where in the first decision support system is a neural network and each of the plurality of first trained neural networks comprises a three-layer network comprising an input layer, a hidden layer and an output layer.

242. The method of claim 234, further comprising:
b1) applying said observation values from said memory means to a plurality of the first decision-support system, wherein each one of the first decision-support systems is trained on the samples of the specified factors with different starting weights for each training;
c1) extracting from the first decision-support system, output value pairs for each one of said first neural networks; and
d) forming a linear combination of said first ones of said output value pairs and forming a linear combination of said second ones of said output value pairs, to obtain a confidence index pair, said confidence index pair being said quantitative objective aid.

243. The method of claim 234, wherein the first decision support system is a neural network that comprises a three-layer network containing an input layer, a hidden layer and an output layer, the input layer having six input nodes, first, second, third, forth and fifth second hidden layer nodes, a hidden layer bias for each hidden layer node, first and second output layer nodes in the output layer, and an output layer bias for each output layer node.

244. The method of claim 234, wherein the first decision support system is a neural network and each of the plurality of first trained neural networks comprises a three-layer network comprising an input layer, a hidden layer and an output layer.

245. The method of claim 234, wherein the clinical factors further comprise the result of a test that detects fetal fibronectin in mammalian body tissue and fluid samples.

246. A method for assessing the risk for delivery in 14 days or fewer days in a patient, comprising the steps of:
  (a) querying and examining the patient to collect observation values reflecting presence and absence of specified factors and storing the observation factors in a storage medium of a computer system, the specified factors comprising: Ethnic Origin Hispanic, Marital Status living with partner, Uterine contractions with or without pain, cervical dilatation, Uterine contractions per hour, and No previous pregnancies;
  (b) performing and obtaining results from the patient of a test that detects fetal fibronectin (fFN) in mammalian body tissue and fluid samples, wherein the test is performed prior to, during or after step (a);
  (c) applying the observation values and the fFN test results from the memory means to a neural network trained on samples of the specified factors and the test results; and
  (d) extracting from the neural network an output value pair that is a preliminary indicator for the risk of delivery in 14 days or few days from obtaining the body tissue of fluid sample.

247. The method of claim 246, further including the steps of:
  (c1) applying the observation values and the relevant biochemical test results from the memory means to a plurality of the second neural networks, each one of the first neural networks being trained on the samples of the specified factors with starting weights for each training being randomly initialized;
  (d1) extracting from each one of the first trained neural networks, output value pairs for each one of the first neural networks; and
  (e) forming a linear combination of the first ones of the output value pairs and forming a linear combination of the second ones of the output value pairs, to obtain a confidence index pair, the confidence index pair being the indicator of the risk for delivery in 14 days or fewer days.

248. The method of claim 246, wherein the first trained neural network comprises a three-layer network containing an input layer, a hidden layer and an output layer, the input layer having seven input nodes, first, second, third, fourth and fifth hidden layer nodes, a hidden layer bias for each hidden layer node, first and second output layer nodes in the output layer, and an output layer bias for each output layer node.

249. The method of claim 246, wherein the sample is a cervico/vaginal sample.

250. A computer system, comprising a neural network or plurality thereof trained for assessing the risk of delivery within a selected time period, wherein the time period is within seven or fourteen days of performing a biochemical test to measure fetal fibronectin in a sample from a pregnant subject or prior to thirty five weeks of gestation.

251. A computer system, comprising a neural network or plurality thereof trained for diagnosing endometriosis.

* * * * *

UNITED STATES PATENT AND TRADEMARK OFFICE
CERTIFICATE OF CORRECTION

PATENT NO. : 6,678,669 B2
DATED : January 13, 2004
INVENTOR(S) : Lapointe et al.

It is certified that error appears in the above-identified patent and that said Letters Patent is hereby corrected as shown below:

Title page,
Item [*] Notice, delete the phrase "by 658 days" and insert -- by 657 days --

Signed and Sealed this

Nineteenth Day of July, 2005

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,678,669 B2 | Page 1 of 11 |
| DATED | : January 13, 2004 | |
| INVENTOR(S) | : Jerome P. LaPointe and Duane Desieno | |

It is certified that error appears in the above-identified patent and that said Letters Patent is hereby corrected as shown below:

<u>Title page,</u>
After Item [57], ABSTRACT, change "251 Claims, 18 Drawing Sheets" to -- 249 Claims, 18 Drawing Sheets --.

<u>Column 239, line 50 through Column 276, line 35,</u>
Replace claims 16, 27, 29, 37, 38, 40-42, 45, 70, 74, 78, 91, 102, 113, 116, 130, 131, 134, 139, 140, 147, 151, 154, 161, 185, 205-207, 224, 229, 233 and 241, with the following:

16. A method of improving the effectiveness of a diagnostic biochemical test, comprising:
 selecting a set of important selected variables according to the method of claim 1 to identify a set of selected variables by collecting candidate variables from test subjects;
 performing the biochemical test on test subjects to obtain test data, wherein the biochemical test is performed before, after or during the selecting step;
 training a decision-support system using the selected final set of important selected variables and the biochemical test data; and
 producing an output that is a test, wherein the output test is more effective than the biochemical test alone.

27. A method for variable selection, comprising:
 (a) collecting a first set of n candidate variables that correspond to measurements, the results of tests, queries or observations and a second set of selected important variables, wherein the second set is initially empty;
 (b) ranking all candidate variables, wherein the ranking is either arbitrary or ordered;
 (c) taking the highest m ranked variables one at a time, wherein m is from 1 up to n, and evaluating each by training a decision-support system on that variable combined with the current set of selected important variables;
 (d) selecting the best of the m variables, wherein the best variable is the one that gives the highest performance of the decision-support system, and if the best variable improves performance compared to the performance of the selected important variables, adding it to the selected important variable set, removing it from the candidate set and continuing evaluating at step (c), if the variable does not improve performance in comparison to the performance of the selected important variables, evaluating is continued at step (e);
 (e) determining if all variables on the candidate set have been evaluated, wherein if they have been evaluated, the process is complete and the set of selected important variables is a completed set, otherwise continuing by taking the next highest m ranked variables one at a time, and evaluating each by training a decision-support-system on that variable combined with the current set of important selected variables and performing step (d); and
 (f) producing an output comprising the set of important variables.

UNITED STATES PATENT AND TRADEMARK OFFICE
CERTIFICATE OF CORRECTION

| | | |
|---|---|---|
| PATENT NO. | : 6,678,669 B2 | |
| DATED | : January 13, 2004 | |
| INVENTOR(S) | : Jerome P. LaPointe and Duane Desieno | |

It is certified that error appears in the above-identified patent and that said Letters Patent is hereby corrected as shown below:

<u>Column 239, line 50 through Column 276, line 35 (cont'd),</u>

29. The method of claim 27, wherein ranking is based on an analysis comprising a sensitivity analysis or other decision-support system-based analysis.

37. A method for variable selection, comprising:
   (a) providing a first set of n candidate variables and a second set of selected important variables, wherein the second set is initially empty;
   (b) taking candidate variables one at a time and evaluating each by training a computer-based decision-support system on that variable combined with the current set of selected important variables;
   (c) selecting the best of the candidate variables, wherein the best variable is any one that gives the highest performance of the decision-support system, and if the best candidate variable improves performance compared to the performance of the selected important variables, adding it to the selected important variable set, removing it from the candidate set and continuing evaluating at step (b), wherein the best candidate variable does not improve performance, the process is completed, wherein the computer-based decision-support system includes a consensus of neural networks; and
   (d) outputting the candidate variables onto a computer display or storing them on computer readable medium.

38. A method for developing a decision-support system-based test to aid in diagnosing a medical condition, disease or disorder in a patient, comprising:
   (a) collecting observations by examining and querying a group of test patients in whom the medical condition is known;
   (b) categorizing the observations into a set of candidate variables having observation values and storing the observation values as an observation data set in a computer;
   (c) selecting a subset of selected important variables from the set of candidate variables by classifying the observation data set using a first decision-support system programmed into the computer system, whereby the subset of selected important variables includes the candidate variables substantially indicative of the medical condition;
   (d) training a computer-based second decision-support system using the observation data corresponding to a subset of selected important variables, whereby the second decision-support system-based system constitutes a decision-support based diagnostic test for the condition, disease or disorder; and
   (e) storing the second decision-support system in a computer memory or on a computer-readable medium.

UNITED STATES PATENT AND TRADEMARK OFFICE
CERTIFICATE OF CORRECTION

| | |
|---|---|
| PATENT NO. | : 6,678,669 B2 |
| DATED | : January 13, 2004 |
| INVENTOR(S) | : Jerome P. LaPointe and Duane Desieno |

It is certified that error appears in the above-identified patent and that said Letters Patent is hereby corrected as shown below:

<u>Column 239, line 50 through Column 276, line 35 (cont'd),</u>

40. The method of claim 38, wherein the second decision-support system includes at least one neural network.

41. The method of claim 38, wherein the step of selecting a subset of selected important variables includes:
    (i) providing a first set of n candidate variables and a second set of selected important variables, wherein the second set is initially empty;
    (ii) taking candidate variables one at a time and evaluating each by training a decision-support system on that variable combined with the current set of selected important variables;
    (iii) selecting the best of the candidate variables, wherein the best variable is any one that gives the highest performance of the decision-support system, and if the best candidate variable improves performance compared to the performance of the selected important variables, adding it to the selected important variable set, removing it from the candidate set and continuing evaluating at step (ii), wherein the best candidate variable does not improve performance, the process is completed.

42. The method of claim 38, wherein the step of selecting a subset of selected important variables includes:
    (i) providing a first set of n candidate variables and a second set of selected important variables, wherein the second set is initially empty;
    (ii) ranking all candidate variables, wherein the ranking is either arbitrary or ordered;
    (iii) taking the highest m ranked variables one at a time, wherein m is from 1 up to n, and evaluating each by training a decision-support system on that variable combined with the current set of selected important variables;
    (iv) selecting the best of the m variables, wherein the best variable is the one that gives the highest performance of the decision-support system, and if the best variable improves performance compared to the performance of the selected important variables, adding it to the selected important variable set, removing it from the candidate set and continuing evaluating at step (iii), if the variable does not improve performance in comparison to the performance of the selected important variables, evaluating is continued at step (v);
    (v) determining if all variables on the candidate set have been evaluated, wherein if they have been evaluated, the process is complete and the set of selected important variables is a completed set, otherwise continuing by taking the next highest m ranked variables one at a time, and evaluating each by training a decision-support-system on that variable combined with the current set of important selected variables and performing step (iv).

UNITED STATES PATENT AND TRADEMARK OFFICE
CERTIFICATE OF CORRECTION

| | | |
|---|---|---|
| PATENT NO. | : 6,678,669 B2 | |
| DATED | : January 13, 2004 | |
| INVENTOR(S) | : Jerome P. LaPointe and Duane Desieno | |

It is certified that error appears in the above-identified patent and that said Letters Patent is hereby corrected as shown below:

<u>Column 239, line 50 through Column 276, line 35 (cont'd),</u>

45. The method of claim 44, wherein the sensitivity analysis comprises:
    (i) determining an average observation value for each of the variables in the observation data set;
    (ii) selecting a training example, and running the example through a decision-support system to produce an output value, designated and stored as the normal output;
    (iii) selecting a first variable in the selected training example, replacing the observation value with the average observation value of the first variable, running the modified example in the decision-support system in the forward mode and recording the output as the modified output;
    (iv) squaring the difference between the normal output and the modified output and accumulating it as a total, wherein the total for each variable designated the selected variable total for each variable;
    (v) repeating steps (iii) and (iv) for each variable in the example;
    (vi) repeating steps (ii)-(v) for each example in the data set, wherein each total for the selected variable represents the relative contribution of each variable to the determination of the decision-support system output.

70. The method of claim 63, wherein the step of selecting a subset of selected important variables includes:
    (i) providing a first set of n candidate variables and a second set of selected important variables, wherein the second set is initially empty;
    (ii) ranking all candidate variables, wherein the ranking is either arbitrary or ordered;
    (iii) taking the highest m ranked variables one at a time, wherein m is from 1 up to n, and evaluating each by training a decision-support system on that variable combined with the current set of selected important variables;
    (iv) selecting the best of the m variables, wherein the best variable is the one that gives the highest performance of the decision-support system, and if the best variable improves performance compared to the performance of the selected important variables, adding it to the selected important variable set, removing it from the candidate set and continuing evaluating at step (iii), if the variable does not improve performance in comparison to the performance of the selected important variables, evaluating is continued at step (v);
    (v) determining if all variables on the candidate set have been evaluated, wherein if they have been evaluated, the process is complete and the set of selected important variables is a completed set, otherwise continuing by taking the next highest m ranked variables one at a time, and evaluating each by training a decision-support-system on that variable combined with the current set of important selected variables and performing step (iv).

UNITED STATES PATENT AND TRADEMARK OFFICE
CERTIFICATE OF CORRECTION

| | | |
|---|---|---|
| PATENT NO. | : 6,678,669 B2 | |
| DATED | : January 13, 2004 | |
| INVENTOR(S) | : Jerome P. LaPointe and Duane Desieno | |

It is certified that error appears in the above-identified patent and that said Letters Patent is hereby corrected as shown below:

Column 239, line 50 through Column 276, line 35 (cont'd),

74. The method of claim 70, wherein ranking is based on a process comprising a statistical analysis.

78. The method of claim 63, wherein the step of selecting a subset of selected important variables includes:
- (i) providing a first set of n candidate variables and a second set of selected important variables, wherein the second set is initially empty;
- (ii) taking candidate variables one at a time and evaluating each by training a decision-support system on that variable combined with the current set of selected important variables;
- (iii) selecting the best of the candidate variables, wherein the best variable is any one that gives the highest performance of the decision-support system, and if the best candidate variable improves performance compared to the performance of the selected important variables, adding it to the selected important variable set, removing it from the candidate set and continuing evaluating at step (ii), wherein the best candidate variable does not improve performance, the process is completed.

91. The method of claim 45, wherein the step of selecting a subset of selected important variables includes:
- (i) providing a first set of n candidate variables and a second set of selected important variables, wherein the second set is initially empty;
- (ii) taking candidate variables one at a time and evaluating each by training a decision-support system on that variable combined with the current set of selected important variables;
- (iii) selecting the best of the candidate variables, wherein the best variable is any one that gives the highest performance of the decision-support system, and if the best candidate variable improves performance compared to the performance of the selected important variables, adding it to the selected important variable set, removing it from the candidate set and continuing evaluating at step (ii), wherein the best candidate variable does not improve performance, the process is completed.

102. The method of claim 60, wherein the step of training a second decision-support system includes partitioning the observation data set into a plurality of partitions comprising at least one testing data partition and a plurality of training data partitions, wherein the second decision-support system is run using the plurality of training data partitions and the testing data partition is used to provide a final performance estimate for the second decision-support system after the training data partitions have been run.

UNITED STATES PATENT AND TRADEMARK OFFICE
CERTIFICATE OF CORRECTION

| | |
|---|---|
| PATENT NO. | : 6,678,669 B2 |
| DATED | : January 13, 2004 |
| INVENTOR(S) | : Jerome P. LaPointe and Duane Desieno |

It is certified that error appears in the above-identified patent and that said Letters Patent is hereby corrected as shown below:

Column 239, line 50 through Column 276, line 35 (cont'd),

113. The method of claim 38, wherein the disorder is endometriosis and the candidate variables comprise at least four of the variables selected from:
    (i) past history of endometriosis, number of births, dysmenorrhea, age, pelvic pain, history of pelvic surgery, smoking quantity per day, medication history, number of pregnancies, number of abortions, abnormal PAP/dysplasia, pregnancy hypertension, genital warts, and diabetes, or
    (ii) age, parity, gravidity, number of abortions, smoking quantity per day, past history of endometriosis, dysmenorrhea, pelvic pain, abnormal PAP, history of pelvic surgery, medication history, pregnancy hypertension, genital warts and diabetes.

116. A method for analyzing effectiveness of a diagnostic test to aid in diagnosing the presence, absence or severity of a medical condition or for assessing a course of treatment or the effectiveness of a particular treatment in a patient comprising:
    (a) collecting observations from a group of test patients in whom the medical condition is known by querying and examining the test patients;
    (b) categorizing the observations into a set of candidate variables having observation values and storing the observation values as an observation data set in a computer;
    (c) selecting a subset of selected important variables from the set of candidate variables by classifying the observation data set using a first decision-support system programmed into the computer system;
    (d) training a second decision-support system using the observation data corresponding to the subset of selected important variables;
    (e) performing the diagnostic test under analysis or treating test patients with the test treatment, wherein the test or treatment is performed before, during or after any of steps (a) - (d);
    (f) collecting results of the diagnostic test under analysis or collecting observations after or during treatment from same the group of test patients;
    (g) categorizing the observations into a second set of candidate variables having observation values, combining them with the observations from step (b), and storing the observation values as an observation data set in a computer;
    (h) selecting a second subset of selected important variables by classifying the observation data set using a first decision-support system programmed into the computer system;
    (i) training a third decision-support system using the observation data corresponding to a subset of selected important variables from step (g); and
    (j) comparing the performance of the second and third systems, thereby assessing the effectiveness of a diagnostic test to aid in diagnosing the presence, absence or severity of a medical condition or assessing the effectiveness of a course of treatment or the effectiveness of a particular treatment in treating a disease, disorder or condition.

UNITED STATES PATENT AND TRADEMARK OFFICE
CERTIFICATE OF CORRECTION

| | | |
|---|---|---|
| PATENT NO. | : 6,678,669 B2 | |
| DATED | : January 13, 2004 | |
| INVENTOR(S) | : Jerome P. LaPointe and Duane Desieno | |

It is certified that error appears in the above-identified patent and that said Letters Patent is hereby corrected as shown below:

<u>Column 239, line 50 through Column 276, line 35 (cont'd),</u>

130. The method of claim 126, wherein the sensitivity analysis, comprises:
  (i) determining an average observation value for each of the variables in the observation data set;
  (ii) selecting a training example, and running the example through a decision-support system to produce an output value, designated and stored as the normal output;
  (iii) selecting a first variable in the selected training example, replacing the observation value with the average observation value of the first variable, running the modified example in the decision-support system in the forward mode and recording the output as the modified output;
  (iv) squaring the difference between the normal output and the modified output and accumulating it as a total, wherein the total for each variable designated the selected variable total for each variable;
  (v) repeating steps (iii) and (iv) for each variable in the example;
  (vi) repeating steps (ii)-(v) for each example in the data set, wherein each total for the selected variable represents the relative contribution of each variable to the determination of the decision-support system output.

131. The method of claim 125, wherein ranking is based on a process comprising a statistical analysis.

134. The method of claim 116, wherein the step of training a second and/or third decision-support system includes partitioning the observation data set into a plurality of partitions comprising at least one testing data partition and a plurality of training data partitions, wherein the second decision-support system is run using the plurality of training data partitions and the testing data partition is used to provide a final performance estimate for the second decision-support system after the training data partitions have been run.

139. The method of claim 116, further comprising:
   collecting additional observations from patients and categorizing them into a set of candidate variables, which are then added to first set of candidate variables at step (b); and then
(j) repeating steps (c) - (i).

140. A method for developing a condition-specific biochemical test to aid in diagnosing the presence, absence, or severity of a medical condition in a patient comprising:
  (a) performing and collecting test results of a biochemical test from a group of test patients in whom the condition is known or suspected;

UNITED STATES PATENT AND TRADEMARK OFFICE
CERTIFICATE OF CORRECTION

| | | |
|---|---|---|
| PATENT NO. | : 6,678,669 B2 | |
| DATED | : January 13, 2004 | |
| INVENTOR(S) | : Jerome P. LaPointe and Duane Desieno | |

It is certified that error appears in the above-identified patent and that said Letters Patent is hereby corrected as shown below:

<u>Column 239, line 50 through Column 276, line 35 (cont'd),</u>

(b) categorizing the test results and other observations into a set of candidate variables having observation values and storing the observation values as an observation data set in a computer;
    (c) selecting a subset of selected important variables from a set of variables comprising the candidate variables by classifying the observation data set using a first decision-support system programmed into the computer system, whereby the subset of selected important variables includes the candidate variables substantially indicative of the medical condition; and
    (d) identifying those variable(s) in the selected important variable set that correspond to biochemical data; and
    (e) producing a biochemical test that assesses the data that corresponds to the identified variable(s).

147. The method of claim 140, wherein the step of selecting a subset of selected important variables includes:
    (i) providing a first set of n candidate variables and a second set of selected important variables, wherein the second set is initially empty;
    (ii) taking candidate variables one at a time and evaluating each by training a decision-support system on that variable combined with the current set of selected important variables;
    (iii) selecting the best of the candidate variables, wherein the best variable is any one that gives the highest performance of the decision-support system, and if the best candidate variable improves performance compared to the performance of the selected important variables, adding it to the selected important variable set, removing it from the candidate set and continuing evaluating at step (ii), wherein the best candidate variable does not improve performance, the process is completed.

151. The method of claim 150, wherein the sensitivity analysis comprises:
    (i) determining an average observation value for each of the variables in the observation data set;
    (ii) selecting a training example, and running the example through a decision-support system to produce an output value, designated and stored as the normal output;
    (iii) selecting a first variable in the selected training example, replacing the observation value with the average observation value of the first variable, running the modified example in the decision-support system in the forward mode and recording the output as the modified output;
    (iv) squaring the difference between the normal output and the modified output and accumulating it as a total, wherein the total for each variable designated the selected variable total for each variable;

UNITED STATES PATENT AND TRADEMARK OFFICE
CERTIFICATE OF CORRECTION

| | | |
|---|---|---|
| PATENT NO. | : 6,678,669 B2 | Page 9 of 11 |
| DATED | : January 13, 2004 | |
| INVENTOR(S) | : Jerome P. LaPointe and Duane Desieno | |

It is certified that error appears in the above-identified patent and that said Letters Patent is hereby corrected as shown below:

Column 239, line 50 through Column 276, line 35 (cont'd), (v) repeating steps (iii) and (iv) for each variable in the example;
      (vi) repeating steps (ii)-(v) for each example in the data set, wherein each total for the selected variable represents the relative contribution of each variable to the determination of the decision-support system output.

154. The method of claim 153, wherein the sensitivity analysis, comprises:
      (i) determining an average observation value for each of the variables in the observation data set;
      (ii) selecting a training example, and running the example through a decision-support system to produce an output value, designated and stored as the normal output;
      (iii) selecting a first variable in the selected training example, replacing the observation value with the average observation value of the first variable, running the modified example in the decision-support system in the forward mode and recording the output as the modified output;
      (iv) squaring the difference between the normal output and the modified output and accumulating it as a total, wherein the total for each variable designated the selected variable total for each variable;
      (v) repeating steps (iii) and (iv) for each variable in the example;
      (vi) repeating steps (ii)-(v) for each example in the data set, wherein each total for the selected variable represents the relative contribution of each variable to the determination of the decision-support system output.

161. The method of claim 140, wherein the observation values are obtained from patient historical data results and/or biochemical test results.

185. A method for assessing the risk of delivery prior to completion of 35 weeks of gestation, comprising assessing a subset of variables containing at least three and up to all of the following variables:
    Ethnic Origin Caucasian;
    Marital Status living with partner;
    EGA by sonogram;
    EGA at sampling;
    estimated date of delivery by best;
    cervical dilatation (CM);
    parity-preterm;
    vaginal bleeding at time of sampling;
    cervical consistency at time of sampling; and
    previous pregnancy without complication,
    by querying and testing the subject;

UNITED STATES PATENT AND TRADEMARK OFFICE
CERTIFICATE OF CORRECTION

| | |
|---|---|
| PATENT NO. | : 6,678,669 B2 |
| DATED | : January 13, 2004 |
| INVENTOR(S) | : Jerome P. LaPointe and Duane Desieno |

It is certified that error appears in the above-identified patent and that said Letters Patent is hereby corrected as shown below:

Column 239, line 50 through Column 276, line 35 (cont'd), entering the results of the queries and tests into a computer system that comprises a decision-support system that has been trained to assesses the risk of delivery prior to 35 weeks of gestation; and
    producing an output that assesses the risk.

205. The method of claim 202, wherein the sample is a cervico/vaginal sample.

206. A method for assessing the risk for delivery in seven or fewer days in a pregnant subject, comprising assessing a subset of variables containing at least three and up to all of the following variables:
Ethnic Origin Caucasian;
Uterine contractions with or without pain;
Parity-abortions;
vaginal bleeding at time of sampling;
uterine contractions per hour; and
No previous pregnancies,
    by querying and testing the subject;
    entering the results of the queries and tests into a computer system that comprises a decision-support system that has been trained to assess the risk of delivery within seven days; and
    producing an output that assesses the risk of delivery within seven days.

207. The method of claim 206, wherein:
    the variables further include the results of a test to detect fetal fibronectin (fFN) in a cervico/vaginal sample;
    the selected variables include the results of the test; and
    the method measures the risk of delivery in 7 days or fewer days from the time of obtaining the sample for the fFN.

224. A method for assessing the risk for delivery in 7 days or fewer days in a subject, comprising the steps of:
    (a) querying and examining the subject to collect observation values reflecting presence and absence of specified factors and storing the observation factors in storage means of the computer system, the specified factors comprising: Ethnic Origin Caucasian, Uterine contractions with or without pain, Parity-abortions, vaginal bleeding at time of sampling, uterine contractions per hour, prior to and No previous pregnancies;
    (b) performing and obtaining results from the patient of a test that detects fetal fibronectin (fFN) in mammalian body tissue and fluid samples, wherein the test is performed before, during or after the querying and examining step;

UNITED STATES PATENT AND TRADEMARK OFFICE
CERTIFICATE OF CORRECTION

| | | |
|---|---|---|
| PATENT NO. | : 6,678,669 B2 | |
| DATED | : January 13, 2004 | |
| INVENTOR(S) | : Jerome P. LaPointe and Duane Desieno | |

It is certified that error appears in the above-identified patent and that said Letters Patent is hereby corrected as shown below:

<u>Column 239, line 50 through Column 276, line 35 (cont'd),</u>

(c) applying the observation values and the fFN test results from the memory means to a neural network trained on samples of the specified factors and the test results; and thereupon (d) obtaining from the neural network an output value pair that is an indicator for the risk of delivery in 7 days or fewer days from obtaining the cervico/vaginal sample.

229.   The method of claim 228, wherein:
    the variables further include the results of a test for to detect fetal fibronectin (fFN) in a cervico/vaginal sample;
    the selected variables include the results of the test; and
    the method measures the risk of delivery in 14 days or fewer days from obtaining the sample for the fFN.

233.   The method of claim 228, wherein:
    the variables further include the results of a test that detects fetal fibronectin in mammalian body tissue and fluid samples;
    the selected variables include the results of the test; and
    the method measures the risk of delivery in 14 days or fewer days from obtaining the sample for the fFN.

241.   The method of claim 238, wherein the first decision support system is a neural network and each of the plurality of first trained neural networks comprises a three-layer network comprising an input layer, a hidden layer and an output layer.

Cancel claims 250 and 251.

Signed and Sealed this

Third Day of January, 2006

JON W. DUDAS
*Director of the United States Patent and Trademark Office*